United States Patent
Shelton, IV et al.

(10) Patent No.: US 11,589,916 B2
(45) Date of Patent: Feb. 28, 2023

(54) ELECTROSURGICAL INSTRUMENTS WITH ELECTRODES HAVING VARIABLE ENERGY DENSITIES

(71) Applicant: Ethicon LLC, Guaynabo, PR (US)

(72) Inventors: Frederick E. Shelton, IV, Hillsboro, OH (US); Kevin M. Fiebig, Cincinnati, OH (US); Taylor W. Aronhalt, Loveland, OH (US); Sarah A. Worthington, Cincinnati, OH (US)

(73) Assignee: Cilag GmbH International, Zug (CH)

(*) Notice: Subject to any disclaimer, the term of this patent is extended or adjusted under 35 U.S.C. 154(b) by 203 days.

(21) Appl. No.: 16/885,879

(22) Filed: May 28, 2020

(65) Prior Publication Data
US 2021/0196360 A1   Jul. 1, 2021

Related U.S. Application Data

(60) Provisional application No. 62/955,299, filed on Dec. 30, 2019.

(51) Int. Cl.
*G09G 5/00* (2006.01)
*A61B 18/14* (2006.01)
(Continued)

(52) U.S. Cl.
CPC ...... *A61B 18/1445* (2013.01); *A61B 18/1206* (2013.01); *A61B 18/16* (2013.01);
(Continued)

(58) Field of Classification Search
CPC .............. A61B 2018/00601; A61B 2018/0063; A61B 2018/00994; A61B 2018/126;
(Continued)

(56) References Cited

U.S. PATENT DOCUMENTS 969,528 A    9/1910  Disbrow
1,570,025 A  1/1926  Young
(Continued)

FOREIGN PATENT DOCUMENTS

CA    2535467 A1    4/1993
CN    2460047 Y    11/2001
(Continued)

OTHER PUBLICATIONS

"ATM-MPLS Network Interworking Version 2.0, af-aic-0178.001" ATM Standard, The ATM Forum Technical Committee, published Aug. 2003.
(Continued)

*Primary Examiner* — Insa Sadio

(57) ABSTRACT

An electrosurgical instrument comprising an end effector is disclosed. The end effector comprises a first jaw and a second jaw. At least one of the first jaw and the second jaw is movable to transition the end effector from an open configuration to a closed configuration to grasp tissue therebetween. The second jaw comprises linear portions cooperating to form an angular profile and a treatment surface comprising segments extending along the angular profile. The segments comprise different geometries and different conductivities. The segments are configured to produce variable energy densities along the treatment surface.

42 Claims, 30 Drawing Sheets

(51) Int. Cl.
*A61B 18/12* (2006.01)
*A61B 90/00* (2016.01)
*A61B 18/16* (2006.01)
*A61B 18/00* (2006.01)
*A61B 17/32* (2006.01)

(52) U.S. Cl.
CPC .............. *A61B 2017/320074* (2017.08); *A61B 2018/0063* (2013.01); *A61B 2018/00077* (2013.01); *A61B 2018/00083* (2013.01); *A61B 2018/00095* (2013.01); *A61B 2018/00101* (2013.01); *A61B 2018/00107* (2013.01); *A61B 2018/00404* (2013.01); *A61B 2018/00589* (2013.01); *A61B 2018/00601* (2013.01); *A61B 2018/00607* (2013.01); *A61B 2018/00791* (2013.01); *A61B 2018/00827* (2013.01); *A61B 2018/00875* (2013.01); *A61B 2018/00892* (2013.01); *A61B 2018/00898* (2013.01); *A61B 2018/00994* (2013.01); *A61B 2018/126* (2013.01); *A61B 2018/1226* (2013.01); *A61B 2018/1253* (2013.01); *A61B 2018/1467* (2013.01); *A61B 2018/162* (2013.01); *A61B 2090/066* (2016.02)

(58) Field of Classification Search
CPC ........ A61B 17/320092; A61B 18/1442; A61B 2017/320095; A61B 18/1445; A61B 2090/065; A61B 17/07207; A61B 2017/00017; A61B 2017/00221; A61B 2017/00398; A61B 2017/0046; A61B 2017/00725; A61B 2017/07271; A61B 2017/07285; A61B 2017/2927; A61B 2017/2929; A61B 2018/1465; A61B 2090/061; A61B 2090/0811; A61B 2090/0812; A61B 90/03; A61B 2090/064; A61B 2090/0803; A61B 2090/0814; A61B 34/30; A61B 17/072; A61B 18/1206; A61B 2017/00039; A61B 2017/00119; A61B 2017/00455; A61B 2018/00083; A61B 2017/07278; A61B 2018/00607; A61B 2018/00875; A61B 2090/034; A61B 90/98; A61B 2017/00477; A61B 2017/07254; A61B 2018/00077; A61B 2018/00136; A61B 2018/00404; A61B 2018/1253; A61B 18/16; A61B 2017/320075; A61B 2017/320094; A61B 2018/00107; A61B 2018/00589; A61B 2018/1412; A61B 2018/1455; A61B 2034/302; A61B 2090/035; A61B 17/320068; A61B 18/00; A61B 2017/07228; A61B 2017/320074; A61B 2018/0019; A61B 2018/1452; A61B 2034/2048; A61B 17/00234; A61B 18/14; A61B 2017/00473; A61B 2017/2825; A61B 2018/0013; A61B 2018/00148; A61B 2018/00202; A61B 2018/00702; A61B 2090/067; A61B 2218/008; A61B 17/068; A61B 17/0686; A61B 17/295; A61B 17/32; A61B 18/1482; A61B 18/149; A61B 18/1815; A61B 2017/00022; A61B 2017/00026; A61B 2017/00075; A61B 2017/00015; A61B 2017/00137; A61B 2017/00154; A61B 2017/00225; A61B 2017/00305; A61B 2017/00367; A61B 2017/00424; A61B 2017/00734; A61B 2017/00876; A61B 2017/07264; A61B 2017/20228; A61B 2017/2829; A61B 2017/2925; A61B 2017/2926; A61B 2018/00095; A61B 2018/00101; A61B 2018/00125; A61B 2018/00208; A61B 2018/00613; A61B 2018/00672; A61B 2018/0072; A61B 2018/00732; A61B 2018/00767; A61B 2018/00791; A61B 2018/00827; A61B 2018/00892; A61B 2018/00898; A61B 2018/00916; A61B 2018/00922; A61B 2018/00958; A61B 2018/1226; A61B 2018/1273; A61B 2018/1405; A61B 2018/1467; A61B 2018/162; A61B 2034/2055; A61B 2034/2072; A61B 2034/256; A61B 2034/258; A61B 2090/066; A61B 2090/0804; A61B 2090/0807; A61B 2090/0808; A61B 2218/002; A61B 2218/007; A61B 2562/0223; A61B 2562/0247; A61B 2562/0261; A61B 34/20; A61B 90/06; A61B 90/08; A61B 90/90; G16H 20/40; G16H 40/63; G16H 40/40; H05K 1/0283; H05K 1/147; H05K 2201/09263; H05K 1/028; H05K 1/148; H05K 2201/056; H05K 2201/10151; H05K 3/103; H05K 3/12; B22F 2003/242; B22F 3/225; B22F 3/24; B33Y 80/00; H04B 15/00; H04B 5/0081; G05B 2219/37094; G01R 33/0094; G01R 33/072; G01R 33/02

See application file for complete search history.

(56) References Cited

U.S. PATENT DOCUMENTS

| | | |
|---|---|---|
| 1,813,902 A | 7/1931 | Bovie |
| 2,188,497 A | 1/1940 | Calva |
| 2,366,274 A | 1/1945 | Luth et al. |
| 2,425,245 A | 8/1947 | Johnson |
| 2,442,966 A | 6/1948 | Wallace |
| 2,458,152 A | 1/1949 | Eakins |
| 2,510,693 A | 6/1950 | Green |
| 2,597,564 A | 5/1952 | Bugg |
| 2,704,333 A | 3/1955 | Calosi et al. |
| 2,736,960 A | 3/1956 | Armstrong |
| 2,748,967 A | 6/1956 | Roach |
| 2,845,072 A | 7/1958 | Shafer |
| 2,849,788 A | 9/1958 | Creek |
| 2,867,039 A | 1/1959 | Zach |
| 2,874,470 A | 2/1959 | Richards |
| 2,990,616 A | 7/1961 | Balamuth et al. |
| RE25,033 E | 8/1961 | Balamuth et al. |
| 3,015,961 A | 1/1962 | Roney |
| 3,033,407 A | 5/1962 | Alfons |
| 3,053,124 A | 9/1962 | Balamuth et al. |
| 3,082,805 A | 3/1963 | Royce |
| 3,166,971 A | 1/1965 | Stoecker |
| 3,322,403 A | 5/1967 | Murphy |
| 3,432,691 A | 3/1969 | Shoh |
| 3,433,226 A | 3/1969 | Boyd |
| 3,489,930 A | 1/1970 | Shoh |
| 3,513,848 A | 5/1970 | Winston et al. |
| 3,514,856 A | 6/1970 | Camp et al. |
| 3,525,912 A | 8/1970 | Wallin |
| 3,526,219 A | 9/1970 | Balamuth |
| 3,554,198 A | 1/1971 | Tatoian et al. |
| 3,580,841 A | 5/1971 | Cadotte et al. |
| 3,606,682 A | 9/1971 | Camp et al. |
| 3,614,484 A | 10/1971 | Shoh |
| 3,616,375 A | 10/1971 | Inoue |
| 3,629,726 A | 12/1971 | Popescu |
| 3,636,943 A | 1/1972 | Balamuth |

(56) References Cited

U.S. PATENT DOCUMENTS

| | | |
|---|---|---|
| 3,668,486 A | 6/1972 | Silver |
| 3,702,948 A | 11/1972 | Balamuth |
| 3,703,651 A | 11/1972 | Blowers |
| 3,776,238 A | 12/1973 | Peyman et al. |
| 3,777,760 A | 12/1973 | Essner |
| 3,805,787 A | 4/1974 | Banko |
| 3,809,977 A | 5/1974 | Balamuth et al. |
| 3,830,098 A | 8/1974 | Antonevich |
| 3,854,737 A | 12/1974 | Gilliam, Sr. |
| 3,862,630 A | 1/1975 | Balamuth |
| 3,875,945 A | 4/1975 | Friedman |
| 3,885,438 A | 5/1975 | Harris, Sr. et al. |
| 3,900,823 A | 8/1975 | Sokal et al. |
| 3,918,442 A | 11/1975 | Nikolaev et al. |
| 3,924,335 A | 12/1975 | Balamuth et al. |
| 3,946,738 A | 3/1976 | Newton et al. |
| 3,955,859 A | 5/1976 | Stella et al. |
| 3,956,826 A | 5/1976 | Perdreaux, Jr. |
| 3,989,952 A | 11/1976 | Hohmann |
| 4,005,714 A | 2/1977 | Hiltebrandt |
| 4,012,647 A | 3/1977 | Balamuth et al. |
| 4,034,762 A | 7/1977 | Cosens et al. |
| 4,058,126 A | 11/1977 | Leveen |
| 4,074,719 A | 2/1978 | Semm |
| 4,156,187 A | 5/1979 | Murry et al. |
| 4,167,944 A | 9/1979 | Banko |
| 4,188,927 A | 2/1980 | Harris |
| 4,200,106 A | 4/1980 | Douvas et al. |
| 4,203,430 A | 5/1980 | Takahashi |
| 4,203,444 A | 5/1980 | Bonnell et al. |
| 4,220,154 A | 9/1980 | Semm |
| 4,237,441 A | 12/1980 | van Konynenburg et al. |
| 4,244,371 A | 1/1981 | Farin |
| 4,281,785 A | 8/1981 | Brooks |
| 4,300,083 A | 11/1981 | Helges |
| 4,302,728 A | 11/1981 | Nakamura |
| 4,304,987 A | 12/1981 | van Konynenburg |
| 4,306,570 A | 12/1981 | Matthews |
| 4,314,559 A | 2/1982 | Allen |
| 4,353,371 A | 10/1982 | Cosman |
| 4,409,981 A | 10/1983 | Lundberg |
| 4,445,063 A | 4/1984 | Smith |
| 4,461,304 A | 7/1984 | Kuperstein |
| 4,463,759 A | 8/1984 | Garito et al. |
| 4,491,132 A | 1/1985 | Aikins |
| 4,492,231 A | 1/1985 | Auth |
| 4,494,759 A | 1/1985 | Kieffer |
| 4,504,264 A | 3/1985 | Kelman |
| 4,512,344 A | 4/1985 | Barber |
| 4,526,571 A | 7/1985 | Wuchinich |
| 4,535,773 A | 8/1985 | Yoon |
| 4,541,638 A | 9/1985 | Ogawa et al. |
| 4,545,374 A | 10/1985 | Jacobson |
| 4,545,926 A | 10/1985 | Fouts, Jr. et al. |
| 4,549,147 A | 10/1985 | Kondo |
| 4,550,870 A | 11/1985 | Krumme et al. |
| 4,553,544 A | 11/1985 | Nomoto et al. |
| 4,562,838 A | 1/1986 | Walker |
| 4,574,615 A | 3/1986 | Bower et al. |
| 4,582,236 A | 4/1986 | Hirose |
| 4,593,691 A | 6/1986 | Lindstrom et al. |
| 4,608,981 A | 9/1986 | Rothfuss et al. |
| 4,617,927 A | 10/1986 | Manes |
| 4,633,119 A | 12/1986 | Thompson |
| 4,633,874 A | 1/1987 | Chow et al. |
| 4,634,420 A | 1/1987 | Spinosa et al. |
| 4,640,279 A | 2/1987 | Beard |
| 4,641,053 A | 2/1987 | Takeda |
| 4,646,738 A | 3/1987 | Trott |
| 4,646,756 A | 3/1987 | Watmough et al. |
| 4,649,919 A | 3/1987 | Thimsen et al. |
| 4,662,068 A | 5/1987 | Polonsky |
| 4,674,502 A | 6/1987 | Imonti |
| 4,694,835 A | 9/1987 | Strand |
| 4,708,127 A | 11/1987 | Abdelghani |
| 4,712,722 A | 12/1987 | Hood et al. |
| 4,735,603 A | 4/1988 | Goodson et al. |
| 4,761,871 A | 8/1988 | O'Connor et al. |
| 4,808,154 A | 2/1989 | Freeman |
| 4,819,635 A | 4/1989 | Shapiro |
| 4,827,911 A | 5/1989 | Broadwin et al. |
| 4,830,462 A | 5/1989 | Karny et al. |
| 4,832,683 A | 5/1989 | Idemoto et al. |
| 4,836,186 A | 6/1989 | Scholz |
| 4,838,853 A | 6/1989 | Parisi |
| 4,844,064 A | 7/1989 | Thimsen et al. |
| 4,849,133 A | 7/1989 | Yoshida et al. |
| 4,850,354 A | 7/1989 | McGurk-Burleson et al. |
| 4,852,578 A | 8/1989 | Companion et al. |
| 4,860,745 A | 8/1989 | Farin et al. |
| 4,862,890 A | 9/1989 | Stasz et al. |
| 4,865,159 A | 9/1989 | Jamison |
| 4,867,157 A | 9/1989 | McGurk-Burleson et al. |
| 4,878,493 A | 11/1989 | Pasternak et al. |
| 4,880,015 A | 11/1989 | Nierman |
| 4,881,550 A | 11/1989 | Kothe |
| 4,896,009 A | 1/1990 | Pawlowski |
| 4,903,696 A | 2/1990 | Stasz et al. |
| 4,910,389 A | 3/1990 | Sherman et al. |
| 4,915,643 A | 4/1990 | Samejima et al. |
| 4,920,978 A | 5/1990 | Colvin |
| 4,922,902 A | 5/1990 | Wuchinich et al. |
| 4,926,860 A | 5/1990 | Stice et al. |
| 4,936,842 A | 6/1990 | D'Amelio et al. |
| 4,954,960 A | 9/1990 | Lo et al. |
| 4,965,532 A | 10/1990 | Sakurai |
| 4,979,952 A | 12/1990 | Kubota et al. |
| 4,981,756 A | 1/1991 | Rhandhawa |
| 5,001,649 A | 3/1991 | Lo et al. |
| 5,009,661 A | 4/1991 | Michelson |
| 5,013,956 A | 5/1991 | Kurozumi et al. |
| 5,015,227 A | 5/1991 | Broadwin et al. |
| 5,020,514 A | 6/1991 | Heckele |
| 5,026,370 A | 6/1991 | Lottick |
| 5,026,387 A | 6/1991 | Thomas |
| 5,035,695 A | 7/1991 | Weber, Jr. et al. |
| 5,042,461 A | 8/1991 | Inoue et al. |
| 5,042,707 A | 8/1991 | Taheri |
| 5,052,145 A | 10/1991 | Wang |
| 5,061,269 A | 10/1991 | Muller |
| 5,075,839 A | 12/1991 | Fisher et al. |
| 5,084,052 A | 1/1992 | Jacobs |
| 5,099,840 A | 3/1992 | Goble et al. |
| 5,104,025 A | 4/1992 | Main et al. |
| 5,105,117 A | 4/1992 | Yamaguchi |
| 5,106,538 A | 4/1992 | Barma et al. |
| 5,108,383 A | 4/1992 | White |
| 5,109,819 A | 5/1992 | Custer et al. |
| 5,112,300 A | 5/1992 | Ureche |
| 5,113,139 A | 5/1992 | Furukawa |
| 5,123,903 A | 6/1992 | Quaid et al. |
| 5,126,618 A | 6/1992 | Takahashi et al. |
| D327,872 S | 7/1992 | McMills et al. |
| 5,152,762 A | 10/1992 | McElhenney |
| 5,156,633 A | 10/1992 | Smith |
| 5,160,334 A | 11/1992 | Billings et al. |
| 5,162,044 A | 11/1992 | Gahn et al. |
| 5,163,421 A | 11/1992 | Bernstein et al. |
| 5,163,537 A | 11/1992 | Radev |
| 5,163,945 A | 11/1992 | Ortiz et al. |
| 5,167,619 A | 12/1992 | Wuchinich |
| 5,167,725 A | 12/1992 | Clark et al. |
| 5,172,344 A | 12/1992 | Ehrlich |
| 5,174,276 A | 12/1992 | Crockard |
| D332,660 S | 1/1993 | Rawson et al. |
| 5,176,677 A | 1/1993 | Wuchinich |
| 5,176,695 A | 1/1993 | Dulebohn |
| 5,184,605 A | 2/1993 | Grzeszykowski |
| 5,188,102 A | 2/1993 | Idemoto et al. |
| D334,173 S | 3/1993 | Liu et al. |
| 5,190,517 A | 3/1993 | Zieve et al. |
| 5,190,518 A | 3/1993 | Takasu |
| 5,190,541 A | 3/1993 | Abele et al. |
| 5,196,007 A | 3/1993 | Ellman et al. |

(56) References Cited

U.S. PATENT DOCUMENTS

| | | |
|---|---|---|
| 5,203,380 A | 4/1993 | Chikama |
| 5,205,459 A | 4/1993 | Brinkerhoff et al. |
| 5,205,817 A | 4/1993 | Idemoto et al. |
| 5,209,719 A | 5/1993 | Baruch et al. |
| 5,213,569 A | 5/1993 | Davis |
| 5,214,339 A | 5/1993 | Naito |
| 5,217,460 A | 6/1993 | Knoepfler |
| 5,218,529 A | 6/1993 | Meyer et al. |
| 5,221,282 A | 6/1993 | Wuchinich |
| 5,222,937 A | 6/1993 | Kagawa |
| 5,226,909 A | 7/1993 | Evans et al. |
| 5,226,910 A | 7/1993 | Kajiyama et al. |
| 5,231,989 A | 8/1993 | Middleman et al. |
| 5,234,428 A | 8/1993 | Kaufman |
| 5,241,236 A | 8/1993 | Sasaki et al. |
| 5,241,968 A | 9/1993 | Slater |
| 5,242,339 A | 9/1993 | Thornton |
| 5,242,460 A | 9/1993 | Klein et al. |
| 5,246,003 A | 9/1993 | DeLonzor |
| 5,254,129 A | 10/1993 | Alexander |
| 5,257,988 A | 11/1993 | L'Esperance, Jr. |
| 5,258,004 A | 11/1993 | Bales et al. |
| 5,258,006 A | 11/1993 | Rydell et al. |
| 5,261,922 A | 11/1993 | Hood |
| 5,263,957 A | 11/1993 | Davison |
| 5,264,925 A | 11/1993 | Shipp et al. |
| 5,269,297 A | 12/1993 | Weng et al. |
| 5,275,166 A | 1/1994 | Vaitekunas et al. |
| 5,275,607 A | 1/1994 | Lo et al. |
| 5,275,609 A | 1/1994 | Pingleton et al. |
| 5,282,800 A | 2/1994 | Foshee et al. |
| 5,282,817 A | 2/1994 | Hoogeboom et al. |
| 5,285,795 A | 2/1994 | Ryan et al. |
| 5,285,945 A | 2/1994 | Brinkerhoff et al. |
| 5,290,286 A | 3/1994 | Parins |
| 5,293,863 A | 3/1994 | Zhu et al. |
| 5,300,068 A | 4/1994 | Rosar et al. |
| 5,304,115 A | 4/1994 | Pflueger et al. |
| D347,474 S | 5/1994 | Olson |
| 5,307,976 A | 5/1994 | Olson et al. |
| 5,309,927 A | 5/1994 | Welch |
| 5,312,023 A | 5/1994 | Green et al. |
| 5,312,425 A | 5/1994 | Evans et al. |
| 5,318,525 A | 6/1994 | West et al. |
| 5,318,563 A | 6/1994 | Malis et al. |
| 5,318,564 A | 6/1994 | Eggers |
| 5,318,570 A | 6/1994 | Hood et al. |
| 5,318,589 A | 6/1994 | Lichtman |
| 5,322,055 A | 6/1994 | Davison et al. |
| 5,324,299 A | 6/1994 | Davison et al. |
| 5,326,013 A | 7/1994 | Green et al. |
| 5,326,342 A | 7/1994 | Pflueger et al. |
| 5,330,471 A | 7/1994 | Eggers |
| 5,330,502 A | 7/1994 | Hassler et al. |
| 5,334,183 A | 8/1994 | Wuchinich |
| 5,339,723 A | 8/1994 | Huitema |
| 5,342,356 A | 8/1994 | Ellman et al. |
| 5,342,359 A | 8/1994 | Rydell |
| 5,344,420 A | 9/1994 | Hilal et al. |
| 5,345,937 A | 9/1994 | Middleman et al. |
| 5,346,502 A | 9/1994 | Estabrook et al. |
| 5,353,474 A | 10/1994 | Good et al. |
| 5,357,164 A | 10/1994 | Imabayashi et al. |
| 5,357,423 A | 10/1994 | Weaver et al. |
| 5,359,994 A | 11/1994 | Krauter et al. |
| 5,361,583 A | 11/1994 | Huitema |
| 5,366,466 A | 11/1994 | Christian et al. |
| 5,368,557 A | 11/1994 | Nita et al. |
| 5,370,645 A | 12/1994 | Klicek et al. |
| 5,371,429 A | 12/1994 | Manna |
| 5,374,813 A | 12/1994 | Shipp |
| D354,564 S | 1/1995 | Medema |
| 5,381,067 A | 1/1995 | Greenstein et al. |
| 5,383,874 A | 1/1995 | Jackson et al. |
| 5,383,917 A | 1/1995 | Desai et al. |
| 5,387,207 A | 2/1995 | Dyer et al. |
| 5,387,215 A | 2/1995 | Fisher |
| 5,389,098 A | 2/1995 | Tsuruta et al. |
| 5,394,187 A | 2/1995 | Shipp |
| 5,395,033 A | 3/1995 | Byrne et al. |
| 5,395,312 A | 3/1995 | Desai |
| 5,395,363 A | 3/1995 | Billings et al. |
| 5,395,364 A | 3/1995 | Anderhub et al. |
| 5,396,266 A | 3/1995 | Brimhall |
| 5,396,900 A | 3/1995 | Slater et al. |
| 5,400,267 A | 3/1995 | Denen et al. |
| 5,403,312 A | 4/1995 | Yates et al. |
| 5,403,334 A | 4/1995 | Evans et al. |
| 5,406,503 A | 4/1995 | Williams, Jr. et al. |
| 5,408,268 A | 4/1995 | Shipp |
| D358,887 S | 5/1995 | Feinberg |
| 5,411,481 A | 5/1995 | Allen et al. |
| 5,417,709 A | 5/1995 | Slater |
| 5,419,761 A | 5/1995 | Narayanan et al. |
| 5,421,829 A | 6/1995 | Olichney et al. |
| 5,423,844 A | 6/1995 | Miller |
| 5,428,504 A | 6/1995 | Bhatia |
| 5,429,131 A | 7/1995 | Scheinman et al. |
| 5,438,997 A | 8/1995 | Sieben et al. |
| 5,441,499 A | 8/1995 | Fritzsch |
| 5,443,463 A | 8/1995 | Stern et al. |
| 5,445,638 A | 8/1995 | Rydell et al. |
| 5,445,639 A | 8/1995 | Kuslich et al. |
| 5,447,509 A | 9/1995 | Mills et al. |
| 5,449,370 A | 9/1995 | Vaitekunas |
| 5,451,053 A | 9/1995 | Garrido |
| 5,451,161 A | 9/1995 | Sharp |
| 5,451,220 A | 9/1995 | Ciervo |
| 5,451,227 A | 9/1995 | Michaelson |
| 5,456,684 A | 10/1995 | Schmidt et al. |
| 5,458,598 A | 10/1995 | Feinberg et al. |
| 5,462,604 A | 10/1995 | Shibano et al. |
| 5,465,895 A | 11/1995 | Knodel et al. |
| 5,471,988 A | 12/1995 | Fujio et al. |
| 5,472,443 A | 12/1995 | Cordis et al. |
| 5,476,479 A | 12/1995 | Green et al. |
| 5,478,003 A | 12/1995 | Green et al. |
| 5,480,409 A | 1/1996 | Riza |
| 5,483,501 A | 1/1996 | Park et al. |
| 5,484,436 A | 1/1996 | Eggers et al. |
| 5,486,162 A | 1/1996 | Brumbach |
| 5,486,189 A | 1/1996 | Mudry et al. |
| 5,490,860 A | 2/1996 | Middle et al. |
| 5,496,317 A | 3/1996 | Goble et al. |
| 5,499,992 A | 3/1996 | Meade et al. |
| 5,500,216 A | 3/1996 | Julian et al. |
| 5,501,654 A | 3/1996 | Failla et al. |
| 5,504,650 A | 4/1996 | Katsui et al. |
| 5,505,693 A | 4/1996 | Mackool |
| 5,507,297 A | 4/1996 | Slater et al. |
| 5,507,738 A | 4/1996 | Ciervo |
| 5,509,922 A | 4/1996 | Aranyi et al. |
| 5,511,556 A | 4/1996 | DeSantis |
| 5,520,704 A | 5/1996 | Castro et al. |
| 5,522,832 A | 6/1996 | Kugo et al. |
| 5,522,839 A | 6/1996 | Pilling |
| 5,527,331 A | 6/1996 | Kresch et al. |
| 5,531,744 A | 7/1996 | Nardella et al. |
| 5,536,267 A | 7/1996 | Edwards et al. |
| 5,540,681 A | 7/1996 | Strul et al. |
| 5,540,693 A | 7/1996 | Fisher |
| 5,542,916 A | 8/1996 | Hirsch et al. |
| 5,548,286 A | 8/1996 | Craven |
| 5,549,637 A | 8/1996 | Crainich |
| 5,553,675 A | 9/1996 | Pitzen et al. |
| 5,558,671 A | 9/1996 | Yates |
| 5,562,609 A | 10/1996 | Brumbach |
| 5,562,610 A | 10/1996 | Brumbach |
| 5,562,659 A | 10/1996 | Morris |
| 5,562,703 A | 10/1996 | Desai |
| 5,563,179 A | 10/1996 | Stone et al. |
| 5,569,164 A | 10/1996 | Lurz |
| 5,571,121 A | 11/1996 | Heifetz |
| 5,573,424 A | 11/1996 | Poppe |

(56) References Cited

U.S. PATENT DOCUMENTS

| | | |
|---|---|---|
| 5,573,533 A | 11/1996 | Strul |
| 5,573,534 A | 11/1996 | Stone |
| 5,577,654 A | 11/1996 | Bishop |
| 5,584,830 A | 12/1996 | Ladd et al. |
| 5,591,187 A | 1/1997 | Dekel |
| 5,593,414 A | 1/1997 | Shipp et al. |
| 5,599,350 A | 2/1997 | Schulze et al. |
| 5,600,526 A | 2/1997 | Russell et al. |
| 5,601,601 A | 2/1997 | Tal et al. |
| 5,603,773 A | 2/1997 | Campbell |
| 5,607,436 A | 3/1997 | Pratt et al. |
| 5,607,450 A | 3/1997 | Zvenyatsky et al. |
| 5,609,573 A | 3/1997 | Sandock |
| 5,611,813 A | 3/1997 | Lichtman |
| 5,618,304 A | 4/1997 | Hart et al. |
| 5,618,307 A | 4/1997 | Donlon et al. |
| 5,618,492 A | 4/1997 | Auten et al. |
| 5,620,447 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,626,608 A | 5/1997 | Cuny et al. |
| 5,628,760 A | 5/1997 | Knoepfler |
| 5,630,420 A | 5/1997 | Vaitekunas |
| 5,632,432 A | 5/1997 | Schulze et al. |
| 5,632,717 A | 5/1997 | Yoon |
| 5,640,741 A | 6/1997 | Yano |
| D381,077 S | 7/1997 | Hunt |
| 5,647,871 A | 7/1997 | Levine et al. |
| 5,649,937 A | 7/1997 | Bito et al. |
| 5,649,955 A | 7/1997 | Hashimoto et al. |
| 5,651,780 A | 7/1997 | Jackson et al. |
| 5,653,713 A | 8/1997 | Michelson |
| 5,655,100 A | 8/1997 | Ebrahim et al. |
| 5,658,281 A | 8/1997 | Heard |
| 5,662,662 A | 9/1997 | Bishop et al. |
| 5,662,667 A | 9/1997 | Knodel |
| 5,665,085 A | 9/1997 | Nardella |
| 5,665,100 A | 9/1997 | Yoon |
| 5,669,922 A | 9/1997 | Hood |
| 5,674,219 A | 10/1997 | Monson et al. |
| 5,674,220 A | 10/1997 | Fox et al. |
| 5,674,235 A | 10/1997 | Parisi |
| 5,678,568 A | 10/1997 | Uchikubo et al. |
| 5,688,270 A | 11/1997 | Yates et al. |
| 5,690,269 A | 11/1997 | Bolanos et al. |
| 5,693,042 A | 12/1997 | Boiarski et al. |
| 5,693,051 A | 12/1997 | Schulze et al. |
| 5,694,936 A | 12/1997 | Fujimoto et al. |
| 5,695,510 A | 12/1997 | Hood |
| 5,700,261 A | 12/1997 | Brinkerhoff |
| 5,704,534 A | 1/1998 | Huitema et al. |
| 5,704,791 A | 1/1998 | Gillio |
| 5,707,369 A | 1/1998 | Vaitekunas et al. |
| 5,709,680 A | 1/1998 | Yates et al. |
| 5,711,472 A | 1/1998 | Bryan |
| 5,713,896 A | 2/1998 | Nardella |
| 5,715,817 A | 2/1998 | Stevens-Wright et al. |
| 5,716,366 A | 2/1998 | Yates |
| 5,717,306 A | 2/1998 | Shipp |
| 5,720,742 A | 2/1998 | Zacharias |
| 5,720,744 A | 2/1998 | Eggleston et al. |
| 5,722,980 A | 3/1998 | Schulz et al. |
| 5,723,970 A | 3/1998 | Bell |
| 5,728,130 A | 3/1998 | Ishikawa et al. |
| 5,730,752 A | 3/1998 | Alden et al. |
| 5,733,074 A | 3/1998 | Stock et al. |
| 5,735,848 A | 4/1998 | Yates et al. |
| 5,741,226 A | 4/1998 | Strukel et al. |
| 5,743,906 A | 4/1998 | Parins et al. |
| 5,752,973 A | 5/1998 | Kieturakis |
| 5,755,717 A | 5/1998 | Yates et al. |
| 5,762,255 A | 6/1998 | Chrisman et al. |
| 5,766,164 A | 6/1998 | Mueller et al. |
| 5,772,659 A | 6/1998 | Becker et al. |
| 5,776,130 A | 7/1998 | Buysse et al. |
| 5,776,155 A | 7/1998 | Beaupre et al. |
| 5,779,130 A | 7/1998 | Alesi et al. |
| 5,779,701 A | 7/1998 | McBrayer et al. |
| 5,782,834 A | 7/1998 | Lucey et al. |
| 5,792,135 A | 8/1998 | Madhani et al. |
| 5,792,138 A | 8/1998 | Shipp |
| 5,792,165 A | 8/1998 | Klieman et al. |
| 5,796,188 A | 8/1998 | Bays |
| 5,797,941 A | 8/1998 | Schulze et al. |
| 5,797,958 A | 8/1998 | Yoon |
| 5,797,959 A | 8/1998 | Castro et al. |
| 5,800,432 A | 9/1998 | Swanson |
| 5,800,448 A | 9/1998 | Banko |
| 5,800,449 A | 9/1998 | Wales |
| 5,805,140 A | 9/1998 | Rosenberg et al. |
| 5,807,393 A | 9/1998 | Williamson, IV et al. |
| 5,808,396 A | 9/1998 | Boukhny |
| 5,810,811 A | 9/1998 | Yates et al. |
| 5,810,828 A | 9/1998 | Lightman et al. |
| 5,810,859 A | 9/1998 | DiMatteo et al. |
| 5,817,033 A | 10/1998 | DeSantis et al. |
| 5,817,084 A | 10/1998 | Jensen |
| 5,817,093 A | 10/1998 | Williamson, IV et al. |
| 5,817,119 A | 10/1998 | Klieman et al. |
| 5,823,197 A | 10/1998 | Edwards |
| 5,827,271 A | 10/1998 | Buysse et al. |
| 5,827,323 A | 10/1998 | Klieman et al. |
| 5,828,160 A | 10/1998 | Sugishita |
| 5,833,696 A | 11/1998 | Whitfield et al. |
| 5,836,897 A | 11/1998 | Sakurai et al. |
| 5,836,909 A | 11/1998 | Cosmescu |
| 5,836,943 A | 11/1998 | Miller, III |
| 5,836,957 A | 11/1998 | Schulz et al. |
| 5,836,990 A | 11/1998 | Li |
| 5,843,109 A | 12/1998 | Mehta et al. |
| 5,851,212 A | 12/1998 | Zirps et al. |
| 5,853,412 A | 12/1998 | Mayenberger |
| 5,854,590 A | 12/1998 | Dalstein |
| 5,858,018 A | 1/1999 | Shipp et al. |
| 5,865,361 A | 2/1999 | Milliman et al. |
| 5,873,873 A | 2/1999 | Smith et al. |
| 5,873,882 A | 2/1999 | Straub et al. |
| 5,876,401 A | 3/1999 | Schulze et al. |
| 5,878,193 A | 3/1999 | Wang et al. |
| 5,879,364 A | 3/1999 | Bromfield et al. |
| 5,880,668 A | 3/1999 | Hall |
| 5,883,615 A | 3/1999 | Fago et al. |
| 5,891,142 A | 4/1999 | Eggers et al. |
| 5,893,835 A | 4/1999 | Witt et al. |
| 5,897,523 A | 4/1999 | Wright et al. |
| 5,897,569 A | 4/1999 | Kellogg et al. |
| 5,903,607 A | 5/1999 | Tailliet |
| 5,904,681 A | 5/1999 | West, Jr. |
| 5,906,625 A | 5/1999 | Bito et al. |
| 5,906,627 A | 5/1999 | Spaulding |
| 5,906,628 A | 5/1999 | Miyawaki et al. |
| 5,910,129 A | 6/1999 | Koblish et al. |
| 5,911,699 A | 6/1999 | Anis et al. |
| 5,913,823 A | 6/1999 | Hedberg et al. |
| 5,916,229 A | 6/1999 | Evans |
| 5,921,956 A | 7/1999 | Grinberg et al. |
| 5,929,846 A | 7/1999 | Rosenberg et al. |
| 5,935,143 A | 8/1999 | Hood |
| 5,935,144 A | 8/1999 | Estabrook |
| 5,938,633 A | 8/1999 | Beaupre |
| 5,944,718 A | 8/1999 | Austin et al. |
| 5,944,737 A | 8/1999 | Tsonton et al. |
| 5,947,984 A | 9/1999 | Whipple |
| 5,954,717 A | 9/1999 | Behl et al. |
| 5,954,736 A | 9/1999 | Bishop et al. |
| 5,954,746 A | 9/1999 | Holthaus et al. |
| 5,957,882 A | 9/1999 | Nita et al. |
| 5,957,943 A | 9/1999 | Vaitekunas |
| 5,968,007 A | 10/1999 | Simon et al. |
| 5,968,060 A | 10/1999 | Kellogg |
| 5,974,342 A | 10/1999 | Petrofsky |
| D416,089 S | 11/1999 | Barton et al. |
| 5,980,510 A | 11/1999 | Tsonton et al. |

(56) References Cited

U.S. PATENT DOCUMENTS

| | | |
|---|---|---|
| 5,980,546 A | 11/1999 | Hood |
| 5,984,938 A | 11/1999 | Yoon |
| 5,987,344 A | 11/1999 | West |
| 5,989,274 A | 11/1999 | Davison et al. |
| 5,989,275 A | 11/1999 | Estabrook et al. |
| 5,993,465 A | 11/1999 | Shipp et al. |
| 5,993,972 A | 11/1999 | Reich et al. |
| 5,994,855 A | 11/1999 | Lundell et al. |
| 6,003,517 A | 12/1999 | Sheffield et al. |
| 6,004,335 A | 12/1999 | Vaitekunas et al. |
| 6,013,052 A | 1/2000 | Durman et al. |
| 6,024,741 A | 2/2000 | Williamson, IV et al. |
| 6,024,744 A | 2/2000 | Kese et al. |
| 6,024,750 A | 2/2000 | Mastri et al. |
| 6,027,515 A | 2/2000 | Cimino |
| 6,031,526 A | 2/2000 | Shipp |
| 6,033,375 A | 3/2000 | Brumbach |
| 6,033,399 A | 3/2000 | Gines |
| 6,036,667 A | 3/2000 | Manna et al. |
| 6,036,707 A | 3/2000 | Spaulding |
| 6,039,734 A | 3/2000 | Goble |
| 6,048,224 A | 4/2000 | Kay |
| 6,050,943 A | 4/2000 | Slayton et al. |
| 6,050,996 A | 4/2000 | Schmaltz et al. |
| 6,051,010 A | 4/2000 | DiMatteo et al. |
| 6,056,735 A | 5/2000 | Okada et al. |
| 6,063,098 A | 5/2000 | Houser et al. |
| 6,066,132 A | 5/2000 | Chen et al. |
| 6,066,151 A | 5/2000 | Miyawaki et al. |
| 6,068,627 A | 5/2000 | Orszulak et al. |
| 6,068,629 A | 5/2000 | Haissaguerre et al. |
| 6,068,647 A | 5/2000 | Witt et al. |
| 6,074,389 A | 6/2000 | Levine et al. |
| 6,077,285 A | 6/2000 | Boukhny |
| 6,080,149 A | 6/2000 | Huang et al. |
| 6,083,191 A | 7/2000 | Rose |
| 6,086,584 A | 7/2000 | Miller |
| 6,090,120 A | 7/2000 | Wright et al. |
| 6,091,995 A | 7/2000 | Ingle et al. |
| 6,096,033 A | 8/2000 | Tu et al. |
| 6,099,483 A | 8/2000 | Palmer et al. |
| 6,099,542 A | 8/2000 | Cohn et al. |
| 6,099,550 A | 8/2000 | Yoon |
| 6,109,500 A | 8/2000 | Alli et al. |
| 6,110,127 A | 8/2000 | Suzuki |
| 6,113,594 A | 9/2000 | Savage |
| 6,113,598 A | 9/2000 | Baker |
| 6,117,152 A | 9/2000 | Huitema |
| H1904 H | 10/2000 | Yates et al. |
| 6,126,629 A | 10/2000 | Perkins |
| 6,126,658 A | 10/2000 | Baker |
| 6,129,735 A | 10/2000 | Okada et al. |
| 6,129,740 A | 10/2000 | Michelson |
| 6,132,368 A | 10/2000 | Cooper |
| 6,132,427 A | 10/2000 | Jones et al. |
| 6,132,429 A | 10/2000 | Baker |
| 6,132,448 A | 10/2000 | Perez et al. |
| 6,139,320 A | 10/2000 | Hahn |
| 6,139,561 A | 10/2000 | Shibata et al. |
| 6,142,615 A | 11/2000 | Qiu et al. |
| 6,142,994 A | 11/2000 | Swanson et al. |
| 6,144,402 A | 11/2000 | Norsworthy et al. |
| 6,147,560 A | 11/2000 | Erhage et al. |
| 6,152,902 A | 11/2000 | Christian et al. |
| 6,152,923 A | 11/2000 | Ryan |
| 6,154,198 A | 11/2000 | Rosenberg |
| 6,156,029 A | 12/2000 | Mueller |
| 6,159,160 A | 12/2000 | Hsei et al. |
| 6,159,175 A | 12/2000 | Strukel et al. |
| 6,162,194 A | 12/2000 | Shipp |
| 6,162,208 A | 12/2000 | Hipps |
| 6,165,150 A | 12/2000 | Banko |
| 6,174,309 B1 | 1/2001 | Wrublewski et al. |
| 6,174,310 B1 | 1/2001 | Kirwan, Jr. |
| 6,176,857 B1 | 1/2001 | Ashley |
| 6,179,853 B1 | 1/2001 | Sachse et al. |
| 6,183,426 B1 | 2/2001 | Akisada et al. |
| 6,187,003 B1 | 2/2001 | Buysse et al. |
| 6,190,386 B1 | 2/2001 | Rydell |
| 6,193,709 B1 | 2/2001 | Miyawaki et al. |
| 6,204,592 B1 | 3/2001 | Hur |
| 6,205,383 B1 | 3/2001 | Hermann |
| 6,205,855 B1 | 3/2001 | Pfeiffer |
| 6,206,844 B1 | 3/2001 | Reichel et al. |
| 6,206,876 B1 | 3/2001 | Levine et al. |
| 6,210,337 B1 | 4/2001 | Dunham et al. |
| 6,210,402 B1 | 4/2001 | Olsen et al. |
| 6,210,403 B1 | 4/2001 | Klicek |
| 6,214,023 B1 | 4/2001 | Whipple et al. |
| 6,228,080 B1 | 5/2001 | Gines |
| 6,231,565 B1 | 5/2001 | Tovey et al. |
| 6,232,899 B1 | 5/2001 | Craven |
| 6,233,476 B1 | 5/2001 | Strommer et al. |
| 6,238,366 B1 | 5/2001 | Savage et al. |
| 6,241,724 B1 | 6/2001 | Fleischman et al. |
| 6,245,065 B1 | 6/2001 | Panescu et al. |
| 6,251,110 B1 | 6/2001 | Wampler |
| 6,252,110 B1 | 6/2001 | Uemura et al. |
| D444,365 S | 7/2001 | Bass et al. |
| D445,092 S | 7/2001 | Lee |
| D445,764 S | 7/2001 | Lee |
| 6,254,623 B1 | 7/2001 | Haibel, Jr. et al. |
| 6,257,241 B1 | 7/2001 | Wampler |
| 6,258,034 B1 | 7/2001 | Hanafy |
| 6,259,230 B1 | 7/2001 | Chou |
| 6,267,761 B1 | 7/2001 | Ryan |
| 6,270,831 B2 | 8/2001 | Kumar et al. |
| 6,273,852 B1 | 8/2001 | Lehe et al. |
| 6,274,963 B1 | 8/2001 | Estabrook et al. |
| 6,277,115 B1 | 8/2001 | Saadat |
| 6,277,117 B1 | 8/2001 | Tetzlaff et al. |
| 6,278,218 B1 | 8/2001 | Madan et al. |
| 6,280,407 B1 | 8/2001 | Manna et al. |
| 6,283,981 B1 | 9/2001 | Beaupre |
| 6,287,344 B1 | 9/2001 | Wampler et al. |
| 6,290,575 B1 | 9/2001 | Shipp |
| 6,292,700 B1 | 9/2001 | Morrison et al. |
| 6,299,591 B1 | 10/2001 | Banko |
| 6,306,131 B1 | 10/2001 | Hareyama et al. |
| 6,306,157 B1 | 10/2001 | Shchervinsky |
| 6,309,400 B2 | 10/2001 | Beaupre |
| 6,311,783 B1 | 11/2001 | Harpell |
| 6,319,221 B1 | 11/2001 | Savage et al. |
| 6,325,795 B1 | 12/2001 | Lindemann et al. |
| 6,325,799 B1 | 12/2001 | Goble |
| 6,325,811 B1 | 12/2001 | Messerly |
| 6,328,751 B1 | 12/2001 | Beaupre |
| 6,332,891 B1 | 12/2001 | Himes |
| 6,338,657 B1 | 1/2002 | Harper et al. |
| 6,340,352 B1 | 1/2002 | Okada et al. |
| 6,340,878 B1 | 1/2002 | Oglesbee |
| 6,350,269 B1 | 2/2002 | Shipp et al. |
| 6,352,532 B1 | 3/2002 | Kramer et al. |
| 6,356,224 B1 | 3/2002 | Wohlfarth |
| 6,358,246 B1 | 3/2002 | Behl et al. |
| 6,358,264 B2 | 3/2002 | Banko |
| 6,364,888 B1 | 4/2002 | Niemeyer et al. |
| 6,379,320 B1 | 4/2002 | Lafon et al. |
| D457,958 S | 5/2002 | Dycus et al. |
| 6,383,194 B1 | 5/2002 | Pothula |
| 6,384,690 B1 | 5/2002 | Wilhelmsson et al. |
| 6,387,094 B1 | 5/2002 | Eitenmuller |
| 6,387,109 B1 | 5/2002 | Davison et al. |
| 6,388,657 B1 | 5/2002 | Natoli |
| 6,390,973 B1 | 5/2002 | Ouchi |
| 6,391,026 B1 | 5/2002 | Hung et al. |
| 6,391,042 B1 | 5/2002 | Cimino |
| 6,398,779 B1 | 6/2002 | Buysse et al. |
| 6,402,743 B1 | 6/2002 | Orszulak et al. |
| 6,402,748 B1 | 6/2002 | Schoenman et al. |
| 6,405,184 B1 | 6/2002 | Bohme et al. |
| 6,405,733 B1 | 6/2002 | Fogarty et al. |
| 6,409,722 B1 | 6/2002 | Hoey et al. |
| H2037 H | 7/2002 | Yates et al. |

(56) References Cited

U.S. PATENT DOCUMENTS

| | | |
|---|---|---|
| 6,416,469 B1 | 7/2002 | Phung et al. |
| 6,416,486 B1 | 7/2002 | Wampler |
| 6,419,675 B1 | 7/2002 | Gallo, Sr. |
| 6,423,073 B2 | 7/2002 | Bowman |
| 6,423,082 B1 | 7/2002 | Houser et al. |
| 6,425,906 B1 | 7/2002 | Young et al. |
| 6,428,538 B1 | 8/2002 | Blewett et al. |
| 6,428,539 B1 | 8/2002 | Baxter et al. |
| 6,430,446 B1 | 8/2002 | Knowlton |
| 6,432,118 B1 | 8/2002 | Messerly |
| 6,436,114 B1 | 8/2002 | Novak et al. |
| 6,436,115 B1 | 8/2002 | Beaupre |
| 6,440,062 B1 | 8/2002 | Ouchi |
| 6,443,968 B1 | 9/2002 | Holthaus et al. |
| 6,443,969 B1 | 9/2002 | Novak et al. |
| 6,449,006 B1 | 9/2002 | Shipp |
| 6,454,781 B1 | 9/2002 | Witt et al. |
| 6,454,782 B1 | 9/2002 | Schwemberger |
| 6,458,128 B1 | 10/2002 | Schulze |
| 6,458,130 B1 | 10/2002 | Frazier et al. |
| 6,458,142 B1 | 10/2002 | Faller et al. |
| 6,459,363 B1 | 10/2002 | Walker et al. |
| 6,461,363 B1 | 10/2002 | Gadberry et al. |
| 6,464,689 B1 | 10/2002 | Qin et al. |
| 6,464,702 B2 | 10/2002 | Schulze et al. |
| 6,468,270 B1 | 10/2002 | Hovda et al. |
| 6,475,211 B2 | 11/2002 | Chess et al. |
| 6,475,215 B1 | 11/2002 | Tanrisever |
| 6,480,796 B2 | 11/2002 | Wiener |
| 6,485,490 B2 | 11/2002 | Wampler et al. |
| 6,491,690 B1 | 12/2002 | Goble et al. |
| 6,491,701 B2 | 12/2002 | Tierney et al. |
| 6,491,708 B2 | 12/2002 | Madan et al. |
| 6,497,715 B2 | 12/2002 | Satou |
| 6,500,112 B1 | 12/2002 | Khouri |
| 6,500,176 B1 | 12/2002 | Truckai et al. |
| 6,500,188 B2 | 12/2002 | Harper et al. |
| 6,500,312 B2 | 12/2002 | Wedekamp |
| 6,503,248 B1 | 1/2003 | Levine |
| 6,506,208 B2 | 1/2003 | Hunt et al. |
| 6,511,478 B1 | 1/2003 | Burnside et al. |
| 6,511,480 B1 | 1/2003 | Tetzlaff et al. |
| 6,511,493 B1 | 1/2003 | Moutafis et al. |
| 6,514,252 B2 | 2/2003 | Nezhat et al. |
| 6,514,267 B2 | 2/2003 | Jewett |
| 6,517,565 B1 | 2/2003 | Whitman et al. |
| 6,524,251 B2 | 2/2003 | Rabiner et al. |
| 6,524,316 B1 | 2/2003 | Nicholson et al. |
| 6,527,736 B1 | 3/2003 | Attinger et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,537,291 B2 | 3/2003 | Friedman et al. |
| 6,543,452 B1 | 4/2003 | Lavigne |
| 6,543,456 B1 | 4/2003 | Freeman |
| 6,544,260 B1 | 4/2003 | Markel et al. |
| 6,551,309 B1 | 4/2003 | LePivert |
| 6,554,829 B2 | 4/2003 | Schulze et al. |
| 6,558,376 B2 | 5/2003 | Bishop |
| 6,558,380 B2 | 5/2003 | Lingenfelder et al. |
| 6,561,983 B2 | 5/2003 | Cronin et al. |
| 6,562,035 B1 | 5/2003 | Levin |
| 6,562,037 B2 | 5/2003 | Paton et al. |
| 6,565,558 B1 | 5/2003 | Lindenmeier et al. |
| 6,572,563 B2 | 6/2003 | Ouchi |
| 6,572,632 B2 | 6/2003 | Zisterer et al. |
| 6,572,639 B1 | 6/2003 | Ingle et al. |
| 6,575,969 B1 | 6/2003 | Rittman, III et al. |
| 6,582,427 B1 | 6/2003 | Goble et al. |
| 6,582,451 B1 | 6/2003 | Marucci et al. |
| 6,584,360 B2 | 6/2003 | Francischelli et al. |
| D477,408 S | 7/2003 | Bromley |
| 6,585,735 B1 | 7/2003 | Frazier et al. |
| 6,588,277 B2 | 7/2003 | Giordano et al. |
| 6,589,200 B1 | 7/2003 | Schwemberger et al. |
| 6,589,239 B2 | 7/2003 | Khandkar et al. |
| 6,590,733 B1 | 7/2003 | Wilson et al. |
| 6,599,288 B2 | 7/2003 | Maguire et al. |
| 6,602,252 B2 | 8/2003 | Mollenauer |
| 6,602,262 B2 | 8/2003 | Griego et al. |
| 6,607,540 B1 | 8/2003 | Shipp |
| 6,610,059 B1 | 8/2003 | West, Jr. |
| 6,610,060 B2 | 8/2003 | Mulier et al. |
| 6,611,793 B1 | 8/2003 | Burnside et al. |
| 6,616,450 B2 | 9/2003 | Mossle et al. |
| 6,619,529 B2 | 9/2003 | Green et al. |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,623,500 B1 | 9/2003 | Cook et al. |
| 6,623,501 B2 | 9/2003 | Heller et al. |
| 6,626,848 B2 | 9/2003 | Neuenfeldt |
| 6,626,926 B2 | 9/2003 | Friedman et al. |
| 6,629,974 B2 | 10/2003 | Penny et al. |
| 6,632,221 B1 | 10/2003 | Edwards et al. |
| 6,633,234 B2 | 10/2003 | Wiener et al. |
| 6,635,057 B2 | 10/2003 | Harano et al. |
| 6,644,532 B2 | 11/2003 | Green et al. |
| 6,651,669 B1 | 11/2003 | Burnside |
| 6,652,513 B2 | 11/2003 | Panescu et al. |
| 6,652,539 B2 | 11/2003 | Shipp et al. |
| 6,652,545 B2 | 11/2003 | Shipp et al. |
| 6,656,132 B1 | 12/2003 | Ouchi |
| 6,656,177 B2 | 12/2003 | Truckai et al. |
| 6,656,198 B2 | 12/2003 | Tsonton et al. |
| 6,660,017 B2 | 12/2003 | Beaupre |
| 6,662,127 B2 | 12/2003 | Wiener et al. |
| 6,663,941 B2 | 12/2003 | Brown et al. |
| 6,666,860 B1 | 12/2003 | Takahashi |
| 6,666,875 B1 | 12/2003 | Sakurai et al. |
| 6,669,690 B1 | 12/2003 | Okada et al. |
| 6,669,710 B2 | 12/2003 | Moutafis et al. |
| 6,673,248 B2 | 1/2004 | Chowdhury |
| 6,676,660 B2 | 1/2004 | Wampler et al. |
| 6,678,621 B2 | 1/2004 | Wiener et al. |
| 6,679,875 B2 | 1/2004 | Honda et al. |
| 6,679,882 B1 | 1/2004 | Kornerup |
| 6,679,899 B2 | 1/2004 | Wiener et al. |
| 6,682,501 B1 | 1/2004 | Nelson et al. |
| 6,682,544 B2 | 1/2004 | Mastri et al. |
| 6,685,700 B2 | 2/2004 | Behl et al. |
| 6,685,701 B2 | 2/2004 | Orszulak et al. |
| 6,685,703 B2 | 2/2004 | Pearson et al. |
| 6,689,145 B2 | 2/2004 | Lee et al. |
| 6,689,146 B1 | 2/2004 | Himes |
| 6,690,960 B2 | 2/2004 | Chen et al. |
| 6,695,840 B2 | 2/2004 | Schulze |
| 6,702,821 B2 | 3/2004 | Bonutti |
| 6,716,215 B1 | 4/2004 | David et al. |
| 6,719,692 B2 | 4/2004 | Kleffner et al. |
| 6,719,765 B2 | 4/2004 | Bonutti |
| 6,719,776 B2 | 4/2004 | Baxter et al. |
| 6,722,552 B2 | 4/2004 | Fenton, Jr. |
| 6,723,091 B2 | 4/2004 | Goble et al. |
| D490,059 S | 5/2004 | Conway et al. |
| 6,730,080 B2 | 5/2004 | Harano et al. |
| 6,731,047 B2 | 5/2004 | Kauf et al. |
| 6,733,498 B2 | 5/2004 | Paton et al. |
| 6,733,506 B1 | 5/2004 | McDevitt et al. |
| 6,736,813 B2 | 5/2004 | Yamauchi et al. |
| 6,739,872 B1 | 5/2004 | Turri |
| 6,740,079 B1 | 5/2004 | Eggers et al. |
| D491,666 S | 6/2004 | Kimmell et al. |
| 6,743,245 B2 | 6/2004 | Lobdell |
| 6,746,284 B1 | 6/2004 | Spink, Jr. |
| 6,746,443 B1 | 6/2004 | Morley et al. |
| 6,752,815 B2 | 6/2004 | Beaupre |
| 6,755,825 B2 | 6/2004 | Shoenman et al. |
| 6,761,698 B2 | 7/2004 | Shibata et al. |
| 6,762,535 B2 | 7/2004 | Take et al. |
| 6,766,202 B2 | 7/2004 | Underwood et al. |
| 6,770,072 B1 | 8/2004 | Truckai et al. |
| 6,773,409 B2 | 8/2004 | Truckai et al. |
| 6,773,434 B2 | 8/2004 | Ciarrocca |

(56) References Cited

U.S. PATENT DOCUMENTS

| | | |
|---|---|---|
| 6,773,435 B2 | 8/2004 | Schulze et al. |
| 6,773,443 B2 | 8/2004 | Truwit et al. |
| 6,773,444 B2 | 8/2004 | Messerly |
| 6,775,575 B2 | 8/2004 | Bommannan et al. |
| 6,778,023 B2 | 8/2004 | Christensen |
| 6,783,524 B2 | 8/2004 | Anderson et al. |
| 6,786,382 B1 | 9/2004 | Hoffman |
| 6,786,383 B2 | 9/2004 | Stegelmann |
| 6,789,939 B2 | 9/2004 | Schrodinger et al. |
| 6,790,173 B2 | 9/2004 | Saadat et al. |
| 6,790,216 B1 | 9/2004 | Ishikawa |
| 6,794,027 B1 | 9/2004 | Araki et al. |
| 6,796,981 B2 | 9/2004 | Wham et al. |
| D496,997 S | 10/2004 | Dycus et al. |
| 6,800,085 B2 | 10/2004 | Selmon et al. |
| 6,802,843 B2 | 10/2004 | Truckai et al. |
| 6,808,525 B2 | 10/2004 | Latterell et al. |
| 6,809,508 B2 | 10/2004 | Donofrio |
| 6,810,281 B2 | 10/2004 | Brock et al. |
| 6,811,842 B1 | 11/2004 | Ehrnsperger et al. |
| 6,814,731 B2 | 11/2004 | Swanson |
| 6,819,027 B2 | 11/2004 | Saraf |
| 6,821,273 B2 | 11/2004 | Mollenauer |
| 6,827,712 B2 | 12/2004 | Tovey et al. |
| 6,828,712 B2 | 12/2004 | Battaglin et al. |
| 6,835,082 B2 | 12/2004 | Gonnering |
| 6,835,199 B2 | 12/2004 | McGuckin, Jr. et al. |
| 6,840,938 B1 | 1/2005 | Morley et al. |
| 6,843,789 B2 | 1/2005 | Goble |
| 6,849,073 B2 | 2/2005 | Hoey et al. |
| 6,860,878 B2 | 3/2005 | Brock |
| 6,860,880 B2 | 3/2005 | Treat et al. |
| 6,863,676 B2 | 3/2005 | Lee et al. |
| 6,866,671 B2 | 3/2005 | Tierney et al. |
| 6,869,439 B2 | 3/2005 | White et al. |
| 6,875,220 B2 | 4/2005 | Du et al. |
| 6,877,647 B2 | 4/2005 | Green et al. |
| 6,882,439 B2 | 4/2005 | Ishijima |
| 6,887,209 B2 | 5/2005 | Kadziauskas et al. |
| 6,887,252 B1 | 5/2005 | Okada et al. |
| 6,893,435 B2 | 5/2005 | Goble |
| 6,898,536 B2 | 5/2005 | Wiener et al. |
| 6,899,685 B2 | 5/2005 | Kermode et al. |
| 6,905,497 B2 | 6/2005 | Truckai et al. |
| 6,908,463 B2 | 6/2005 | Treat et al. |
| 6,908,472 B2 | 6/2005 | Wiener et al. |
| 6,913,579 B2 | 7/2005 | Truckai et al. |
| 6,915,623 B2 | 7/2005 | Dey et al. |
| 6,923,804 B2 | 8/2005 | Eggers et al. |
| 6,923,806 B2 | 8/2005 | Hooven et al. |
| 6,926,712 B2 | 8/2005 | Phan |
| 6,926,716 B2 | 8/2005 | Baker et al. |
| 6,926,717 B1 | 8/2005 | Garito et al. |
| 6,929,602 B2 | 8/2005 | Hirakui et al. |
| 6,929,622 B2 | 8/2005 | Chian |
| 6,929,632 B2 | 8/2005 | Nita et al. |
| 6,929,644 B2 | 8/2005 | Truckai et al. |
| 6,933,656 B2 | 8/2005 | Matsushita et al. |
| D509,589 S | 9/2005 | Wells |
| 6,942,660 B2 | 9/2005 | Pantera et al. |
| 6,942,677 B2 | 9/2005 | Nita et al. |
| 6,945,981 B2 | 9/2005 | Donofrio et al. |
| 6,946,779 B2 | 9/2005 | Birgel |
| 6,948,503 B2 | 9/2005 | Refior et al. |
| 6,953,461 B2 | 10/2005 | McClurken et al. |
| 6,958,070 B2 | 10/2005 | Witt et al. |
| D511,145 S | 11/2005 | Donofrio et al. |
| 6,974,450 B2 | 12/2005 | Weber et al. |
| 6,976,844 B2 | 12/2005 | Hickok et al. |
| 6,976,969 B2 | 12/2005 | Messerly |
| 6,977,495 B2 | 12/2005 | Donofrio |
| 6,979,332 B2 | 12/2005 | Adams |
| 6,981,628 B2 | 1/2006 | Wales |
| 6,984,220 B2 | 1/2006 | Wuchinich |
| 6,984,231 B2 | 1/2006 | Goble et al. |
| 6,988,295 B2 | 1/2006 | Tillim |
| 6,994,708 B2 | 2/2006 | Manzo |
| 6,994,709 B2 | 2/2006 | Iida |
| 7,000,818 B2 | 2/2006 | Shelton, IV et al. |
| 7,001,335 B2 | 2/2006 | Adachi et al. |
| 7,001,379 B2 | 2/2006 | Behl et al. |
| 7,001,382 B2 | 2/2006 | Gallo, Sr. |
| 7,004,951 B2 | 2/2006 | Gibbens, III |
| 7,011,657 B2 | 3/2006 | Truckai et al. |
| 7,014,638 B2 | 3/2006 | Michelson |
| 7,018,389 B2 | 3/2006 | Camerlengo |
| 7,025,732 B2 | 4/2006 | Thompson et al. |
| 7,033,356 B2 | 4/2006 | Latterell et al. |
| 7,033,357 B2 | 4/2006 | Baxter et al. |
| 7,037,306 B2 | 5/2006 | Podany et al. |
| 7,041,083 B2 | 5/2006 | Chu et al. |
| 7,041,088 B2 | 5/2006 | Nawrocki et al. |
| 7,041,102 B2 | 5/2006 | Truckai et al. |
| 7,044,949 B2 | 5/2006 | Orszulak et al. |
| 7,052,494 B2 | 5/2006 | Goble et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,893 B2 | 6/2006 | Hibner et al. |
| 7,066,895 B2 | 6/2006 | Podany |
| 7,066,936 B2 | 6/2006 | Ryan |
| 7,070,597 B2 | 7/2006 | Truckai et al. |
| 7,074,218 B2 | 7/2006 | Washington et al. |
| 7,074,219 B2 | 7/2006 | Levine et al. |
| 7,077,039 B2 | 7/2006 | Gass et al. |
| 7,077,845 B2 | 7/2006 | Hacker et al. |
| 7,077,853 B2 | 7/2006 | Kramer et al. |
| 7,083,075 B2 | 8/2006 | Swayze et al. |
| 7,083,613 B2 | 8/2006 | Treat |
| 7,083,618 B2 | 8/2006 | Couture et al. |
| 7,083,619 B2 | 8/2006 | Truckai et al. |
| 7,087,054 B2 | 8/2006 | Truckai et al. |
| 7,090,637 B2 | 8/2006 | Danitz et al. |
| 7,090,672 B2 | 8/2006 | Underwood et al. |
| 7,094,235 B2 | 8/2006 | Francischelli |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,101,378 B2 | 9/2006 | Salameh et al. |
| 7,104,834 B2 | 9/2006 | Robinson et al. |
| 7,108,695 B2 | 9/2006 | Witt et al. |
| 7,111,769 B2 | 9/2006 | Wales et al. |
| 7,112,201 B2 | 9/2006 | Truckai et al. |
| 7,113,831 B2 | 9/2006 | Hooven |
| D531,311 S | 10/2006 | Guerra et al. |
| 7,117,034 B2 | 10/2006 | Kronberg |
| 7,118,564 B2 | 10/2006 | Ritchie et al. |
| 7,118,570 B2 | 10/2006 | Tetzlaff et al. |
| 7,118,587 B2 | 10/2006 | Dycus et al. |
| 7,119,516 B2 | 10/2006 | Denning |
| 7,124,932 B2 | 10/2006 | Isaacson et al. |
| 7,125,409 B2 | 10/2006 | Truckai et al. |
| 7,128,720 B2 | 10/2006 | Podany |
| 7,131,860 B2 | 11/2006 | Sartor et al. |
| 7,131,970 B2 | 11/2006 | Moses et al. |
| 7,135,018 B2 | 11/2006 | Ryan et al. |
| 7,135,030 B2 | 11/2006 | Schwemberger et al. |
| 7,137,980 B2 | 11/2006 | Buysse et al. |
| 7,143,925 B2 | 12/2006 | Shelton, IV et al. |
| 7,144,403 B2 | 12/2006 | Booth |
| 7,147,138 B2 | 12/2006 | Shelton, IV |
| 7,153,315 B2 | 12/2006 | Miller |
| D536,093 S | 1/2007 | Nakajima et al. |
| 7,156,189 B1 | 1/2007 | Bar-Cohen et al. |
| 7,156,846 B2 | 1/2007 | Dycus et al. |
| 7,156,853 B2 | 1/2007 | Ratsu |
| 7,157,058 B2 | 1/2007 | Marhasin et al. |
| 7,159,750 B2 | 1/2007 | Racenet et al. |
| 7,160,259 B2 | 1/2007 | Tardy et al. |
| 7,160,296 B2 | 1/2007 | Pearson et al. |
| 7,160,298 B2 | 1/2007 | Lawes et al. |
| 7,160,299 B2 | 1/2007 | Baily |
| 7,163,548 B2 | 1/2007 | Stulen et al. |
| 7,166,103 B2 | 1/2007 | Carmel et al. |

(56) References Cited

U.S. PATENT DOCUMENTS

| | | |
|---|---|---|
| 7,169,144 B2 | 1/2007 | Hoey et al. |
| 7,169,146 B2 | 1/2007 | Truckai et al. |
| 7,169,156 B2 | 1/2007 | Hart |
| 7,179,254 B2 | 2/2007 | Pendekanti et al. |
| 7,179,271 B2 | 2/2007 | Friedman et al. |
| 7,186,253 B2 | 3/2007 | Truckai et al. |
| 7,189,233 B2 | 3/2007 | Truckai et al. |
| 7,195,631 B2 | 3/2007 | Dumbauld |
| D541,418 S | 4/2007 | Schechter et al. |
| 7,198,635 B2 | 4/2007 | Danek et al. |
| 7,204,820 B2 | 4/2007 | Akahoshi |
| 7,207,471 B2 | 4/2007 | Heinrich et al. |
| 7,207,997 B2 | 4/2007 | Shipp et al. |
| 7,208,005 B2 | 4/2007 | Frecker et al. |
| 7,210,881 B2 | 5/2007 | Greenberg |
| 7,211,079 B2 | 5/2007 | Treat |
| 7,217,128 B2 | 5/2007 | Atkin et al. |
| 7,217,269 B2 | 5/2007 | El-Galley et al. |
| 7,220,951 B2 | 5/2007 | Truckai et al. |
| 7,223,229 B2 | 5/2007 | Inman et al. |
| 7,225,964 B2 | 6/2007 | Mastri et al. |
| 7,226,447 B2 | 6/2007 | Uchida et al. |
| 7,226,448 B2 | 6/2007 | Bertolero et al. |
| 7,229,455 B2 | 6/2007 | Sakurai et al. |
| 7,232,440 B2 | 6/2007 | Dumbauld et al. |
| 7,235,071 B2 | 6/2007 | Gonnering |
| 7,235,073 B2 | 6/2007 | Levine et al. |
| 7,241,294 B2 | 7/2007 | Reschke |
| 7,244,262 B2 | 7/2007 | Wiener et al. |
| 7,251,531 B2 | 7/2007 | Mosher et al. |
| 7,252,641 B2 | 8/2007 | Thompson et al. |
| 7,252,667 B2 | 8/2007 | Moses et al. |
| 7,258,688 B1 | 8/2007 | Shah et al. |
| 7,264,618 B2 | 9/2007 | Murakami et al. |
| 7,267,677 B2 | 9/2007 | Johnson et al. |
| 7,267,685 B2 | 9/2007 | Butaric et al. |
| 7,269,873 B2 | 9/2007 | Brewer et al. |
| 7,273,483 B2 | 9/2007 | Wiener et al. |
| D552,241 S | 10/2007 | Bromley et al. |
| 7,282,048 B2 | 10/2007 | Goble et al. |
| 7,285,895 B2 | 10/2007 | Beaupre |
| 7,287,682 B1 | 10/2007 | Ezzat et al. |
| 7,297,149 B2 | 11/2007 | Vitali et al. |
| 7,300,431 B2 | 11/2007 | Dubrovsky |
| 7,300,435 B2 | 11/2007 | Wham et al. |
| 7,300,446 B2 | 11/2007 | Beaupre |
| 7,300,450 B2 | 11/2007 | Vleugels et al. |
| 7,303,531 B2 | 12/2007 | Lee et al. |
| 7,303,557 B2 | 12/2007 | Wham et al. |
| 7,306,597 B2 | 12/2007 | Manzo |
| 7,307,313 B2 | 12/2007 | Ohyanagi et al. |
| 7,309,849 B2 | 12/2007 | Truckai et al. |
| 7,311,706 B2 | 12/2007 | Schoenman et al. |
| 7,311,709 B2 | 12/2007 | Truckai et al. |
| 7,317,955 B2 | 1/2008 | McGreevy |
| 7,318,831 B2 | 1/2008 | Alvarez et al. |
| 7,318,832 B2 | 1/2008 | Young et al. |
| 7,326,236 B2 | 2/2008 | Andreas et al. |
| 7,329,257 B2 | 2/2008 | Kanehira et al. |
| 7,331,410 B2 | 2/2008 | Yong et al. |
| 7,335,165 B2 | 2/2008 | Truwit et al. |
| 7,335,997 B2 | 2/2008 | Wiener |
| 7,337,010 B2 | 2/2008 | Howard et al. |
| 7,353,068 B2 | 4/2008 | Tanaka et al. |
| 7,354,440 B2 | 4/2008 | Truckal et al. |
| 7,357,287 B2 | 4/2008 | Shelton, IV et al. |
| 7,357,802 B2 | 4/2008 | Palanker et al. |
| 7,361,172 B2 | 4/2008 | Cimino |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,380,695 B2 | 6/2008 | Doll et al. |
| 7,380,696 B2 | 6/2008 | Shelton, IV et al. |
| 7,381,209 B2 | 6/2008 | Truckai et al. |
| 7,384,420 B2 | 6/2008 | Dycus et al. |
| 7,390,317 B2 | 6/2008 | Taylor et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,408,288 B2 | 8/2008 | Hara |
| 7,412,008 B2 | 8/2008 | Lliev |
| 7,416,101 B2 | 8/2008 | Shelton, IV et al. |
| 7,416,437 B2 | 8/2008 | Sartor et al. |
| D576,725 S | 9/2008 | Shumer et al. |
| 7,419,490 B2 | 9/2008 | Falkenstein et al. |
| 7,422,139 B2 | 9/2008 | Shelton, IV et al. |
| 7,422,463 B2 | 9/2008 | Kuo |
| 7,422,582 B2 | 9/2008 | Malackowski et al. |
| D578,643 S | 10/2008 | Shumer et al. |
| D578,644 S | 10/2008 | Shumer et al. |
| D578,645 S | 10/2008 | Shumer et al. |
| 7,431,694 B2 | 10/2008 | Stefanchik et al. |
| 7,431,704 B2 | 10/2008 | Babaev |
| 7,431,720 B2 | 10/2008 | Pendekanti et al. |
| 7,435,582 B2 | 10/2008 | Zimmermann et al. |
| 7,441,684 B2 | 10/2008 | Shelton, IV et al. |
| 7,442,193 B2 | 10/2008 | Shields et al. |
| 7,445,621 B2 | 11/2008 | Dumbauld et al. |
| 7,449,004 B2 | 11/2008 | Yamada et al. |
| 7,451,904 B2 | 11/2008 | Shelton, IV |
| 7,455,208 B2 | 11/2008 | Wales et al. |
| 7,455,641 B2 | 11/2008 | Yamada et al. |
| 7,462,181 B2 | 12/2008 | Kraft et al. |
| 7,464,846 B2 | 12/2008 | Shelton, IV et al. |
| 7,464,849 B2 | 12/2008 | Shelton, IV et al. |
| 7,472,815 B2 | 1/2009 | Shelton, IV et al. |
| 7,473,145 B2 | 1/2009 | Ehr et al. |
| 7,473,253 B2 | 1/2009 | Dycus et al. |
| 7,473,263 B2 | 1/2009 | Johnston et al. |
| 7,479,148 B2 | 1/2009 | Beaupre |
| 7,479,160 B2 | 1/2009 | Branch et al. |
| 7,481,775 B2 | 1/2009 | Weikel, Jr. et al. |
| 7,488,285 B2 | 2/2009 | Honda et al. |
| 7,488,319 B2 | 2/2009 | Yates |
| 7,491,201 B2 | 2/2009 | Shields et al. |
| 7,491,202 B2 | 2/2009 | Odom et al. |
| 7,494,468 B2 | 2/2009 | Rabiner et al. |
| 7,494,501 B2 | 2/2009 | Ahlberg et al. |
| 7,498,080 B2 | 3/2009 | Tung et al. |
| 7,502,234 B2 | 3/2009 | Goliszek et al. |
| 7,503,893 B2 | 3/2009 | Kucklick |
| 7,503,895 B2 | 3/2009 | Rabiner et al. |
| 7,506,790 B2 | 3/2009 | Shelton, IV |
| 7,506,791 B2 | 3/2009 | Omaits et al. |
| 7,507,239 B2 | 3/2009 | Shadduck |
| 7,510,107 B2 | 3/2009 | Timm et al. |
| 7,510,556 B2 | 3/2009 | Nguyen et al. |
| 7,513,025 B2 | 4/2009 | Fischer |
| 7,517,349 B2 | 4/2009 | Truckai et al. |
| 7,520,865 B2 | 4/2009 | Radley Young et al. |
| 7,524,320 B2 | 4/2009 | Tierney et al. |
| 7,525,309 B2 | 4/2009 | Sherman et al. |
| 7,530,986 B2 | 5/2009 | Beaupre et al. |
| 7,534,243 B1 | 5/2009 | Chin et al. |
| 7,535,233 B2 | 5/2009 | Kojovic et al. |
| D594,983 S | 6/2009 | Price et al. |
| 7,540,871 B2 | 6/2009 | Gonnering |
| 7,540,872 B2 | 6/2009 | Schechter et al. |
| 7,543,730 B1 | 6/2009 | Marczyk |
| 7,544,200 B2 | 6/2009 | Houser |
| 7,549,564 B2 | 6/2009 | Boudreaux |
| 7,550,216 B2 | 6/2009 | Ofer et al. |
| 7,553,309 B2 | 6/2009 | Buysse et al. |
| 7,554,343 B2 | 6/2009 | Bromfield |
| 7,559,450 B2 | 7/2009 | Wales et al. |
| 7,559,452 B2 | 7/2009 | Wales et al. |
| 7,563,259 B2 | 7/2009 | Takahashi |
| 7,566,318 B2 | 7/2009 | Haefner |
| 7,567,012 B2 | 7/2009 | Namikawa |
| 7,568,603 B2 | 8/2009 | Shelton, IV et al. |
| 7,569,057 B2 | 8/2009 | Liu et al. |
| 7,572,266 B2 | 8/2009 | Young et al. |

(56) References Cited

U.S. PATENT DOCUMENTS

| | | |
|---|---|---|
| 7,572,268 B2 | 8/2009 | Babaev |
| 7,578,820 B2 | 8/2009 | Moore et al. |
| 7,582,084 B2 | 9/2009 | Swanson et al. |
| 7,582,086 B2 | 9/2009 | Privitera et al. |
| 7,582,087 B2 | 9/2009 | Tetzlaff et al. |
| 7,582,095 B2 | 9/2009 | Shipp et al. |
| 7,585,181 B2 | 9/2009 | Olsen |
| 7,586,289 B2 | 9/2009 | Andruk et al. |
| 7,587,536 B2 | 9/2009 | McLeod |
| 7,588,176 B2 | 9/2009 | Timm et al. |
| 7,588,177 B2 | 9/2009 | Racenet |
| 7,594,925 B2 | 9/2009 | Danek et al. |
| 7,597,693 B2 | 10/2009 | Garrison |
| 7,601,119 B2 | 10/2009 | Shahinian |
| 7,601,136 B2 | 10/2009 | Akahoshi |
| 7,604,150 B2 | 10/2009 | Boudreaux |
| 7,607,557 B2 | 10/2009 | Shelton, IV et al. |
| 7,617,961 B2 | 11/2009 | Viola |
| 7,621,930 B2 | 11/2009 | Houser |
| 7,625,370 B2 | 12/2009 | Hart et al. |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,637,410 B2 | 12/2009 | Marczyk |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,240 B2 | 1/2010 | Thompson et al. |
| 7,645,277 B2 | 1/2010 | McClurken et al. |
| 7,645,278 B2 | 1/2010 | Ichihashi et al. |
| 7,648,499 B2 | 1/2010 | Orszulak et al. |
| 7,649,410 B2 | 1/2010 | Andersen et al. |
| 7,654,431 B2 | 2/2010 | Hueil et al. |
| 7,655,003 B2 | 2/2010 | Lorang et al. |
| 7,658,311 B2 | 2/2010 | Boudreaux |
| 7,659,833 B2 | 2/2010 | Warner et al. |
| 7,662,151 B2 | 2/2010 | Crompton, Jr. et al. |
| 7,665,647 B2 | 2/2010 | Shelton, IV et al. |
| 7,666,206 B2 | 2/2010 | Taniguchi et al. |
| 7,667,592 B2 | 2/2010 | Ohyama et al. |
| 7,670,334 B2 | 3/2010 | Hueil et al. |
| 7,670,338 B2 | 3/2010 | Albrecht et al. |
| 7,674,263 B2 | 3/2010 | Ryan |
| 7,678,069 B1 | 3/2010 | Baker et al. |
| 7,678,105 B2 | 3/2010 | McGreevy et al. |
| 7,678,125 B2 | 3/2010 | Shipp |
| 7,682,366 B2 | 3/2010 | Sakurai et al. |
| 7,686,770 B2 | 3/2010 | Cohen |
| 7,686,826 B2 | 3/2010 | Lee et al. |
| 7,688,028 B2 | 3/2010 | Phillips et al. |
| 7,691,095 B2 | 4/2010 | Bednarek et al. |
| 7,691,098 B2 | 4/2010 | Wallace et al. |
| 7,696,441 B2 | 4/2010 | Kataoka |
| 7,699,846 B2 | 4/2010 | Ryan |
| 7,703,459 B2 | 4/2010 | Saadat et al. |
| 7,703,653 B2 | 4/2010 | Shah et al. |
| 7,708,735 B2 | 5/2010 | Chapman et al. |
| 7,708,751 B2 | 5/2010 | Hughes et al. |
| 7,708,758 B2 | 5/2010 | Lee et al. |
| 7,708,768 B2 | 5/2010 | Danek et al. |
| 7,713,202 B2 | 5/2010 | Boukhny et al. |
| 7,713,267 B2 | 5/2010 | Pozzato |
| 7,714,481 B2 | 5/2010 | Sakai |
| 7,717,312 B2 | 5/2010 | Beetel |
| 7,717,914 B2 | 5/2010 | Kimura |
| 7,717,915 B2 | 5/2010 | Miyazawa |
| 7,721,935 B2 | 5/2010 | Racenet et al. |
| 7,722,527 B2 | 5/2010 | Bouchier et al. |
| 7,722,607 B2 | 5/2010 | Dumbauld et al. |
| D618,797 S | 6/2010 | Price et al. |
| 7,726,537 B2 | 6/2010 | Olson et al. |
| 7,727,177 B2 | 6/2010 | Bayat |
| 7,731,717 B2 | 6/2010 | Odom et al. |
| 7,738,969 B2 | 6/2010 | Bleich |
| 7,740,594 B2 | 6/2010 | Hibner |
| 7,744,615 B2 | 6/2010 | Couture |
| 7,749,240 B2 | 7/2010 | Takahashi et al. |
| 7,751,115 B2 | 7/2010 | Song |
| 7,753,245 B2 | 7/2010 | Boudreaux et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| D621,503 S | 8/2010 | Otten et al. |
| 7,766,210 B2 | 8/2010 | Shelton, IV et al. |
| 7,766,693 B2 | 8/2010 | Sartor et al. |
| 7,766,910 B2 | 8/2010 | Hixson et al. |
| 7,768,510 B2 | 8/2010 | Tsai et al. |
| 7,770,774 B2 | 8/2010 | Mastri et al. |
| 7,770,775 B2 | 8/2010 | Shelton, IV et al. |
| 7,771,425 B2 | 8/2010 | Dycus et al. |
| 7,771,444 B2 | 8/2010 | Patel et al. |
| 7,775,972 B2 | 8/2010 | Brock et al. |
| 7,776,036 B2 | 8/2010 | Schechter et al. |
| 7,776,037 B2 | 8/2010 | Odom |
| 7,778,733 B2 | 8/2010 | Nowlin et al. |
| 7,780,054 B2 | 8/2010 | Wales |
| 7,780,593 B2 | 8/2010 | Ueno et al. |
| 7,780,651 B2 | 8/2010 | Madhani et al. |
| 7,780,659 B2 | 8/2010 | Okada et al. |
| 7,780,663 B2 | 8/2010 | Yates et al. |
| 7,784,662 B2 | 8/2010 | Wales et al. |
| 7,784,663 B2 | 8/2010 | Shelton, IV |
| 7,789,883 B2 | 9/2010 | Takashino et al. |
| 7,793,814 B2 | 9/2010 | Racenet et al. |
| 7,794,475 B2 | 9/2010 | Hess et al. |
| 7,796,969 B2 | 9/2010 | Kelly et al. |
| 7,798,386 B2 | 9/2010 | Schall et al. |
| 7,799,020 B2 | 9/2010 | Shores et al. |
| 7,799,027 B2 | 9/2010 | Hafner |
| 7,799,045 B2 | 9/2010 | Masuda |
| 7,803,152 B2 | 9/2010 | Honda et al. |
| 7,803,156 B2 | 9/2010 | Eder et al. |
| 7,803,168 B2 | 9/2010 | Gifford et al. |
| 7,806,891 B2 | 10/2010 | Nowlin et al. |
| 7,810,693 B2 | 10/2010 | Broehl et al. |
| 7,811,283 B2 | 10/2010 | Moses et al. |
| 7,815,238 B2 | 10/2010 | Cao |
| 7,815,641 B2 | 10/2010 | Dodde et al. |
| 7,819,298 B2 | 10/2010 | Hall et al. |
| 7,819,299 B2 | 10/2010 | Shelton, IV et al. |
| 7,819,819 B2 | 10/2010 | Quick et al. |
| 7,819,872 B2 | 10/2010 | Johnson et al. |
| 7,821,143 B2 | 10/2010 | Wiener |
| D627,066 S | 11/2010 | Romero |
| 7,824,401 B2 | 11/2010 | Manzo et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,834,484 B2 | 11/2010 | Sartor |
| 7,837,699 B2 | 11/2010 | Yamada et al. |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,846,160 B2 | 12/2010 | Payne et al. |
| 7,846,161 B2 | 12/2010 | Dumbauld et al. |
| 7,854,735 B2 | 12/2010 | Houser et al. |
| D631,155 S | 1/2011 | Peine et al. |
| 7,861,906 B2 | 1/2011 | Doll et al. |
| 7,862,560 B2 | 1/2011 | Marion |
| 7,862,561 B2 | 1/2011 | Swanson et al. |
| 7,867,228 B2 | 1/2011 | Nobis et al. |
| 7,871,392 B2 | 1/2011 | Sartor |
| 7,871,423 B2 | 1/2011 | Livneh |
| 7,876,030 B2 | 1/2011 | Taki et al. |
| D631,965 S | 2/2011 | Price et al. |
| 7,877,852 B2 | 2/2011 | Unger et al. |
| 7,878,991 B2 | 2/2011 | Babaev |
| 7,879,029 B2 | 2/2011 | Jimenez |
| 7,879,033 B2 | 2/2011 | Sartor et al. |
| 7,879,035 B2 | 2/2011 | Garrison et al. |
| 7,879,070 B2 | 2/2011 | Ortiz et al. |
| 7,883,475 B2 | 2/2011 | Dupont et al. |
| 7,892,606 B2 | 2/2011 | Thies et al. |

(56) References Cited

U.S. PATENT DOCUMENTS

| | | |
|---|---|---|
| 7,896,875 B2 | 3/2011 | Heim et al. |
| 7,897,792 B2 | 3/2011 | Iikura et al. |
| 7,901,400 B2 | 3/2011 | Wham et al. |
| 7,901,423 B2 | 3/2011 | Stulen et al. |
| 7,905,881 B2 | 3/2011 | Masuda et al. |
| 7,909,220 B2 | 3/2011 | Viola |
| 7,909,820 B2 | 3/2011 | Lipson et al. |
| 7,909,824 B2 | 3/2011 | Masuda et al. |
| 7,918,848 B2 | 4/2011 | Lau et al. |
| 7,919,184 B2 | 4/2011 | Mohapatra et al. |
| 7,922,061 B2 | 4/2011 | Shelton, IV et al. |
| 7,922,651 B2 | 4/2011 | Yamada et al. |
| 7,931,611 B2 | 4/2011 | Novak et al. |
| 7,931,649 B2 | 4/2011 | Couture et al. |
| D637,288 S | 5/2011 | Houghton |
| D638,540 S | 5/2011 | Ijiri et al. |
| 7,935,114 B2 | 5/2011 | Takashino et al. |
| 7,936,203 B2 | 5/2011 | Zimlich |
| 7,951,095 B2 | 5/2011 | Makin et al. |
| 7,951,165 B2 | 5/2011 | Golden et al. |
| 7,955,331 B2 | 6/2011 | Truckai et al. |
| 7,956,620 B2 | 6/2011 | Gilbert |
| 7,959,050 B2 | 6/2011 | Smith et al. |
| 7,959,626 B2 | 6/2011 | Hong et al. |
| 7,963,963 B2 | 6/2011 | Francischelli et al. |
| 7,967,602 B2 | 6/2011 | Lindquist |
| 7,972,328 B2 | 7/2011 | Wham et al. |
| 7,972,329 B2 | 7/2011 | Refior et al. |
| 7,975,895 B2 | 7/2011 | Milliman |
| 7,976,544 B2 | 7/2011 | McClurken et al. |
| 7,980,443 B2 | 7/2011 | Scheib et al. |
| 7,981,050 B2 | 7/2011 | Ritchart et al. |
| 7,981,113 B2 | 7/2011 | Truckai et al. |
| 7,997,278 B2 | 8/2011 | Utley et al. |
| 7,998,157 B2 | 8/2011 | Culp et al. |
| 8,002,732 B2 | 8/2011 | Visconti |
| 8,002,770 B2 | 8/2011 | Swanson et al. |
| 8,020,743 B2 | 9/2011 | Shelton, IV |
| 8,025,672 B2 | 9/2011 | Novak et al. |
| 8,028,885 B2 | 10/2011 | Smith et al. |
| 8,033,173 B2 | 10/2011 | Ehlert et al. |
| 8,034,049 B2 | 10/2011 | Odom et al. |
| 8,038,693 B2 | 10/2011 | Allen |
| 8,048,070 B2 | 11/2011 | O'Brien et al. |
| 8,052,672 B2 | 11/2011 | Laufer et al. |
| 8,055,208 B2 | 11/2011 | Lilja et al. |
| 8,056,720 B2 | 11/2011 | Hawkes |
| 8,056,787 B2 | 11/2011 | Boudreaux et al. |
| 8,057,468 B2 | 11/2011 | Konesky |
| 8,057,498 B2 | 11/2011 | Robertson |
| 8,058,771 B2 | 11/2011 | Giordano et al. |
| 8,061,014 B2 | 11/2011 | Smith et al. |
| 8,066,167 B2 | 11/2011 | Measamer et al. |
| 8,070,036 B1 | 12/2011 | Knodel |
| 8,070,711 B2 | 12/2011 | Bassinger et al. |
| 8,070,762 B2 | 12/2011 | Escudero et al. |
| 8,075,555 B2 | 12/2011 | Truckai et al. |
| 8,075,558 B2 | 12/2011 | Truckai et al. |
| 8,089,197 B2 | 1/2012 | Rinner et al. |
| 8,092,475 B2 | 1/2012 | Cotter et al. |
| 8,096,459 B2 | 1/2012 | Ortiz et al. |
| 8,097,012 B2 | 1/2012 | Kagarise |
| 8,100,894 B2 | 1/2012 | Mucko et al. |
| 8,105,230 B2 | 1/2012 | Honda et al. |
| 8,105,323 B2 | 1/2012 | Buysse et al. |
| 8,105,324 B2 | 1/2012 | Palanker et al. |
| 8,114,104 B2 | 2/2012 | Young et al. |
| 8,118,276 B2 | 2/2012 | Sanders et al. |
| 8,128,624 B2 | 3/2012 | Couture et al. |
| 8,133,218 B2 | 3/2012 | Daw et al. |
| 8,136,712 B2 | 3/2012 | Zingman |
| 8,141,762 B2 | 3/2012 | Bedi et al. |
| 8,142,421 B2 | 3/2012 | Cooper et al. |
| 8,142,461 B2 | 3/2012 | Houser et al. |
| 8,147,485 B2 | 4/2012 | Wham et al. |
| 8,147,488 B2 | 4/2012 | Masuda |
| 8,147,508 B2 | 4/2012 | Madan et al. |
| 8,152,801 B2 | 4/2012 | Goldberg et al. |
| 8,152,825 B2 | 4/2012 | Madan et al. |
| 8,157,145 B2 | 4/2012 | Shelton, IV et al. |
| 8,161,977 B2 | 4/2012 | Shelton, IV et al. |
| 8,162,966 B2 | 4/2012 | Connor et al. |
| 8,170,717 B2 | 5/2012 | Sutherland et al. |
| 8,172,846 B2 | 5/2012 | Brunnett et al. |
| 8,172,870 B2 | 5/2012 | Shipp |
| 8,177,800 B2 | 5/2012 | Spitz et al. |
| 8,182,502 B2 | 5/2012 | Stulen et al. |
| 8,186,560 B2 | 5/2012 | Hess et al. |
| 8,186,877 B2 | 5/2012 | Klimovitch et al. |
| 8,187,267 B2 | 5/2012 | Pappone et al. |
| D661,801 S | 6/2012 | Price et al. |
| D661,802 S | 6/2012 | Price et al. |
| D661,803 S | 6/2012 | Price et al. |
| D661,804 S | 6/2012 | Price et al. |
| 8,197,472 B2 | 6/2012 | Lau et al. |
| 8,197,479 B2 | 6/2012 | Olson et al. |
| 8,197,502 B2 | 6/2012 | Smith et al. |
| 8,207,651 B2 | 6/2012 | Gilbert |
| 8,210,411 B2 | 7/2012 | Yates et al. |
| 8,211,100 B2 | 7/2012 | Podhajsky et al. |
| 8,220,688 B2 | 7/2012 | Laurent et al. |
| 8,221,306 B2 | 7/2012 | Okada et al. |
| 8,221,415 B2 | 7/2012 | Francischelli |
| 8,221,418 B2 | 7/2012 | Prakash et al. |
| 8,226,580 B2 | 7/2012 | Govari et al. |
| 8,226,665 B2 | 7/2012 | Cohen |
| 8,226,675 B2 | 7/2012 | Houser et al. |
| 8,231,607 B2 | 7/2012 | Takuma |
| 8,235,917 B2 | 8/2012 | Joseph et al. |
| 8,236,018 B2 | 8/2012 | Yoshimine et al. |
| 8,236,019 B2 | 8/2012 | Houser |
| 8,236,020 B2 | 8/2012 | Smith et al. |
| 8,241,235 B2 | 8/2012 | Kahler et al. |
| 8,241,271 B2 | 8/2012 | Millman et al. |
| 8,241,282 B2 | 8/2012 | Unger et al. |
| 8,241,283 B2 | 8/2012 | Guerra et al. |
| 8,241,284 B2 | 8/2012 | Dycus et al. |
| 8,241,312 B2 | 8/2012 | Messerly |
| 8,246,575 B2 | 8/2012 | Viola |
| 8,246,615 B2 | 8/2012 | Behnke |
| 8,246,616 B2 | 8/2012 | Amoah et al. |
| 8,246,618 B2 | 8/2012 | Bucciaglia et al. |
| 8,246,642 B2 | 8/2012 | Houser et al. |
| 8,251,994 B2 | 8/2012 | McKenna et al. |
| 8,252,012 B2 | 8/2012 | Stulen |
| 8,253,303 B2 | 8/2012 | Giordano et al. |
| 8,257,377 B2 | 9/2012 | Wiener et al. |
| 8,257,387 B2 | 9/2012 | Cunningham |
| 8,262,563 B2 | 9/2012 | Bakos et al. |
| 8,267,300 B2 | 9/2012 | Boudreaux |
| 8,267,935 B2 | 9/2012 | Couture et al. |
| 8,273,087 B2 | 9/2012 | Kimura et al. |
| D669,992 S | 10/2012 | Schafer et al. |
| D669,993 S | 10/2012 | Merchant et al. |
| 8,277,446 B2 | 10/2012 | Heard |
| 8,277,447 B2 | 10/2012 | Garrison et al. |
| 8,277,471 B2 | 10/2012 | Wiener et al. |
| 8,282,581 B2 | 10/2012 | Zhao et al. |
| 8,282,669 B2 | 10/2012 | Gerber et al. |
| 8,286,846 B2 | 10/2012 | Smith et al. |
| 8,287,485 B2 | 10/2012 | Kimura et al. |
| 8,287,528 B2 | 10/2012 | Wham et al. |
| 8,287,532 B2 | 10/2012 | Carroll et al. |
| 8,292,886 B2 | 10/2012 | Kerr et al. |
| 8,292,888 B2 | 10/2012 | Whitman |
| 8,292,905 B2 | 10/2012 | Taylor et al. |
| 8,295,902 B2 | 10/2012 | Salahieh et al. |
| 8,298,223 B2 | 10/2012 | Wham et al. |
| 8,298,225 B2 | 10/2012 | Gilbert |
| 8,298,232 B2 | 10/2012 | Unger |
| 8,298,233 B2 | 10/2012 | Mueller |
| 8,303,576 B2 | 11/2012 | Brock |
| 8,303,579 B2 | 11/2012 | Shibata |
| 8,303,580 B2 | 11/2012 | Wham et al. |

(56) References Cited

U.S. PATENT DOCUMENTS

| | | |
|---|---|---|
| 8,303,583 B2 | 11/2012 | Hosier et al. |
| 8,303,613 B2 | 11/2012 | Crandall et al. |
| 8,306,629 B2 | 11/2012 | Mioduski et al. |
| 8,308,040 B2 | 11/2012 | Huang et al. |
| 8,319,400 B2 | 11/2012 | Houser et al. |
| 8,323,302 B2 | 12/2012 | Robertson et al. |
| 8,323,310 B2 | 12/2012 | Kingsley |
| 8,328,061 B2 | 12/2012 | Kasvikis |
| 8,328,761 B2 | 12/2012 | Widenhouse et al. |
| 8,328,802 B2 | 12/2012 | Deville et al. |
| 8,328,833 B2 | 12/2012 | Cuny |
| 8,328,834 B2 | 12/2012 | Isaacs et al. |
| 8,333,764 B2 | 12/2012 | Francischelli et al. |
| 8,333,778 B2 | 12/2012 | Smith et al. |
| 8,333,779 B2 | 12/2012 | Smith et al. |
| 8,334,468 B2 | 12/2012 | Palmer et al. |
| 8,334,635 B2 | 12/2012 | Voegele et al. |
| 8,337,407 B2 | 12/2012 | Quistgaard et al. |
| 8,338,726 B2 | 12/2012 | Palmer et al. |
| 8,343,146 B2 | 1/2013 | Godara et al. |
| 8,344,596 B2 | 1/2013 | Nield et al. |
| 8,348,880 B2 | 1/2013 | Messerly et al. |
| 8,348,947 B2 | 1/2013 | Takashino et al. |
| 8,348,967 B2 | 1/2013 | Stulen |
| 8,353,297 B2 | 1/2013 | Dacquay et al. |
| 8,357,103 B2 | 1/2013 | Mark et al. |
| 8,357,144 B2 | 1/2013 | Whitman et al. |
| 8,357,149 B2 | 1/2013 | Govari et al. |
| 8,357,158 B2 | 1/2013 | McKenna et al. |
| 8,360,299 B2 | 1/2013 | Zemlok et al. |
| 8,361,066 B2 | 1/2013 | Long et al. |
| 8,361,072 B2 | 1/2013 | Dumbauld et al. |
| 8,361,569 B2 | 1/2013 | Saito et al. |
| 8,366,727 B2 | 2/2013 | Witt et al. |
| 8,372,064 B2 | 2/2013 | Douglass et al. |
| 8,372,099 B2 | 2/2013 | Deville et al. |
| 8,372,101 B2 | 2/2013 | Smith et al. |
| 8,372,102 B2 | 2/2013 | Stulen et al. |
| 8,374,670 B2 | 2/2013 | Selkee |
| 8,377,044 B2 | 2/2013 | Coe et al. |
| 8,377,059 B2 | 2/2013 | Deville et al. |
| 8,377,085 B2 | 2/2013 | Smith et al. |
| 8,382,748 B2 | 2/2013 | Geisei |
| 8,382,775 B1 | 2/2013 | Bender et al. |
| 8,382,782 B2 | 2/2013 | Robertson et al. |
| 8,382,792 B2 | 2/2013 | Chojin |
| 8,388,646 B2 | 3/2013 | Chojin |
| 8,388,647 B2 | 3/2013 | Nau, Jr. et al. |
| 8,393,514 B2 | 3/2013 | Shelton, IV et al. |
| 8,394,115 B2 | 3/2013 | Houser et al. |
| 8,397,971 B2 | 3/2013 | Yates et al. |
| 8,398,394 B2 | 3/2013 | Sauter et al. |
| 8,403,926 B2 | 3/2013 | Nobis et al. |
| 8,403,945 B2 | 3/2013 | Whitfield et al. |
| 8,403,948 B2 | 3/2013 | Deville et al. |
| 8,403,949 B2 | 3/2013 | Palmer et al. |
| 8,403,950 B2 | 3/2013 | Palmer et al. |
| 8,409,234 B2 | 4/2013 | Stabler et al. |
| 8,414,577 B2 | 4/2013 | Boudreaux et al. |
| 8,418,073 B2 | 4/2013 | Mohr et al. |
| 8,418,349 B2 | 4/2013 | Smith et al. |
| 8,419,757 B2 | 4/2013 | Smith et al. |
| 8,419,758 B2 | 4/2013 | Smith et al. |
| 8,419,759 B2 | 4/2013 | Dietz |
| 8,423,182 B2 | 4/2013 | Robinson et al. |
| 8,425,410 B2 | 4/2013 | Murray et al. |
| 8,425,545 B2 | 4/2013 | Smith et al. |
| 8,430,811 B2 | 4/2013 | Hess et al. |
| 8,430,874 B2 | 4/2013 | Newton et al. |
| 8,430,876 B2 | 4/2013 | Kappus et al. |
| 8,430,897 B2 | 4/2013 | Novak et al. |
| 8,430,898 B2 | 4/2013 | Wiener et al. |
| 8,435,257 B2 | 5/2013 | Smith et al. |
| 8,437,832 B2 | 5/2013 | Govari et al. |
| 8,439,912 B2 | 5/2013 | Cunningham et al. |
| 8,439,939 B2 | 5/2013 | Deville et al. |
| 8,444,036 B2 | 5/2013 | Shelton, IV |
| 8,444,637 B2 | 5/2013 | Podmore et al. |
| 8,444,662 B2 | 5/2013 | Palmer et al. |
| 8,444,663 B2 | 5/2013 | Houser et al. |
| 8,444,664 B2 | 5/2013 | Balanev et al. |
| 8,453,906 B2 | 6/2013 | Huang et al. |
| 8,454,599 B2 | 6/2013 | Inagaki et al. |
| 8,454,639 B2 | 6/2013 | Du et al. |
| 8,459,525 B2 | 6/2013 | Yates et al. |
| 8,460,284 B2 | 6/2013 | Aronow et al. |
| 8,460,288 B2 | 6/2013 | Tamai et al. |
| 8,460,292 B2 | 6/2013 | Truckai et al. |
| 8,461,744 B2 | 6/2013 | Wiener et al. |
| 8,469,981 B2 | 6/2013 | Robertson et al. |
| 8,471,685 B2 | 6/2013 | Shingai |
| 8,479,969 B2 | 7/2013 | Shelton, IV |
| 8,480,703 B2 | 7/2013 | Nicholas et al. |
| 8,484,833 B2 | 7/2013 | Cunningham et al. |
| 8,485,413 B2 | 7/2013 | Scheib et al. |
| 8,485,970 B2 | 7/2013 | Widenhouse et al. |
| 8,486,057 B2 | 7/2013 | Behnke, II |
| 8,486,096 B2 | 7/2013 | Robertson et al. |
| 8,491,578 B2 | 7/2013 | Manwaring et al. |
| 8,491,625 B2 | 7/2013 | Horner |
| 8,496,682 B2 | 7/2013 | Guerra et al. |
| D687,549 S | 8/2013 | Johnson et al. |
| 8,506,555 B2 | 8/2013 | Ruiz Morales |
| 8,509,318 B2 | 8/2013 | Tailliet |
| 8,512,336 B2 | 8/2013 | Couture |
| 8,512,337 B2 | 8/2013 | Francischelli et al. |
| 8,512,359 B2 | 8/2013 | Whitman et al. |
| 8,512,364 B2 | 8/2013 | Kowalski et al. |
| 8,512,365 B2 | 8/2013 | Wiener et al. |
| 8,518,067 B2 | 8/2013 | Masuda et al. |
| 8,521,331 B2 | 8/2013 | Itkowitz |
| 8,523,043 B2 | 9/2013 | Ullrich et al. |
| 8,523,882 B2 | 9/2013 | Huitema et al. |
| 8,523,889 B2 | 9/2013 | Stulen et al. |
| 8,528,563 B2 | 9/2013 | Gruber |
| 8,529,437 B2 | 9/2013 | Taylor et al. |
| 8,529,565 B2 | 9/2013 | Masuda et al. |
| 8,531,064 B2 | 9/2013 | Robertson et al. |
| 8,535,308 B2 | 9/2013 | Govari et al. |
| 8,535,311 B2 | 9/2013 | Schall |
| 8,535,340 B2 | 9/2013 | Allen |
| 8,535,341 B2 | 9/2013 | Allen |
| 8,540,128 B2 | 9/2013 | Shelton, IV et al. |
| 8,546,996 B2 | 10/2013 | Messerly et al. |
| 8,546,999 B2 | 10/2013 | Houser et al. |
| 8,551,077 B2 | 10/2013 | Main et al. |
| 8,551,086 B2 | 10/2013 | Kimura et al. |
| 8,556,929 B2 | 10/2013 | Harper et al. |
| 8,561,870 B2 | 10/2013 | Baxter, III et al. |
| 8,562,592 B2 | 10/2013 | Conlon et al. |
| 8,562,598 B2 | 10/2013 | Falkenstein et al. |
| 8,562,600 B2 | 10/2013 | Kirkpatrick et al. |
| 8,562,604 B2 | 10/2013 | Nishimura |
| 8,568,390 B2 | 10/2013 | Mueller |
| 8,568,397 B2 | 10/2013 | Horner et al. |
| 8,568,400 B2 | 10/2013 | Gilbert |
| 8,568,412 B2 | 10/2013 | Brandt et al. |
| 8,569,997 B2 | 10/2013 | Lee |
| 8,573,461 B2 | 11/2013 | Shelton, IV et al. |
| 8,573,465 B2 | 11/2013 | Shelton, IV |
| 8,574,231 B2 | 11/2013 | Boudreaux et al. |
| 8,574,253 B2 | 11/2013 | Gruber et al. |
| 8,579,176 B2 | 11/2013 | Smith et al. |
| 8,579,897 B2 | 11/2013 | Vakharia et al. |
| 8,579,928 B2 | 11/2013 | Robertson et al. |
| 8,579,937 B2 | 11/2013 | Gresham |
| 8,585,727 B2 | 11/2013 | Polo |
| 8,588,371 B2 | 11/2013 | Ogawa et al. |
| 8,591,459 B2 | 11/2013 | Clymer et al. |
| 8,591,506 B2 | 11/2013 | Wham et al. |
| 8,591,536 B2 | 11/2013 | Robertson |
| D695,407 S | 12/2013 | Price et al. |
| D696,631 S | 12/2013 | Price et al. |
| 8,596,513 B2 | 12/2013 | Olson et al. |

(56) References Cited

U.S. PATENT DOCUMENTS

| | | |
|---|---|---|
| 8,597,193 B2 | 12/2013 | Grunwald et al. |
| 8,597,287 B2 | 12/2013 | Benamou et al. |
| 8,602,031 B2 | 12/2013 | Reis et al. |
| 8,602,288 B2 | 12/2013 | Shelton, IV et al. |
| 8,603,085 B2 | 12/2013 | Jimenez |
| 8,603,089 B2 | 12/2013 | Viola |
| 8,608,044 B2 | 12/2013 | Hueil et al. |
| 8,608,045 B2 | 12/2013 | Smith et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,617,152 B2 | 12/2013 | Werneth et al. |
| 8,617,194 B2 | 12/2013 | Beaupre |
| 8,622,274 B2 | 1/2014 | Yates et al. |
| 8,623,011 B2 | 1/2014 | Spivey |
| 8,623,016 B2 | 1/2014 | Fischer |
| 8,623,027 B2 | 1/2014 | Price et al. |
| 8,623,040 B2 | 1/2014 | Artsyukhovich et al. |
| 8,623,044 B2 | 1/2014 | Timm et al. |
| 8,628,529 B2 | 1/2014 | Aldridge et al. |
| 8,628,534 B2 | 1/2014 | Jones et al. |
| 8,632,461 B2 | 1/2014 | Glossop |
| 8,636,736 B2 | 1/2014 | Yates et al. |
| 8,638,428 B2 | 1/2014 | Brown |
| 8,640,788 B2 | 2/2014 | Dachs, II et al. |
| 8,641,663 B2 | 2/2014 | Kirschenman et al. |
| 8,647,350 B2 | 2/2014 | Mohan et al. |
| 8,650,728 B2 | 2/2014 | Wan et al. |
| 8,652,120 B2 | 2/2014 | Giordano et al. |
| 8,652,132 B2 | 2/2014 | Tsuchiya et al. |
| 8,652,155 B2 | 2/2014 | Houser et al. |
| 8,657,489 B2 | 2/2014 | Ladurner et al. |
| 8,659,208 B1 | 2/2014 | Rose et al. |
| 8,663,214 B2 | 3/2014 | Weinberg et al. |
| 8,663,220 B2 | 3/2014 | Wiener et al. |
| 8,663,222 B2 | 3/2014 | Anderson et al. |
| 8,663,223 B2 | 3/2014 | Masuda et al. |
| 8,663,262 B2 | 3/2014 | Smith et al. |
| 8,668,691 B2 | 3/2014 | Heard |
| 8,668,710 B2 | 3/2014 | Slipszenko et al. |
| 8,684,253 B2 | 4/2014 | Giordano et al. |
| 8,685,016 B2 | 4/2014 | Wham et al. |
| 8,685,020 B2 | 4/2014 | Weizman et al. |
| 8,690,582 B2 | 4/2014 | Rohrbach et al. |
| 8,695,866 B2 | 4/2014 | Leimbach et al. |
| 8,696,366 B2 | 4/2014 | Chen et al. |
| 8,696,665 B2 | 4/2014 | Hunt et al. |
| 8,696,666 B2 | 4/2014 | Sanai et al. |
| 8,696,917 B2 | 4/2014 | Petisce et al. |
| 8,702,609 B2 | 4/2014 | Hadjicostis |
| 8,702,704 B2 | 4/2014 | Shelton, IV et al. |
| 8,704,425 B2 | 4/2014 | Giordano et al. |
| 8,708,213 B2 | 4/2014 | Shelton, IV et al. |
| 8,709,008 B2 | 4/2014 | Willis et al. |
| 8,709,031 B2 | 4/2014 | Stulen |
| 8,709,035 B2 | 4/2014 | Johnson et al. |
| 8,715,270 B2 | 5/2014 | Weitzner et al. |
| 8,715,277 B2 | 5/2014 | Weizman |
| 8,721,640 B2 | 5/2014 | Taylor et al. |
| 8,721,657 B2 | 5/2014 | Kondoh et al. |
| 8,733,613 B2 | 5/2014 | Huitema et al. |
| 8,733,614 B2 | 5/2014 | Ross et al. |
| 8,734,443 B2 | 5/2014 | Hixson et al. |
| 8,738,110 B2 | 5/2014 | Tabada et al. |
| 8,747,238 B2 | 6/2014 | Shelton, IV et al. |
| 8,747,351 B2 | 6/2014 | Schultz |
| 8,747,404 B2 | 6/2014 | Boudreaux et al. |
| 8,749,116 B2 | 6/2014 | Messerly et al. |
| 8,752,264 B2 | 6/2014 | Ackley et al. |
| 8,752,749 B2 | 6/2014 | Moore et al. |
| 8,753,338 B2 | 6/2014 | Widenhouse et al. |
| 8,754,570 B2 | 6/2014 | Voegele et al. |
| 8,758,342 B2 | 6/2014 | Bales et al. |
| 8,758,352 B2 | 6/2014 | Cooper et al. |
| 8,758,391 B2 | 6/2014 | Swayze et al. |
| 8,764,735 B2 | 7/2014 | Coe et al. |
| 8,764,747 B2 | 7/2014 | Cummings et al. |
| 8,767,970 B2 | 7/2014 | Eppolito |
| 8,770,459 B2 | 7/2014 | Racenet et al. |
| 8,771,269 B2 | 7/2014 | Sherman et al. |
| 8,771,270 B2 | 7/2014 | Burbank |
| 8,771,293 B2 | 7/2014 | Surti et al. |
| 8,773,001 B2 | 7/2014 | Wiener et al. |
| 8,777,944 B2 | 7/2014 | Frankhouser et al. |
| 8,777,945 B2 | 7/2014 | Floume et al. |
| 8,779,648 B2 | 7/2014 | Giordano et al. |
| 8,783,541 B2 | 7/2014 | Shelton, IV et al. |
| 8,784,415 B2 | 7/2014 | Malackowski et al. |
| 8,784,418 B2 | 7/2014 | Romero |
| 8,790,342 B2 | 7/2014 | Stulen et al. |
| 8,795,274 B2 | 8/2014 | Hanna |
| 8,795,275 B2 | 8/2014 | Hafner |
| 8,795,276 B2 | 8/2014 | Dietz et al. |
| 8,795,327 B2 | 8/2014 | Dietz et al. |
| 8,800,838 B2 | 8/2014 | Shelton, IV |
| 8,801,710 B2 | 8/2014 | Ullrich et al. |
| 8,801,752 B2 | 8/2014 | Fortier et al. |
| 8,807,414 B2 | 8/2014 | Ross et al. |
| 8,808,204 B2 | 8/2014 | Irisawa et al. |
| 8,808,319 B2 | 8/2014 | Houser et al. |
| 8,814,856 B2 | 8/2014 | Elmouelhi et al. |
| 8,814,870 B2 | 8/2014 | Paraschiv et al. |
| 8,820,605 B2 | 9/2014 | Shelton, IV |
| 8,821,388 B2 | 9/2014 | Naito et al. |
| 8,827,992 B2 | 9/2014 | Koss et al. |
| 8,827,995 B2 | 9/2014 | Schaller et al. |
| 8,834,466 B2 | 9/2014 | Cummings et al. |
| 8,834,518 B2 | 9/2014 | Faller et al. |
| 8,844,789 B2 | 9/2014 | Shelton, IV et al. |
| 8,845,537 B2 | 9/2014 | Tanaka et al. |
| 8,845,630 B2 | 9/2014 | Mehta et al. |
| 8,848,808 B2 | 9/2014 | Dress |
| 8,851,354 B2 | 10/2014 | Swensgard et al. |
| 8,852,184 B2 | 10/2014 | Kucklick |
| 8,858,547 B2 | 10/2014 | Brogna |
| 8,862,955 B2 | 10/2014 | Cesari |
| 8,864,749 B2 | 10/2014 | Okada |
| 8,864,757 B2 | 10/2014 | Klimovitch et al. |
| 8,864,761 B2 | 10/2014 | Johnson et al. |
| 8,870,865 B2 | 10/2014 | Frankhouser et al. |
| 8,874,220 B2 | 10/2014 | Draghici et al. |
| 8,876,726 B2 | 11/2014 | Amit et al. |
| 8,876,858 B2 | 11/2014 | Braun |
| 8,882,766 B2 | 11/2014 | Couture et al. |
| 8,882,791 B2 | 11/2014 | Stulen |
| 8,888,776 B2 | 11/2014 | Dietz et al. |
| 8,888,783 B2 | 11/2014 | Young |
| 8,888,809 B2 | 11/2014 | Davison et al. |
| 8,899,462 B2 | 12/2014 | Kostrzewski et al. |
| 8,900,259 B2 | 12/2014 | Houser et al. |
| 8,906,016 B2 | 12/2014 | Boudreaux et al. |
| 8,906,017 B2 | 12/2014 | Rioux et al. |
| 8,911,438 B2 | 12/2014 | Swoyer et al. |
| 8,911,460 B2 | 12/2014 | Neurohr et al. |
| 8,920,412 B2 | 12/2014 | Fritz et al. |
| 8,920,414 B2 | 12/2014 | Stone et al. |
| 8,920,421 B2 | 12/2014 | Rupp |
| 8,926,607 B2 | 1/2015 | Norvell et al. |
| 8,926,608 B2 | 1/2015 | Bacher et al. |
| 8,926,620 B2 | 1/2015 | Chasmawala et al. |
| 8,931,682 B2 | 1/2015 | Timm et al. |
| 8,932,282 B2 | 1/2015 | Gilbert |
| 8,932,299 B2 | 1/2015 | Bono et al. |
| 8,936,614 B2 | 1/2015 | Allen, IV |
| 8,939,974 B2 | 1/2015 | Boudreaux et al. |
| 8,945,126 B2 | 2/2015 | Garrison et al. |
| 8,951,248 B2 | 2/2015 | Messerly et al. |
| 8,951,272 B2 | 2/2015 | Robertson et al. |
| 8,956,349 B2 | 2/2015 | Aldridge et al. |
| 8,960,520 B2 | 2/2015 | McCuen |
| 8,961,515 B2 | 2/2015 | Twomey et al. |
| 8,961,547 B2 | 2/2015 | Dietz et al. |
| 8,967,443 B2 | 3/2015 | McCuen |
| 8,968,283 B2 | 3/2015 | Kharin |

(56) References Cited

U.S. PATENT DOCUMENTS

| | | |
|---|---|---|
| 8,968,294 B2 | 3/2015 | Maass et al. |
| 8,968,296 B2 | 3/2015 | McPherson |
| 8,968,355 B2 | 3/2015 | Malkowski et al. |
| 8,974,447 B2 | 3/2015 | Kimball et al. |
| 8,974,477 B2 | 3/2015 | Yamada |
| 8,974,479 B2 | 3/2015 | Ross et al. |
| 8,974,932 B2 | 3/2015 | McGahan et al. |
| 8,979,843 B2 | 3/2015 | Timm et al. |
| 8,979,844 B2 | 3/2015 | White et al. |
| 8,979,890 B2 | 3/2015 | Boudreaux |
| 8,986,287 B2 | 3/2015 | Park et al. |
| 8,986,297 B2 | 3/2015 | Daniel et al. |
| 8,986,302 B2 | 3/2015 | Aldridge et al. |
| 8,989,855 B2 | 3/2015 | Murphy et al. |
| 8,989,903 B2 | 3/2015 | Weir et al. |
| 8,991,678 B2 | 3/2015 | Wellman et al. |
| 8,992,422 B2 | 3/2015 | Spivey et al. |
| 8,992,526 B2 | 3/2015 | Brodbeck et al. |
| 8,998,891 B2 | 4/2015 | Garito et al. |
| 9,005,199 B2 | 4/2015 | Beckman et al. |
| 9,011,437 B2 | 4/2015 | Woodruff et al. |
| 9,011,471 B2 | 4/2015 | Timm et al. |
| 9,017,326 B2 | 4/2015 | DiNardo et al. |
| 9,017,355 B2 | 4/2015 | Smith et al. |
| 9,017,372 B2 | 4/2015 | Artale et al. |
| 9,023,035 B2 | 5/2015 | Allen, IV et al. |
| 9,023,070 B2 | 5/2015 | Levine et al. |
| 9,023,071 B2 | 5/2015 | Miller et al. |
| 9,028,397 B2 | 5/2015 | Naito |
| 9,028,476 B2 | 5/2015 | Bonn |
| 9,028,478 B2 | 5/2015 | Mueller |
| 9,028,481 B2 | 5/2015 | Behnke, II |
| 9,028,494 B2 | 5/2015 | Shelton, IV et al. |
| 9,028,519 B2 | 5/2015 | Yates et al. |
| 9,031,667 B2 | 5/2015 | Williams |
| 9,033,973 B2 | 5/2015 | Krapohl et al. |
| 9,035,741 B2 | 5/2015 | Hamel et al. |
| 9,037,259 B2 | 5/2015 | Mathur |
| 9,039,690 B2 | 5/2015 | Kersten et al. |
| 9,039,691 B2 | 5/2015 | Moua et al. |
| 9,039,695 B2 | 5/2015 | Giordano et al. |
| 9,039,696 B2 | 5/2015 | Assmus et al. |
| 9,039,705 B2 | 5/2015 | Takashino |
| 9,039,731 B2 | 5/2015 | Joseph |
| 9,043,018 B2 | 5/2015 | Mohr |
| 9,044,227 B2 | 6/2015 | Shelton, IV et al. |
| 9,044,230 B2 | 6/2015 | Morgan et al. |
| 9,044,238 B2 | 6/2015 | Orszulak |
| 9,044,243 B2 | 6/2015 | Johnson et al. |
| 9,044,245 B2 | 6/2015 | Condie et al. |
| 9,044,256 B2 | 6/2015 | Cadeddu et al. |
| 9,044,261 B2 | 6/2015 | Houser |
| 9,050,083 B2 | 6/2015 | Yates et al. |
| 9,050,093 B2 | 6/2015 | Aldridge et al. |
| 9,050,098 B2 | 6/2015 | Deville et al. |
| 9,050,123 B2 | 6/2015 | Krause et al. |
| 9,050,124 B2 | 6/2015 | Houser |
| 9,055,961 B2 | 6/2015 | Manzo et al. |
| 9,059,547 B2 | 6/2015 | McLawhorn |
| 9,060,770 B2 | 6/2015 | Shelton, IV et al. |
| 9,060,775 B2 | 6/2015 | Wiener et al. |
| 9,060,776 B2 | 6/2015 | Yates et al. |
| 9,060,778 B2 | 6/2015 | Condie et al. |
| 9,066,720 B2 | 6/2015 | Ballakur et al. |
| 9,066,723 B2 | 6/2015 | Beller et al. |
| 9,066,747 B2 | 6/2015 | Robertson |
| 9,072,523 B2 | 7/2015 | Houser et al. |
| 9,072,535 B2 | 7/2015 | Shelton, IV et al. |
| 9,072,536 B2 | 7/2015 | Shelton, IV et al. |
| 9,072,538 B2 | 7/2015 | Suzuki et al. |
| 9,072,539 B2 | 7/2015 | Messerly et al. |
| 9,084,624 B2 | 7/2015 | Larkin et al. |
| 9,089,327 B2 | 7/2015 | Worrell et al. |
| 9,089,360 B2 | 7/2015 | Messerly et al. |
| 9,095,362 B2 | 8/2015 | Dachs, II et al. |
| 9,095,367 B2 | 8/2015 | Olson et al. |
| 9,099,863 B2 | 8/2015 | Smith et al. |
| 9,101,358 B2 | 8/2015 | Kerr et al. |
| 9,101,385 B2 | 8/2015 | Shelton, IV et al. |
| 9,107,684 B2 | 8/2015 | Ma |
| 9,107,689 B2 | 8/2015 | Robertson et al. |
| 9,107,690 B2 | 8/2015 | Bales, Jr. et al. |
| 9,113,900 B2 | 8/2015 | Buysse et al. |
| 9,113,907 B2 | 8/2015 | Allen, IV et al. |
| 9,113,940 B2 | 8/2015 | Twomey |
| 9,119,657 B2 | 9/2015 | Shelton, IV et al. |
| 9,119,957 B2 | 9/2015 | Gantz et al. |
| 9,125,662 B2 | 9/2015 | Shelton, IV |
| 9,125,667 B2 | 9/2015 | Stone et al. |
| 9,144,453 B2 | 9/2015 | Rencher et al. |
| 9,147,965 B2 | 9/2015 | Lee |
| 9,149,324 B2 | 10/2015 | Huang et al. |
| 9,149,325 B2 | 10/2015 | Worrell et al. |
| 9,161,803 B2 | 10/2015 | Yates et al. |
| 9,165,114 B2 | 10/2015 | Jain et al. |
| 9,168,054 B2 | 10/2015 | Turner et al. |
| 9,168,085 B2 | 10/2015 | Juzkiw et al. |
| 9,168,089 B2 | 10/2015 | Buysse et al. |
| 9,173,656 B2 | 11/2015 | Schurr et al. |
| 9,179,912 B2 | 11/2015 | Yates et al. |
| 9,186,199 B2 | 11/2015 | Strauss et al. |
| 9,186,204 B2 | 11/2015 | Nishimura et al. |
| 9,186,796 B2 | 11/2015 | Ogawa |
| 9,192,380 B2 | 11/2015 | Racenet et al. |
| 9,192,421 B2 | 11/2015 | Garrison |
| 9,192,428 B2 | 11/2015 | Houser et al. |
| 9,192,431 B2 | 11/2015 | Woodruff et al. |
| 9,198,714 B2 | 12/2015 | Worrell et al. |
| 9,198,715 B2 | 12/2015 | Livneh |
| 9,198,718 B2 | 12/2015 | Marczyk et al. |
| 9,198,776 B2 | 12/2015 | Young |
| 9,204,879 B2 | 12/2015 | Shelton, IV |
| 9,204,891 B2 | 12/2015 | Weitzman |
| 9,204,918 B2 | 12/2015 | Germain et al. |
| 9,204,923 B2 | 12/2015 | Manzo et al. |
| 9,216,050 B2 | 12/2015 | Condie et al. |
| 9,216,051 B2 | 12/2015 | Fischer et al. |
| 9,216,062 B2 | 12/2015 | Duque et al. |
| 9,220,483 B2 | 12/2015 | Frankhouser et al. |
| 9,220,527 B2 | 12/2015 | Houser et al. |
| 9,220,559 B2 | 12/2015 | Worrell et al. |
| 9,226,750 B2 | 1/2016 | Weir et al. |
| 9,226,751 B2 | 1/2016 | Shelton, IV et al. |
| 9,226,766 B2 | 1/2016 | Aldridge et al. |
| 9,226,767 B2 | 1/2016 | Stulen et al. |
| 9,232,979 B2 | 1/2016 | Parihar et al. |
| 9,237,891 B2 | 1/2016 | Shelton, IV |
| 9,237,921 B2 | 1/2016 | Messerly et al. |
| 9,241,060 B1 | 1/2016 | Fujisaki |
| 9,241,692 B2 | 1/2016 | Gunday et al. |
| 9,241,728 B2 | 1/2016 | Price et al. |
| 9,241,730 B2 | 1/2016 | Babaev |
| 9,241,731 B2 | 1/2016 | Boudreaux et al. |
| 9,241,768 B2 | 1/2016 | Sandhu et al. |
| 9,247,953 B2 | 2/2016 | Palmer et al. |
| 9,254,165 B2 | 2/2016 | Aronow et al. |
| 9,259,234 B2 | 2/2016 | Robertson et al. |
| 9,259,265 B2 | 2/2016 | Harris et al. |
| 9,265,567 B2 | 2/2016 | Orban, III et al. |
| 9,265,926 B2 | 2/2016 | Strobl et al. |
| 9,265,973 B2 | 2/2016 | Akagane |
| 9,277,962 B2 | 3/2016 | Koss et al. |
| 9,282,974 B2 | 3/2016 | Shelton, IV |
| 9,283,027 B2 | 3/2016 | Monson et al. |
| 9,283,045 B2 | 3/2016 | Rhee et al. |
| 9,283,054 B2 | 3/2016 | Morgan et al. |
| 9,289,256 B2 | 3/2016 | Shelton, IV et al. |
| 9,295,514 B2 | 3/2016 | Shelton, IV et al. |
| 9,301,759 B2 | 4/2016 | Spivey et al. |
| 9,305,497 B2 | 4/2016 | Seo et al. |
| 9,307,388 B2 | 4/2016 | Liang et al. |
| 9,307,986 B2 | 4/2016 | Hall et al. |
| 9,308,009 B2 | 4/2016 | Madan et al. |
| 9,308,014 B2 | 4/2016 | Fischer |

(56) References Cited

U.S. PATENT DOCUMENTS

| | | |
|---|---|---|
| 9,314,261 B2 | 4/2016 | Bales, Jr. et al. |
| 9,314,292 B2 | 4/2016 | Trees et al. |
| 9,314,301 B2 | 4/2016 | Ben-Haim et al. |
| 9,326,754 B2 | 5/2016 | Polster |
| 9,326,767 B2 | 5/2016 | Koch et al. |
| 9,326,787 B2 | 5/2016 | Sanai et al. |
| 9,326,788 B2 | 5/2016 | Batross et al. |
| 9,332,987 B2 | 5/2016 | Leimbach et al. |
| 9,333,025 B2 | 5/2016 | Monson et al. |
| 9,333,034 B2 | 5/2016 | Hancock |
| 9,339,289 B2 | 5/2016 | Robertson |
| 9,339,323 B2 | 5/2016 | Eder et al. |
| 9,339,326 B2 | 5/2016 | McCullagh et al. |
| 9,345,481 B2 | 5/2016 | Hall et al. |
| 9,345,534 B2 | 5/2016 | Artale et al. |
| 9,345,900 B2 | 5/2016 | Wu et al. |
| 9,351,642 B2 | 5/2016 | Nadkarni et al. |
| 9,351,726 B2 | 5/2016 | Leimbach et al. |
| 9,351,727 B2 | 5/2016 | Leimbach et al. |
| 9,351,754 B2 | 5/2016 | Vakharia et al. |
| 9,352,173 B2 | 5/2016 | Yamada et al. |
| 9,358,003 B2 | 6/2016 | Hall et al. |
| 9,358,065 B2 | 6/2016 | Ladtkow et al. |
| 9,364,171 B2 | 6/2016 | Harris et al. |
| 9,364,230 B2 | 6/2016 | Shelton, IV et al. |
| 9,364,279 B2 | 6/2016 | Houser et al. |
| 9,370,364 B2 | 6/2016 | Smith et al. |
| 9,370,400 B2 | 6/2016 | Parihar |
| 9,370,611 B2 | 6/2016 | Ross et al. |
| 9,375,230 B2 | 6/2016 | Ross et al. |
| 9,375,232 B2 | 6/2016 | Hunt et al. |
| 9,375,256 B2 | 6/2016 | Cunningham et al. |
| 9,375,264 B2 | 6/2016 | Horner et al. |
| 9,375,267 B2 | 6/2016 | Kerr et al. |
| 9,385,831 B2 | 7/2016 | Marr et al. |
| 9,386,983 B2 | 7/2016 | Swensgard et al. |
| 9,393,037 B2 | 7/2016 | Olson et al. |
| 9,393,070 B2 | 7/2016 | Gelfand et al. |
| 9,398,911 B2 | 7/2016 | Auld |
| 9,402,680 B2 | 8/2016 | Ginnebaugh et al. |
| 9,402,682 B2 | 8/2016 | Worrell et al. |
| 9,408,606 B2 | 8/2016 | Shelton, IV |
| 9,408,622 B2 | 8/2016 | Stulen et al. |
| 9,408,660 B2 | 8/2016 | Strobl et al. |
| 9,414,853 B2 | 8/2016 | Stulen et al. |
| 9,414,880 B2 | 8/2016 | Monson et al. |
| 9,421,014 B2 | 8/2016 | Ingmanson et al. |
| 9,421,060 B2 | 8/2016 | Monson et al. |
| 9,427,249 B2 | 8/2016 | Robertson et al. |
| 9,427,279 B2 | 8/2016 | Muniz-Medina et al. |
| 9,439,668 B2 | 9/2016 | Timm et al. |
| 9,439,669 B2 | 9/2016 | Wiener et al. |
| 9,439,671 B2 | 9/2016 | Akagane |
| 9,442,288 B2 | 9/2016 | Tanimura |
| 9,445,784 B2 | 9/2016 | O'Keeffe |
| 9,445,832 B2 | 9/2016 | Wiener et al. |
| 9,451,967 B2 | 9/2016 | Jordan et al. |
| 9,456,863 B2 | 10/2016 | Moua |
| 9,456,864 B2 | 10/2016 | Witt et al. |
| 9,468,438 B2 | 10/2016 | Baber et al. |
| 9,468,498 B2 | 10/2016 | Sigmon, Jr. |
| 9,474,542 B2 | 10/2016 | Slipszenko et al. |
| 9,474,568 B2 | 10/2016 | Akagane |
| 9,486,236 B2 | 11/2016 | Price et al. |
| 9,492,146 B2 | 11/2016 | Kostrzewski et al. |
| 9,492,224 B2 | 11/2016 | Boudreaux et al. |
| 9,498,245 B2 | 11/2016 | Voegele et al. |
| 9,498,275 B2 | 11/2016 | Wham et al. |
| 9,504,483 B2 | 11/2016 | Houser et al. |
| 9,504,520 B2 | 11/2016 | Worrell et al. |
| 9,504,524 B2 | 11/2016 | Behnke, II |
| 9,504,855 B2 | 11/2016 | Messerly et al. |
| 9,510,850 B2 | 12/2016 | Robertson et al. |
| 9,510,906 B2 | 12/2016 | Boudreaux et al. |
| 9,522,029 B2 | 12/2016 | Yates et al. |
| 9,522,032 B2 | 12/2016 | Behnke |
| 9,526,564 B2 | 12/2016 | Rusin |
| 9,526,565 B2 | 12/2016 | Strobl |
| 9,545,253 B2 | 1/2017 | Worrell et al. |
| 9,545,497 B2 | 1/2017 | Wenderow et al. |
| 9,554,465 B1 | 1/2017 | Liu et al. |
| 9,554,794 B2 | 1/2017 | Baber et al. |
| 9,554,846 B2 | 1/2017 | Boudreaux |
| 9,554,854 B2 | 1/2017 | Yates et al. |
| 9,560,995 B2 | 2/2017 | Addison et al. |
| 9,561,038 B2 | 2/2017 | Shelton, IV et al. |
| 9,572,592 B2 | 2/2017 | Price et al. |
| 9,574,644 B2 | 2/2017 | Parihar |
| 9,585,714 B2 | 3/2017 | Livneh |
| 9,592,056 B2 | 3/2017 | Mozdzierz et al. |
| 9,592,072 B2 | 3/2017 | Akagane |
| 9,597,143 B2 | 3/2017 | Madan et al. |
| 9,603,669 B2 | 3/2017 | Govari et al. |
| 9,610,091 B2 | 4/2017 | Johnson et al. |
| 9,610,114 B2 | 4/2017 | Baxter, III et al. |
| 9,615,877 B2 | 4/2017 | Tyrrell et al. |
| 9,623,237 B2 | 4/2017 | Turner et al. |
| 9,629,623 B2 | 4/2017 | Lytle, IV et al. |
| 9,629,629 B2 | 4/2017 | Leimbach et al. |
| 9,632,573 B2 | 4/2017 | Ogawa et al. |
| 9,636,135 B2 | 5/2017 | Stulen |
| 9,636,165 B2 | 5/2017 | Larson et al. |
| 9,636,167 B2 | 5/2017 | Gregg |
| 9,638,770 B2 | 5/2017 | Dietz et al. |
| 9,642,644 B2 | 5/2017 | Houser et al. |
| 9,642,669 B2 | 5/2017 | Takashino et al. |
| 9,643,052 B2 | 5/2017 | Tchao et al. |
| 9,649,110 B2 | 5/2017 | Parihar et al. |
| 9,649,111 B2 | 5/2017 | Shelton, IV et al. |
| 9,649,126 B2 | 5/2017 | Robertson et al. |
| 9,649,173 B2 | 5/2017 | Choi et al. |
| 9,655,670 B2 | 5/2017 | Larson et al. |
| 9,662,131 B2 | 5/2017 | Omori et al. |
| 9,668,806 B2 | 6/2017 | Unger et al. |
| 9,671,860 B2 | 6/2017 | Ogawa et al. |
| 9,674,949 B1 | 6/2017 | Liu et al. |
| 9,675,374 B2 | 6/2017 | Stulen et al. |
| 9,675,375 B2 | 6/2017 | Houser et al. |
| 9,681,884 B2 | 6/2017 | Clem et al. |
| 9,687,230 B2 | 6/2017 | Leimbach et al. |
| 9,687,290 B2 | 6/2017 | Keller |
| 9,690,362 B2 | 6/2017 | Leimbach et al. |
| 9,693,817 B2 | 7/2017 | Mehta et al. |
| 9,700,309 B2 | 7/2017 | Jaworek et al. |
| 9,700,339 B2 | 7/2017 | Nield |
| 9,700,343 B2 | 7/2017 | Messerly et al. |
| 9,705,456 B2 | 7/2017 | Gilbert |
| 9,707,004 B2 | 7/2017 | Houser et al. |
| 9,707,027 B2 | 7/2017 | Ruddenklau et al. |
| 9,707,030 B2 | 7/2017 | Davison et al. |
| 9,713,507 B2 | 7/2017 | Stulen et al. |
| 9,717,548 B2 | 8/2017 | Couture |
| 9,717,552 B2 | 8/2017 | Cosman et al. |
| 9,724,094 B2 | 8/2017 | Baber et al. |
| 9,724,118 B2 | 8/2017 | Schulte et al. |
| 9,724,120 B2 | 8/2017 | Faller et al. |
| 9,724,152 B2 | 8/2017 | Horlle et al. |
| 9,730,695 B2 | 8/2017 | Leimbach et al. |
| 9,733,663 B2 | 8/2017 | Leimbach et al. |
| 9,737,301 B2 | 8/2017 | Baber et al. |
| 9,737,326 B2 | 8/2017 | Worrell et al. |
| 9,737,355 B2 | 8/2017 | Yates et al. |
| 9,737,358 B2 | 8/2017 | Beckman et al. |
| 9,743,929 B2 | 8/2017 | Leimbach et al. |
| 9,743,946 B2 | 8/2017 | Faller et al. |
| 9,743,947 B2 | 8/2017 | Price et al. |
| 9,750,499 B2 | 9/2017 | Leimbach et al. |
| 9,757,128 B2 | 9/2017 | Baber et al. |
| 9,757,142 B2 | 9/2017 | Shimizu |
| 9,757,150 B2 | 9/2017 | Alexander et al. |
| 9,757,186 B2 | 9/2017 | Boudreaux et al. |
| 9,764,164 B2 | 9/2017 | Wiener et al. |
| 9,770,285 B2 | 9/2017 | Zoran et al. |
| 9,782,169 B2 | 10/2017 | Kimsey et al. |

(56) References Cited

U.S. PATENT DOCUMENTS

| | | |
|---|---|---|
| 9,782,214 B2 | 10/2017 | Houser et al. |
| 9,788,836 B2 | 10/2017 | Overmyer et al. |
| 9,788,851 B2 | 10/2017 | Dannaher et al. |
| 9,795,405 B2 | 10/2017 | Price et al. |
| 9,795,436 B2 | 10/2017 | Yates et al. |
| 9,795,808 B2 | 10/2017 | Messerly et al. |
| 9,801,626 B2 | 10/2017 | Parihar et al. |
| 9,801,648 B2 | 10/2017 | Houser et al. |
| 9,802,033 B2 | 10/2017 | Hibner et al. |
| 9,804,618 B2 | 10/2017 | Leimbach et al. |
| 9,808,244 B2 | 11/2017 | Leimbach et al. |
| 9,808,246 B2 | 11/2017 | Shelton, IV et al. |
| 9,808,308 B2 | 11/2017 | Faller et al. |
| 9,814,460 B2 | 11/2017 | Kimsey et al. |
| 9,814,514 B2 | 11/2017 | Shelton, IV et al. |
| 9,815,211 B2 | 11/2017 | Cao et al. |
| 9,820,738 B2 | 11/2017 | Lytle, IV et al. |
| 9,820,768 B2 | 11/2017 | Gee et al. |
| 9,820,771 B2 | 11/2017 | Norton et al. |
| 9,820,806 B2 | 11/2017 | Lee et al. |
| 9,826,976 B2 | 11/2017 | Parihar et al. |
| 9,826,977 B2 | 11/2017 | Leimbach et al. |
| 9,839,443 B2 | 12/2017 | Brockman et al. |
| 9,844,368 B2 | 12/2017 | Boudreaux et al. |
| 9,844,374 B2 | 12/2017 | Lytle, IV et al. |
| 9,844,375 B2 | 12/2017 | Overmyer et al. |
| 9,848,901 B2 | 12/2017 | Robertson et al. |
| 9,848,902 B2 | 12/2017 | Price et al. |
| 9,848,937 B2 | 12/2017 | Trees et al. |
| 9,861,381 B2 | 1/2018 | Johnson |
| 9,861,428 B2 | 1/2018 | Trees et al. |
| 9,867,612 B2 | 1/2018 | Parihar et al. |
| 9,867,651 B2 | 1/2018 | Wham |
| 9,867,670 B2 | 1/2018 | Brannan et al. |
| 9,872,722 B2 | 1/2018 | Lech |
| 9,872,725 B2 | 1/2018 | Worrell et al. |
| 9,872,726 B2 | 1/2018 | Morisaki |
| 9,877,720 B2 | 1/2018 | Worrell et al. |
| 9,877,776 B2 | 1/2018 | Boudreaux |
| 9,878,184 B2 | 1/2018 | Beaupre |
| 9,883,860 B2 | 2/2018 | Leimbach |
| 9,883,884 B2 | 2/2018 | Neurohr et al. |
| 9,888,919 B2 | 2/2018 | Leimbach et al. |
| 9,888,958 B2 | 2/2018 | Evans et al. |
| 9,895,148 B2 | 2/2018 | Shelton, IV et al. |
| 9,901,321 B2 | 2/2018 | Harks et al. |
| 9,901,342 B2 | 2/2018 | Shelton, IV et al. |
| 9,901,383 B2 | 2/2018 | Hassler, Jr. |
| 9,901,754 B2 | 2/2018 | Yamada |
| 9,907,563 B2 | 3/2018 | Germain et al. |
| 9,913,642 B2 | 3/2018 | Leimbach et al. |
| 9,913,656 B2 | 3/2018 | Stulen |
| 9,913,680 B2 | 3/2018 | Voegele et al. |
| 9,918,730 B2 | 3/2018 | Trees et al. |
| 9,924,961 B2 | 3/2018 | Shelton, IV et al. |
| 9,925,003 B2 | 3/2018 | Parihar et al. |
| 9,931,118 B2 | 4/2018 | Shelton, IV et al. |
| 9,943,309 B2 | 4/2018 | Shelton, IV et al. |
| 9,949,785 B2 | 4/2018 | Price et al. |
| 9,949,788 B2 | 4/2018 | Boudreaux |
| 9,962,182 B2 | 5/2018 | Dietz et al. |
| 9,968,355 B2 | 5/2018 | Shelton, IV et al. |
| 9,974,539 B2 | 5/2018 | Yates et al. |
| 9,987,000 B2 | 6/2018 | Shelton, IV et al. |
| 9,987,033 B2 | 6/2018 | Neurohr et al. |
| 9,993,248 B2 | 6/2018 | Shelton, IV et al. |
| 9,993,258 B2 | 6/2018 | Shelton, IV et al. |
| 10,004,497 B2 | 6/2018 | Overmyer et al. |
| 10,004,501 B2 | 6/2018 | Shelton, IV et al. |
| 10,004,526 B2 | 6/2018 | Dycus et al. |
| 10,004,527 B2 | 6/2018 | Gee et al. |
| D822,206 S | 7/2018 | Shelton, IV et al. |
| 10,010,339 B2 | 7/2018 | Witt et al. |
| 10,010,341 B2 | 7/2018 | Houser et al. |
| 10,013,049 B2 | 7/2018 | Leimbach et al. |
| 10,016,199 B2 | 7/2018 | Baber et al. |
| 10,016,207 B2 | 7/2018 | Suzuki et al. |
| 10,022,142 B2 | 7/2018 | Aranyi et al. |
| 10,022,567 B2 | 7/2018 | Messerly et al. |
| 10,022,568 B2 | 7/2018 | Messerly et al. |
| 10,028,761 B2 | 7/2018 | Leimbach et al. |
| 10,028,786 B2 | 7/2018 | Mucilli et al. |
| 10,034,684 B2 | 7/2018 | Weisenburgh, II et al. |
| 10,034,704 B2 | 7/2018 | Asher et al. |
| D826,405 S | 8/2018 | Shelton, IV et al. |
| 10,039,588 B2 | 8/2018 | Harper et al. |
| 10,041,822 B2 | 8/2018 | Zemlok |
| 10,045,776 B2 | 8/2018 | Shelton, IV et al. |
| 10,045,779 B2 | 8/2018 | Savage et al. |
| 10,045,794 B2 | 8/2018 | Witt et al. |
| 10,045,810 B2 | 8/2018 | Schall et al. |
| 10,045,819 B2 | 8/2018 | Jensen et al. |
| 10,052,044 B2 | 8/2018 | Shelton, IV et al. |
| 10,052,102 B2 | 8/2018 | Baxter, III et al. |
| 10,070,916 B2 | 9/2018 | Artale |
| 10,080,609 B2 | 9/2018 | Hancock et al. |
| 10,085,748 B2 | 10/2018 | Morgan et al. |
| 10,085,762 B2 | 10/2018 | Timm et al. |
| 10,085,792 B2 | 10/2018 | Johnson et al. |
| 10,092,310 B2 | 10/2018 | Boudreaux et al. |
| 10,092,344 B2 | 10/2018 | Mohr et al. |
| 10,092,348 B2 | 10/2018 | Boudreaux |
| 10,092,350 B2 | 10/2018 | Rothweiler et al. |
| 10,105,140 B2 | 10/2018 | Malinouskas et al. |
| 10,111,679 B2 | 10/2018 | Baber et al. |
| 10,111,699 B2 | 10/2018 | Boudreaux |
| 10,111,703 B2 | 10/2018 | Cosman, Jr. et al. |
| 10,117,649 B2 | 11/2018 | Baxter et al. |
| 10,117,667 B2 | 11/2018 | Robertson et al. |
| 10,117,702 B2 | 11/2018 | Danziger et al. |
| 10,123,835 B2 | 11/2018 | Keller et al. |
| 10,130,367 B2 | 11/2018 | Cappola et al. |
| 10,130,410 B2 | 11/2018 | Strobl et al. |
| 10,130,412 B2 | 11/2018 | Wham |
| 10,135,242 B2 | 11/2018 | Baber et al. |
| 10,136,887 B2 | 11/2018 | Shelton, IV et al. |
| 10,149,680 B2 | 12/2018 | Parihar et al. |
| 10,154,848 B2 | 12/2018 | Chernov et al. |
| 10,154,852 B2 | 12/2018 | Conlon et al. |
| 10,159,483 B2 | 12/2018 | Beckman et al. |
| 10,159,524 B2 | 12/2018 | Yates et al. |
| 10,166,060 B2 | 1/2019 | Johnson et al. |
| 10,172,665 B2 | 1/2019 | Heckel et al. |
| 10,172,669 B2 | 1/2019 | Felder et al. |
| 10,178,992 B2 | 1/2019 | Wise et al. |
| 10,179,022 B2 | 1/2019 | Yates et al. |
| 10,180,463 B2 | 1/2019 | Beckman et al. |
| 10,182,816 B2 | 1/2019 | Shelton, IV et al. |
| 10,182,818 B2 | 1/2019 | Hensel et al. |
| 10,188,385 B2 | 1/2019 | Kerr et al. |
| 10,188,455 B2 | 1/2019 | Hancock et al. |
| 10,194,907 B2 | 2/2019 | Marczyk et al. |
| 10,194,972 B2 | 2/2019 | Yates et al. |
| 10,194,973 B2 | 2/2019 | Wiener et al. |
| 10,194,976 B2 | 2/2019 | Boudreaux |
| 10,194,977 B2 | 2/2019 | Yang |
| 10,194,999 B2 | 2/2019 | Bacher et al. |
| 10,201,364 B2 | 2/2019 | Leimbach et al. |
| 10,201,365 B2 | 2/2019 | Boudreaux et al. |
| 10,201,382 B2 | 2/2019 | Wiener et al. |
| 10,226,250 B2 | 3/2019 | Beckman et al. |
| 10,226,273 B2 | 3/2019 | Messerly et al. |
| 10,231,747 B2 | 3/2019 | Stulen et al. |
| 10,238,385 B2 | 3/2019 | Yates et al. |
| 10,238,391 B2 | 3/2019 | Leimbach et al. |
| 10,245,027 B2 | 4/2019 | Shelton, IV et al. |
| 10,245,028 B2 | 4/2019 | Shelton, IV et al. |
| 10,245,029 B2 | 4/2019 | Hunter et al. |
| 10,245,030 B2 | 4/2019 | Hunter et al. |
| 10,245,033 B2 | 4/2019 | Overmyer et al. |
| 10,245,095 B2 | 4/2019 | Boudreaux |
| 10,245,104 B2 | 4/2019 | McKenna et al. |
| 10,251,664 B2 | 4/2019 | Shelton, IV et al. |
| 10,258,331 B2 | 4/2019 | Shelton, IV et al. |

(56) References Cited

U.S. PATENT DOCUMENTS

| | | |
|---|---|---|
| 10,258,505 B2 | 4/2019 | Ovchinnikov |
| 10,263,171 B2 | 4/2019 | Wiener et al. |
| 10,265,068 B2 | 4/2019 | Harris et al. |
| 10,265,117 B2 | 4/2019 | Wiener et al. |
| 10,265,118 B2 | 4/2019 | Gerhardt |
| 10,271,840 B2 | 4/2019 | Sapre |
| 10,271,851 B2 | 4/2019 | Shelton, IV et al. |
| D847,989 S | 5/2019 | Shelton, IV et al. |
| 10,278,721 B2 | 5/2019 | Dietz et al. |
| 10,285,705 B2 | 5/2019 | Shelton, IV et al. |
| 10,285,724 B2 | 5/2019 | Faller et al. |
| 10,285,750 B2 | 5/2019 | Coulson et al. |
| 10,292,704 B2 | 5/2019 | Harris et al. |
| 10,299,810 B2 | 5/2019 | Robertson et al. |
| 10,299,821 B2 | 5/2019 | Shelton, IV et al. |
| D850,617 S | 6/2019 | Shelton, IV et al. |
| D851,762 S | 6/2019 | Shelton, IV et al. |
| 10,307,159 B2 | 6/2019 | Harris et al. |
| 10,314,579 B2 | 6/2019 | Chowaniec et al. |
| 10,314,582 B2 | 6/2019 | Shelton, IV et al. |
| 10,314,638 B2 | 6/2019 | Gee et al. |
| 10,321,907 B2 | 6/2019 | Shelton, IV et al. |
| 10,321,950 B2 | 6/2019 | Yates et al. |
| D854,151 S | 7/2019 | Shelton, IV et al. |
| 10,335,149 B2 | 7/2019 | Baxter, III et al. |
| 10,335,182 B2 | 7/2019 | Stulen et al. |
| 10,335,183 B2 | 7/2019 | Worrell et al. |
| 10,335,614 B2 | 7/2019 | Messerly et al. |
| 10,342,543 B2 | 7/2019 | Shelton, IV et al. |
| 10,342,602 B2 | 7/2019 | Strobl et al. |
| 10,342,606 B2 | 7/2019 | Cosman et al. |
| 10,342,623 B2 | 7/2019 | Huelman et al. |
| 10,348,941 B2 | 7/2019 | Elliot, Jr. et al. |
| 10,349,999 B2 | 7/2019 | Yates et al. |
| 10,350,016 B2 | 7/2019 | Burbank et al. |
| 10,350,025 B1 | 7/2019 | Loyd et al. |
| 10,357,246 B2 | 7/2019 | Shelton, IV et al. |
| 10,357,247 B2 | 7/2019 | Shelton, IV et al. |
| 10,357,303 B2 | 7/2019 | Conlon et al. |
| 10,363,084 B2 | 7/2019 | Friedrichs |
| 10,368,861 B2 | 8/2019 | Baxter, III et al. |
| 10,368,865 B2 | 8/2019 | Harris et al. |
| 10,376,263 B2 | 8/2019 | Morgan et al. |
| 10,376,305 B2 | 8/2019 | Yates et al. |
| 10,390,841 B2 | 8/2019 | Shelton, IV et al. |
| 10,398,439 B2 | 9/2019 | Cabrera et al. |
| 10,398,466 B2 | 9/2019 | Stulen et al. |
| 10,398,497 B2 | 9/2019 | Batross et al. |
| 10,405,857 B2 | 9/2019 | Shelton, IV et al. |
| 10,405,863 B2 | 9/2019 | Wise et al. |
| 10,413,291 B2 | 9/2019 | Worthington et al. |
| 10,413,293 B2 | 9/2019 | Shelton, IV et al. |
| 10,413,297 B2 | 9/2019 | Harris et al. |
| 10,413,352 B2 | 9/2019 | Thomas et al. |
| 10,413,353 B2 | 9/2019 | Kerr et al. |
| 10,420,552 B2 | 9/2019 | Shelton, IV et al. |
| 10,420,579 B2 | 9/2019 | Wiener et al. |
| 10,420,607 B2 | 9/2019 | Woloszko et al. |
| D865,175 S | 10/2019 | Widenhouse et al. |
| 10,426,471 B2 | 10/2019 | Shelton, IV et al. |
| 10,426,507 B2 | 10/2019 | Wiener et al. |
| 10,426,978 B2 | 10/2019 | Akagane |
| 10,433,837 B2 | 10/2019 | Worthington et al. |
| 10,433,849 B2 | 10/2019 | Shelton, IV et al. |
| 10,433,865 B2 | 10/2019 | Witt et al. |
| 10,433,866 B2 | 10/2019 | Witt et al. |
| 10,433,900 B2 | 10/2019 | Harris et al. |
| 10,441,279 B2 | 10/2019 | Shelton, IV et al. |
| 10,441,308 B2 | 10/2019 | Robertson |
| 10,441,310 B2 | 10/2019 | Olson et al. |
| 10,441,345 B2 | 10/2019 | Aldridge et al. |
| 10,448,948 B2 | 10/2019 | Shelton, IV et al. |
| 10,448,950 B2 | 10/2019 | Shelton, IV et al. |
| 10,448,986 B2 | 10/2019 | Zikorus et al. |
| 10,456,140 B2 | 10/2019 | Shelton, IV et al. |
| 10,456,193 B2 | 10/2019 | Yates et al. |
| 10,463,421 B2 | 11/2019 | Boudreaux et al. |
| 10,463,887 B2 | 11/2019 | Witt et al. |
| 10,470,762 B2 | 11/2019 | Leimbach et al. |
| 10,470,764 B2 | 11/2019 | Baxter, III et al. |
| 10,478,182 B2 | 11/2019 | Taylor |
| 10,478,190 B2 | 11/2019 | Miller et al. |
| 10,485,542 B2 | 11/2019 | Shelton, IV et al. |
| 10,485,543 B2 | 11/2019 | Shelton, IV et al. |
| 10,485,607 B2 | 11/2019 | Strobl et al. |
| D869,655 S | 12/2019 | Shelton, IV et al. |
| 10,492,785 B2 | 12/2019 | Overmyer et al. |
| 10,492,849 B2 | 12/2019 | Juergens et al. |
| 10,499,914 B2 | 12/2019 | Huang et al. |
| 10,507,033 B2 | 12/2019 | Dickerson et al. |
| 10,512,795 B2 | 12/2019 | Voegele et al. |
| 10,517,595 B2 | 12/2019 | Hunter et al. |
| 10,517,596 B2 | 12/2019 | Hunter et al. |
| 10,517,627 B2 | 12/2019 | Timm et al. |
| 10,524,787 B2 | 1/2020 | Shelton, IV et al. |
| 10,524,789 B2 | 1/2020 | Swayze et al. |
| 10,524,854 B2 | 1/2020 | Woodruff et al. |
| 10,524,872 B2 | 1/2020 | Stewart et al. |
| 10,531,874 B2 | 1/2020 | Morgan et al. |
| 10,537,324 B2 | 1/2020 | Shelton, IV et al. |
| 10,537,325 B2 | 1/2020 | Bakos et al. |
| 10,537,351 B2 | 1/2020 | Shelton, IV et al. |
| 10,542,979 B2 | 1/2020 | Shelton, IV et al. |
| 10,542,982 B2 | 1/2020 | Beckman et al. |
| 10,542,991 B2 | 1/2020 | Shelton, IV et al. |
| 10,543,008 B2 | 1/2020 | Vakharia et al. |
| 10,548,504 B2 | 2/2020 | Shelton, IV et al. |
| 10,548,655 B2 | 2/2020 | Scheib et al. |
| 10,555,769 B2 | 2/2020 | Worrell et al. |
| 10,561,560 B2 | 2/2020 | Boutoussov et al. |
| 10,568,624 B2 | 2/2020 | Shelton, IV et al. |
| 10,568,625 B2 | 2/2020 | Harris et al. |
| 10,568,626 B2 | 2/2020 | Shelton, IV et al. |
| 10,568,632 B2 | 2/2020 | Miller et al. |
| 10,575,892 B2 | 3/2020 | Danziger et al. |
| 10,582,928 B2 | 3/2020 | Hunter et al. |
| 10,588,625 B2 | 3/2020 | Weaner et al. |
| 10,588,630 B2 | 3/2020 | Shelton, IV et al. |
| 10,588,631 B2 | 3/2020 | Shelton, IV et al. |
| 10,588,632 B2 | 3/2020 | Shelton, IV et al. |
| 10,588,633 B2 | 3/2020 | Shelton, IV et al. |
| 10,595,929 B2 | 3/2020 | Boudreaux et al. |
| 10,595,930 B2 | 3/2020 | Scheib et al. |
| 10,603,036 B2 | 3/2020 | Hunter et al. |
| 10,610,224 B2 | 4/2020 | Shelton, IV et al. |
| 10,610,286 B2 | 4/2020 | Wiener et al. |
| 10,610,313 B2 | 4/2020 | Bailey et al. |
| 10,617,412 B2 | 4/2020 | Shelton, IV et al. |
| 10,617,420 B2 | 4/2020 | Shelton, IV et al. |
| 10,617,464 B2 | 4/2020 | Duppuis |
| 10,624,635 B2 | 4/2020 | Harris et al. |
| 10,624,691 B2 | 4/2020 | Wiener et al. |
| 10,631,858 B2 | 4/2020 | Burbank |
| 10,631,859 B2 | 4/2020 | Shelton, IV et al. |
| 10,632,630 B2 | 4/2020 | Cao et al. |
| RE47,996 E | 5/2020 | Turner et al. |
| 10,639,034 B2 | 5/2020 | Harris et al. |
| 10,639,035 B2 | 5/2020 | Shelton, IV et al. |
| 10,639,037 B2 | 5/2020 | Shelton, IV et al. |
| 10,639,092 B2 | 5/2020 | Corbett et al. |
| 10,639,098 B2 | 5/2020 | Cosman et al. |
| 10,646,269 B2 | 5/2020 | Worrell et al. |
| 10,646,292 B2 | 5/2020 | Solomon et al. |
| 10,653,413 B2 | 5/2020 | Worthington et al. |
| 10,667,809 B2 | 6/2020 | Bakos et al. |
| 10,667,810 B2 | 6/2020 | Shelton, IV et al. |
| 10,667,811 B2 | 6/2020 | Harris et al. |
| 10,675,021 B2 | 6/2020 | Harris et al. |
| 10,675,024 B2 | 6/2020 | Shelton, IV et al. |
| 10,675,025 B2 | 6/2020 | Swayze et al. |
| 10,675,026 B2 | 6/2020 | Harris et al. |
| 10,677,764 B2 | 6/2020 | Ross et al. |
| 10,682,136 B2 | 6/2020 | Harris et al. |
| 10,682,138 B2 | 6/2020 | Shelton, IV et al. |

(56) References Cited

U.S. PATENT DOCUMENTS

| | | |
|---|---|---|
| 10,687,806 B2 | 6/2020 | Shelton, IV et al. |
| 10,687,809 B2 | 6/2020 | Shelton, IV et al. |
| 10,687,810 B2 | 6/2020 | Shelton, IV et al. |
| 10,687,884 B2 | 6/2020 | Wiener et al. |
| 10,688,321 B2 | 6/2020 | Wiener et al. |
| 10,695,055 B2 | 6/2020 | Shelton, IV et al. |
| 10,695,057 B2 | 6/2020 | Shelton, IV et al. |
| 10,695,058 B2 | 6/2020 | Lytle, IV et al. |
| 10,695,119 B2 | 6/2020 | Smith |
| 10,702,270 B2 | 7/2020 | Shelton, IV et al. |
| 10,702,329 B2 | 7/2020 | Strobl et al. |
| 10,709,446 B2 | 7/2020 | Harris et al. |
| 10,709,469 B2 | 7/2020 | Shelton, IV et al. |
| 10,709,906 B2 | 7/2020 | Nield |
| 10,716,615 B2 | 7/2020 | Shelton, IV et al. |
| 10,722,233 B2 | 7/2020 | Wellman |
| D893,717 S | 8/2020 | Messerly et al. |
| 10,729,458 B2 | 8/2020 | Stoddard et al. |
| 10,729,494 B2 | 8/2020 | Parihar et al. |
| 10,736,629 B2 | 8/2020 | Shelton, IV et al. |
| 10,736,685 B2 | 8/2020 | Wiener et al. |
| 10,751,108 B2 | 8/2020 | Yates et al. |
| 10,758,229 B2 | 9/2020 | Shelton, IV et al. |
| 10,758,230 B2 | 9/2020 | Shelton, IV et al. |
| 10,758,232 B2 | 9/2020 | Shelton, IV et al. |
| 10,758,294 B2 | 9/2020 | Jones |
| 10,765,427 B2 | 9/2020 | Shelton, IV et al. |
| 10,765,470 B2 | 9/2020 | Yates et al. |
| 10,772,629 B2 | 9/2020 | Shelton, IV et al. |
| 10,772,630 B2 | 9/2020 | Wixey |
| 10,779,821 B2 | 9/2020 | Harris et al. |
| 10,779,823 B2 | 9/2020 | Shelton, IV et al. |
| 10,779,824 B2 | 9/2020 | Shelton, IV et al. |
| 10,779,825 B2 | 9/2020 | Shelton, IV et al. |
| 10,779,845 B2 | 9/2020 | Timm et al. |
| 10,779,849 B2 | 9/2020 | Shelton, IV et al. |
| 10,779,879 B2 | 9/2020 | Yates et al. |
| 10,786,253 B2 | 9/2020 | Shelton, IV et al. |
| 10,806,454 B2 | 10/2020 | Kopp |
| 10,813,638 B2 | 10/2020 | Shelton, IV et al. |
| 10,820,938 B2 | 11/2020 | Fischer et al. |
| 10,828,058 B2 | 11/2020 | Shelton, IV et al. |
| 10,835,245 B2 | 11/2020 | Swayze et al. |
| 10,835,246 B2 | 11/2020 | Shelton, IV et al. |
| 10,835,247 B2 | 11/2020 | Shelton, IV et al. |
| 10,835,307 B2 | 11/2020 | Shelton, IV et al. |
| 10,842,492 B2 | 11/2020 | Shelton, IV et al. |
| 10,842,523 B2 | 11/2020 | Shelton, IV et al. |
| 10,842,563 B2 | 11/2020 | Gilbert et al. |
| D906,355 S | 12/2020 | Messerly et al. |
| 10,856,867 B2 | 12/2020 | Shelton, IV et al. |
| 10,856,868 B2 | 12/2020 | Shelton, IV et al. |
| 10,856,869 B2 | 12/2020 | Shelton, IV et al. |
| 10,856,870 B2 | 12/2020 | Harris et al. |
| 10,856,896 B2 | 12/2020 | Eichmann et al. |
| 10,856,929 B2 | 12/2020 | Yates et al. |
| 10,856,934 B2 | 12/2020 | Trees et al. |
| 10,874,465 B2 | 12/2020 | Weir et al. |
| D908,216 S | 1/2021 | Messerly et al. |
| 10,881,399 B2 | 1/2021 | Shelton, IV et al. |
| 10,881,401 B2 | 1/2021 | Baber et al. |
| 10,881,409 B2 | 1/2021 | Cabrera |
| 10,881,449 B2 | 1/2021 | Boudreaux et al. |
| 10,888,322 B2 | 1/2021 | Morgan et al. |
| 10,888,347 B2 | 1/2021 | Witt et al. |
| 10,893,863 B2 | 1/2021 | Shelton, IV et al. |
| 10,893,864 B2 | 1/2021 | Harris et al. |
| 10,893,883 B2 | 1/2021 | Dannaher |
| 10,898,186 B2 | 1/2021 | Bakos et al. |
| 10,898,256 B2 | 1/2021 | Yates et al. |
| 10,912,559 B2 | 2/2021 | Harris et al. |
| 10,912,580 B2 | 2/2021 | Green et al. |
| 10,912,603 B2 | 2/2021 | Boudreaux et al. |
| 10,918,385 B2 | 2/2021 | Overmyer et al. |
| 10,925,659 B2 | 2/2021 | Shelton, IV et al. |
| D914,878 S | 3/2021 | Shelton, IV et al. |
| 10,932,766 B2 | 3/2021 | Tesar et al. |
| 10,932,847 B2 | 3/2021 | Yates et al. |
| 10,945,727 B2 | 3/2021 | Shelton, IV et al. |
| 10,952,788 B2 | 3/2021 | Asher et al. |
| 10,959,727 B2 | 3/2021 | Hunter et al. |
| 10,966,741 B2 | 4/2021 | Illizaliturri-Sanchez et al. |
| 10,966,747 B2 | 4/2021 | Worrell et al. |
| 10,973,516 B2 | 4/2021 | Shelton, IV et al. |
| 10,973,517 B2 | 4/2021 | Wixey |
| 10,973,520 B2 | 4/2021 | Shelton, IV et al. |
| 10,980,536 B2 | 4/2021 | Weaner et al. |
| 10,987,123 B2 | 4/2021 | Weir et al. |
| 10,987,156 B2 | 4/2021 | Trees et al. |
| 10,993,715 B2 | 5/2021 | Shelton, IV et al. |
| 10,993,716 B2 | 5/2021 | Shelton, IV et al. |
| 10,993,763 B2 | 5/2021 | Batross et al. |
| 11,000,278 B2 | 5/2021 | Shelton, IV et al. |
| 11,000,279 B2 | 5/2021 | Shelton, IV et al. |
| 11,020,114 B2 | 6/2021 | Shelton, IV et al. |
| 11,020,140 B2 | 6/2021 | Gee et al. |
| 11,033,322 B2 | 6/2021 | Wiener et al. |
| 11,039,834 B2 | 6/2021 | Harris et al. |
| 11,045,191 B2 | 6/2021 | Shelton, IV et al. |
| 11,045,192 B2 | 6/2021 | Harris et al. |
| 11,051,840 B2 | 7/2021 | Shelton, IV et al. |
| 11,051,873 B2 | 7/2021 | Wiener et al. |
| 11,058,424 B2 | 7/2021 | Shelton, IV et al. |
| 11,058,447 B2 | 7/2021 | Houser |
| 11,058,448 B2 | 7/2021 | Shelton, IV et al. |
| 11,058,475 B2 | 7/2021 | Wiener et al. |
| 11,064,997 B2 | 7/2021 | Shelton, IV et al. |
| 11,065,048 B2 | 7/2021 | Messerly et al. |
| 11,083,455 B2 | 8/2021 | Shelton, IV et al. |
| 11,083,458 B2 | 8/2021 | Harris et al. |
| 11,090,048 B2 | 8/2021 | Fanelli et al. |
| 11,090,049 B2 | 8/2021 | Bakos et al. |
| 11,090,104 B2 | 8/2021 | Wiener et al. |
| 11,096,688 B2 | 8/2021 | Shelton, IV et al. |
| 11,096,752 B2 | 8/2021 | Stulen et al. |
| 11,109,866 B2 | 9/2021 | Shelton, IV et al. |
| 11,129,611 B2 | 9/2021 | Shelton, IV et al. |
| 11,129,666 B2 | 9/2021 | Messerly et al. |
| 11,129,669 B2 | 9/2021 | Stulen et al. |
| 11,129,670 B2 | 9/2021 | Shelton, IV et al. |
| 11,134,942 B2 | 10/2021 | Harris et al. |
| 11,134,978 B2 | 10/2021 | Shelton, IV et al. |
| 11,141,154 B2 | 10/2021 | Shelton, IV et al. |
| 11,141,213 B2 | 10/2021 | Yates et al. |
| 11,147,551 B2 | 10/2021 | Shelton, IV |
| 11,147,553 B2 | 10/2021 | Shelton, IV |
| 11,160,551 B2 | 11/2021 | Shelton, IV et al. |
| 11,166,716 B2 | 11/2021 | Shelton, IV et al. |
| 11,172,929 B2 | 11/2021 | Shelton, IV |
| 11,179,155 B2 | 11/2021 | Shelton, IV et al. |
| 11,179,173 B2 | 11/2021 | Price et al. |
| 11,191,539 B2 | 12/2021 | Overmyer et al. |
| 11,191,540 B2 | 12/2021 | Aronhalt et al. |
| 11,197,668 B2 | 12/2021 | Shelton, IV et al. |
| 11,202,670 B2 | 12/2021 | Worrell et al. |
| 11,207,065 B2 | 12/2021 | Harris et al. |
| 11,207,067 B2 | 12/2021 | Shelton, IV et al. |
| 11,213,293 B2 | 1/2022 | Worthington et al. |
| 11,213,294 B2 | 1/2022 | Shelton, IV et al. |
| 11,219,453 B2 | 1/2022 | Shelton, IV et al. |
| 11,224,426 B2 | 1/2022 | Shelton, IV et al. |
| 11,224,497 B2 | 1/2022 | Shelton, IV et al. |
| 11,229,437 B2 | 1/2022 | Shelton, IV et al. |
| 11,229,450 B2 | 1/2022 | Shelton, IV et al. |
| 11,229,471 B2 | 1/2022 | Shelton, IV et al. |
| 11,229,472 B2 | 1/2022 | Shelton, IV et al. |
| 11,234,698 B2 | 2/2022 | Shelton, IV et al. |
| 11,241,235 B2 | 2/2022 | Shelton, IV et al. |
| 11,246,592 B2 | 2/2022 | Shelton, IV et al. |
| 11,246,625 B2 | 2/2022 | Kane et al. |
| 11,246,678 B2 | 2/2022 | Shelton, IV et al. |
| 11,253,256 B2 | 2/2022 | Harris et al. |
| 11,259,803 B2 | 3/2022 | Shelton, IV et al. |
| 11,259,805 B2 | 3/2022 | Shelton, IV et al. |

(56) References Cited

U.S. PATENT DOCUMENTS

| | | | |
|---|---|---|---|
| 11,259,806 B2 | 3/2022 | Shelton, IV et al. |
| 11,259,807 B2 | 3/2022 | Shelton, IV et al. |
| 11,266,405 B2 | 3/2022 | Shelton, IV et al. |
| 11,266,430 B2 | 3/2022 | Clauda et al. |
| 11,272,931 B2 | 3/2022 | Boudreaux et al. |
| 11,278,280 B2 | 3/2022 | Shelton, IV et al. |
| 11,284,890 B2 | 3/2022 | Nalagatla et al. |
| 11,291,440 B2 | 4/2022 | Harris et al. |
| 11,291,444 B2 | 4/2022 | Boudreaux et al. |
| 11,291,445 B2 | 4/2022 | Shelton, IV et al. |
| 11,291,447 B2 | 4/2022 | Shelton, IV et al. |
| 11,291,451 B2 | 4/2022 | Shelton, IV |
| 11,298,127 B2 | 4/2022 | Shelton, IV |
| 11,298,129 B2 | 4/2022 | Bakos et al. |
| 11,298,130 B2 | 4/2022 | Bakos et al. |
| 11,304,695 B2 | 4/2022 | Shelton, IV et al. |
| 11,304,696 B2 | 4/2022 | Shelton, IV et al. |
| 11,304,699 B2 | 4/2022 | Shelton, IV et al. |
| 11,311,306 B2 | 4/2022 | Shelton, IV et al. |
| 11,311,326 B2 | 4/2022 | Boudreaux |
| 11,311,342 B2 | 4/2022 | Parihar et al. |
| D950,728 S | 5/2022 | Bakos et al. |
| D952,144 S | 5/2022 | Boudreaux |
| 11,317,915 B2 | 5/2022 | Boudreaux et al. |
| 11,324,503 B2 | 5/2022 | Shelton, IV et al. |
| 11,324,527 B2 | 5/2022 | Aldridge et al. |
| 11,324,557 B2 | 5/2022 | Shelton, IV et al. |
| 11,331,100 B2 | 5/2022 | Boudreaux et al. |
| 11,331,101 B2 | 5/2022 | Harris et al. |
| 11,337,747 B2 | 5/2022 | Voegele et al. |
| 11,344,362 B2 | 5/2022 | Yates et al. |
| 11,350,938 B2 | 6/2022 | Shelton, IV et al. |
| 11,357,503 B2 | 6/2022 | Bakos et al. |
| 11,361,176 B2 | 6/2022 | Shelton, IV et al. |
| 11,369,377 B2 | 6/2022 | Boudreaux et al. |
| 11,376,098 B2 | 7/2022 | Shelton, IV et al. |
| 11,382,642 B2 | 7/2022 | Robertson et al. |
| 11,389,161 B2 | 7/2022 | Shelton, IV et al. |
| 11,389,164 B2 | 7/2022 | Yates et al. |
| 11,399,837 B2 | 8/2022 | Shelton, IV et al. |
| 11,399,855 B2 | 8/2022 | Boudreaux et al. |
| 11,406,382 B2 | 8/2022 | Shelton, IV et al. |
| 11,413,060 B2 | 8/2022 | Faller et al. |
| 11,419,606 B2 | 8/2022 | Overmyer et al. |
| 11,419,626 B2 | 8/2022 | Timm et al. |
| 11,424,027 B2 | 8/2022 | Shelton, IV |
| 11,426,167 B2 | 8/2022 | Shelton, IV et al. |
| 11,426,191 B2 | 8/2022 | Vakharia et al. |
| 11,446,029 B2 | 9/2022 | Shelton, IV et al. |
| 2001/0025173 A1 | 9/2001 | Ritchie et al. |
| 2001/0025183 A1 | 9/2001 | Shahidi |
| 2001/0025184 A1 | 9/2001 | Messerly |
| 2001/0031950 A1 | 10/2001 | Ryan |
| 2001/0039419 A1 | 11/2001 | Francischelli et al. |
| 2002/0002377 A1 | 1/2002 | Cimino |
| 2002/0002380 A1 | 1/2002 | Bishop |
| 2002/0019649 A1 | 2/2002 | Sikora et al. |
| 2002/0022836 A1 | 2/2002 | Goble et al. |
| 2002/0029036 A1 | 3/2002 | Goble et al. |
| 2002/0029055 A1 | 3/2002 | Bonutti |
| 2002/0032452 A1 | 3/2002 | Tierney et al. |
| 2002/0049551 A1 | 4/2002 | Friedman et al. |
| 2002/0052617 A1 | 5/2002 | Anis et al. |
| 2002/0077550 A1 | 6/2002 | Rabiner et al. |
| 2002/0107517 A1 | 8/2002 | Witt et al. |
| 2002/0156466 A1 | 10/2002 | Sakurai et al. |
| 2002/0156493 A1 | 10/2002 | Houser et al. |
| 2002/0165577 A1 | 11/2002 | Witt et al. |
| 2002/0177862 A1 | 11/2002 | Aranyi et al. |
| 2003/0009164 A1 | 1/2003 | Woloszko et al. |
| 2003/0014053 A1 | 1/2003 | Nguyen et al. |
| 2003/0014087 A1 | 1/2003 | Fang et al. |
| 2003/0036705 A1 | 2/2003 | Hare et al. |
| 2003/0040758 A1 | 2/2003 | Wang et al. |
| 2003/0050572 A1 | 3/2003 | Brautigam et al. |
| 2003/0055443 A1 | 3/2003 | Spotnitz |
| 2003/0073981 A1 | 4/2003 | Whitman et al. |
| 2003/0109778 A1 | 6/2003 | Rashidi |
| 2003/0109875 A1 | 6/2003 | Tetzlaff et al. |
| 2003/0114851 A1 | 6/2003 | Truckai et al. |
| 2003/0130693 A1 | 7/2003 | Levin et al. |
| 2003/0139741 A1 | 7/2003 | Goble et al. |
| 2003/0144680 A1 | 7/2003 | Kellogg et al. |
| 2003/0158548 A1 | 8/2003 | Phan et al. |
| 2003/0171747 A1 | 9/2003 | Kanehira et al. |
| 2003/0181898 A1 | 9/2003 | Bowers |
| 2003/0199794 A1 | 10/2003 | Sakurai et al. |
| 2003/0204199 A1 | 10/2003 | Novak et al. |
| 2003/0208186 A1 | 11/2003 | Moreyra |
| 2003/0212332 A1 | 11/2003 | Fenton et al. |
| 2003/0212363 A1 | 11/2003 | Shipp |
| 2003/0212392 A1 | 11/2003 | Fenton et al. |
| 2003/0212422 A1 | 11/2003 | Fenton et al. |
| 2003/0225332 A1 | 12/2003 | Okada et al. |
| 2003/0229344 A1 | 12/2003 | Dycus et al. |
| 2004/0030254 A1 | 2/2004 | Babaev |
| 2004/0030330 A1 | 2/2004 | Brassell et al. |
| 2004/0047485 A1 | 3/2004 | Sherrit et al. |
| 2004/0054364 A1 | 3/2004 | Aranyi et al. |
| 2004/0064151 A1 | 4/2004 | Mollenauer |
| 2004/0087943 A1 | 5/2004 | Dycus et al. |
| 2004/0092921 A1 | 5/2004 | Kadziauskas et al. |
| 2004/0092992 A1 | 5/2004 | Adams et al. |
| 2004/0097911 A1 | 5/2004 | Murakami et al. |
| 2004/0097912 A1 | 5/2004 | Gonnering |
| 2004/0097919 A1 | 5/2004 | Wellman et al. |
| 2004/0097996 A1 | 5/2004 | Rabiner et al. |
| 2004/0116952 A1 | 6/2004 | Sakurai et al. |
| 2004/0122423 A1 | 6/2004 | Dycus et al. |
| 2004/0132383 A1 | 7/2004 | Langford et al. |
| 2004/0138621 A1 | 7/2004 | Jahns et al. |
| 2004/0142667 A1 | 7/2004 | Lochhead et al. |
| 2004/0147934 A1 | 7/2004 | Kiester |
| 2004/0147945 A1 | 7/2004 | Fritzsch |
| 2004/0158237 A1 | 8/2004 | Abboud et al. |
| 2004/0167508 A1 | 8/2004 | Wham et al. |
| 2004/0176686 A1 | 9/2004 | Hare et al. |
| 2004/0176751 A1 | 9/2004 | Weitzner et al. |
| 2004/0193150 A1 | 9/2004 | Sharkey et al. |
| 2004/0193153 A1 | 9/2004 | Sartor et al. |
| 2004/0199193 A1 | 10/2004 | Hayashi et al. |
| 2004/0215132 A1 | 10/2004 | Yoon |
| 2004/0243147 A1 | 12/2004 | Lipow |
| 2004/0249374 A1 | 12/2004 | Tetzlaff et al. |
| 2004/0260273 A1 | 12/2004 | Wan |
| 2004/0260300 A1 | 12/2004 | Gorensek et al. |
| 2004/0267311 A1 | 12/2004 | Viola et al. |
| 2005/0015125 A1 | 1/2005 | Mioduski et al. |
| 2005/0020967 A1 | 1/2005 | Ono |
| 2005/0021018 A1 | 1/2005 | Anderson et al. |
| 2005/0021065 A1 | 1/2005 | Yamada et al. |
| 2005/0021078 A1 | 1/2005 | Vleugels et al. |
| 2005/0033278 A1 | 2/2005 | McClurken et al. |
| 2005/0033337 A1 | 2/2005 | Muir et al. |
| 2005/0070800 A1 | 3/2005 | Takahashi |
| 2005/0080427 A1 | 4/2005 | Govari et al. |
| 2005/0088285 A1 | 4/2005 | Jei |
| 2005/0090817 A1 | 4/2005 | Phan |
| 2005/0096683 A1 | 5/2005 | Ellins et al. |
| 2005/0099824 A1 | 5/2005 | Dowling et al. |
| 2005/0107777 A1 | 5/2005 | West et al. |
| 2005/0131390 A1 | 6/2005 | Heinrich et al. |
| 2005/0143769 A1 | 6/2005 | White et al. |
| 2005/0149108 A1 | 7/2005 | Cox |
| 2005/0165429 A1 | 7/2005 | Douglas et al. |
| 2005/0171522 A1 | 8/2005 | Christopherson |
| 2005/0177184 A1 | 8/2005 | Easley |
| 2005/0182339 A1 | 8/2005 | Lee et al. |
| 2005/0188743 A1 | 9/2005 | Land |
| 2005/0192610 A1 | 9/2005 | Houser et al. |
| 2005/0192611 A1 | 9/2005 | Houser |
| 2005/0206583 A1 | 9/2005 | Lemelson et al. |
| 2005/0222598 A1 | 10/2005 | Ho et al. |
| 2005/0234484 A1 | 10/2005 | Houser et al. |

(56) References Cited

U.S. PATENT DOCUMENTS

| | | |
|---|---|---|
| 2005/0249667 A1 | 11/2005 | Tuszynski et al. |
| 2005/0256405 A1 | 11/2005 | Makin et al. |
| 2005/0261588 A1 | 11/2005 | Makin et al. |
| 2005/0262175 A1 | 11/2005 | Iino et al. |
| 2005/0267464 A1 | 12/2005 | Truckai et al. |
| 2005/0271807 A1 | 12/2005 | Iijima et al. |
| 2005/0273090 A1 | 12/2005 | Nieman et al. |
| 2005/0288659 A1 | 12/2005 | Kimura et al. |
| 2006/0025757 A1 | 2/2006 | Heim |
| 2006/0030797 A1 | 2/2006 | Zhou et al. |
| 2006/0030848 A1 | 2/2006 | Craig et al. |
| 2006/0058825 A1 | 3/2006 | Ogura et al. |
| 2006/0063130 A1 | 3/2006 | Hayman et al. |
| 2006/0064086 A1 | 3/2006 | Odom |
| 2006/0066181 A1 | 3/2006 | Bromfield et al. |
| 2006/0074442 A1 | 4/2006 | Noriega et al. |
| 2006/0079874 A1 | 4/2006 | Faller et al. |
| 2006/0079879 A1 | 4/2006 | Faller et al. |
| 2006/0095046 A1 | 5/2006 | Trieu et al. |
| 2006/0109061 A1 | 5/2006 | Dobson et al. |
| 2006/0159731 A1 | 7/2006 | Shoshan |
| 2006/0190034 A1 | 8/2006 | Nishizawa et al. |
| 2006/0206100 A1 | 9/2006 | Eskridge et al. |
| 2006/0206115 A1 | 9/2006 | Schomer et al. |
| 2006/0211943 A1 | 9/2006 | Beaupre |
| 2006/0217729 A1 | 9/2006 | Eskridge et al. |
| 2006/0224160 A1 | 10/2006 | Trieu et al. |
| 2006/0247558 A1 | 11/2006 | Yamada |
| 2006/0253050 A1 | 11/2006 | Yoshimine et al. |
| 2006/0259026 A1 | 11/2006 | Godara et al. |
| 2006/0264809 A1 | 11/2006 | Hansmann et al. |
| 2006/0264995 A1 | 11/2006 | Fanton et al. |
| 2006/0265035 A1 | 11/2006 | Yachi et al. |
| 2006/0270916 A1 | 11/2006 | Skwarek et al. |
| 2006/0271030 A1 | 11/2006 | Francis et al. |
| 2006/0293656 A1 | 12/2006 | Shadduck et al. |
| 2007/0016235 A1 | 1/2007 | Tanaka et al. |
| 2007/0016236 A1 | 1/2007 | Beaupre |
| 2007/0021738 A1 | 1/2007 | Hasser et al. |
| 2007/0027468 A1 | 2/2007 | Wales et al. |
| 2007/0032704 A1 | 2/2007 | Gandini et al. |
| 2007/0055228 A1 | 3/2007 | Berg et al. |
| 2007/0056596 A1 | 3/2007 | Fanney et al. |
| 2007/0060935 A1 | 3/2007 | Schwardt et al. |
| 2007/0063618 A1 | 3/2007 | Bromfield |
| 2007/0066971 A1 | 3/2007 | Podhajsky |
| 2007/0067123 A1 | 3/2007 | Jungerman |
| 2007/0073185 A1 | 3/2007 | Nakao |
| 2007/0073341 A1 | 3/2007 | Smith et al. |
| 2007/0074584 A1 | 4/2007 | Talarico et al. |
| 2007/0106317 A1 | 5/2007 | Shelton et al. |
| 2007/0118115 A1 | 5/2007 | Artale et al. |
| 2007/0130771 A1 | 6/2007 | Ehlert et al. |
| 2007/0135803 A1 | 6/2007 | Belson |
| 2007/0149881 A1 | 6/2007 | Rabin |
| 2007/0156163 A1 | 7/2007 | Davison et al. |
| 2007/0166663 A1 | 7/2007 | Telles et al. |
| 2007/0173803 A1 | 7/2007 | Wham et al. |
| 2007/0173813 A1 | 7/2007 | Odom |
| 2007/0173872 A1 | 7/2007 | Neuenfeldt |
| 2007/0175955 A1 | 8/2007 | Shelton et al. |
| 2007/0185474 A1 | 8/2007 | Nahen |
| 2007/0191712 A1 | 8/2007 | Messerly et al. |
| 2007/0191713 A1 | 8/2007 | Eichmann et al. |
| 2007/0203483 A1 | 8/2007 | Kim et al. |
| 2007/0208336 A1 | 9/2007 | Kim et al. |
| 2007/0208340 A1 | 9/2007 | Ganz et al. |
| 2007/0219481 A1 | 9/2007 | Babaev |
| 2007/0232926 A1 | 10/2007 | Stulen et al. |
| 2007/0232928 A1 | 10/2007 | Wiener et al. |
| 2007/0236213 A1 | 10/2007 | Paden et al. |
| 2007/0239101 A1 | 10/2007 | Kellogg |
| 2007/0249941 A1 | 10/2007 | Salehi et al. |
| 2007/0260242 A1 | 11/2007 | Dycus et al. |
| 2007/0265560 A1 | 11/2007 | Soltani et al. |
| 2007/0265613 A1 | 11/2007 | Edelstein et al. |
| 2007/0265616 A1 | 11/2007 | Couture et al. |
| 2007/0265620 A1 | 11/2007 | Kraas et al. |
| 2007/0275348 A1 | 11/2007 | Lemon |
| 2007/0287933 A1 | 12/2007 | Phan et al. |
| 2007/0288055 A1 | 12/2007 | Lee |
| 2007/0299895 A1 | 12/2007 | Johnson et al. |
| 2008/0005213 A1 | 1/2008 | Holtzman |
| 2008/0013809 A1 | 1/2008 | Zhu et al. |
| 2008/0015575 A1 | 1/2008 | Odom et al. |
| 2008/0033465 A1 | 2/2008 | Schmitz et al. |
| 2008/0039746 A1 | 2/2008 | Hissong et al. |
| 2008/0051812 A1 | 2/2008 | Schmitz et al. |
| 2008/0058775 A1 | 3/2008 | Darian et al. |
| 2008/0058845 A1 | 3/2008 | Shimizu et al. |
| 2008/0071269 A1 | 3/2008 | Hilario et al. |
| 2008/0077145 A1 | 3/2008 | Boyden et al. |
| 2008/0082039 A1 | 4/2008 | Babaev |
| 2008/0082098 A1 | 4/2008 | Tanaka et al. |
| 2008/0097501 A1 | 4/2008 | Blier |
| 2008/0114355 A1 | 5/2008 | Whayne et al. |
| 2008/0114364 A1 | 5/2008 | Goldin et al. |
| 2008/0122496 A1 | 5/2008 | Wagner |
| 2008/0125768 A1 | 5/2008 | Tahara et al. |
| 2008/0147058 A1 | 6/2008 | Horrell et al. |
| 2008/0147062 A1 | 6/2008 | Truckai et al. |
| 2008/0147092 A1 | 6/2008 | Rogge et al. |
| 2008/0171938 A1 | 7/2008 | Masuda et al. |
| 2008/0177268 A1 | 7/2008 | Daum et al. |
| 2008/0188755 A1 | 8/2008 | Hart |
| 2008/0200940 A1 | 8/2008 | Eichmann et al. |
| 2008/0208108 A1 | 8/2008 | Kimura |
| 2008/0208231 A1 | 8/2008 | Ota et al. |
| 2008/0214967 A1 | 9/2008 | Aranyi et al. |
| 2008/0234709 A1 | 9/2008 | Houser |
| 2008/0243162 A1 | 10/2008 | Shibata et al. |
| 2008/0255413 A1 | 10/2008 | Zemlok et al. |
| 2008/0275440 A1 | 11/2008 | Kratoska et al. |
| 2008/0281200 A1 | 11/2008 | Voic et al. |
| 2008/0281315 A1 | 11/2008 | Gines |
| 2008/0287944 A1 | 11/2008 | Pearson et al. |
| 2008/0287948 A1 | 11/2008 | Newton et al. |
| 2008/0296346 A1 | 12/2008 | Shelton, IV et al. |
| 2008/0300588 A1 | 12/2008 | Groth et al. |
| 2009/0012516 A1 | 1/2009 | Curtis et al. |
| 2009/0023985 A1 | 1/2009 | Ewers |
| 2009/0043293 A1 | 2/2009 | Pankratov et al. |
| 2009/0048537 A1 | 2/2009 | Lydon et al. |
| 2009/0048589 A1 | 2/2009 | Takashino et al. |
| 2009/0054886 A1 | 2/2009 | Yachi et al. |
| 2009/0054889 A1 | 2/2009 | Newton et al. |
| 2009/0054894 A1 | 2/2009 | Yachi |
| 2009/0065565 A1 | 3/2009 | Cao |
| 2009/0076506 A1 | 3/2009 | Baker |
| 2009/0082716 A1 | 3/2009 | Akahoshi |
| 2009/0082766 A1 | 3/2009 | Unger et al. |
| 2009/0088785 A1 | 4/2009 | Masuda |
| 2009/0090763 A1 | 4/2009 | Zemlok et al. |
| 2009/0101692 A1 | 4/2009 | Whitman et al. |
| 2009/0112206 A1 | 4/2009 | Dumbauld et al. |
| 2009/0118751 A1 | 5/2009 | Wiener et al. |
| 2009/0131885 A1 | 5/2009 | Akahoshi |
| 2009/0143678 A1 | 6/2009 | Keast et al. |
| 2009/0143799 A1 | 6/2009 | Smith et al. |
| 2009/0143800 A1 | 6/2009 | Deville et al. |
| 2009/0157064 A1 | 6/2009 | Hodel |
| 2009/0163807 A1 | 6/2009 | Sliwa |
| 2009/0177119 A1 | 7/2009 | Heidner et al. |
| 2009/0179923 A1 | 7/2009 | Amundson et al. |
| 2009/0182322 A1 | 7/2009 | D'Amelio et al. |
| 2009/0182331 A1 | 7/2009 | D'Amelio et al. |
| 2009/0182332 A1 | 7/2009 | Long et al. |
| 2009/0192441 A1 | 7/2009 | Gelbart et al. |
| 2009/0198272 A1 | 8/2009 | Kerver et al. |
| 2009/0204114 A1 | 8/2009 | Odom |
| 2009/0216157 A1 | 8/2009 | Yamada |
| 2009/0223033 A1 | 9/2009 | Houser |
| 2009/0240244 A1 | 9/2009 | Malis et al. |
| 2009/0248021 A1 | 10/2009 | McKenna |

(56) References Cited

U.S. PATENT DOCUMENTS

| | | |
|---|---|---|
| 2009/0254077 A1 | 10/2009 | Craig |
| 2009/0254080 A1 | 10/2009 | Honda |
| 2009/0259149 A1 | 10/2009 | Tahara et al. |
| 2009/0264909 A1 | 10/2009 | Beaupre |
| 2009/0270771 A1 | 10/2009 | Takahashi |
| 2009/0270812 A1 | 10/2009 | Litscher et al. |
| 2009/0270853 A1 | 10/2009 | Yachi et al. |
| 2009/0270891 A1 | 10/2009 | Beaupre |
| 2009/0270899 A1 | 10/2009 | Carusillo et al. |
| 2009/0287205 A1 | 11/2009 | Ingle |
| 2009/0292283 A1 | 11/2009 | Odom |
| 2009/0299141 A1 | 12/2009 | Downey et al. |
| 2009/0306639 A1 | 12/2009 | Nevo et al. |
| 2009/0327715 A1 | 12/2009 | Smith et al. |
| 2010/0004508 A1 | 1/2010 | Naito et al. |
| 2010/0022825 A1 | 1/2010 | Yoshie |
| 2010/0030233 A1 | 2/2010 | Whitman et al. |
| 2010/0034605 A1 | 2/2010 | Huckins et al. |
| 2010/0036370 A1 | 2/2010 | Mirel et al. |
| 2010/0042093 A9 | 2/2010 | Wham et al. |
| 2010/0049180 A1 | 2/2010 | Wells et al. |
| 2010/0057081 A1 | 3/2010 | Hanna |
| 2010/0057118 A1 | 3/2010 | Dietz et al. |
| 2010/0063437 A1 | 3/2010 | Nelson et al. |
| 2010/0063525 A1 | 3/2010 | Beaupre et al. |
| 2010/0063528 A1 | 3/2010 | Beaupre |
| 2010/0081863 A1 | 4/2010 | Hess et al. |
| 2010/0081864 A1 | 4/2010 | Hess et al. |
| 2010/0081883 A1 | 4/2010 | Murray et al. |
| 2010/0094323 A1 | 4/2010 | Isaacs et al. |
| 2010/0106173 A1 | 4/2010 | Yoshimine |
| 2010/0109480 A1 | 5/2010 | Forslund et al. |
| 2010/0158307 A1 | 6/2010 | Kubota et al. |
| 2010/0168741 A1 | 7/2010 | Sanai et al. |
| 2010/0181966 A1 | 7/2010 | Sakakibara |
| 2010/0187283 A1 | 7/2010 | Crainich et al. |
| 2010/0204721 A1 | 8/2010 | Young et al. |
| 2010/0222714 A1 | 9/2010 | Muir et al. |
| 2010/0222752 A1 | 9/2010 | Collins, Jr. et al. |
| 2010/0228250 A1 | 9/2010 | Brogna |
| 2010/0234906 A1 | 9/2010 | Koh |
| 2010/0274160 A1 | 10/2010 | Yachi et al. |
| 2010/0274278 A1 | 10/2010 | Fleenor et al. |
| 2010/0280368 A1 | 11/2010 | Can et al. |
| 2010/0298743 A1 | 11/2010 | Nield et al. |
| 2010/0331742 A1 | 12/2010 | Masuda |
| 2011/0004233 A1 | 1/2011 | Muir et al. |
| 2011/0015650 A1 | 1/2011 | Choi et al. |
| 2011/0022032 A1 | 1/2011 | Zemlok et al. |
| 2011/0028964 A1 | 2/2011 | Edwards |
| 2011/0071523 A1 | 3/2011 | Dickhans |
| 2011/0082494 A1 | 4/2011 | Kerr et al. |
| 2011/0106141 A1 | 5/2011 | Nakamura |
| 2011/0112400 A1 | 5/2011 | Emery et al. |
| 2011/0125149 A1 | 5/2011 | El-Galley et al. |
| 2011/0125151 A1 | 5/2011 | Strauss et al. |
| 2011/0144640 A1 | 6/2011 | Heinrich et al. |
| 2011/0160725 A1 | 6/2011 | Kabaya et al. |
| 2011/0238010 A1 | 9/2011 | Kirschenman et al. |
| 2011/0238079 A1 | 9/2011 | Hannaford et al. |
| 2011/0273465 A1 | 11/2011 | Konishi et al. |
| 2011/0278343 A1 | 11/2011 | Knodel et al. |
| 2011/0279268 A1 | 11/2011 | Konishi et al. |
| 2011/0284014 A1 | 11/2011 | Cadeddu et al. |
| 2011/0290856 A1 | 12/2011 | Shelton, IV et al. |
| 2011/0295295 A1 | 12/2011 | Shelton, IV et al. |
| 2011/0306967 A1 | 12/2011 | Payne et al. |
| 2011/0313415 A1 | 12/2011 | Fernandez et al. |
| 2012/0004655 A1 | 1/2012 | Kim et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022583 A1 | 1/2012 | Sugalski et al. |
| 2012/0041358 A1 | 2/2012 | Mann et al. |
| 2012/0053597 A1 | 3/2012 | Anvari et al. |
| 2012/0059286 A1 | 3/2012 | Hastings et al. |
| 2012/0059289 A1 | 3/2012 | Nield et al. |
| 2012/0071863 A1 | 3/2012 | Lee et al. |
| 2012/0078244 A1 | 3/2012 | Worrell et al. |
| 2012/0080344 A1 | 4/2012 | Shelton, IV |
| 2012/0101495 A1 | 4/2012 | Young et al. |
| 2012/0109186 A1 | 5/2012 | Parrott et al. |
| 2012/0116222 A1 | 5/2012 | Sawada et al. |
| 2012/0116265 A1 | 5/2012 | Houser et al. |
| 2012/0116266 A1 | 5/2012 | Houser et al. |
| 2012/0116381 A1 | 5/2012 | Houser et al. |
| 2012/0136279 A1 | 5/2012 | Tanaka et al. |
| 2012/0136347 A1 | 5/2012 | Brustad et al. |
| 2012/0136386 A1 | 5/2012 | Kishida et al. |
| 2012/0143211 A1 | 6/2012 | Kishi |
| 2012/0150049 A1 | 6/2012 | Zielinski et al. |
| 2012/0150169 A1 | 6/2012 | Zielinksi et al. |
| 2012/0172904 A1 | 7/2012 | Muir et al. |
| 2012/0191091 A1 | 7/2012 | Allen |
| 2012/0193396 A1 | 8/2012 | Zemlok et al. |
| 2012/0211542 A1 | 8/2012 | Racenet |
| 2012/0234893 A1 | 9/2012 | Schuckmann et al. |
| 2012/0253328 A1 | 10/2012 | Cunningham et al. |
| 2012/0265241 A1 | 10/2012 | Hart et al. |
| 2012/0296325 A1 | 11/2012 | Takashino |
| 2012/0296371 A1 | 11/2012 | Kappus et al. |
| 2013/0023925 A1 | 1/2013 | Mueller |
| 2013/0085510 A1 | 4/2013 | Stefanchik et al. |
| 2013/0123776 A1 | 5/2013 | Monson et al. |
| 2013/0158659 A1 | 6/2013 | Bergs et al. |
| 2013/0158660 A1 | 6/2013 | Bergs et al. |
| 2013/0165929 A1 | 6/2013 | Muir et al. |
| 2013/0214025 A1 | 8/2013 | Zemlok et al. |
| 2013/0253256 A1 | 9/2013 | Griffith et al. |
| 2013/0253480 A1 | 9/2013 | Kimball et al. |
| 2013/0267874 A1 | 10/2013 | Marcotte et al. |
| 2013/0277410 A1 | 10/2013 | Fernandez et al. |
| 2013/0296843 A1 | 11/2013 | Boudreaux et al. |
| 2013/0334989 A1 | 12/2013 | Kataoka |
| 2013/0345701 A1 | 12/2013 | Allen, IV et al. |
| 2014/0001231 A1 | 1/2014 | Shelton, IV et al. |
| 2014/0001234 A1 | 1/2014 | Shelton, IV et al. |
| 2014/0005640 A1 | 1/2014 | Shelton, IV et al. |
| 2014/0005663 A1 | 1/2014 | Heard et al. |
| 2014/0005678 A1 | 1/2014 | Shelton, IV et al. |
| 2014/0005702 A1 | 1/2014 | Timm et al. |
| 2014/0005705 A1 | 1/2014 | Weir et al. |
| 2014/0005718 A1 | 1/2014 | Shelton, IV et al. |
| 2014/0014544 A1 | 1/2014 | Bugnard et al. |
| 2014/0077426 A1 | 3/2014 | Park |
| 2014/0121569 A1 | 5/2014 | Schafer et al. |
| 2014/0135804 A1 | 5/2014 | Weisenburgh, II et al. |
| 2014/0163541 A1 | 6/2014 | Shelton, IV et al. |
| 2014/0163549 A1 | 6/2014 | Yates et al. |
| 2014/0180274 A1 | 6/2014 | Kabaya et al. |
| 2014/0194868 A1 | 7/2014 | Sanai et al. |
| 2014/0194874 A1 | 7/2014 | Dietz et al. |
| 2014/0194875 A1 | 7/2014 | Reschke et al. |
| 2014/0207124 A1 | 7/2014 | Aldridge et al. |
| 2014/0207135 A1 | 7/2014 | Winter |
| 2014/0221994 A1 | 8/2014 | Reschke |
| 2014/0246475 A1 | 9/2014 | Hall et al. |
| 2014/0249557 A1 | 9/2014 | Koch et al. |
| 2014/0263541 A1 | 9/2014 | Leimbach et al. |
| 2014/0263552 A1 | 9/2014 | Hall et al. |
| 2014/0276794 A1 | 9/2014 | Batchelor et al. |
| 2014/0276797 A1 | 9/2014 | Batchelor et al. |
| 2014/0276798 A1 | 9/2014 | Batchelor et al. |
| 2014/0373003 A1 | 12/2014 | Grez et al. |
| 2015/0014392 A1 | 1/2015 | Williams et al. |
| 2015/0032150 A1 | 1/2015 | Ishida et al. |
| 2015/0048140 A1 | 2/2015 | Penna et al. |
| 2015/0066027 A1 | 3/2015 | Garrison et al. |
| 2015/0080876 A1 | 3/2015 | Worrell et al. |
| 2015/0080887 A1 | 3/2015 | Sobajima et al. |
| 2015/0088122 A1 | 3/2015 | Jensen |
| 2015/0112335 A1 | 4/2015 | Boudreaux et al. |
| 2015/0157356 A1 | 6/2015 | Gee |
| 2015/0164533 A1 | 6/2015 | Felder et al. |

(56) References Cited

U.S. PATENT DOCUMENTS

| | | |
|---|---|---|
| 2015/0164534 A1 | 6/2015 | Felder et al. |
| 2015/0164535 A1 | 6/2015 | Felder et al. |
| 2015/0164536 A1 | 6/2015 | Czarnecki et al. |
| 2015/0164537 A1 | 6/2015 | Cagle et al. |
| 2015/0238260 A1 | 8/2015 | Nau, Jr. |
| 2015/0272557 A1 | 10/2015 | Overmyer et al. |
| 2015/0272571 A1 | 10/2015 | Leimbach et al. |
| 2015/0272580 A1 | 10/2015 | Leimbach et al. |
| 2015/0272582 A1 | 10/2015 | Leimbach et al. |
| 2015/0272659 A1 | 10/2015 | Boudreaux et al. |
| 2015/0282879 A1 | 10/2015 | Ruelas |
| 2015/0289364 A1 | 10/2015 | Ilkko et al. |
| 2015/0313667 A1 | 11/2015 | Allen, IV |
| 2015/0317899 A1 | 11/2015 | Dumbauld et al. |
| 2015/0351765 A1 | 12/2015 | Valentine et al. |
| 2015/0374430 A1 | 12/2015 | Weiler et al. |
| 2016/0038228 A1 | 2/2016 | Daniel et al. |
| 2016/0044841 A1 | 2/2016 | Chamberlain |
| 2016/0045248 A1 | 2/2016 | Unger et al. |
| 2016/0051316 A1 | 2/2016 | Boudreaux |
| 2016/0066913 A1 | 3/2016 | Swayze et al. |
| 2016/0175025 A1 | 6/2016 | Strobl |
| 2016/0175029 A1 | 6/2016 | Witt et al. |
| 2016/0206342 A1 | 7/2016 | Robertson et al. |
| 2016/0249910 A1 | 9/2016 | Shelton, IV et al. |
| 2016/0262786 A1 | 9/2016 | Madan et al. |
| 2016/0270842 A1 | 9/2016 | Strobl et al. |
| 2016/0296251 A1 | 10/2016 | Olson et al. |
| 2016/0296252 A1 | 10/2016 | Olson et al. |
| 2016/0296270 A1 | 10/2016 | Strobl et al. |
| 2016/0358849 A1 | 12/2016 | Jur et al. |
| 2017/0065331 A1 | 3/2017 | Mayer et al. |
| 2017/0086909 A1 | 3/2017 | Yates et al. |
| 2017/0119426 A1 | 5/2017 | Akagane |
| 2017/0135751 A1 | 5/2017 | Rothweiler et al. |
| 2017/0164972 A1 | 6/2017 | Johnson et al. |
| 2017/0164997 A1 | 6/2017 | Johnson et al. |
| 2017/0189095 A1 | 7/2017 | Danziger et al. |
| 2017/0202595 A1 | 7/2017 | Shelton, IV |
| 2017/0224332 A1 | 8/2017 | Hunter et al. |
| 2017/0231628 A1 | 8/2017 | Shelton, IV et al. |
| 2017/0281186 A1 | 10/2017 | Shelton, IV et al. |
| 2017/0296177 A1 | 10/2017 | Harris et al. |
| 2017/0296180 A1 | 10/2017 | Harris et al. |
| 2017/0303954 A1 | 10/2017 | Ishii |
| 2017/0312018 A1 | 11/2017 | Trees et al. |
| 2017/0325874 A1 | 11/2017 | Noack et al. |
| 2017/0333073 A1 | 11/2017 | Faller et al. |
| 2017/0348044 A1 | 12/2017 | Wang et al. |
| 2018/0014872 A1 | 1/2018 | Dickerson |
| 2018/0132850 A1 | 5/2018 | Leimbach et al. |
| 2018/0168575 A1 | 6/2018 | Simms et al. |
| 2018/0168577 A1 | 6/2018 | Aronhalt et al. |
| 2018/0168579 A1 | 6/2018 | Aronhalt et al. |
| 2018/0168598 A1 | 6/2018 | Shelton, IV et al. |
| 2018/0168608 A1 | 6/2018 | Shelton, IV et al. |
| 2018/0168609 A1 | 6/2018 | Fanelli et al. |
| 2018/0168610 A1 | 6/2018 | Shelton, IV et al. |
| 2018/0168615 A1 | 6/2018 | Shelton, IV et al. |
| 2018/0168618 A1 | 6/2018 | Scott et al. |
| 2018/0168619 A1 | 6/2018 | Scott et al. |
| 2018/0168623 A1 | 6/2018 | Simms et al. |
| 2018/0168625 A1 | 6/2018 | Posada et al. |
| 2018/0168633 A1 | 6/2018 | Shelton, IV et al. |
| 2018/0168647 A1 | 6/2018 | Shelton, IV et al. |
| 2018/0168648 A1 | 6/2018 | Shelton, IV et al. |
| 2018/0168650 A1 | 6/2018 | Shelton, IV et al. |
| 2018/0188125 A1 | 7/2018 | Park et al. |
| 2018/0221045 A1* | 8/2018 | Zimmerman .......... A61B 1/005 |
| 2018/0289432 A1 | 10/2018 | Kostrzewski et al. |
| 2018/0303493 A1 | 10/2018 | Chapolini |
| 2018/0325517 A1 | 11/2018 | Wingardner et al. |
| 2018/0353245 A1* | 12/2018 | Mccloud ................ A61B 34/25 |
| 2018/0368844 A1 | 12/2018 | Bakos et al. |
| 2019/0000459 A1 | 1/2019 | Shelton, IV et al. |
| 2019/0000461 A1 | 1/2019 | Shelton, IV et al. |
| 2019/0000462 A1 | 1/2019 | Shelton, IV et al. |
| 2019/0000475 A1 | 1/2019 | Shelton, IV et al. |
| 2019/0000476 A1 | 1/2019 | Shelton, IV et al. |
| 2019/0000477 A1 | 1/2019 | Shelton, IV et al. |
| 2019/0038282 A1 | 2/2019 | Shelton, IV et al. |
| 2019/0038283 A1 | 2/2019 | Shelton, IV et al. |
| 2019/0104919 A1 | 4/2019 | Shelton, IV et al. |
| 2019/0125384 A1 | 5/2019 | Scheib et al. |
| 2019/0125390 A1 | 5/2019 | Shelton, IV et al. |
| 2019/0183504 A1 | 6/2019 | Shelton, IV et al. |
| 2019/0200844 A1 | 7/2019 | Shelton, IV et al. |
| 2019/0200977 A1 | 7/2019 | Shelton, IV et al. |
| 2019/0200981 A1 | 7/2019 | Harris et al. |
| 2019/0201030 A1 | 7/2019 | Shelton, IV et al. |
| 2019/0201045 A1 | 7/2019 | Yates et al. |
| 2019/0201046 A1 | 7/2019 | Shelton, IV et al. |
| 2019/0201047 A1 | 7/2019 | Yates et al. |
| 2019/0201048 A1 | 7/2019 | Stulen et al. |
| 2019/0201104 A1 | 7/2019 | Shelton, IV et al. |
| 2019/0201136 A1 | 7/2019 | Shelton, IV et al. |
| 2019/0201137 A1 | 7/2019 | Shelton, IV et al. |
| 2019/0201594 A1 | 7/2019 | Shelton, IV et al. |
| 2019/0206562 A1 | 7/2019 | Shelton, IV et al. |
| 2019/0206564 A1 | 7/2019 | Shelton, IV et al. |
| 2019/0206569 A1 | 7/2019 | Shelton, IV et al. |
| 2019/0209201 A1 | 7/2019 | Boudreaux et al. |
| 2019/0223941 A1 | 7/2019 | Kitamura et al. |
| 2019/0269455 A1 | 9/2019 | Mensch et al. |
| 2019/0290265 A1 | 9/2019 | Shelton, IV et al. |
| 2019/0298350 A1 | 10/2019 | Shelton, IV et al. |
| 2019/0298352 A1 | 10/2019 | Shelton, IV et al. |
| 2019/0298353 A1 | 10/2019 | Shelton, IV et al. |
| 2019/0366562 A1 | 12/2019 | Zhang et al. |
| 2019/0388091 A1 | 12/2019 | Eschbach et al. |
| 2020/0054321 A1 | 2/2020 | Harris et al. |
| 2020/0054382 A1 | 2/2020 | Yates et al. |
| 2020/0078076 A1 | 3/2020 | Henderson et al. |
| 2020/0078085 A1 | 3/2020 | Yates et al. |
| 2020/0078106 A1 | 3/2020 | Henderson et al. |
| 2020/0078609 A1 | 3/2020 | Messerly et al. |
| 2020/0100825 A1 | 4/2020 | Henderson et al. |
| 2020/0100830 A1 | 4/2020 | Henderson et al. |
| 2020/0129261 A1 | 4/2020 | Eschbach |
| 2020/0138473 A1 | 5/2020 | Shelton, IV et al. |
| 2020/0188047 A1 | 6/2020 | Itkowitz et al. |
| 2020/0222111 A1 | 7/2020 | Yates et al. |
| 2020/0222112 A1 | 7/2020 | Hancock et al. |
| 2020/0229834 A1 | 7/2020 | Olson et al. |
| 2020/0237434 A1 | 7/2020 | Scheib et al. |
| 2020/0261078 A1 | 8/2020 | Bakos et al. |
| 2020/0261086 A1 | 8/2020 | Zeiner et al. |
| 2020/0261087 A1 | 8/2020 | Timm et al. |
| 2020/0261141 A1 | 8/2020 | Wiener et al. |
| 2020/0268433 A1 | 8/2020 | Wiener et al. |
| 2020/0305870 A1 | 10/2020 | Shelton, IV |
| 2020/0315623 A1 | 10/2020 | Eisinger et al. |
| 2020/0315712 A1 | 10/2020 | Jasperson et al. |
| 2020/0405296 A1 | 12/2020 | Shelton, IV et al. |
| 2020/0405302 A1 | 12/2020 | Shelton, IV et al. |
| 2020/0405316 A1 | 12/2020 | Shelton, IV et al. |
| 2020/0405409 A1 | 12/2020 | Shelton, IV et al. |
| 2020/0405410 A1 | 12/2020 | Shelton, IV |
| 2020/0405437 A1 | 12/2020 | Shelton, IV et al. |
| 2020/0405439 A1 | 12/2020 | Shelton, IV et al. |
| 2020/0410177 A1 | 12/2020 | Shelton, IV |
| 2021/0052313 A1 | 2/2021 | Shelton, IV et al. |
| 2021/0100578 A1 | 4/2021 | Weir et al. |
| 2021/0100579 A1 | 4/2021 | Shelton, IV et al. |
| 2021/0177481 A1 | 6/2021 | Shelton, IV et al. |
| 2021/0177494 A1 | 6/2021 | Houser et al. |
| 2021/0177496 A1 | 6/2021 | Shelton, IV et al. |
| 2021/0186492 A1 | 6/2021 | Shelton, IV et al. |
| 2021/0186493 A1 | 6/2021 | Shelton, IV et al. |
| 2021/0186494 A1 | 6/2021 | Shelton, IV et al. |
| 2021/0186495 A1 | 6/2021 | Shelton, IV et al. |
| 2021/0186497 A1 | 6/2021 | Shelton, IV et al. |
| 2021/0186498 A1 | 6/2021 | Boudreaux et al. |
| 2021/0186499 A1 | 6/2021 | Shelton, IV et al. |

(56) References Cited

U.S. PATENT DOCUMENTS

| | | | |
|---|---|---|---|
| 2021/0186500 A1 | 6/2021 | Shelton, IV et al. |
| 2021/0186501 A1 | 6/2021 | Shelton, IV et al. |
| 2021/0186502 A1 | 6/2021 | Shelton, IV et al. |
| 2021/0186504 A1 | 6/2021 | Shelton, IV et al. |
| 2021/0186507 A1 | 6/2021 | Shelton, IV et al. |
| 2021/0186553 A1 | 6/2021 | Green et al. |
| 2021/0186554 A1 | 6/2021 | Green et al. |
| 2021/0196263 A1 | 7/2021 | Shelton, IV et al. |
| 2021/0196265 A1 | 7/2021 | Shelton, IV et al. |
| 2021/0196266 A1 | 7/2021 | Shelton, IV et al. |
| 2021/0196267 A1 | 7/2021 | Shelton, IV et al. |
| 2021/0196268 A1 | 7/2021 | Shelton, IV et al. |
| 2021/0196269 A1 | 7/2021 | Shelton, IV et al. |
| 2021/0196270 A1 | 7/2021 | Shelton, IV et al. |
| 2021/0196271 A1 | 7/2021 | Shelton, IV et al. |
| 2021/0196301 A1 | 7/2021 | Shelton, IV et al. |
| 2021/0196302 A1 | 7/2021 | Shelton, IV et al. |
| 2021/0196305 A1 | 7/2021 | Strobl |
| 2021/0196306 A1 | 7/2021 | Estera et al. |
| 2021/0196307 A1 | 7/2021 | Shelton, IV |
| 2021/0196334 A1 | 7/2021 | Sarley et al. |
| 2021/0196335 A1 | 7/2021 | Messerly et al. |
| 2021/0196336 A1 | 7/2021 | Faller et al. |
| 2021/0196343 A1 | 7/2021 | Shelton, IV et al. |
| 2021/0196344 A1 | 7/2021 | Shelton, IV et al. |
| 2021/0196345 A1 | 7/2021 | Messerly et al. |
| 2021/0196346 A1 | 7/2021 | Leuck et al. |
| 2021/0196349 A1 | 7/2021 | Fiebig et al. |
| 2021/0196350 A1 | 7/2021 | Fiebig et al. |
| 2021/0196351 A1 | 7/2021 | Sarley et al. |
| 2021/0196352 A1 | 7/2021 | Messerly et al. |
| 2021/0196353 A1 | 7/2021 | Gee et al. |
| 2021/0196354 A1 | 7/2021 | Shelton, IV et al. |
| 2021/0196355 A1 | 7/2021 | Shelton, IV et al. |
| 2021/0196356 A1 | 7/2021 | Shelton, IV et al. |
| 2021/0196357 A1 | 7/2021 | Shelton, IV et al. |
| 2021/0196358 A1 | 7/2021 | Shelton, IV et al. |
| 2021/0196359 A1 | 7/2021 | Shelton, IV et al. |
| 2021/0196361 A1 | 7/2021 | Shelton, IV et al. |
| 2021/0196362 A1 | 7/2021 | Shelton, IV et al. |
| 2021/0196363 A1 | 7/2021 | Shelton, IV et al. |
| 2021/0196364 A1 | 7/2021 | Shelton, IV et al. |
| 2021/0196365 A1 | 7/2021 | Shelton, IV et al. |
| 2021/0196366 A1 | 7/2021 | Shelton, IV et al. |
| 2021/0196367 A1 | 7/2021 | Salguero et al. |
| 2021/0212744 A1 | 7/2021 | Shelton, IV et al. |
| 2021/0220036 A1 | 7/2021 | Shelton, IV et al. |
| 2021/0236195 A1 | 8/2021 | Asher et al. |
| 2021/0282804 A1 | 9/2021 | Worrell et al. |
| 2021/0393288 A1 | 12/2021 | Shelton, IV et al. |
| 2021/0393314 A1 | 12/2021 | Wiener et al. |
| 2021/0393319 A1 | 12/2021 | Shelton, IV et al. |
| 2022/0039891 A1 | 2/2022 | Stulen et al. |
| 2022/0071655 A1 | 3/2022 | Price et al. |
| 2022/0168005 A1 | 6/2022 | Aldridge et al. |
| 2022/0168039 A1 | 6/2022 | Worrell et al. |
| 2022/0226014 A1 | 7/2022 | Clauda, IV et al. |

FOREIGN PATENT DOCUMENTS

| | | | |
|---|---|---|---|
| CN | 1634601 A | 7/2005 |
| CN | 1775323 A | 5/2006 |
| CN | 1922563 A | 2/2007 |
| CN | 2868227 Y | 2/2007 |
| CN | 201029899 Y | 3/2008 |
| CN | 101474081 A | 7/2009 |
| CN | 101516285 A | 8/2009 |
| CN | 101522112 A | 9/2009 |
| CN | 102100582 A | 6/2011 |
| CN | 102149312 A | 8/2011 |
| CN | 202027624 U | 11/2011 |
| CN | 102792181 A | 11/2012 |
| CN | 103281982 A | 9/2013 |
| CN | 103379853 A | 10/2013 |
| CN | 203468630 U | 3/2014 |
| CN | 104001276 A | 8/2014 |
| CN | 104013444 A | 9/2014 |
| CN | 104434298 A | 3/2015 |
| CN | 107374752 A | 11/2017 |
| DE | 3904558 A1 | 8/1990 |
| DE | 9210327 U1 | 11/1992 |
| DE | 4300307 A1 | 7/1994 |
| DE | 29623113 U1 | 10/1997 |
| DE | 20004812 U1 | 9/2000 |
| DE | 20021619 U1 | 3/2001 |
| DE | 10042606 A1 | 8/2001 |
| DE | 10201569 A1 | 7/2003 |
| DE | 102012109037 A1 | 4/2014 |
| EP | 0171967 A2 | 2/1986 |
| EP | 0336742 A2 | 10/1989 |
| EP | 0136855 B1 | 11/1989 |
| EP | 0705571 A1 | 4/1996 |
| EP | 1698289 A2 | 9/2006 |
| EP | 1862133 A1 | 12/2007 |
| EP | 1972264 A1 | 9/2008 |
| EP | 2060238 A1 | 5/2009 |
| EP | 1747761 B1 | 10/2009 |
| EP | 2131760 A1 | 12/2009 |
| EP | 1214913 B1 | 7/2010 |
| EP | 1946708 B1 | 6/2011 |
| EP | 1767164 B1 | 1/2013 |
| EP | 2578172 A2 | 4/2013 |
| EP | 2668922 A1 | 12/2013 |
| EP | 2076195 B1 | 12/2015 |
| EP | 2510891 B1 | 6/2016 |
| EP | 3476302 A2 | 5/2019 |
| EP | 3476331 A1 | 5/2019 |
| EP | 3694298 A1 | 8/2020 |
| GB | 2032221 A | 4/1980 |
| GB | 2317566 A | 4/1998 |
| JP | S50100891 A | 8/1975 |
| JP | S5968513 U | 5/1984 |
| JP | S59141938 A | 8/1984 |
| JP | S62221343 A | 9/1987 |
| JP | S62227343 A | 10/1987 |
| JP | S62292153 A | 12/1987 |
| JP | S62292154 A | 12/1987 |
| JP | S63109386 A | 5/1988 |
| JP | S63315049 A | 12/1988 |
| JP | H01151452 A | 6/1989 |
| JP | H01198540 A | 8/1989 |
| JP | H0271510 U | 5/1990 |
| JP | H02286149 A | 11/1990 |
| JP | H02292193 A | 12/1990 |
| JP | H0337061 A | 2/1991 |
| JP | H0425707 U | 2/1992 |
| JP | H0464351 A | 2/1992 |
| JP | H0430508 U | 3/1992 |
| JP | H04152942 A | 5/1992 |
| JP | H 0541716 A | 2/1993 |
| JP | H0595955 A | 4/1993 |
| JP | H05115490 A | 5/1993 |
| JP | H0670938 A | 3/1994 |
| JP | H06104503 A | 4/1994 |
| JP | H0824266 A | 1/1996 |
| JP | H08229050 A | 9/1996 |
| JP | H08275951 A | 10/1996 |
| JP | H08299351 A | 11/1996 |
| JP | H08336545 A | 12/1996 |
| JP | H09130655 A | 5/1997 |
| JP | H09135553 A | 5/1997 |
| JP | H09140722 A | 6/1997 |
| JP | H105237 A | 1/1998 |
| JP | 10127654 A | 5/1998 |
| JP | H10295700 A | 11/1998 |
| JP | H11128238 A | 5/1999 |
| JP | H11169381 A | 6/1999 |
| JP | 2000210299 A | 8/2000 |
| JP | 2000271142 A | 10/2000 |
| JP | 2000271145 A | 10/2000 |
| JP | 2000287987 A | 10/2000 |
| JP | 2001029353 A | 2/2001 |
| JP | 2002059380 A | 2/2002 |
| JP | 2002186901 A | 7/2002 |

(56) References Cited

FOREIGN PATENT DOCUMENTS

| | | |
|---|---|---|
| JP | 2002263579 A | 9/2002 |
| JP | 2002330977 A | 11/2002 |
| JP | 2003000612 A | 1/2003 |
| JP | 2003010201 A | 1/2003 |
| JP | 2003116870 A | 4/2003 |
| JP | 2003126104 A | 5/2003 |
| JP | 2003126110 A | 5/2003 |
| JP | 2003153919 A | 5/2003 |
| JP | 2003339730 A | 12/2003 |
| JP | 2004129871 A | 4/2004 |
| JP | 2004147701 A | 5/2004 |
| JP | 2005003496 A | 1/2005 |
| JP | 2005027026 A | 1/2005 |
| JP | 2005074088 A | 3/2005 |
| JP | 2005337119 A | 12/2005 |
| JP | 2006068396 A | 3/2006 |
| JP | 2006081664 A | 3/2006 |
| JP | 2006114072 A | 4/2006 |
| JP | 2006217716 A | 8/2006 |
| JP | 2006288431 A | 10/2006 |
| JP | 2007037568 A | 2/2007 |
| JP | 200801876 A | 1/2008 |
| JP | 200833644 A | 2/2008 |
| JP | 2008188160 A | 8/2008 |
| JP | D1339835 S | 8/2008 |
| JP | 2010009686 A | 1/2010 |
| JP | 2010121865 A | 6/2010 |
| JP | 2012071186 A | 4/2012 |
| JP | 2012235658 A | 11/2012 |
| KR | 100789356 B1 | 12/2007 |
| RU | 2154437 C1 | 8/2000 |
| RU | 22035 U1 | 3/2002 |
| RU | 2201169 C2 | 3/2003 |
| RU | 2405603 C1 | 12/2010 |
| RU | 2013119977 A | 11/2014 |
| SU | 850068 A1 | 7/1981 |
| WO | WO-8103272 A1 | 11/1981 |
| WO | WO-9308757 A1 | 5/1993 |
| WO | WO-9314708 A1 | 8/1993 |
| WO | WO-9421183 A1 | 9/1994 |
| WO | WO-9424949 A1 | 11/1994 |
| WO | WO-9639086 A1 | 12/1996 |
| WO | WO-9800069 A1 | 1/1998 |
| WO | WO-9840015 A2 | 9/1998 |
| WO | WO-9920213 A1 | 4/1999 |
| WO | WO-9923960 A1 | 5/1999 |
| WO | WO-0024330 A1 | 5/2000 |
| WO | WO-0064358 A2 | 11/2000 |
| WO | WO-0128444 A1 | 4/2001 |
| WO | WO-0167970 A1 | 9/2001 |
| WO | WO-0172251 A1 | 10/2001 |
| WO | WO-0195810 A2 | 12/2001 |
| WO | WO-03095028 A1 | 11/2003 |
| WO | WO-2004037095 A2 | 5/2004 |
| WO | WO-2004078051 A2 | 9/2004 |
| WO | WO-2004098426 A1 | 11/2004 |
| WO | WO-2006091494 A1 | 8/2006 |
| WO | WO-2007008710 A2 | 1/2007 |
| WO | WO-2008118709 A1 | 10/2008 |
| WO | WO-2008130793 A1 | 10/2008 |
| WO | WO-2010027109 A1 | 3/2010 |
| WO | WO-2010104755 A1 | 9/2010 |
| WO | WO-2011008672 A2 | 1/2011 |
| WO | WO-2011044343 A2 | 4/2011 |
| WO | WO-2011052939 A2 | 5/2011 |
| WO | WO-2011060031 A1 | 5/2011 |
| WO | WO-2012044606 A2 | 4/2012 |
| WO | WO-2012088535 A1 | 6/2012 |
| WO | WO-2012150567 A1 | 11/2012 |
| WO | WO-2016130844 A1 | 8/2016 |
| WO | WO-2019130090 A1 | 7/2019 |
| WO | WO-2019130113 A1 | 7/2019 |

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).

AST Products, Inc., "Principles of Video Contact Angle Analysis," 20 pages, (2006).

Campbell et al., "Thermal Imaging in Surgery," p. 19-3, in Medical Infrared Imaging, N. A. Diakides and J. D. Bronzino, Eds. (2008).

Chen et al., "Heat-Induced Changes in the Mechanics of a Collagenous Tissue: Isothermal Free Shrinkage," Transactions of the ASME, vol. 119, pp. 372-378 (Nov. 1997).

Chen et al., "Heat-Induced Changes in the Mechanics of a Collagenous Tissue: Isothermal, Isotonic Shrinkage," Transactions of the ASME, vol. 120, pp. 382-388 (Jun. 1998).

Chen et al., "Heat-induced changes in the mechanics of a collagenous tissue: pseudoelastic behavior at 37° C.," Journal of Biomechanics, 31, pp. 211-216 (1998).

Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).

Covidien 501 (k) Summary Sonicision, dated Feb. 24, 2011 (7 pages).

Covidien Brochure, [Value Analysis Brief], LigaSure Advance™ Pistol Grip, dated Rev. Apr. 2010 (7 pages).

Covidien Brochure, LigaSure Atlas™ Hand Switching Instruments, dated Dec. 2008 (2 pages).

Covidien Brochure, LigaSure Impact™ Instrument LF4318, dated Feb. 2013 (3 pages).

Covidien Brochure, The LigaSure Precise™ Instrument, dated Mar. 2011 (2 pages).

Covidien Brochure, The LigaSure™ 5 mm Blunt Tip Sealer/Divider Family, dated Apr. 2013 (2 pages).

Dean, D.A., "Electrical Impedance Spectroscopy Study of Biological Tissues," J. Electrostat, 66(3-4), Mar. 2008, pp. 165-177. Accessed Apr. 10, 2018: https://www.ncbi.nlm.nih.gov/pmc/articles/PMC2597841/.

Douglas, S.C. "Introduction to Adaptive Filter". Digital Signal Processing Handbook. Ed. Vijay K. Madisetti and Douglas B. Williams. Boca Raton: CRC Press LLC, 1999.

Erbe Electrosurgery VIO® 200 S, (2012), p. 7, 12 pages, accessed Mar. 31, 2014 at http://www.erbe-med. com/erbe/media/Marketing materialien/85140170 ERBE EN VIO 200 S D027541.

F. A. Duck, "Optical Properties of Tissue Including Ultraviolet and Infrared Radiation," pp. 43-71 in Physical Properties of Tissue (1990).

Fowler, K.R., "A Programmable, Arbitrary Waveform Electrosurgical Device," IEEE Engineering in Medicine and Biology Society 10th Annual International Conference, pp. 1324, 1325 (1988).

Gerhard, Glen C., "Surgical Electrotechnology: Quo Vadis?," IEEE Transactions on Biomedical Engineering, vol. BME-31, No. 12, pp. 787-792, Dec. 1984.

Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).

Glaser and Subak-Sharpe,Integrated Circuit Engineering, Addison-Wesley Publishing, Reading, MA (1979).

Gooch et al., "Recommended Infection-Control Practices for Dentistry, 1993," Published: May 28, 1993; [retrieved on Aug. 23, 2008], Retrieved from the internet: URL: http//wonder.cdc.gov/wonder/prevguid/p0000191/p0000191.asp (15 pages).

Graff, K.F., "Elastic Wave Propagation in a Curved Sonic Transmission Line," IEEE Transactions on Sonics and Ultrasonics, SU-17(1), 1-6 (1970).

Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).

(56) References Cited

OTHER PUBLICATIONS

Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Henriques. F.C., "Studies in thermal injury V. The predictability and the significance of thermally induced rate processes leading to irreversible epidermal injury." Archives of Pathology, 434, pp. 489-502 (1947).
http://www.4-traders.com/JOHNSON-JOHNSON-4832/news/Johnson-Johnson-Ethicon-E . . . .
http://www.apicalinstr.com/generators.htm.
http://www.dotmed.eom/listing/electrosurical-unit/ethicon/ultracision-g110-/1466724.
http://www.medicalexpo.com/medical-manufacturer/electrosurgical-generator-6951.html.
http://www.megadyne.com/es_generator.php.
http://www.valleylab.com/product/es/generators/index.html.
http:/www.ethicon.com/GB-en/healthcare-professionals/products/energy-devices/capital/l/ge . . . .
https://www.kjmagnetics.com/fieldcalculator.asp, retrieved Jul. 11, 2016, backdated to Nov. 11, 2011 via https://web.archive.org/web/20111116164447/http://www.kjmagnetics.com/fieldcalculator.asp.
Humphrey, J.D., "Continuum Thermomechanics and the Clinical Treatment of Disease and Injury," Appl. Mech. Rev., vol. 56, No. 2 pp. 231-260 (Mar. 2003).
Huston et al., "Magnetic and Magnetostrictive Properties of Cube Textured Nickel for Magnetostrictive Transducer Applications," IEEE Transactions on Magnetics, vol. 9(4), pp. 636-640 (Dec. 1973).
Hörmann et al., "Reversible and irreversible denaturation of collagen fibers." Biochemistry, 10, pp. 932-937 (1971).
IEEE Std 802.3-2012 (Revision of IEEE Std 802.3-2008, published Dec. 28, 2012.
Incropera et al., Fundamentals of Heat and Mass Transfer, Wiley, New York (1990).
Jang, J. et al. "Neuro-fuzzy and Soft Computing." Prentice Hall, 1997, pp. 13-89, 199-293, 335-393, 453-496, 535-549.
Kurt Gieck & Reiner Gieck, *Engineering Formulas* § Z.7 (7th ed. 1997).
LaCourse, J.R.; Vogt, M.C.; Miller, W.T., III; Selikowitz, S.M., "Spectral Analysis Interpretation of Electrosurgical Generator Nerve and Muscle Stimulation," IEEE Transactions on Biomedical Engineering, vol. 35, No. 7, pp. 505-509, Jul. 1988.
Lee et al., "A multi-sample denaturation temperature tester for collagenous biomaterials," Med. Eng. Phy., vol. 17, No. 2, pp. 115-121 (Mar. 1995).
Leonard I. Malis, M.D., "The Value of Irrigation During Bipolar Coagulation," 1989.
Lim et al., "A Review of Mechanism Used in Laparoscopic Surgical Instruments," Mechanism and Machine Theory, vol. 38, pp. 1133-1147, (2003).
Makarov, S. N., Ochmann, M., Desinger, K., "The longitudinal vibration response of a curved fiber used for laser ultrasound surgical therapy," Journal of the Acoustical Society of America 102, 1191-1199 (1997).
Missinne, et al. "Stretchable Optical Waveguides," vol. 22, No. 4, Feb. 18, 2014, pp. 4168-4179 (12 pages).
Moraleda et al., A Temperature Sensor Based on a Polymer Optical Fiber Macro-Bend, Sensors 2013, 13, 13076-13089, doi: 10.3390/S131013076, ISSN 1424-8220.
Moran et al., "Thermally Induced Shrinkage of Joint Capsule," Clinical Orthopaedics and Related Research, No. 281, pp. 248-255 (Dec. 2000).
Morley, L. S. D., "Elastic Waves in a Naturally Curved Rod," Quarterly Journal of Mechanics and Applied Mathematics, 14: 155-172 (1961).
National Semiconductors Temperature Sensor Handbook—http://www.national.com/appinfo/tempsensors/files/temphb.pdf; accessed online: Apr. 1, 2011.
Orr et al., "Overview of Bioheat Transfer," pp. 367-384 in Optical-Thermal Response of Laser-Irradiated Tissue, A. J. Welch and M. J. C. van Gemert, eds., Plenum, New York (1995).
Sherrit et al., "Novel Horn Designs for Ultrasonic/Sonic Cleaning Welding, Soldering, Cutting and Drilling," Proc. SPIE Smart Structures Conference, vol. 4701, Paper No. 34, San Diego, CA, pp. 353-360, Mar. 2002.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Technology Overview, printed from www.harmonicscalpel.com, Internet site, website accessed on Jun. 13, 2007, (3 pages).
Wall et al., "Thermal modification of collagen," J Shoulder Elbow Surg, No. 8, pp. 339-344 (Jul./Aug. 1999).
Walsh, S. J., White, R. G., "Vibrational Power Transmission in Curved Beams," Journal of Sound and Vibration, 233(3), 455-488 (2000).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wells et al., "Altered Mechanical Behavior of Epicardium Under Isothermal Biaxial Loading," Transactions of the ASME, Journal of Biomedical Engineering, vol. 126, pp. 492-497 (Aug. 2004).
Wright, et al., "Time-Temperature Equivalence of Heat-Induced Changes in Cells and Proteins," Feb. 1998. ASME Journal of Biomechanical Engineering, vol. 120, pp. 22-26.

\* cited by examiner

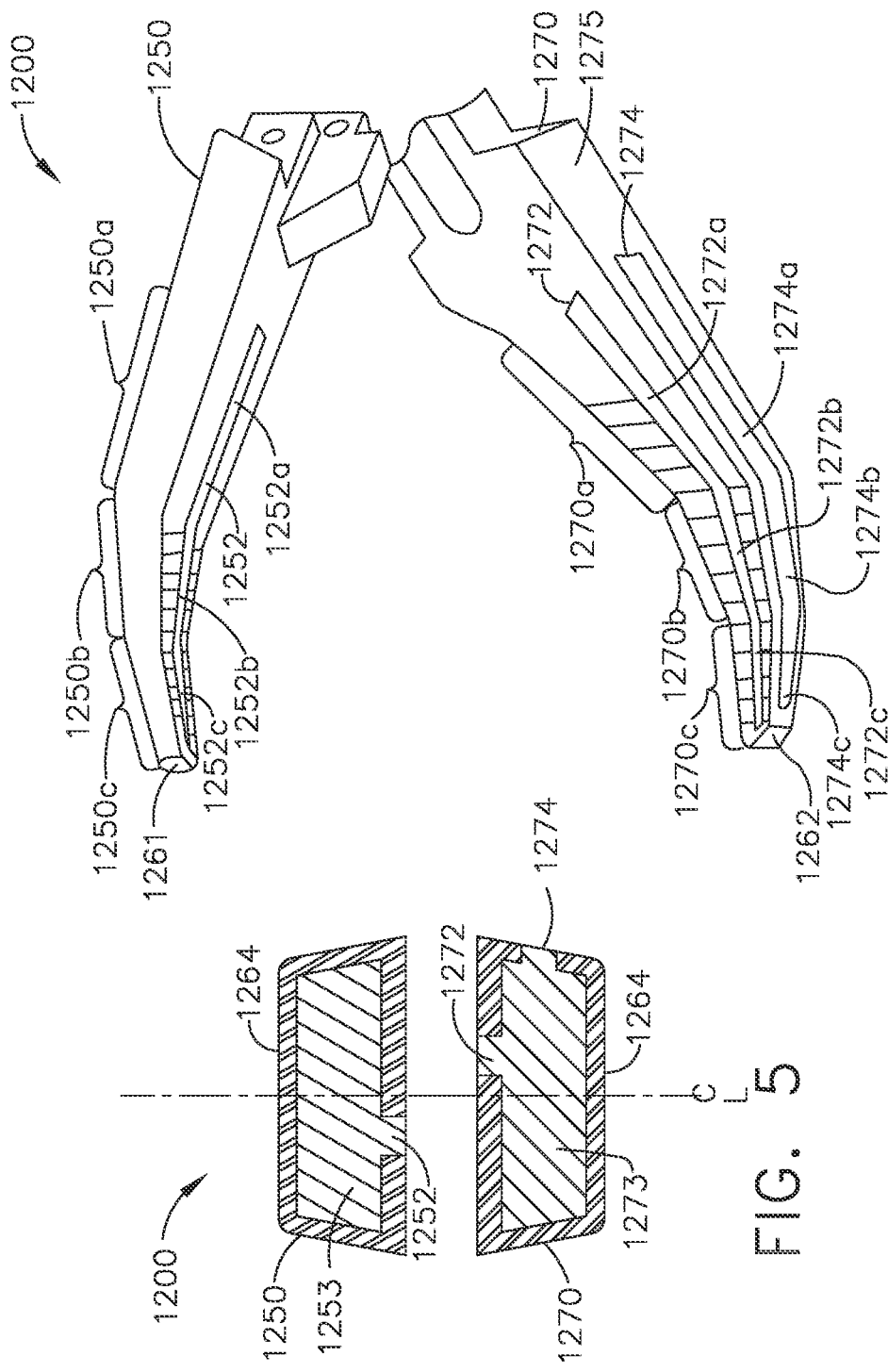

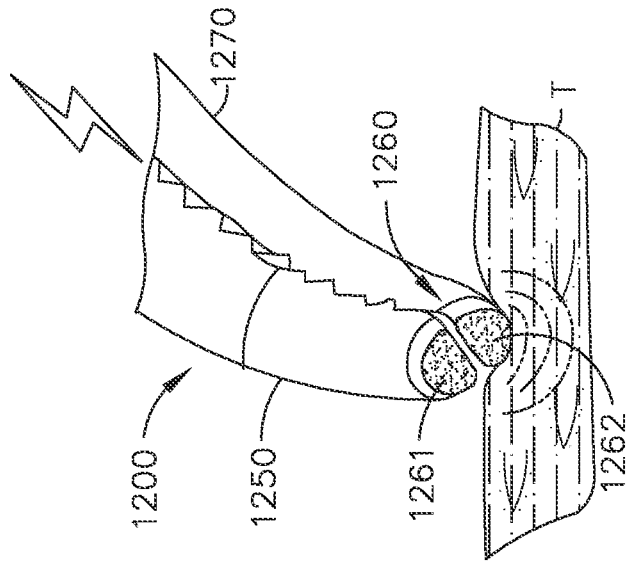
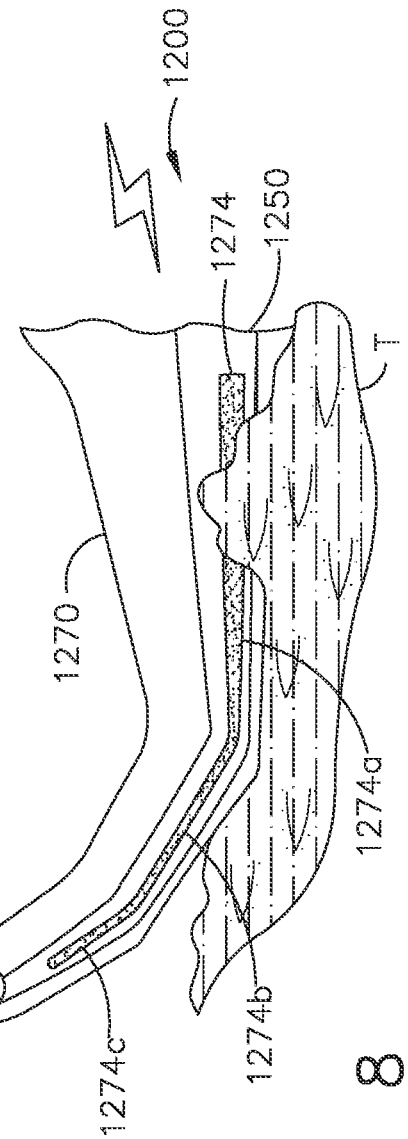
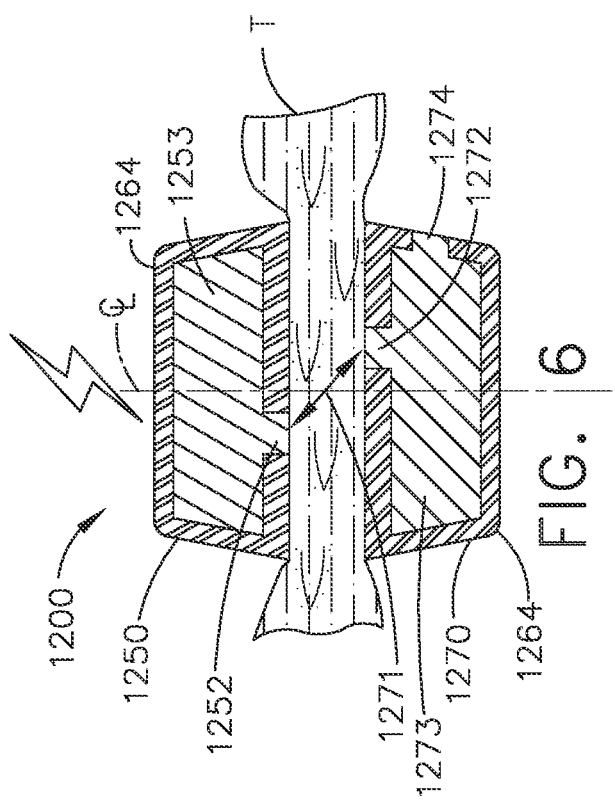

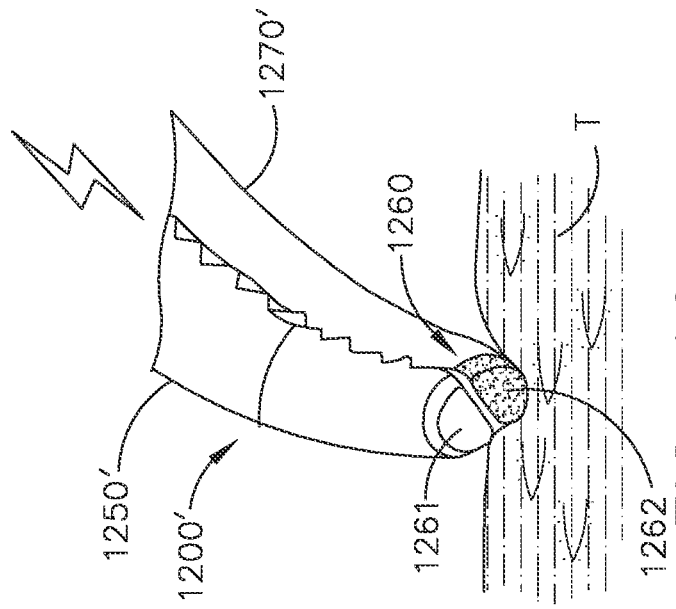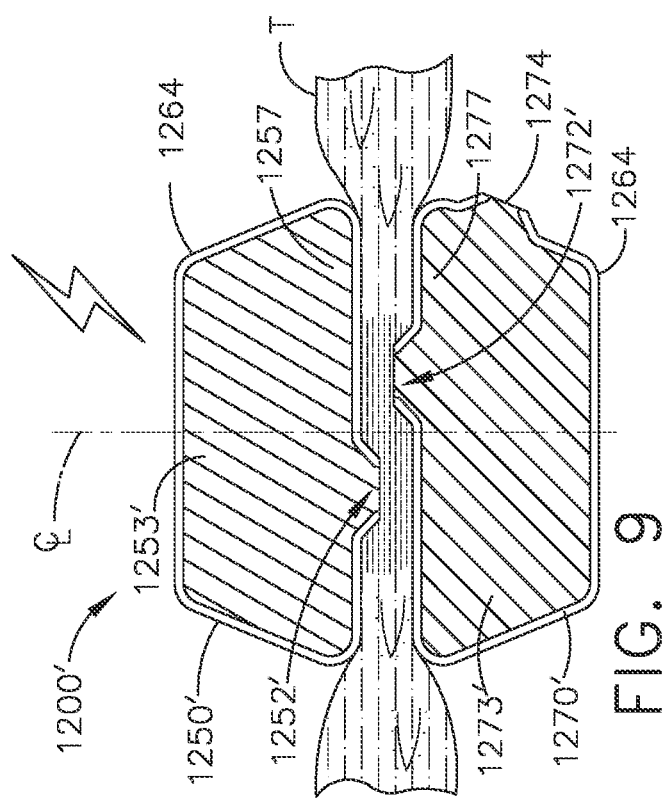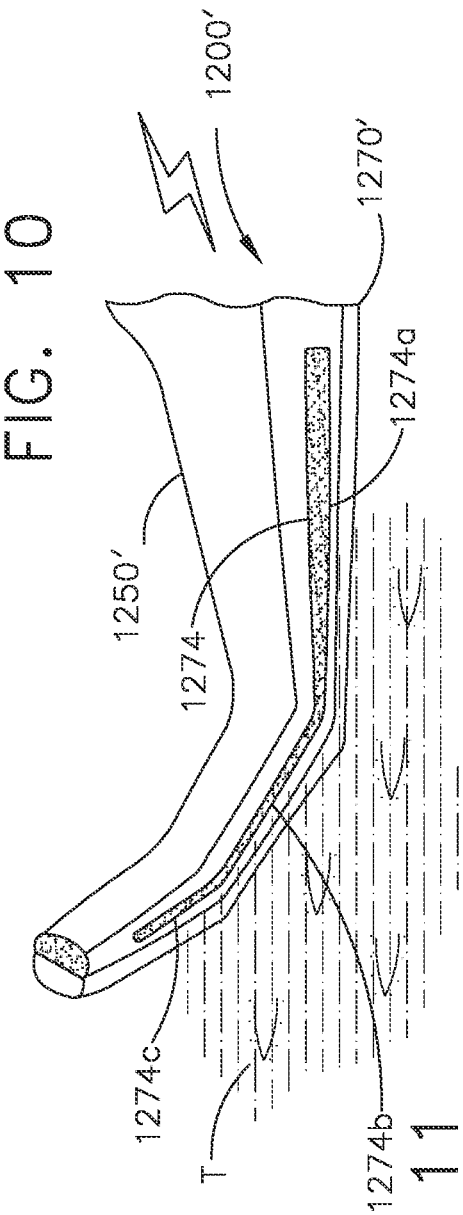

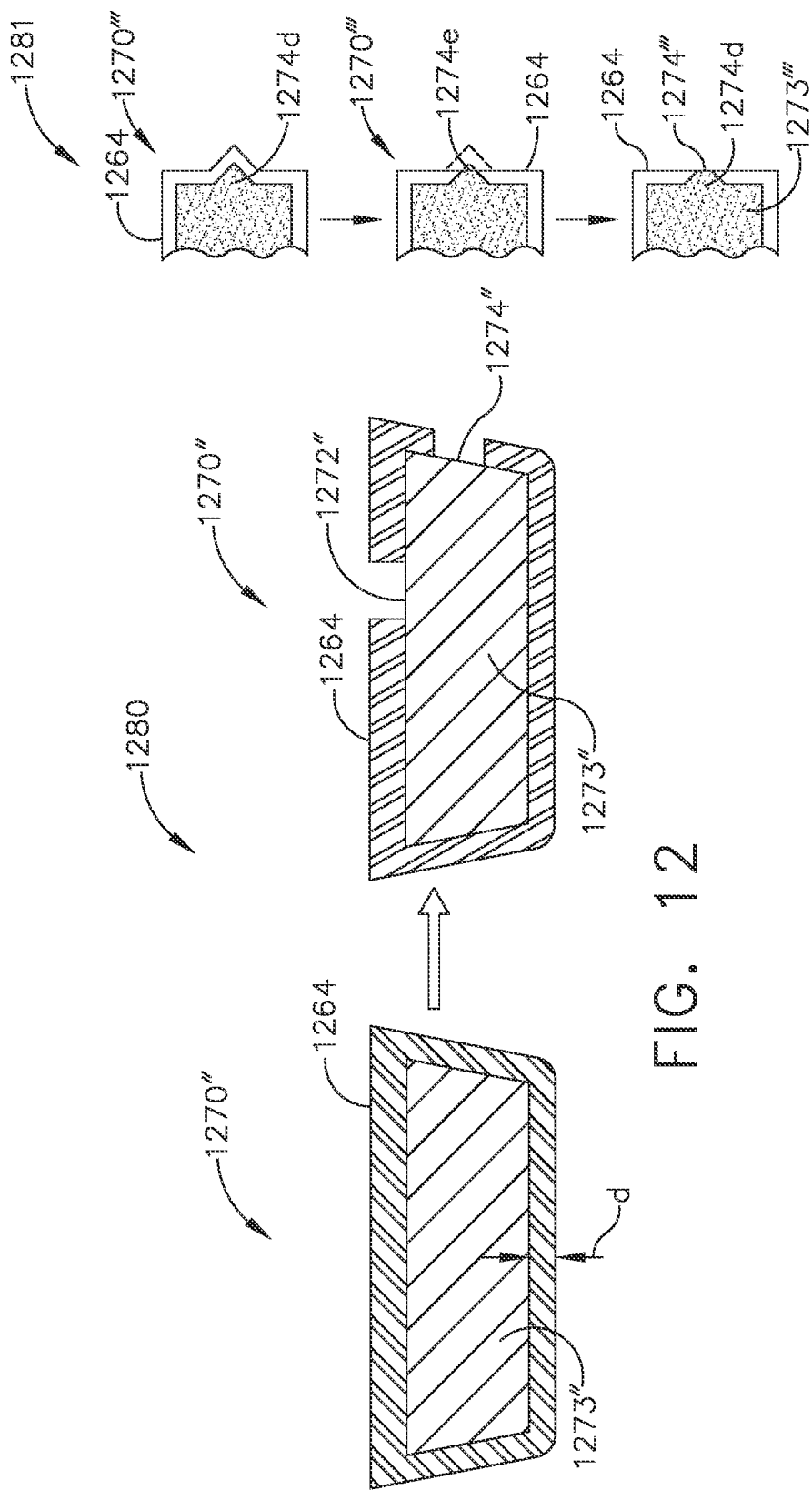

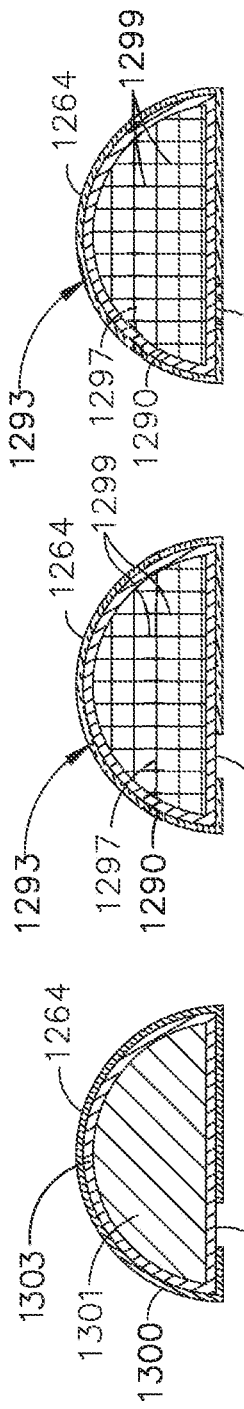
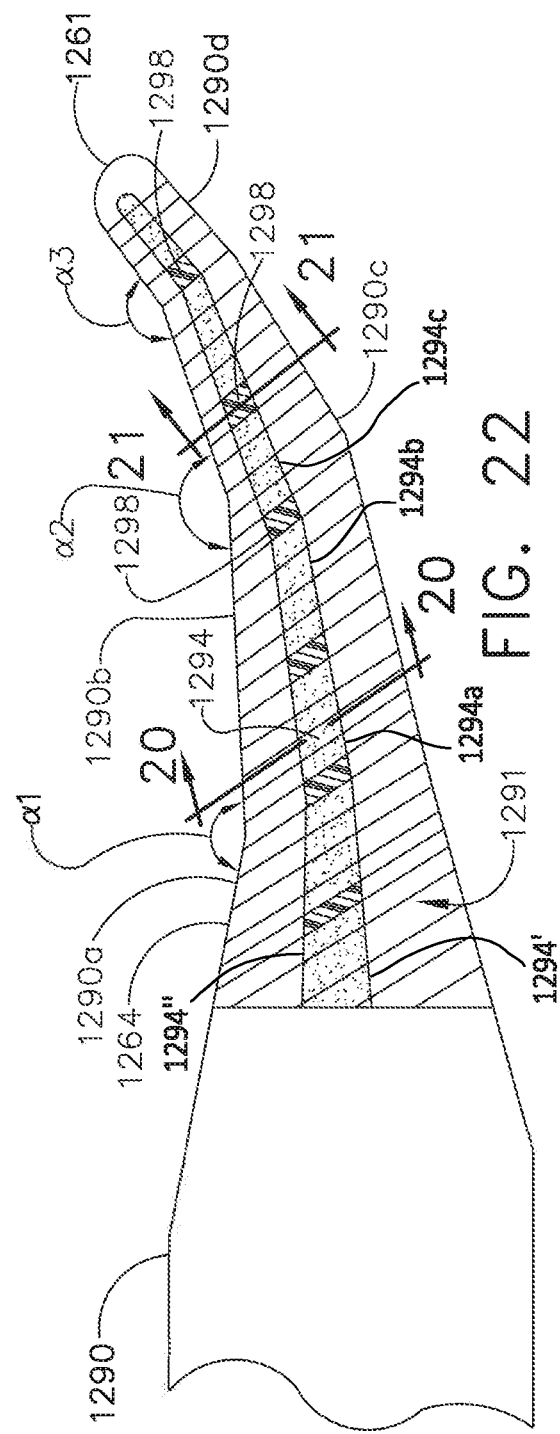

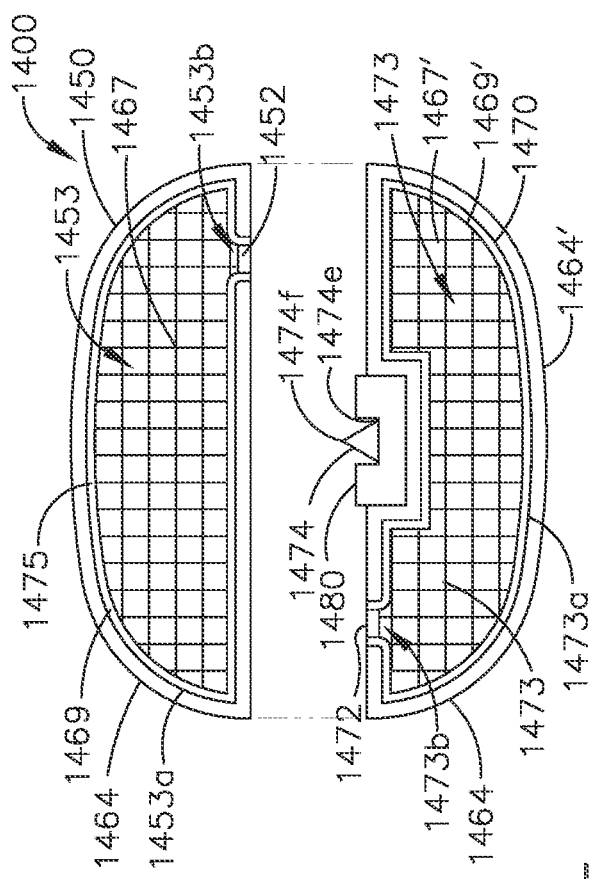
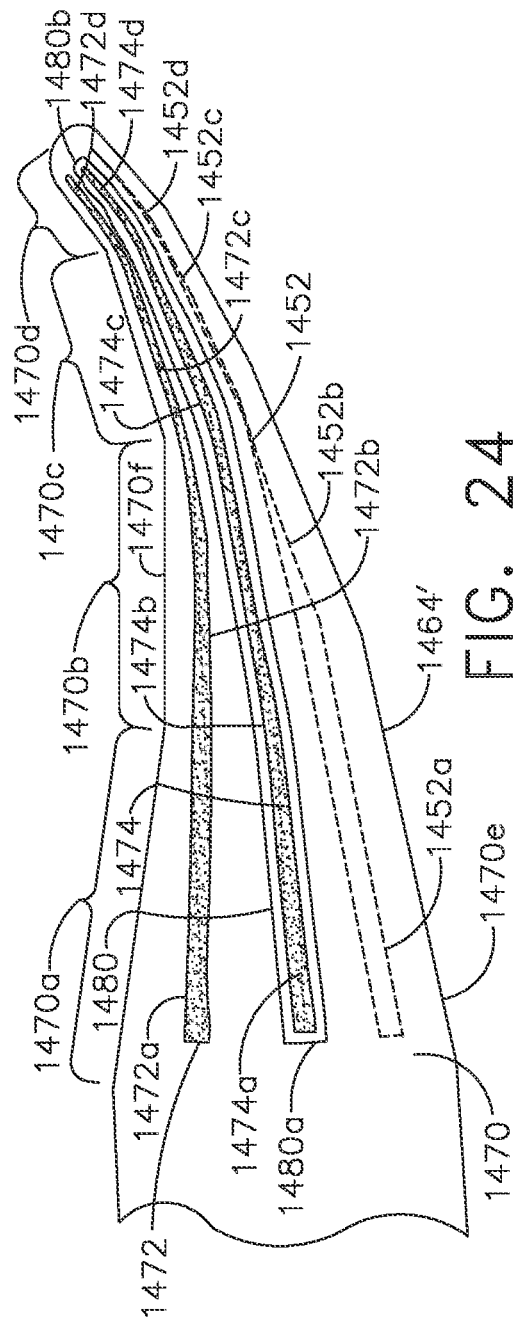
FIG. 25
FIG. 24

| Time | Tissue Operation | Energy type | Jaw aperture | image |
|---|---|---|---|---|
| $t_0$ | No tissue contact | n/a | 0.700"–0.500" | $d_0$ 0.700" |
| $t_1$ | Feathering 3008 | Bipolar | 0.500"–0.030" | 0.500" |
| $t_2$ | Tissue Warming power 3009 | Bipolar & Monopolar | 0.030"–0.010" | $d_2$ 0.030" |
| $t_3$ | Sealing 3010 | Monopolar & Bipolar | 0.010"–0.003" | $d_3$ 0.010" |
| $t_4$ | Cutting 3007 | Monopolar | 0.010"–0.003" | $d_4$ 0.010" |

FIG. 37

ELECTROSURGICAL INSTRUMENTS WITH ELECTRODES HAVING VARIABLE ENERGY DENSITIES

CROSS REFERENCE TO RELATED APPLICATION

This non-provisional application claims the benefit under 35 U.S.C. § 119(e) of U.S. Provisional Patent Application Ser. No. 62/955,299, entitled DEVICES AND SYSTEMS FOR ELECTROSURGERY, filed Dec. 30, 2019, the disclosure of which is incorporated by reference herein in its entirety.

BACKGROUND

The present invention relates to surgical instruments designed to treat tissue, including but not limited to surgical instruments that are configured to cut and fasten tissue. The surgical instruments may include electrosurgical instruments powered by generators to effect tissue dissecting, cutting, and/or coagulation during surgical procedures. The surgical instruments may include instruments that are configured to cut and staple tissue using surgical staples and/or fasteners. The surgical instruments may be configured for use in open surgical procedures, but have applications in other types of surgery, such as laparoscopic, endoscopic, and robotic-assisted procedures and may include end effectors that are articulatable relative to a shaft portion of the instrument to facilitate precise positioning within a patient.

SUMMARY

In various embodiments, an electrosurgical instrument comprising an end effector is disclosed. The end effector comprises a first jaw and a second jaw. At least one of the first jaw and the second jaw is movable to transition the end effector from an open configuration to a closed configuration to grasp tissue therebetween. The second jaw comprises linear portions cooperating to form an angular profile and a treatment surface comprising segments extending along the angular profile. The segments comprise different geometries and different conductivities. The segments are configured to produce variable energy densities along the treatment surface.

In various embodiments, an electrosurgical instrument comprising an end effector is disclosed. The end effector comprises a first jaw and a second jaw. At least one of the first jaw and the second jaw is movable to transition the end effector from an open configuration to a closed configuration to grasp tissue therebetween. The second jaw comprises a gradually narrowing body extending from a proximal end to a distal end. The gradually narrowing body comprises a tissue contacting surface. The tissue contacting surface comprises an insulative layer comprising a first material. The insulative layer extends on opposite sides of an intermediate area extending along a length of the gradually narrowing body. The tissue contacting surface further comprises segments configured to yield variable energy densities along the tissue contacting surface. The segments comprise conductive segments and insulative segments alternating with the conductive segments along the intermediate area. The insulative segments comprise a second material different from the first material.

DRAWINGS

The novel features of the various aspects are set forth with particularity in the appended claims. The described aspects, however, both as to organization and methods of operation, may be best understood by reference to the following description, taken in conjunction with the accompanying drawings in which:

FIG. 4 is an exploded view of an end effector of an electro surgical instrument, in accordance with at least one aspect of the present disclosure;

FIG. 5 is a cross-sectional view of the of the end effector of FIG. 4;

FIGS. 6-8 depict three different operational modes of the end effector of FIG. 4 prior to energy application to tissue;

FIGS. 9-11 depict three different operational modes of the end effector of FIG. 4 during energy application to tissue;

FIG. 12 illustrates a method of manufacturing a jaw of an end effector, in accordance with at least one aspect of the present disclosure;

FIG. 13 illustrates a method of manufacturing a jaw of an end effector, in accordance with at least one aspect of the present disclosure;

FIG. 20 illustrates a cross-sectional view of a jaw of an end effector of an electrosurgical instrument taken through line 20-20 in FIG. 22, in accordance with at least one aspect of the present disclosure;

FIG. 21 illustrates a cross-sectional view of the jaw of the end effector of the electrosurgical instrument taken through line 21-21 in FIG. 22;

FIG. 22 illustrates a perspective view of the jaw of the end effector of the electrosurgical instrument of FIG. 20;

FIG. 23 illustrates a cross-sectional view of a jaw of an end effector of an electrosurgical instrument, in accordance with at least one aspect of the present disclosure;

FIG. 24 illustrates a partial perspective view of a jaw of an end effector of an electrosurgical instrument, in accordance with at least one aspect of the present disclosure;

FIG. 25 illustrates a cross-sectional view of an end effector of an electrosurgical instrument, in accordance with at least one aspect of the present disclosure;

FIG. 37 is a table illustrating a power scheme for coagulating and cutting a tissue treatment region in a treatment cycle applied by an end effector, in accordance with at least one aspect of the present disclosure;

Figure 48:
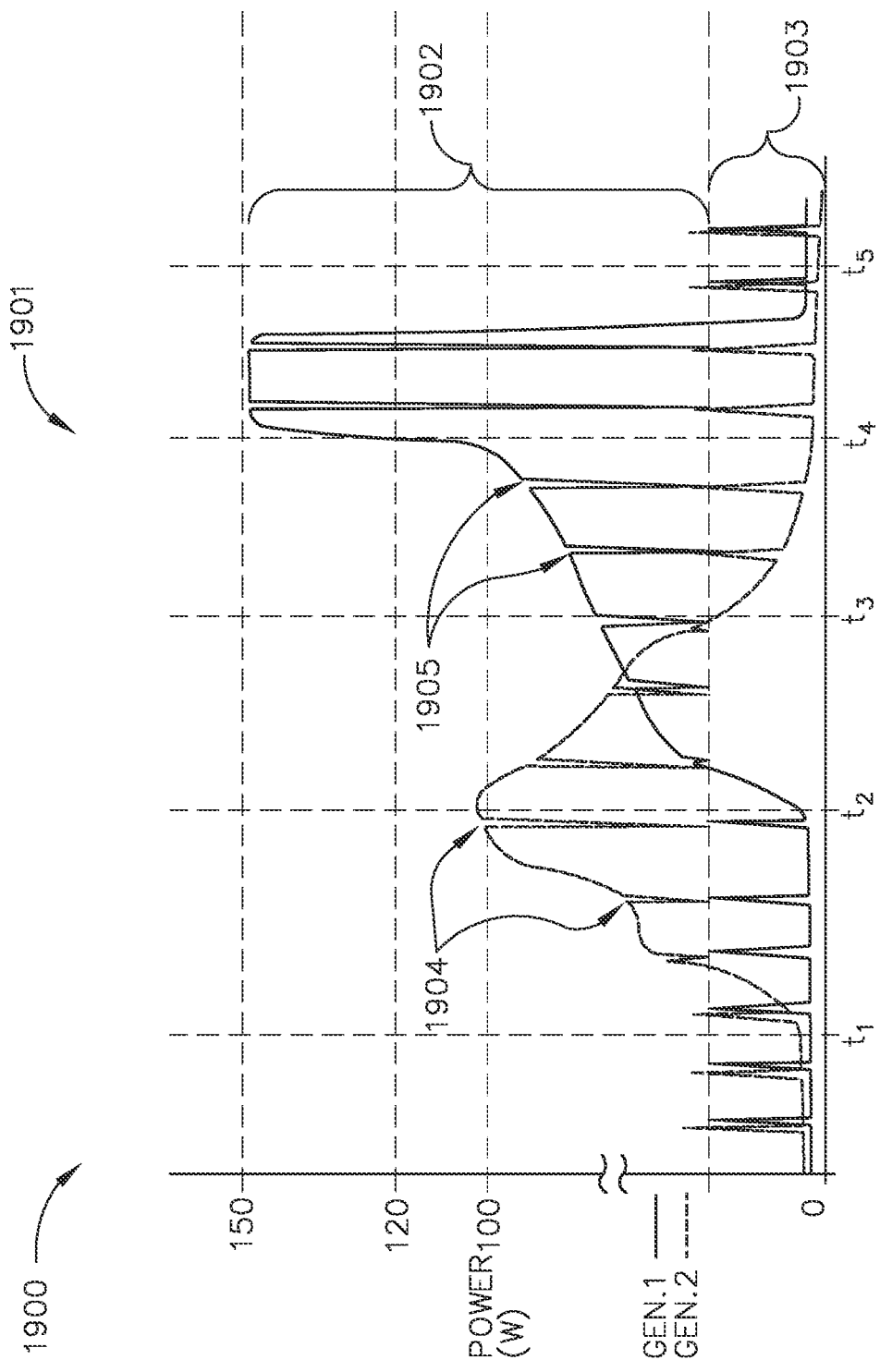
Figure 49:
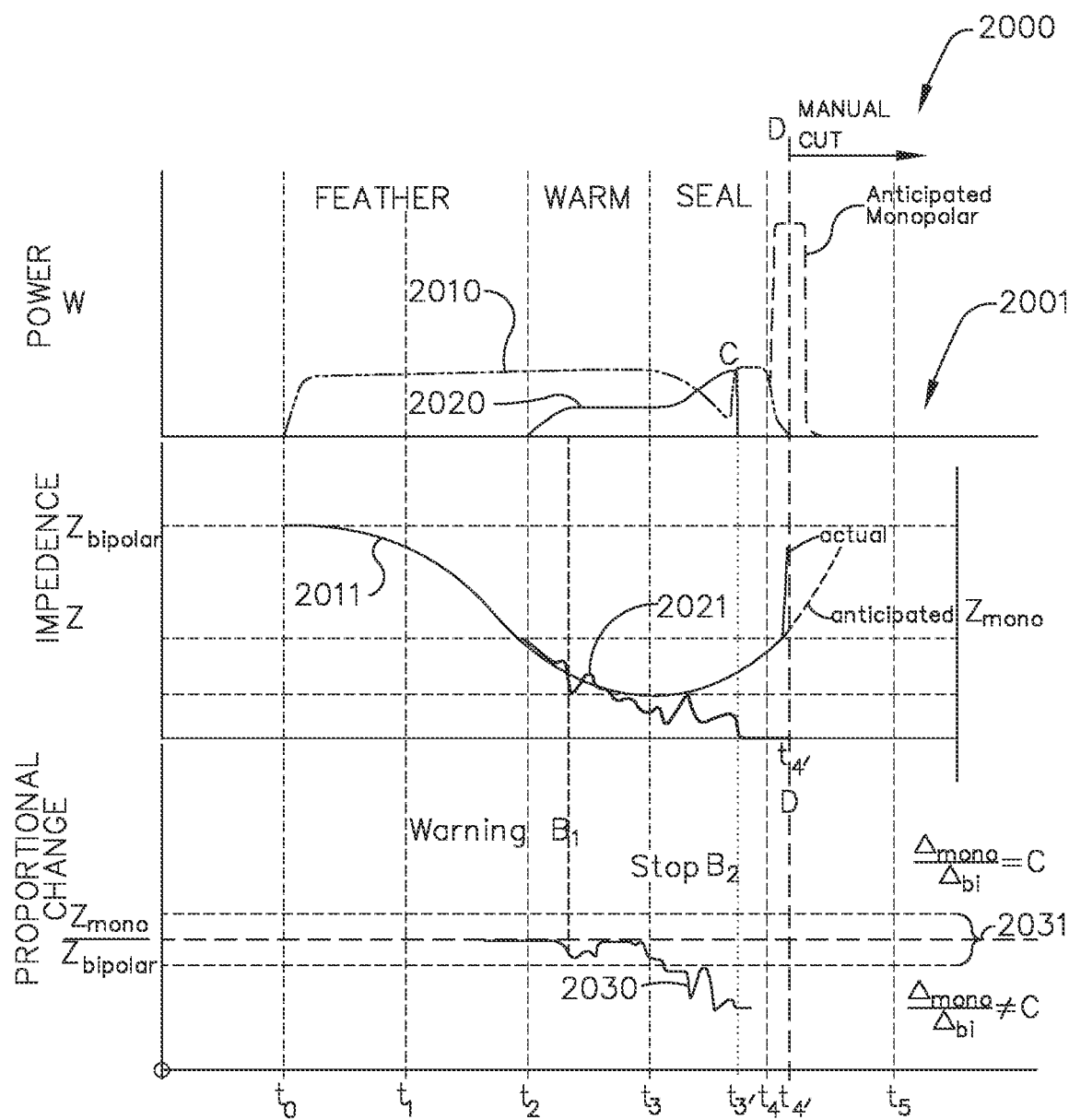

FIG. 48 is a graph illustrating a power scheme including a therapeutic portion for coagulating and cutting a tissue treatment range in a treatment cycle applied by an end effector, and non-therapeutic range, in accordance with at least one aspect of the present disclosure; and FIG. 49 is a graph illustrating a power scheme including for coagulating and cutting a tissue treatment range in a treatment cycle applied by an end effector, and corresponding monopolar and bipolar impedances and a ratio thereof, in accordance with at least one aspect of the present disclosure.

DESCRIPTION

Applicant of the present application owns the following U.S. Patent Applications that are filed on May 28, 2020 and which are each herein incorporated by reference in their respective entireties:

U.S. patent application Ser. No. 16/885,813, entitled METHOD FOR AN ELECTROSURGICAL PROCEDURE, now U.S. Patent Application Publication No. 2021/0196354;

U.S. patent application Ser. No. 16/885,820, entitled ARTICULATABLE SURGICAL INSTRUMENT, now U.S. Patent Application Publication No. 2021/0196301;

U.S. patent application Ser. No. 16/885,823, entitled SURGICAL INSTRUMENT WITH JAW ALIGNMENT FEATURES, now U.S. Patent Application Publication No. 2021/0196355;

U.S. patent application Ser. No. 16/885,826, entitled SURGICAL INSTRUMENT WITH ROTATABLE AND ARTICULATABLE SURGICAL END EFFECTOR, now U.S. Patent Application Publication No. 2021/0196356;

U.S. patent application Ser. No. 16/885,838, entitled ELECTROSURGICAL INSTRUMENT WITH ASYNCHRONOUS ENERGIZING ELECTRODES, now U.S. Patent Application Publication No. 2021/0196357;

U.S. patent application Ser. No. 16/885,851, entitled ELECTROSURGICAL INSTRUMENT WITH ELECTRODES BIASING SUPPORT, now U.S. Patent Application Publication No. 2021/0196358;

U.S. patent application Ser. No. 16/885,860, entitled ELECTROSURGICAL INSTRUMENT WITH FLEXIBLE WIRING ASSEMBLIES, now U.S. Patent Application Publication No. 2021/0196349;

U.S. patent application Ser. No. 16/885,866, entitled ELECTROSURGICAL INSTRUMENT WITH VARIABLE CONTROL MECHANISMS, now U.S. Patent Application Publication No. 2021/0196350;

U.S. patent application Ser. No. 16/885,870, entitled ELECTROSURGICAL SYSTEMS WITH INTEGRATED AND EXTERNAL POWER SOURCES, now U.S. Patent Application Publication No. 2021/0196343;

U.S. patent application Ser. No. 16/885,873, entitled ELECTROSURGICAL INSTRUMENTS WITH ELECTRODES HAVING ENERGY FOCUSING FEATURES, now U.S. Patent Application Publication No. 2021/0196359;

U.S. patent application Ser. No. 16/885,881, entitled ELECTROSURGICAL INSTRUMENT WITH MONOPOLAR AND BIPOLAR ENERGY CAPABILITIES, now U.S. Patent Application Publication No. 2021/0196361;

U.S. patent application Ser. No. 16/885,888, entitled ELECTROSURGICAL END EFFECTORS WITH THERMALLY INSULATIVE AND THERMALLY CONDUCTIVE PORTIONS, now U.S. Patent Application Publication No. 2021/0196362;

U.S. patent application Ser. No. 16/885,893, entitled ELECTROSURGICAL INSTRUMENT WITH ELECTRODES OPERABLE IN BIPOLAR AND MONOPOLAR MODES, now U.S. Patent Application Publication No. 2021/0196363;

U.S. patent application Ser. No. 16/885,900, entitled ELECTROSURGICAL INSTRUMENT FOR DELIVERING BLENDED ENERGY MODALITIES TO TISSUE, now U.S. Patent Application Publication No. 2021/0196364;

U.S. patent application Ser. No. 16/885,917, entitled CONTROL PROGRAM ADAPTATION BASED ON DEVICE STATUS AND USER INPUT, now U.S. Patent Application Publication No. 2021/0196365;

U.S. patent application Ser. No. 16/885,923, entitled CONTROL PROGRAM FOR MODULAR COMBINATION ENERGY DEVICE, now U.S. Patent Application Publication No. 2021/0196366; and U.S. patent application Ser. No. 16/885,931, entitled SURGICAL SYSTEM COMMUNICATION PATHWAYS, now U.S. Patent Application Publication No. 2021/0196344.

Applicant of the present application owns the following U.S. Provisional Patent Applications that were filed on Dec. 30, 2019, the disclosure of each of which is herein incorporated by reference in its entirety:

U.S. Provisional Patent Application Ser. No. 62/955,294, entitled USER INTERFACE FOR SURGICAL INSTRUMENT WITH COMBINATION ENERGY MODALITY END-EFFECTOR;

U.S. Provisional Patent Application Ser. No. 62/955,292, entitled COMBINATION ENERGY MODALITY END-EFFECTOR; and U.S. Provisional Patent Application Ser. No. 62/955,306, entitled SURGICAL INSTRUMENT SYSTEMS.

Applicant of the present application owns the following U.S. Patent Applications, the disclosure of each of which is herein incorporated by reference in its entirety:

U.S. patent application Ser. No. 16/209,395, titled METHOD OF HUB COMMUNICATION, now U.S. Patent Application Publication No. 2019/0201136;

U.S. patent application Ser. No. 16/209,403, titled METHOD OF CLOUD BASED DATA ANALYTICS FOR USE WITH THE HUB, now U.S. Patent Application Publication No. 2019/0206569;

U.S. patent application Ser. No. 16/209,407, titled METHOD OF ROBOTIC HUB COMMUNICATION, DETECTION, AND CONTROL, now U.S. Patent Application Publication No. 2019/0201137;

U.S. patent application Ser. No. 16/209,416, titled METHOD OF HUB COMMUNICATION, PROCESSING, DISPLAY, AND CLOUD ANALYTICS, now U.S. Patent Application Publication No. 2019/0206562;

U.S. patent application Ser. No. 16/209,423, titled METHOD OF COMPRESSING TISSUE WITHIN A STAPLING DEVICE AND SIMULTANEOUSLY DISPLAYING THE LOCATION OF THE TISSUE WITHIN THE JAWS, now U.S. Patent Application Publication No. 2019/0200981;

U.S. patent application Ser. No. 16/209,427, titled METHOD OF USING REINFORCED FLEXIBLE CIRCUITS WITH MULTIPLE SENSORS TO OPTIMIZE PERFORMANCE OF RADIO FREQUENCY DEVICES, now U.S. Patent Application Publication No. 2019/0208641;

U.S. patent application Ser. No. 16/209,433, titled METHOD OF SENSING PARTICULATE FROM SMOKE EVACUATED FROM A PATIENT, ADJUSTING THE PUMP SPEED BASED ON THE SENSED INFORMATION, AND COMMUNICATING THE FUNCTIONAL PARAMETERS OF THE SYSTEM TO THE HUB, now U.S. Patent Application Publication No. 2019/0201594;

U.S. patent application Ser. No. 16/209,447, titled METHOD FOR SMOKE EVACUATION FOR SURGICAL HUB, now U.S. Patent Application Publication No. 2019/0201045;

U.S. patent application Ser. No. 16/209,453, titled METHOD FOR CONTROLLING SMART ENERGY DEVICES, now U.S. Patent Application Publication No. 2019/0201046;

U.S. patent application Ser. No. 16/209,458, titled METHOD FOR SMART ENERGY DEVICE INFRASTRUCTURE, now U.S. Patent Application Publication No. 2019/0201047;

U.S. patent application Ser. No. 16/209,465, titled METHOD FOR ADAPTIVE CONTROL SCHEMES FOR SURGICAL NETWORK CONTROL AND INTERACTION, now U.S. Patent Application Publication No. 2019/0206563;

U.S. patent application Ser. No. 16/209,478, titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, now U.S. Patent Application Publication No. 2019/0104919;

U.S. patent application Ser. No. 16/209,490, titled METHOD FOR FACILITY DATA COLLECTION AND INTERPRETATION, now U.S. Patent Application Publication No. 2019/0206564;

U.S. patent application Ser. No. 16/209,491, titled METHOD FOR CIRCULAR STAPLER CONTROL ALGORITHM ADJUSTMENT BASED ON SITUATIONAL AWARENESS, now U.S. Patent Application Publication No. 2019/0200998;

U.S. patent application Ser. No. 16/562,123, titled METHOD FOR CONSTRUCTING AND USING A MODULAR SURGICAL ENERGY SYSTEM WITH MULTIPLE DEVICES;

U.S. patent application Ser. No. 16/562,135, titled METHOD FOR CONTROLLING AN ENERGY MODULE OUTPUT;

U.S. patent application Ser. No. 16/562,144, titled METHOD FOR CONTROLLING A MODULAR ENERGY SYSTEM USER INTERFACE; and U.S. patent application Ser. No. 16/562,125, titled METHOD FOR COMMUNICATING BETWEEN MODULES AND DEVICES IN A MODULAR SURGICAL SYSTEM.

Before explaining various aspects of an electrosurgical system in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

Various aspects are directed to electrosurgical systems that include electrosurgical instruments powered by generators to effect tissue dissecting, cutting, and/or coagulation during surgical procedures. The electrosurgical instruments may be configured for use in open surgical procedures, but has applications in other types of surgery, such as laparoscopic, endoscopic, and robotic-assisted procedures.

As described below in greater detail, an electrosurgical instrument generally includes a shaft having a distally-mounted end effector (e.g., one or more electrodes). The end effector can be positioned against the tissue such that electrical current is introduced into the tissue. Electrosurgical instruments can be configured for bipolar or monopolar operation. During bipolar operation, current is introduced into and returned from the tissue by active and return electrodes, respectively, of the end effector. During monopolar operation, current is introduced into the tissue by an active electrode of the end effector and returned through a return electrode (e.g., a grounding pad) separately located on a patient's body. Heat generated by the current flowing through the tissue may form hemostatic seals within the tissue and/or between tissues and thus may be particularly useful for sealing blood vessels, for example.

Figure 1:
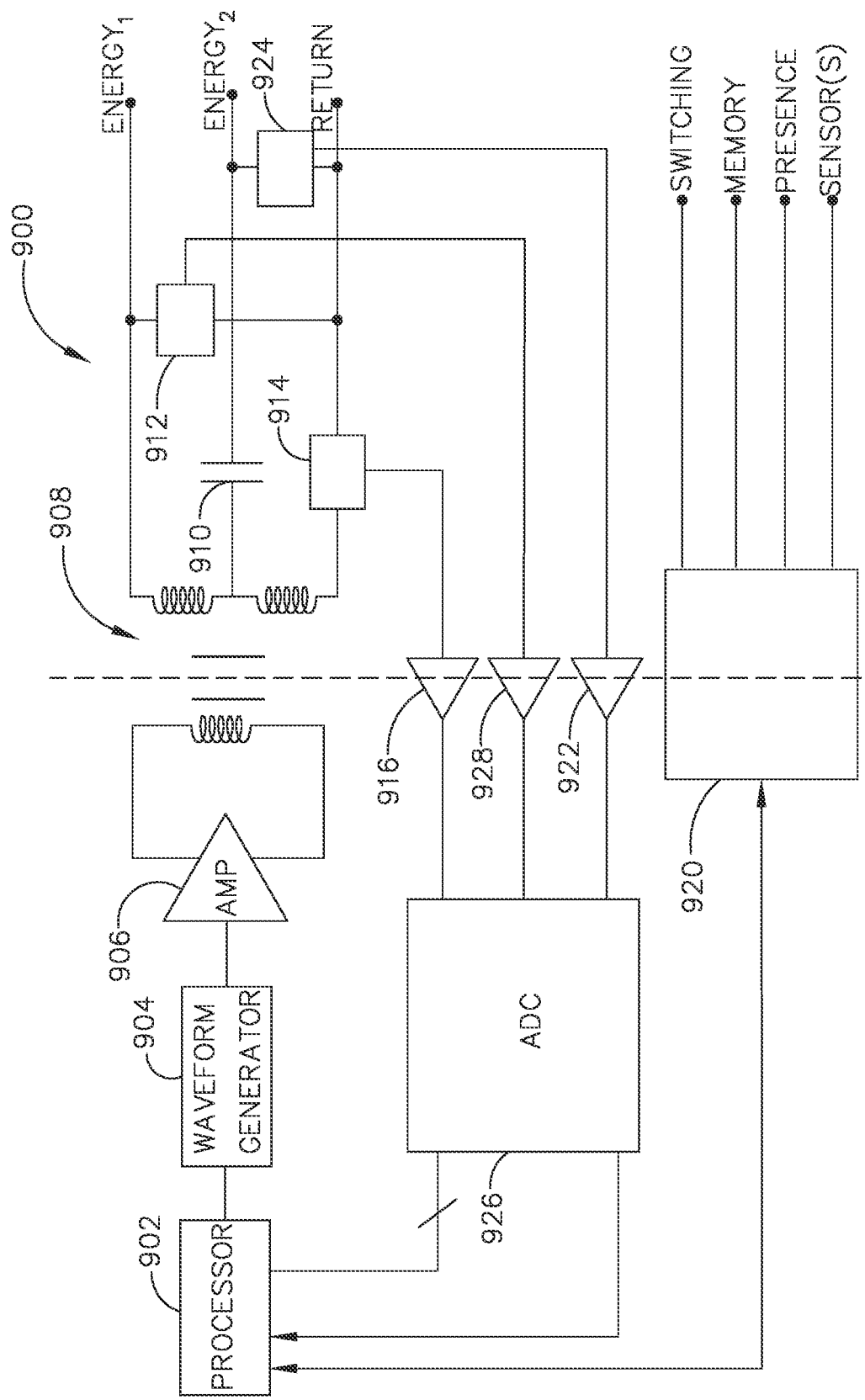
FIG. 1 illustrates an example of a generator for use with a surgical system, in accordance with at least one aspect of the present disclosure.

FIG. 1 illustrates an example of a generator 900 configured to deliver multiple energy modalities to a surgical instrument. The generator 900 provides RF and/or ultrasonic signals for delivering energy to a surgical instrument. The generator 900 comprises at least one generator output that can deliver multiple energy modalities (e.g., ultrasonic, bipolar or monopolar RF, irreversible and/or reversible electroporation, and/or microwave energy, among others) through a single port, and these signals can be delivered separately or simultaneously to an end effector to treat tissue. The generator 900 comprises a processor 902 coupled to a waveform generator 904. The processor 902 and waveform generator 904 are configured to generate a variety of signal waveforms based on information stored in a memory coupled to the processor 902, not shown for clarity of disclosure. The digital information associated with a waveform is provided to the waveform generator 904 which includes one or more DAC circuits to convert the digital input into an analog output. The analog output is fed to an amplifier 906 for signal conditioning and amplification. The conditioned and amplified output of the amplifier 906 is coupled to a power transformer 908. The signals are coupled across the power transformer 908 to the secondary side, which is in the patient isolation side. A first signal of a first energy modality is provided to the surgical instrument between the terminals labeled $ENERGY_1$ and RETURN. A second signal of a second energy modality is coupled across a capacitor 910 and is provided to the surgical instrument between the terminals labeled $ENERGY_2$ and RETURN. It will be appreciated that more than two energy modalities may be output and thus the subscript "n" may be used to designate that up to n $ENERGY_n$ terminals may be provided, where n is a positive integer greater than 1. It also will be appreciated that up to "n" return paths $RETURN_n$ may be provided without departing from the scope of the present disclosure.

A first voltage sensing circuit 912 is coupled across the terminals labeled $ENERGY_1$ and the RETURN path to measure the output voltage therebetween. A second voltage sensing circuit 924 is coupled across the terminals labeled $ENERGY_2$ and the RETURN path to measure the output voltage therebetween. A current sensing circuit 914 is disposed in series with the RETURN leg of the secondary side of the power transformer 908 as shown to measure the output current for either energy modality. If different return paths are provided for each energy modality, then a separate current sensing circuit should be provided in each return leg. The outputs of the first and second voltage sensing circuits 912, 924 are provided to respective isolation transformers 928, 922 and the output of the current sensing circuit 914 is provided to another isolation transformer 916. The outputs of the isolation transformers 916, 928, 922 on the primary side of the power transformer 908 (non-patient isolated side) are provided to a one or more ADC circuit 926. The digitized output of the ADC circuit 926 is provided to the processor 902 for further processing and computation. The output voltages and output current feedback information can be employed to adjust the output voltage and current provided to the surgical instrument and to compute output impedance, among other parameters. Input/output communications between the processor 902 and patient isolated circuits is provided through an interface circuit 920. Sensors also may be in electrical communication with the processor 902 by way of the interface circuit 920.

In one aspect, the impedance may be determined by the processor 902 by dividing the output of either the first voltage sensing circuit 912 coupled across the terminals labeled $ENERGY_1$/RETURN or the second voltage sensing circuit 924 coupled across the terminals labeled $ENERGY_2$/RETURN by the output of the current sensing circuit 914 disposed in series with the RETURN leg of the secondary side of the power transformer 908. The outputs of the first and second voltage sensing circuits 912, 924 are provided to separate isolations transformers 928, 922 and the output of the current sensing circuit 914 is provided to another isolation transformer 916. The digitized voltage and current sensing measurements from the ADC circuit 926 are provided the processor 902 for computing impedance. As an example, the first energy modality $ENERGY_1$ may be RF monopolar energy and the second energy modality $ENERGY_2$ may be RF bipolar energy. Nevertheless, in addition to bipolar and monopolar RF energy modalities, other energy modalities include ultrasonic energy, irreversible and/or reversible electroporation and/or microwave energy, among others. Also, although the example illustrated in FIG. 1 shows a single return path RETURN may be provided for two or more energy modalities, in other aspects, multiple return paths $RETURN_n$ may be provided for each energy modality $ENERGY_n$.

As shown in FIG. 1, the generator 900 comprising at least one output port can include a power transformer 908 with a single output and with multiple taps to provide power in the form of one or more energy modalities, such as ultrasonic, bipolar or monopolar RF, irreversible and/or reversible electroporation, and/or microwave energy, among others, for example, to the end effector depending on the type of treatment of tissue being performed. For example, the generator 900 can deliver energy with higher voltage and lower current to drive an ultrasonic transducer, with lower voltage and higher current to drive RF electrodes for sealing tissue, or with a coagulation waveform for spot coagulation using either monopolar or bipolar RF electrosurgical electrodes. The output waveform from the generator 900 can be steered, switched, or filtered to provide the frequency to the end effector of the surgical instrument. In one example, a connection of RF bipolar electrodes to the generator 900 output would be preferably located between the output labeled $ENERGY_2$ and RETURN. In the case of monopolar output, the preferred connections would be active electrode (e.g., pencil or other probe) to the $ENERGY_2$ output and a suitable return pad connected to the RETURN output.

Additional details are disclosed in U.S. Patent Application Publication No. 2017/0086914, titled TECHNIQUES FOR OPERATING GENERATOR FOR DIGITALLY GENERATING ELECTRICAL SIGNAL WAVEFORMS AND SURGICAL INSTRUMENTS, which published on Mar. 30, 2017, which is herein incorporated by reference in its entirety.

Figure 2:
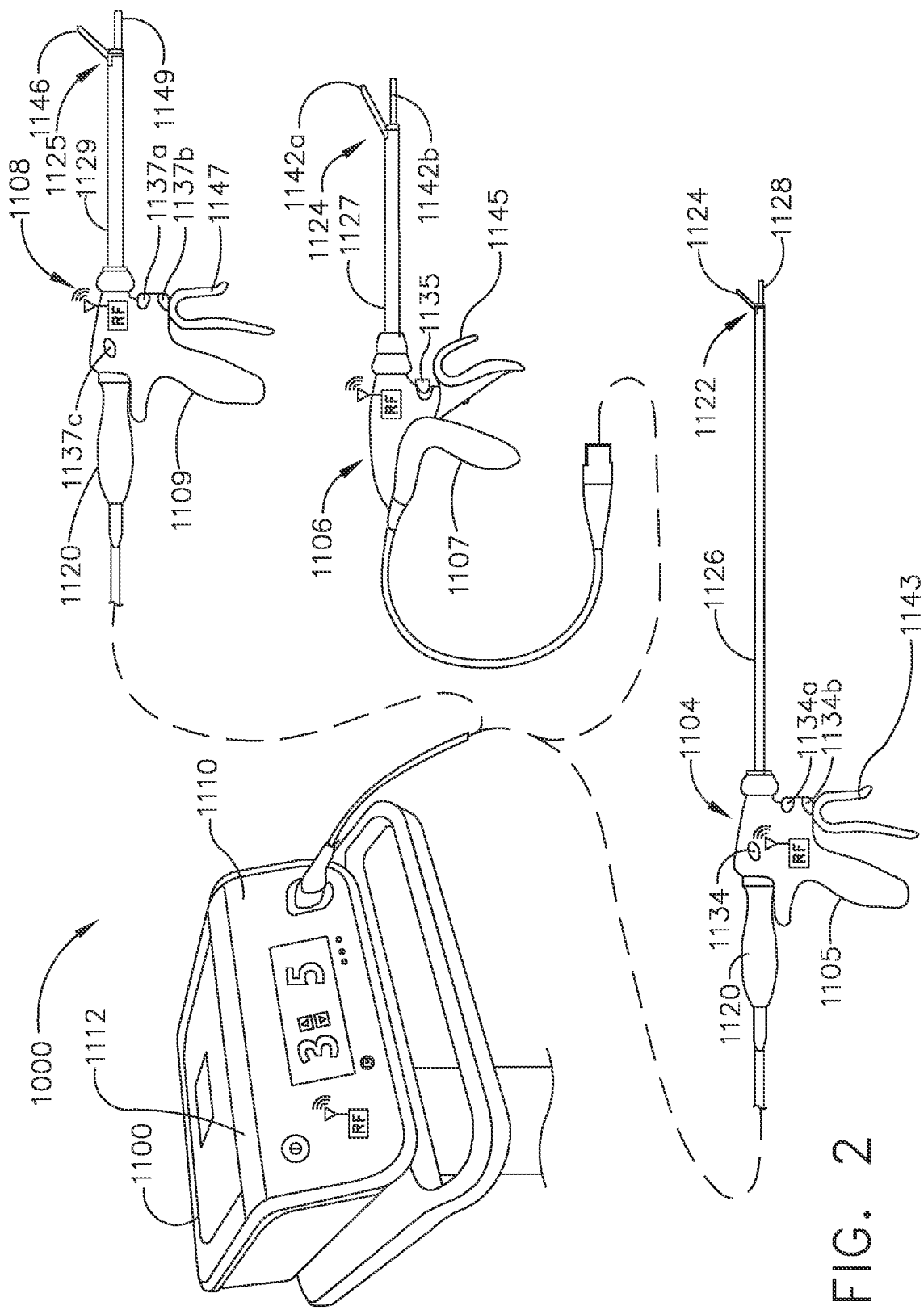
FIG. 2 illustrates one form of a surgical system comprising a generator and an electrosurgical instrument usable therewith, in accordance with at least one aspect of the present disclosure.

FIG. 2 illustrates one form of a surgical system 1000 comprising a generator 1100 and various surgical instruments 1104, 1106, 1108 usable therewith, where the surgical instrument 1104 is an ultrasonic surgical instrument, the surgical instrument 1106 is an RF electrosurgical instrument, and the multifunction surgical instrument 1108 is a combination ultrasonic/RF electrosurgical instrument. The generator 1100 is configurable for use with a variety of surgical instruments. According to various forms, the generator 1100 may be configurable for use with different surgical instruments of different types including, for example, ultrasonic surgical instruments 1104, RF electrosurgical instruments 1106, and multifunction surgical instruments 1108 that integrate RF and ultrasonic energies delivered simultaneously from the generator 1100. Although in the form of FIG. 2 the generator 1100 is shown separate from the surgical instruments 1104, 1106, 1108 in one form, the generator 1100 may be formed integrally with any of the surgical instruments 1104, 1106, 1108 to form a unitary surgical system. The generator 1100 comprises an input device 1110 located on a front panel of the generator 1100 console. The input device 1110 may comprise any suitable device that generates signals suitable for programming the operation of the generator 1100. The generator 1100 may be configured for wired or wireless communication.

The generator 1100 is configured to drive multiple surgical instruments 1104, 1106, 1108. The first surgical instrument is an ultrasonic surgical instrument 1104 and comprises a handpiece 1105 (HP), an ultrasonic transducer 1120, a shaft 1126, and an end effector 1122. The end effector 1122 comprises an ultrasonic blade 1128 acoustically coupled to the ultrasonic transducer 1120 and a clamp arm 1140. The handpiece 1105 comprises a trigger 1143 to operate the clamp arm 1140 and a combination of the toggle buttons 1137, 1134b, 1134c to energize and drive the ultrasonic blade 1128 or other function. The toggle buttons 1137, 1134b, 1134c can be configured to energize the ultrasonic transducer 1120 with the generator 1100.

The generator 1100 also is configured to drive a second surgical instrument 1106. The second surgical instrument 1106 is an RF electrosurgical instrument and comprises a handpiece 1107 (HP), a shaft 1127, and an end effector 1124. The end effector 1124 comprises electrodes in clamp arms 1145, 1142b and return through an electrical conductor portion of the shaft 1127. The electrodes are coupled to and energized by a bipolar energy source within the generator 1100. The handpiece 1107 comprises a trigger 1145 to operate the clamp arms 1145, 1142b and an energy button 1135 to actuate an energy switch to energize the electrodes in the end effector 1124. The second surgical instrument 1106 can also be used with a return pad to deliver monopolar energy to tissue.

The generator 1100 also is configured to drive a multifunction surgical instrument 1108. The multifunction surgical instrument 1108 comprises a handpiece 1109 (HP), a shaft 1129, and an end effector 1125. The end effector 1125 comprises an ultrasonic blade 1149 and a clamp arm 1146. The ultrasonic blade 1149 is acoustically coupled to the ultrasonic transducer 1120. The handpiece 1109 comprises a trigger 1147 to operate the clamp arm 1146 and a combination of the toggle buttons 11310, 1137b, 1137c to energize and drive the ultrasonic blade 1149 or other function. The toggle buttons 11310, 1137b, 1137c can be configured to energize the ultrasonic transducer 1120 with the generator 1100 and energize the ultrasonic blade 1149 with a bipolar energy source also contained within the generator 1100. Monopolar energy can be delivered to the tissue in combination with, or separately from, the bipolar energy.

The generator 1100 is configurable for use with a variety of surgical instruments. According to various forms, the generator 1100 may be configurable for use with different surgical instruments of different types including, for example, the ultrasonic surgical instrument 1104, the RF electrosurgical instrument 1106, and the multifunction surgical instrument 1108 that integrates RF and ultrasonic energies delivered simultaneously from the generator 1100. Although in the form of FIG. 2, the generator 1100 is shown separate from the surgical instruments 1104, 1106, 1108, in another form the generator 1100 may be formed integrally with any one of the surgical instruments 1104, 1106, 1108 to form a unitary surgical system. As discussed above, the generator 1100 comprises an input device 1110 located on a front panel of the generator 1100 console. The input device 1110 may comprise any suitable device that generates signals suitable for programming the operation of the generator 1100. The generator 1100 also may comprise one or more output devices 1112. Further aspects of generators for digitally generating electrical signal waveforms and surgical instruments are described in US patent application publication US-2017-0086914-A1, which is herein incorporated by reference in its entirety.

Figure 3:
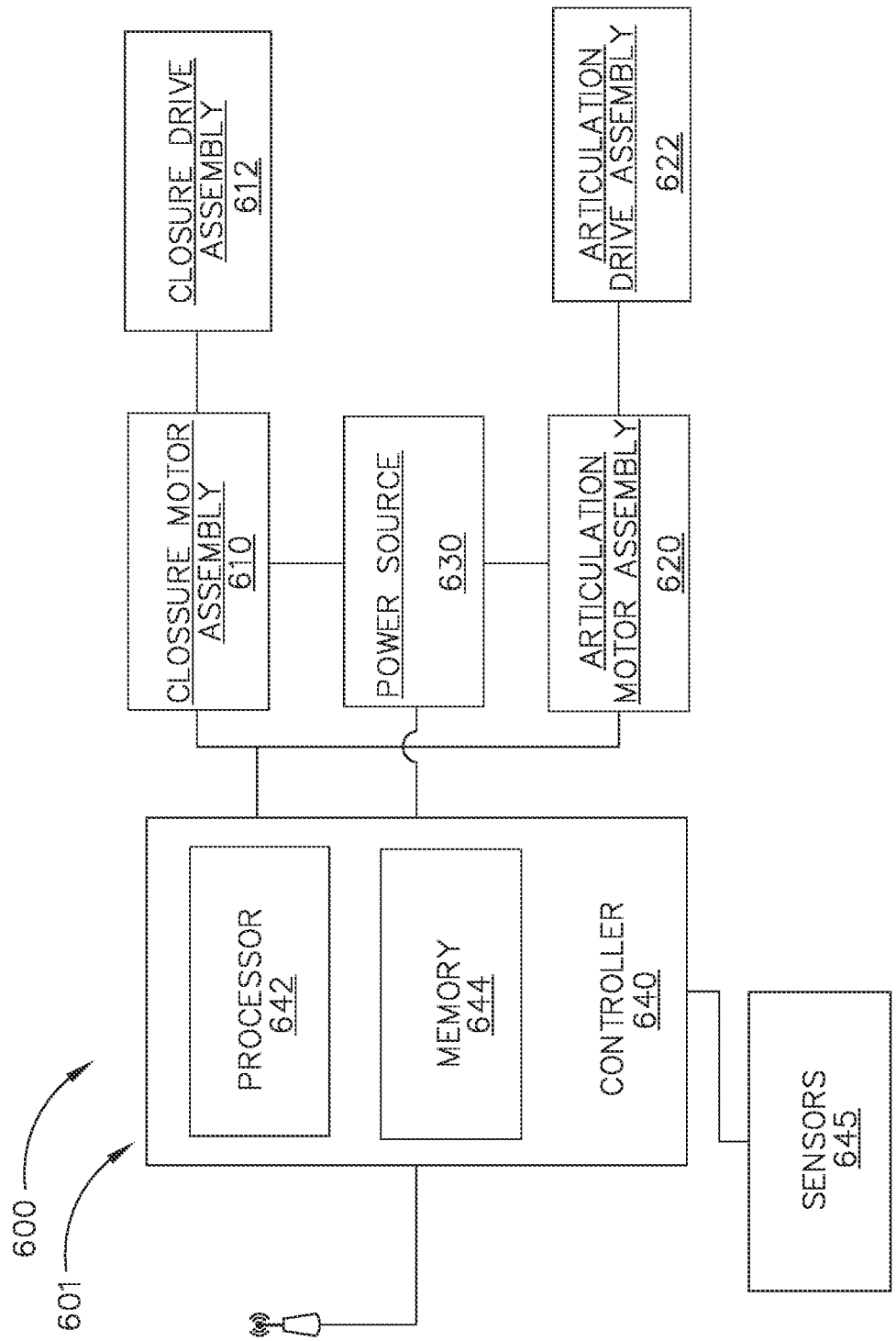
FIG. 3 illustrates a schematic diagram of a surgical instrument or tool, in accordance with at least one aspect of the present disclosure.

FIG. 3 illustrates a schematic diagram of a surgical instrument or tool 600 comprising a plurality of motor assemblies that can be activated to perform various functions. In the illustrated example, a closure motor assembly 610 is operable to transition an end effector between an open configuration and a closed configuration, and an articulation motor assembly 620 is operable to articulate the end effector relative to a shaft assembly. In certain instances, the plurality of motors assemblies can be individually activated to cause firing, closure, and/or articulation motions in the end effector. The firing, closure, and/or articulation motions can be transmitted to the end effector through a shaft assembly, for example.

In certain instances, the closure motor assembly 610 includes a closure motor. The closure 603 may be operably coupled to a closure motor drive assembly 612 which can be configured to transmit closure motions, generated by the motor to the end effector, in particular to displace a closure member to close to transition the end effector to the closed configuration. The closure motions may cause the end effector to transition from an open configuration to a closed configuration to capture tissue, for example. The end effector may be transitioned to an open position by reversing the direction of the motor.

In certain instances, the articulation motor assembly 620 includes an articulation motor that be operably coupled to an articulation drive assembly 622 which can be configured to transmit articulation motions, generated by the motor to the end effector. In certain instances, the articulation motions may cause the end effector to articulate relative to the shaft, for example.

One or more of the motors of the surgical instrument 600 may comprise a torque sensor to measure the output torque on the shaft of the motor. The force on an end effector may be sensed in any conventional manner, such as by force sensors on the outer sides of the jaws or by a torque sensor for the motor actuating the jaws.

In various instances, the motor assemblies 610, 620 include one or more motor drivers that may comprise one or more H-Bridge FETs. The motor drivers may modulate the power transmitted from a power source 630 to a motor based on input from a microcontroller 640 (the "controller"), for example, of a control circuit 601. In certain instances, the microcontroller 640 can be employed to determine the current drawn by the motor, for example.

In certain instances, the microcontroller 640 may include a microprocessor 642 (the "processor") and one or more non-transitory computer-readable mediums or memory units 644 (the "memory"). In certain instances, the memory 644 may store various program instructions, which when executed may cause the processor 642 to perform a plurality of functions and/or calculations described herein. In certain instances, one or more of the memory units 644 may be coupled to the processor 642, for example. In various aspects, the microcontroller 640 may communicate over a wired or wireless channel, or combinations thereof.

In certain instances, the power source 630 can be employed to supply power to the microcontroller 640, for example. In certain instances, the power source 630 may comprise a battery (or "battery pack" or "power pack"), such as a lithium-ion battery, for example. In certain instances, the battery pack may be configured to be releasably mounted to a handle for supplying power to the surgical instrument 600. A number of battery cells connected in series may be used as the power source 630. In certain instances, the power source 630 may be replaceable and/or rechargeable, for example.

In various instances, the processor 642 may control a motor driver to control the position, direction of rotation, and/or velocity of a motor of the assemblies 610, 620. In certain instances, the processor 642 can signal the motor driver to stop and/or disable the motor. It should be understood that the term "processor" as used herein includes any suitable microprocessor, microcontroller, or other basic computing device that incorporates the functions of a computer's central processing unit (CPU) on an integrated circuit or, at most, a few integrated circuits. The processor 642 is a multipurpose, programmable device that accepts digital data as input, processes it according to instructions stored in its memory, and provides results as output. It is an example of sequential digital logic, as it has internal memory. Processors operate on numbers and symbols represented in the binary numeral system.

In one instance, the processor 642 may be any single-core or multicore processor such as those known under the trade name ARM Cortex by Texas Instruments. In certain instances, the microcontroller 620 may be an LM 4F230H5QR, available from Texas Instruments, for example. In at least one example, the Texas Instruments LM4F230H5QR is an ARM Cortex-M4F Processor Core comprising an on-chip memory of 256 KB single-cycle flash memory, or other non-volatile memory, up to 40 MHz, a prefetch buffer to improve performance above 40 MHz, a 32 KB single-cycle SRAM, an internal ROM loaded with StellarisWare® software, a 2 KB EEPROM, one or more PWM modules, one or more QEI analogs, one or more 12-bit ADCs with 12 analog input channels, among other features that are readily available for the product datasheet. Other microcontrollers may be readily substituted for use with the surgical instrument 600. Accordingly, the present disclosure should not be limited in this context.

In certain instances, the memory 644 may include program instructions for controlling each of the motors of the surgical instrument 600. For example, the memory 644 may include program instructions for controlling the closure motor and the articulation motor. Such program instructions may cause the processor 642 to control the closure and articulation functions in accordance with inputs from algorithms or control programs of the surgical instrument 600.

In certain instances, one or more mechanisms and/or sensors such as, for example, sensors 645 can be employed to alert the processor 642 to the program instructions that should be used in a particular setting. For example, the sensors 645 may alert the processor 642 to use the program instructions associated with closing and articulating the end effector. In certain instances, the sensors 645 may comprise position sensors which can be employed to sense the position of a closure actuator, for example. Accordingly, the processor 642 may use the program instructions associated with closing the end effector to activate the motor of the closure drive assembly 620 if the processor 642 receives a signal from the sensors 630 indicative of actuation of the closure actuator.

In some examples, the motors may be brushless DC electric motors, and the respective motor drive signals may comprise a PWM signal provided to one or more stator windings of the motors. Also, in some examples, the motor drivers may be omitted and the control circuit 601 may generate the motor drive signals directly.

It is common practice during various laparoscopic surgical procedures to insert a surgical end effector portion of a surgical instrument through a trocar that has been installed in the abdominal wall of a patient to access a surgical site located inside the patient's abdomen. In its simplest form, a trocar is a pen-shaped instrument with a sharp triangular point at one end that is typically used inside a hollow tube, known as a cannula or sleeve, to create an opening into the body through which surgical end effectors may be introduced. Such arrangement forms an access port into the body cavity through which surgical end effectors may be inserted. The inner diameter of the trocar's cannula necessarily limits the size of the end effector and drive-supporting shaft of the surgical instrument that may be inserted through the trocar.

Regardless of the specific type of surgical procedure being performed, once the surgical end effector has been inserted into the patient through the trocar cannula, it is often necessary to move the surgical end effector relative to the shaft assembly that is positioned within the trocar cannula in order to properly position the surgical end effector relative to the tissue or organ to be treated. This movement or positioning of the surgical end effector relative to the portion of the shaft that remains within the trocar cannula is often referred to as "articulation" of the surgical end effector. A variety of articulation joints have been developed to attach a surgical end effector to an associated shaft in order to facilitate such articulation of the surgical end effector. As one might expect, in many surgical procedures, it is desirable to employ a surgical end effector that has as large a range of articulation as possible.

Due to the size constraints imposed by the size of the trocar cannula, the articulation joint components must be sized so as to be freely insertable through the trocar cannula. These size constraints also limit the size and composition of various drive members and components that operably interface with the motors and/or other control systems that are supported in a housing that may be handheld or comprise a portion of a larger automated system. In many instances, these drive members must operably pass through the articulation joint to be operably coupled to or operably interface with the surgical end effector. For example, one such drive member is commonly employed to apply articulation control motions to the surgical end effector. During use, the articulation drive member may be unactuated to position the surgical end effector in an unarticulated position to facilitate insertion of the surgical end effector through the trocar and then be actuated to articulate the surgical end effector to a desired position once the surgical end effector has entered the patient.

Thus, the aforementioned size constraints form many challenges to developing an articulation system that can effectuate a desired range of articulation, yet accommodate a variety of different drive systems that are necessary to operate various features of the surgical end effector. Further, once the surgical end effector has been positioned in a desired articulated position, the articulation system and articulation joint must be able to retain the surgical end effector in that position during the actuation of the end effector and completion of the surgical procedure. Such articulation joint arrangements must also be able to withstand external forces that are experienced by the end effector during use.

Various modes of one or more surgical devices are often used throughout a particular surgical procedure. Communication pathways extending between the surgical devices and a centralized surgical hub can promote efficiency and increase success of the surgical procedure, for example. In various instances, each surgical device within a surgical system comprises a display, wherein the display communicates a presence and/or an operating status of other surgical devices within the surgical system. The surgical hub can use the information received through the communication pathways to assess compatibility of the surgical devices for use with one another, assess compatibility of the surgical devices for use during a particular surgical procedure, and/or optimize operating parameters of the surgical devices. As described in greater detail herein, the operating parameters of the one or more surgical devices can be optimized based on patient demographics, a particular surgical procedure, and/or detected environmental conditions such as tissue thickness, for example.

FIGS. 4 and 5 illustrate an exploded view (FIG. 4) and a cross-sectional view (FIG. 5) of an end effector 1200 of an electrosurgical instrument (e.g. surgical instruments described in U.S. patent application Ser. No. 16/885,820, now U.S. Patent Application Publication No. 2021/0196301). For example, the end effector 1200 can be, actuated, articulated, and/or rotated with respect to a shaft assembly of a surgical instrument in a similar manner to end effectors described in U.S. patent application Ser. No. 16/885,820, now U.S. Patent Application Publication No. 2021/0196301. Additionally, the end effectors 1200 and other similar end effectors, which are described elsewhere herein, can be powered by one or more generators of a surgical system. Example surgical systems for use with the surgical instrument are described in U.S. application Ser. No. 16/562,123, filed Sep. 5, 2019, and titled METHOD FOR CONSTRUCTING AND USING A MODULAR SURGICAL ENERGY SYSTEM WITH MULTIPLE DEVICES, which is hereby incorporated herein in its entirety.

Referring to FIGS. 6-8, the end effector 1200 includes a first jaw 1250 and a second jaw 1270. At least one of the first jaw 1250 and the second jaw 1270 is pivotable toward and away from the other jaw to transition the end effector 1200 between an open configuration and a closed configuration. The jaws 1250, 1270 are configured to grasp tissue therebetween to apply at least one of a therapeutic energy and a non-therapeutic energy to the tissue. Energy delivery to the tissue grasped by the jaws 1250, 1270 of the end effector 1200 is achieved by electrodes 1252, 1272, 1274, which are configured to deliver the energy in a monopolar mode, bipolar mode, and/or a combination mode with alternating or blended bipolar and monopolar energies. The different energy modalities that can be delivered to the tissue by the end effector 1200 are described in greater detail elsewhere in the present disclosure.

In addition to the electrodes 1252, 1272, 1274, a patient return pad is employed with the application of monopolar energy. Furthermore, the bipolar and monopolar energies are delivered using electrically isolated generators. During use, the patient return pad can detect unexpected power crossover by monitoring power transmission to the return pad via one or more suitable sensors on the return pad. The unexpected power crossover can occur where the bipolar and monopolar energy modalities are used simultaneously. In at least one example, the bipolar mode uses a higher current (e.g. 2-3 amp) than the monopolar mode (e.g. 1 amp). In at least one example, the return pad includes a control circuit and at least one sensor (e.g. current sensor) coupled thereto. In use, the control circuit can receive an input indicative of an unexpected power crossover based on measurements of the at least one sensor. In response, the control circuit may employ a feedback system to issue an alert and/or pause application of one or both of the bipolar and monopolar energy modalities to tissue.

Further to the above, the jaws 1250, 1270 of the end effector 1200 comprise angular profiles where a plurality of angles are defined between discrete portions of each of the jaws 1250, 1270. For example, a first angle is defined by portions 1250a, 1250b (FIG. 4), and a second angle is defined by portions 1250b, 1250c of the first jaw 1250. Similarly, a first angle is defined by portions 1270a, 1270b, and a second angle is defined by portions 1270b, 1270c of the second jaw 1270. In various aspects, the discrete portions of the jaws 1250, 1270 are linear segments. Consecutive linear segments intersect at angles such as, for example, the first angle, or the second angle. The linear segments cooperate to form a generally angular profile of each of the jaws 1250, 1270. The angular profile is general bent away from a central axis.

In one example, the first angles and the second angles are the same, or at least substantially the same. In another example, the first angles and the second angles are different. In another example, the first angle and the second angle comprise values selected from a range of about 120° to about 175°. In yet another example, the first angle and the second angle comprise values selected from a range of about 130° to about 170°.

Furthermore, the portions 1250a, 1270a, which are proximal portions, are larger than the portions 1250b, 1270b, which are intermediate portions. Similarly, the intermediate portions 1250b, 1270b are larger than the portions 1250c, 1270c. In other examples, the distal portions can be larger than the intermediate and/or proximal portions. In other examples, the intermediate portions are larger than the proximal and/or distal portions.

Further to the above, the electrodes 1252, 1272, 1274 of the jaws 1250, 1270 comprise angular profiles that are similar to the angular profiles of the jaws 1250, 1270. In the example of FIGS. 4, 5, the electrodes 1252, 1272, 1274 include discrete segments 1252a, 1252b, 1252c, 1272a, 1272*b*, 1272*c*, 1274*a*, 1274*b*, 1274*c*, respectively, which define first and second angles at their respective intersections, as described above.

When in the closed configuration, the jaws 1250, 1270 cooperate to define a tip electrode 1260 formed of electrode portions 1261, 1262 at the distal ends of the jaws 1250, 1270, respectively. The tip electrode 1260 can be energized to deliver monopolar energy to tissue in contact therewith. Both of the electrode portions 1261, 1262 can be activated simultaneously to deliver the monopolar energy, as illustrated in FIG. 6 or, alternatively, only one of the electrode portions 1261, 1262 can be selectively activated to deliver the monopolar energy on one side of the distal tip electrode 1260, as illustrated in FIG. 10, for example.

The angular profiles of the jaws 1250, 1270 cause the tip electrode 1260 to be on one side of a plane extending laterally between the proximal portion 1252*c* and the proximal portion 1272*c* in the closed configuration. The angular profiles may also cause the intersections between portions 1252*b*, 1252*c*, portions, 1272*b*, 1272*c*, and portions 1274*b*, 1274*c* to be on the same side of the plane as the tip electrode 1260.

In at least one example, the jaws 1250, 1270 include conductive skeletons 1253, 1273, which can be comprised, or at least partially comprised, of a conductive material such as, for example, Titanium. The skeletons 1253, 1273 can be comprised of other conductive materials such as, for example, Aluminum. In at least one example, the skeletons 1253, 1273 are prepared by injection molding. In various examples, the skeletons 1253, 1273 are selectively coated/ covered with an insulative material to prevent thermal conduction and electrical conduction in all but predefined thin energizable zones forming the electrodes 1252, 1272, 1274, 1260. The skeletons 1253, 1273 act as electrodes with electron focusing where the jaws 1250, 1270 have built-in isolation from one jaw to the other. The insulative material can be an insulative polymer such as, for example, PolyTetraFluoroEthylene (e.g. Teflon®). The energizable zones that are defined by the electrodes 1252, 1272 are on the inside of the jaws 1250, 1270, and are operable independently in a bipolar mode to deliver energy to tissue grasped between the jaws 1250, 1270. Meanwhile, the energizable zones that are defined by the electrode tip 1260 and the electrode 1274 are on the outside of the jaws 1250, 1270, and are operable to deliver energy to tissue adjacent an external surface of the end effector 1200 in a monopolar mode. Both of the jaws 1250, 1270 can be energized to deliver the energy in the monopolar mode.

In various aspects, the coating 1264 is a high temperature PolyTetraFluoroEthylene (e.g. Teflon®) coating that is selectively applied to a conductive skeleton yielding selective exposed metallic internal portions that define a three-dimensional geometric electron modulation (GEM) for a focused dissection and coagulation. In at least one example, the coating 1264 comprises a thickness of about 0.003 inches, about 0.0035 inches, or about 0.0025 inches. In various examples, the thickness of the coating 1264 can be any value selected from a range of about 0.002 inches to about 0.004 inches, a range of about 0.0025 inches to about 0.0035 inches, or a range of about 0.0027 inches to about 0.0033 inches. Other thicknesses for the coating 1263 that are capable of three-dimensional geometric electron modulation (GEM) are contemplated by the present disclosure.

The electrodes 1252, 1272, which cooperate to transmit bipolar energy through the tissue, are offset to prevent circuit shorting. As energy flows between the offset electrodes 1252, 1272, the tissue-grasped therebetween is heated generating a seal at the area between electrodes 1252, 1272. Meanwhile, regions of the jaws 1250, 1270 surrounding the electrodes 1252, 1272 provide non-conductive tissue contact surfaces owing to an insulative coating 1264 selectively deposited onto the jaws 1250, 1270 on such regions but not the electrodes 1252, 1272. Accordingly, the electrodes 1252, 1272 are defined by regions of the metallic jaws 1250, 1270, which remain exposed following application of the insulative coating 1264 to the jaws 1250, 1270. While the jaws 1250, 1270 are generally formed of electrically conductive material in this example, the non-conductive regions are defined by the electrically insulative coating 1264.

FIG. 6 illustrates an application of a bipolar energy mode to tissue grasped between the jaws 1250, 1270. In the bipolar energy mode, RF energy flows through the tissue along a path 1271 that is oblique relative to a curved plane (CL) extending centrally, and longitudinally bisecting, the jaws 1250, 1270 such that the electrodes 1252, 1272 are on opposite sides of the curved plane (CL). In other words, the region of tissue that actually receives bipolar RF energy will only be the tissue that is contacting and extending between the electrodes 1252, 1257. Thus, the tissue grasped by the jaws 1250, 1270 will not receive RF energy across the entire lateral width of jaws 1250, 1270. This configuration may thus minimize the thermal spread of heat caused by the application of bipolar RF energy to the tissue. Such minimization of thermal spread may in turn minimize potential collateral damage to tissue that is adjacent to the particular tissue region that the surgeon wishes to weld/seal/coagulate and/or cut.

In at least one example, a lateral gap is defined between the offset electrodes 1252, 1272 in a closed configuration without tissue therebetween. In at least one example, the lateral gap is defined between the offset electrodes 1252, 1272 in the closed configuration by any distance selected from a range of about 0.01 inch to about 0.025 inch, a range of about 0.015 inch to about 0.020 inch, or a range of about 0.016 inch to about 0.019 inch. In at least one example, the lateral gap is defined by a distance of about 0.017 inch.

In the example illustrated in FIGS. 4 and 5, the electrodes 1252, 1272, 1274 comprise gradually narrowing widths as each of the electrodes 1252, 1272, 1274 extends from a proximal end to a distal end. Consequently, the proximal segments 1252*a*, 1272*a*, 1274*a* comprise surface areas that are greater than the intermediate portions 1252*b*, 1272*b*, 1274*b*, respectively. Also, the intermediate segments 1252*b*, 1272*b*, 1274*b* comprise surfaces that are greater than the distal segments 1252*c*, 1272*c*, 1274*c*.

The angular and narrowing profiles of the jaws 1250, 1270 gives the end effector 1200 a bent finger-like shape or an angular hook shape in the closed configuration. This shape permits accurate delivery of energy to a small portion of the tissue using the tip electrode 1260 (FIG. 10) by orienting the end effector 1200 such that the electrode tip 1260 is pointed down toward the tissue. In such orientation, only the electrode tip 1260 is in contact with the tissue, which focuses the energy delivery to the tissue.

Furthermore, as illustrated in FIG. 8, the electrode 1274 extends on an outer surface on a peripheral side 1275 of the second jaw 1270, which affords it the ability effectively separate tissue in contact therewith while the end effector 1200 is in the closed configuration. To separate the tissue, the end effector 1200 is positioned, at least partially, on the peripheral side 1275 that includes the electrode 1274. Activation of the monopolar energy mode through the jaw 1270 cause monopolar energy to flow through the electrode 1274 into the tissue in contact therewith.

FIGS. 9-11 illustrate an end effector 1200' in use to deliver bipolar energy to tissue through electrodes 1252', 1272' (FIG. 9) in a bipolar energy mode of operation, to deliver monopolar energy to tissue through the electrode tip 1261 in a first monopolar mode of operation, and/or to deliver monopolar energy to tissue through the external electrode 1274 in a second monopolar mode of operation. The end effector 1200' is similar in many respects to the end effector 1200. Accordingly, various features of the end effector 1200' that are previously described with respect to the end effector 1200 are not repeated herein in the same level of detail for brevity.

The electrodes 1252', 1272' are different from the electrodes 1252", 1272" in that they define stepped, or uneven, tissue contacting surfaces 1257, 1277. Electrically conductive skeletons 1253', 1273' of the jaws 1250', 1270' include bulging, or protruding, portions that form the conductive tissue contacting surfaces of the electrodes 1252', 1272'. The coating 1264 partially wraps around the bulging, or protruding portions, that form the electrodes 1252', 1272', only leaving exposed the conductive tissue contacting surfaces of the electrodes 1252', 1272'. Accordingly, in the example illustrated in FIG. 9, each of the tissue-contacting surfaces 1257, 1277 includes a step comprising a conductive tissue-contacting surface positioned between two insulative tissue-contacting surfaces that gradually descend the step. Said another way, each of the tissue-contacting surfaces 1257, 1277 includes a first partially conductive tissue-contacting surface and a second insulative tissue-contacting surface stepped down with respect to the first partially conductive tissue-contacting surface. Methods for forming the electrodes 1252', 1272' are later described in connection with FIG. 12.

Furthermore, in a closed configuration without tissue therebetween, the offset electrodes 1252', 1272' overlap defining a gap between opposing insulative outer surfaces of the jaws 1250', 1270'. Accordingly, this configuration provides electrode surfaces that are both vertically offset from each other and laterally offset from each other when jaws 1250', 1270' are closed. In one example, the gap is about 0.01 inch to about 0.025 inch. In addition, while overlapping, the electrodes 1252', 1272' are spaced apart by a lateral gap. To prevent circuit shorting, the lateral gap is less than or equal to a predetermined threshold. In one example, the predetermined threshold is selected from a range of 0.006 inch to 0.008 inch. In one example, the predetermined threshold is about 0.006 inch.

Referring again to FIGS. 7, 10, the tip electrode 1260 is defined by uncoated electrode portions 1261, 1262 that are directly preceded by proximal coated portions that are circumferentially coated to allow for tip coagulation and otomy creation from either or both jaws 1250, 1270. In certain examples, the electrode portions 1261, 1262 are covered by spring-biased, or compliant, insulative housings that allow the electrode portions 1261, 1262 to be exposed only when the distal end of the end effector 1200 is pressed against the tissue to be treated.

Additionally, the segments 1274a, 1274b, 1274c define an angular profile extending along the peripheral side 1275 of the jaw 1270. The segments 1274a, 1274b, 1274c are defined by uncoated linear portions protruding from an angular body of the skeleton 1273 on the peripheral side 1275. The segments 1274a, 1274b, 1274c comprise outer surfaces that are flush with an outer surface of the coating 1264 defined on the peripheral side 1275. In various examples, a horizontal plane extends through the segments 1274a, 1274b, 1274c. The angular profile of the electrode 1274 is defined in the horizontal plane such that the electrode 1274 does not extend more than 45 degrees off a curvature centerline to prevent unintended lateral thermal damage while using the electrode 1274 to dissect or separate tissue.

Figure 14:
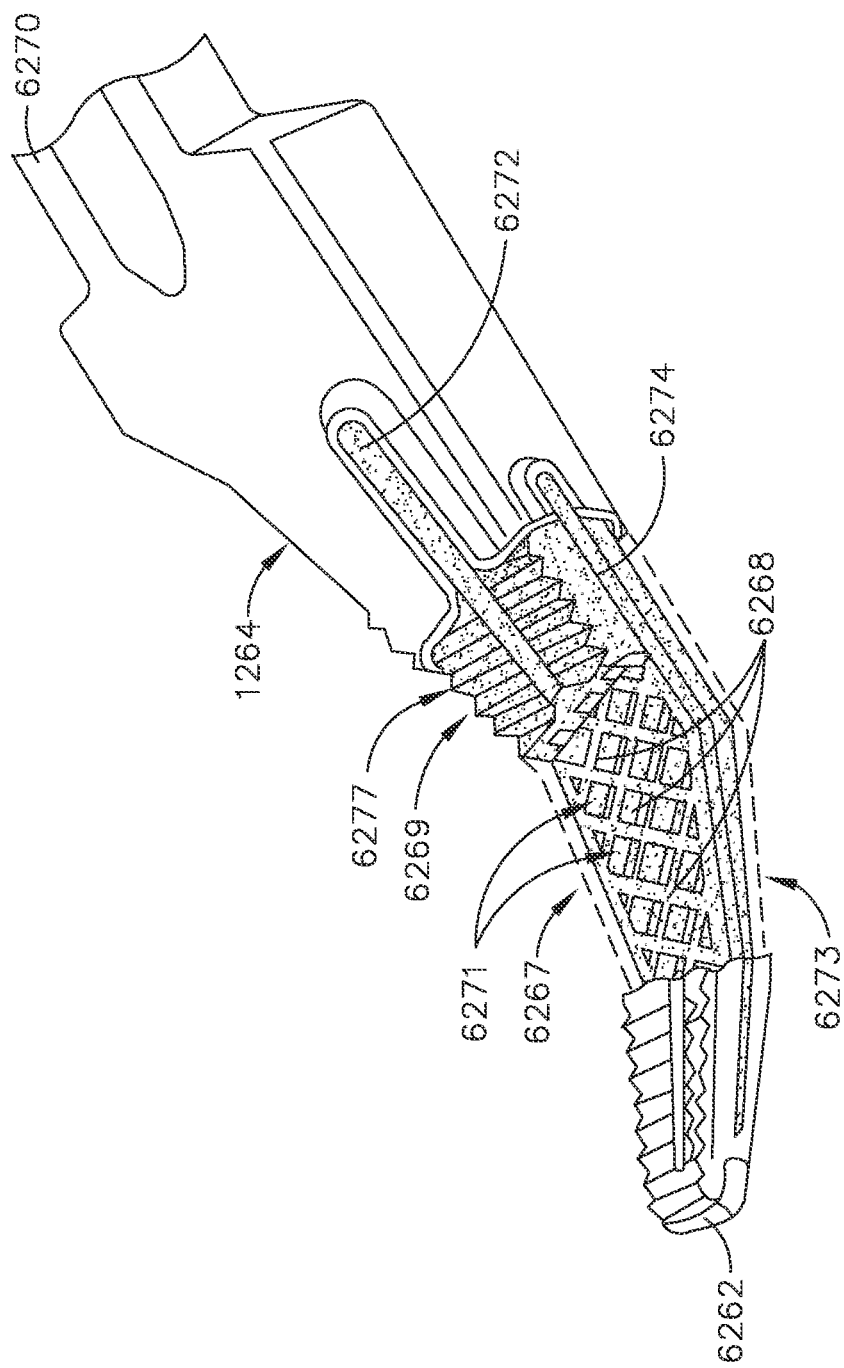
FIG. 14 illustrates a partial perspective view of a jaw of an end effector of an electrosurgical instrument, in accordance with at least one aspect of the present disclosure.

FIG. 14 illustrates a jaw 6270 for use with an end effector (e.g. 1200) of an electrosurgical instrument (e.g. electrosurgical instrument 1106) to treat tissue using RF energy. Further, the jaw 6270 is electrically couplable to a generator (e.g. generator 1100), and is energizable by the generator to deliver a monopolar RF energy to the tissue and/or cooperate with another jaw of the end effector to deliver a bipolar RF energy to the tissue. In addition, the jaw 6270 is similar in many respects to the jaws 1250, 1270. For example, the jaw 6270 comprises an angular profile that is similar to the angular profile of the jaw 1270. In addition, the jaw 6270 presents a thermal mitigation improvement that can be applied to one or both of the jaws 1250, 1270.

In use, jaws of an end effector of an electrosurgical instrument are subjected to a thermal load that can interfere with the performance of their electrode(s). To minimize the thermal load interference without negatively affecting the electrode(s) tissue treatment capabilities, the jaw 6270 includes an electrically conductive skeleton 6273 that has a thermally insulative portion and a thermally conductive portion integral with the thermally insulative portion. The thermally conductive portion defines a heat sink and the thermally insulative portion resists heat transfer. In certain examples, the thermally insulative portion includes inner gaps, voids, or pockets that effectively isolate the thermal mass of the outer surfaces of the jaw 6270 that are directly in contact with the tissue without compromising the electrical conductivity of the jaw 6270.

In the illustrated example, the thermally conductive portion defines a conductive outer layer 6269 that surrounds, or at least partially surrounds, an inner conductive core. In at least one example, the inner conductive core comprises gap-setting members, which can be in the form of pillars, columns, and/or walls extending between opposite sides of the outer layer 6269 with gaps, voids, or pockets extending between the gap setting members.

In at least one example, the gap-setting members form honeycomb-like lattice structures 6267 to provide directional force capabilities as the jaws (i.e. the jaw 6270 and another jaw of the end effector) are transitioned into a closed configuration to grasp tissue therebetween (similar to the jaws 1250, 1270 of FIG. 6). The directional force can be accomplished by aligning the lattices 6267 in a direction that intersects the tissue-contacting surface of the jaw 6270 such that their honeycomb walls 6268 are positioned perpendicularly with respect to the tissue-contacting surface.

Alternatively, or additionally, the conductive inner core of jaw 6270 may include micro pockets of air, which could be more homogeneously distributed and shaped with no predefined organization relative to exterior shape of the jaw to create a more homogeneous stress-strain distribution within the jaw. In various aspects, the electrically conductive skeleton 6273 can be prepared by three-dimensional printing, and may include three dimensionally printed interior pockets that produce electrically conductive but proportionally thermally insulated cores.

Referring still to FIG. 14, the electrically conductive skeleton 6273 is connectable to an energy source (e.g. generator 1100), and comprises electrodes 6262, 6272, and 6274 that are defined on portions of the outer layer 6273 that are selectively not covered by the coating 1264. Accordingly, the jaw 6270 selective thermal and electrical conductivity that controls/focuses energy interaction with tissue through the electrodes 6272, 6274, while reducing thermal spread and thermal mass. The thermally insulated portions of the conductive skeleton 6273 limit the thermal load on the electrodes 6262, 6272, and 6274 during use.

Furthermore, the outer layer 6273 defines gripping features 6277 that extend on opposite sides of the electrode 6272, and are at least partially covered by the coating 1264. The gripping features 6277 improve the ability of the jaw 6270 to adhere to tissue, and resist tissue slippage with respect to the jaw 6270.

In the illustrated examples, the walls 6268 extend diagonally from a first lateral side of the jaw 6270 to a second lateral side of the jaw 6270. The walls 6268 intersect at structural nodes. In the illustrated example, intersecting walls 6268 define pockets 6271 that are covered from the top and/or bottom by the outer layer 6269. Various methods for manufacturing the jaw 6270 are described below.

FIGS. 12, 13 illustrate methods 1280, 1281 for manufacturing jaws 1273", 1273'". In various examples, one more of the jaws 1250, 1270, 1250', 1270' are manufactured in accordance with the methods 1280, 1281. The jaws 1273", 1273'" are prepared by applying a coating 1264 (e.g. with a thickness d) to their entire external surfaces. Then, electrodes are defined by selectively removing portions of the coating 1264 from desired zones to expose the external surface of the skeletons 1273", 1273'" at such zones. In at least one example, selective removal of the coating can be performed by etching (FIG. 12) or by partially cutting away (FIG. 13) tapered portions of the skeleton 1273'" along with their respective coating portions to form flush conductive and non-conductive surfaces. In the example illustrated FIG. 12, electrodes 1272", 1274" are formed by etching. In the example illustrated FIG. 13, an electrode 1274'" is formed from a raised narrow band or ridge 1274d extending alongside the skeleton 1273'". A portion of the ridge 1274D and the coating 1264, directly covering the ridge 1274D, are cut away yielding an external surface of the electrode 1274'" that is flush with an external surface of the coating 1264.

Accordingly, a jaw 1270'" manufactured by the method 1281 includes a tapered electrode 1274'" that is comprised of narrow raised electrically conductive portion 1274e extending alongside the skeleton 1273'", which can help focus the energy delivered from the skeleton 1273'" to the tissue, wherein the portion 1274e has a conductive external surface that is flush with the coating 1264.

Figure 15:
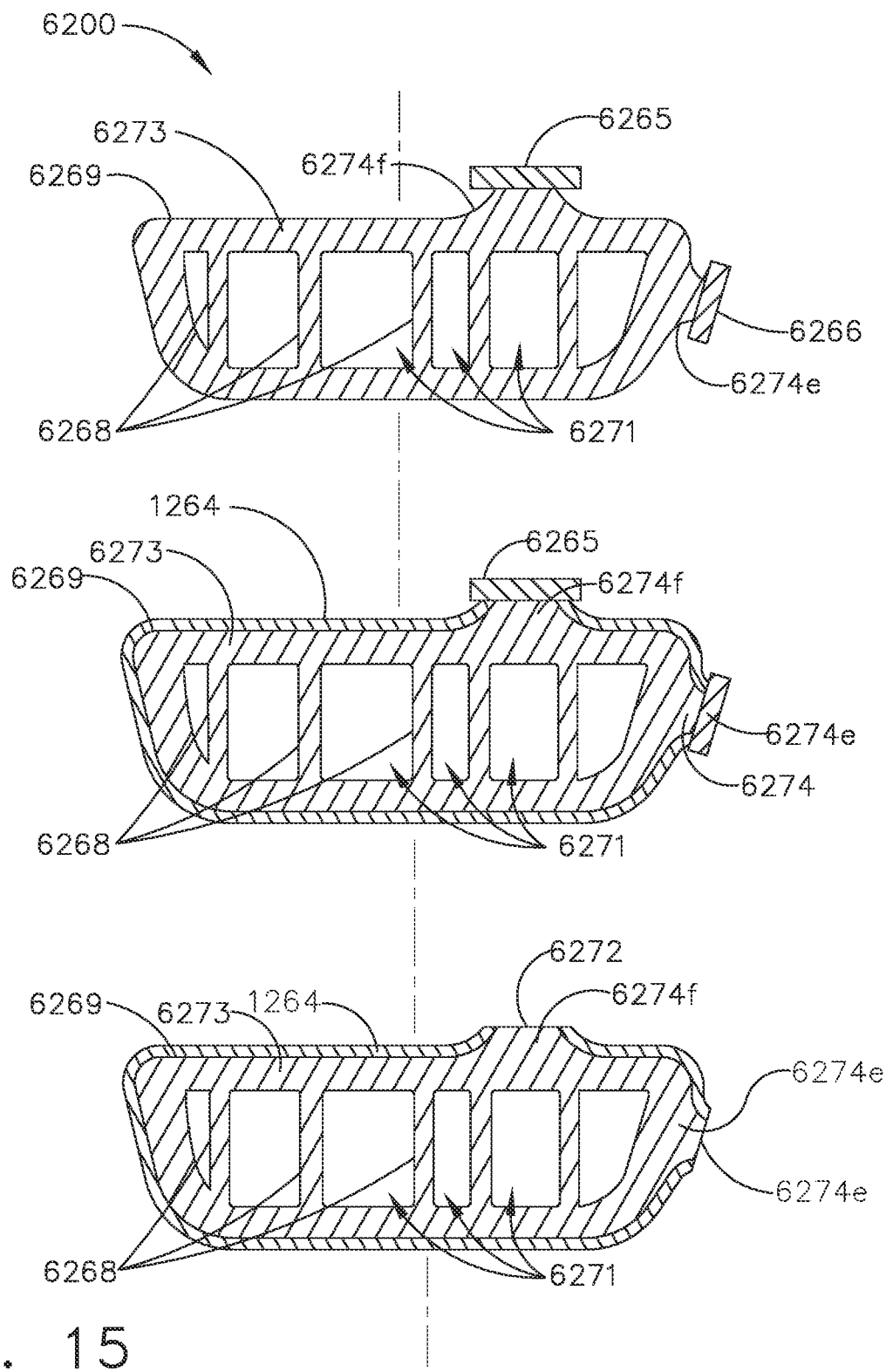
FIG. 15 illustrates steps of a process of manufacturing the jaw of FIG. 14.

In another manufacturing process 6200, the jaw 6270 can be prepared as depicted in FIG. 15. The electrically conductive skeleton 6273 is formed with narrow raised bands or ridges 6274e, 6274f that define the electrodes 6272, and 6274. In the illustrated example, the skeleton 6273 of the jaw 6270 includes ridges 6274e, 6274f, with flat, or at least substantially flat, outer surfaces that are configured to define the electrodes 6272, 6274. In at least one example, the skeleton 6273 is prepared by 3D printing. Masks 6265, 6266 are applied to the ridges 6274e, 6274f, and a coating 1264, which is similar to the coating 1264, is applied to the skeleton 6273. After coating, the masks 6265, 6266 are removed exposing outer surfaces of the electrodes 6272, 6274 that are flush with the outer surface of the coating 1264.

Referring to FIGS. 14 and 15, in various examples, the outer layer 6269 comprises gripping features 6277 extending laterally on one or both sides of each of the electrode 6272. The gripping features 6277 are covered by the coating 1264. In one example, the coating 1264 defines compressible features causing the gap between the jaws of an end effector to vary depending on clamping loads applied to the end effector 1200. In at least one example, the coating 1264 on the jaws yields at least a 0.010"-0.020" overlap of insulation along the centerline of the jaws. The coating 1264 could be applied directly over the gripping features 6277 and/or clamp induced jaw re-alignment features.

In various aspects, the coating 1264 may comprise coating materials such as Titanium Nitride, Diamond-Like coating (DLC), Chromium Nitride, Graphit iC™, etc. In at least one example, the DLC is comprised of an amorphous carbon-hydrogen network with graphite and diamond bondings between the carbon atoms. The DLC coating 1264 can form films with low friction and high hardness characteristics around the skeletons 1253, 1273 (FIG. 6). The DLC coating 1264 can be doped or undoped, and is generally in the form of amorphous carbon (a-C) or hydrogenated amorphous carbon (a-C:H) containing a large fraction of sp3 bonds. Various surface coating technologies can be utilized to form the DLC coating 1264 such as the surface coating technologies developed by Oerlikon Balzers. In at least one example, the DLC coating 1264 is generated using Plasma-assisted Chemical Vapor Deposition (PACVD).

Referring still to FIG. 15, in use, electrical energy flows from the electrically conductive skeleton 6269 to tissue through the electrode 6272. The coating 1264 prevents transfer of the electrical energy to the tissue from other regions of the outer layer 6269 that are covered with the coating 1264. As the surface of the electrode 6272 increases in temperature during a tissue treatment, the thermal energy transfer from the outer layer 6269 to the inner core of the skeleton 6273 is slowed down, or dampened, due to the gaps, voids, or pockets defined by the walls 6268 of the inner core.

Figure 16:
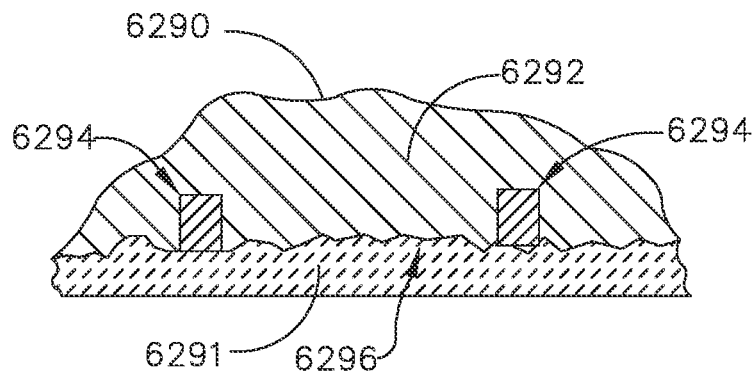
FIG. 16 illustrates steps of a process of manufacturing the jaw of FIG. 14.

FIG. 16 illustrates a skeleton 6290 manufactured for use with a jaw of an end effector of an electrosurgical instrument. One more of the skeletons 1253, 1273, 1253', 1273', 1273", 1273'" can comprise a material composition and/or can be manufactured in a similar manner to the skeleton 6290. In the illustrated example, the skeleton 6290 is comprised of at least two materials: an electrically conductive material such as, for example, Titanium, and a thermally insulative material such as, for example, a ceramic material (e.g. Ceramic Oxide). The Titanium and Ceramic Oxide combination yields jaw components with composite thermal, mechanical, and electrical properties.

In the illustrated example, the composite skeleton 6290 comprises a ceramic base 6291 formed by three-dimensional printing, for example. Additionally, the composite skeleton 6290 includes a titanium crown 6292 prepared separately from the ceramic base 6291 using, for example, three-dimensional printing. The base 6291 and the crown 6292 include complementing attachment features 6294. In the illustrated example, the base 6291 includes posts or projections that are received in corresponding apertures of the crown 6292. The attachment features 6294 also control shrinking. Additionally, or alternatively, contacting surfaces of the base 6291 and the crown 6292 include complementing surface irregularities 6296 specifically design for a mating engagement with one another. The surface irregularities 6296 also resist shrinking caused by the different material compositions of the base 6291 and the crown 6292. In various examples, the composite skeleton 6290 is selectively coated with an insulative coating 1264 leaving exposed certain portions of the crown 6292, which define electrodes, as described above in connection with the jaws 1250, 1270, for example.

Figure 17:
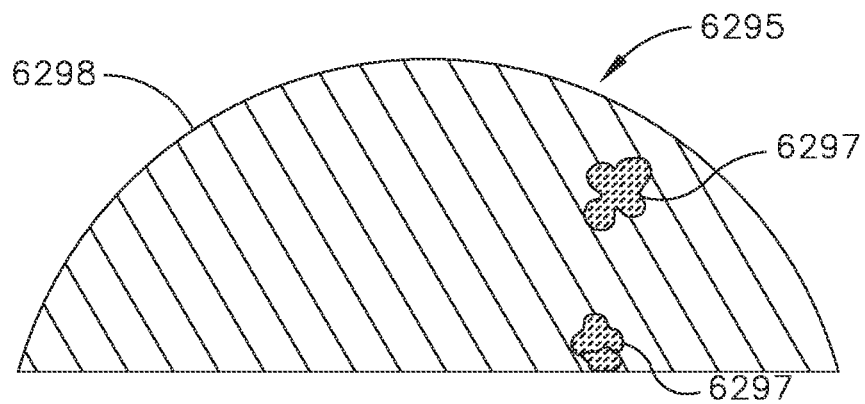
FIGS. 17-19 illustrates steps of a process of manufacturing the jaw of FIG. 14.
Figure 18:
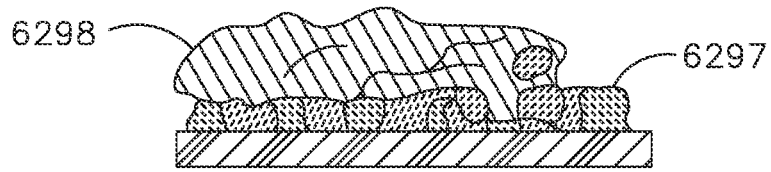
Figure 19:

FIGS. 17 and 18 illustrate a manufacturing process for making a skeleton 6296 for use with a jaw of an end effector of an electrosurgical instrument. One more of the skeletons 1253, 1273, 1253', 1273', 1273", 1273''' can comprise a material composition and/or can be manufactured in a similar manner to the skeleton 6295. In the illustrated example, the composite skeleton 6295 is produced by injection molding utilizing a ceramic powder 6297 and a titanium powder 6298. The powders are fused together (FIG. 18) to form the titanium-ceramic composite 6299 (FIG. 19). In at least one example, a PolyTetraFluoroEthylene (e.g. Teflon®) coating can be selectively applied to the metallic regions of the composite skeleton 6295 for thermal insulation as well as electrical insulation.

FIGS. 20-22 illustrate a jaw 1290 for use with an end effector (e.g. 1200) of an electrosurgical instrument (e.g. electrosurgical instrument 1106) to treat tissue using RF energy. Further, the jaw 6270 is electrically couplable to a generator (e.g. generator 1100), and is energizable by the generator to deliver a monopolar RF energy to the tissue and/or cooperate with another jaw of the end effector to deliver a bipolar RF energy to the tissue. In addition, the jaw 1290 is similar in many respects to the jaws 1250, 1270. For example, the jaw 1290 comprises an angular profile that is similar to the angular or curved profile of the jaw 1270.

In addition, the jaw 1290 is similar to the jaw 6270 in that the jaw 1290 also presents a thermal mitigation improvement. Like the jaw 6270, the jaw 1290 includes a conductive skeleton 1293 that has a thermally insulative portion and a thermally conductive portion integral with, or attached to, the thermally insulative portion. The thermally conductive portion defines a heat sink and the thermally insulative portion resists heat transfer. In certain examples, the thermally insulative portion of the conductive skeleton 1293 comprises a conductive inner core 1297 with inner gaps, voids, or pockets that effectively isolate the thermal mass of the outer surface of the jaw 1290, which defines an electrode 1294 that is directly in contact with the tissue, without compromising the electrical conductivity of the jaw 1290. The thermally conductive portions define a conductive outer layer 1303 that surrounds, or at least partially surrounds, the conductive inner core 1297. In at least one example, the conductive inner core 1297 comprises gap-setting members 1299, which can be in the form of pillars, columns, and/or walls extending between opposite sides of the outer layer 1303 of the jaw 1290 with gaps, voids, or pockets extending between the gap setting members.

Alternatively, or additionally, the conductive inner core 1297 may include micro pockets of air, which could be homogeneously, or non-homogenously, distributed in the conductive inner core 1297. The pockets can comprise predefined, or random shapes, and can be dispersed at predetermined, or random, portions of the conductive inner core 1297. In at least one example, the pockets are dispersed in a manner that creates a more homogeneous stress-strain distribution within the jaw 1290. In various aspects, the skeleton 1293 can be prepared by three-dimensional printing, and may include three dimensionally printed interior pockets that produce electrically conductive but proportionally thermally insulated cores.

Accordingly, the jaw 1290 comprises selective thermal and electrical conductivity that controls/focuses the energy interaction with tissue, while reducing thermal spread and thermal mass. The thermally insulated portions of the conductive skeleton 1293 limit the thermal load on the electrodes of the jaw 1290 during use.

FIG. 22 illustrates an expanded portion of a tissue-contacting surface 1291 of the jaw 1290. In various aspects, the outer layer 1303 of the skeleton 1293 is selectively coated/covered with a first insulative layer 1264 comprising a first material such as, for example, DLC. In the illustrated example, the DLC coating causes the tissue-contacting surface 1291 to be electrically insulated except an intermediate area extending along a length of the tissue-contacting surface 1291, which defines the electrode 1294. In at least one example, the DLC coating extends around the skeleton 1293 covering the jaw 1290 up to perimeters defined on opposite sides 1294', 1294" of the electrode 1294. Conductive zones 1294a, 1294b, 1294c remain exposed, and alternate with insulative zones 1298 along a length of the electrode 1294. In various aspects, the insulative zones 1298 comprise a high temperature PolyTetraFluoroEthylene (e.g. Teflon®). Since the DLC coating is thermally conductive, only the portions of the tissue-contacting surface 1291 that comprise the insulative regions 1298 are thermally insulated. The portions of the issue-contacting surface 1291 that are covered with the DLC coating and the thin conductive energizable zones 1294a, 1294b, 1294c are thermally conductive. Further, only the thin conductive energizable zones 1294a, 1294b, 1294c are electrically conductive. The remaining portions of the tissue-contacting surface 1291, which are covered with either the DLC coating or the PolyTetraFluoroEthylene (e.g. Teflon®), are electrically insulated.

The conductive zones 1294a, 1294b, 1294c define energy concentration locations along the jaw 1290 based on the geometry of the zones 1294a, 1294b, 1294c. Further, the size, shape, and arrangement of the conductive zones 1294a, 1294b, 1294c and insulative zones 1298 causes coagulation energy transmitted through the electrode 1294 to be directed into the tissue in predefined treatment regions thereby preventing parasitic leaching of both the energy and heat from the treatment regions. Furthermore, the thermally insulative conductive inner core 1297 resists heat transfer to portions of the jaw 1290 that do not form treatment regions, which prevents inadvertent collateral thermal damage by incidental contact of tissue with non-treatment areas of the jaw 1290.

The electrode 1294 is selectively interrupted by the regions 1298. Selective application of the high temperature PolyTetraFluoroEthylene (e.g. Teflon®) coating to portions of the electrode 1294 yields selectively exposed metallic internal portions that define a three-dimensional geometric electron modulation (GEM) for a focused dissection and coagulation at the conductive zones 1294a, 1294b, 1294c of the electrode 1294. The regions 1298 are selectively deposited onto the electrode 1294, as illustrated in FIG. 22, yielding a treatment surface with alternating thermally and electrically conductive regions and thermally and electrically insulative regions surrounded by a thermally conductive but electrically insulative outer perimeter region defined by the DLC coating.

Referring to FIG. 22, the jaw 1290 comprises an angular profile where a plurality of angles are defined between discrete portions 1290a, 1290b, 1290c, 1290d of the jaw 1290. For example, a first angle ($\alpha 1$) is defined by portions 1290a, 1290b, a second angle ($\alpha 2$) is defined by portions 1290b, 1290c, and a third angle ($\alpha 3$) is defined by portions 1290c, 1290d of the first jaw 1250. In other examples, at least a portion of a jaw 1290 comprises a smooth curved profile with no angles. In various aspects, the discrete portions 1290a, 1290b, 1290c, 1290d of the jaw 1290 are linear segments. Consecutive linear segments intersect at angles such as, for example, the first angle ($\alpha 1$), or the second angle (α2), and the third angle (α3). The linear segments cooperate to form a generally curved profile of each of the jaw 1290.

In one example, the angles (α1, α2, α3) comprise the same, or at least substantially the same, values. In another example, at least two of the angles (α1, α2, α3) comprise different values. In another example, at least one of the angles (α1, α2, α3) comprises a value selected from a range of about 120° to about 175°. In yet another example, at least one of the angles (α1, α2, α3) comprises a value selected from a range of about 130° to about 170°.

Furthermore, due to the gradually narrowing profile of the jaw 1290, the portion 1290*a*, which is a proximal portion, is larger than the portion 1290*b*, which is an intermediate portion. Similarly, the intermediate portion 1290*b* is larger than the portion 1290*d* that defines a distal portion of the jaw 1290. In other examples, the distal portion can be larger than the intermediate and/or proximal portions. In other examples, the intermediate portion is larger than the proximal and/or distal portions. In addition, the electrode 1294 of the jaw 1290 comprises an angular profile that is similar to the angular profile of the jaw 1290.

Referring to FIG. 23, in certain aspects, a jaw 1300 includes a solid conductive skeleton 1301 that is partially surrounded by a DLC coating 1264. The exposed regions of the skeleton 1301 define one or more electrodes 1302. This arrangement yields a thermally conductive and electrically conductive portion of the jaw 1300, wherein the thermal energy is delivered indiscriminately, but the electrical energy is exclusively delivered through the one or more electrodes 1302.

Figure 26:
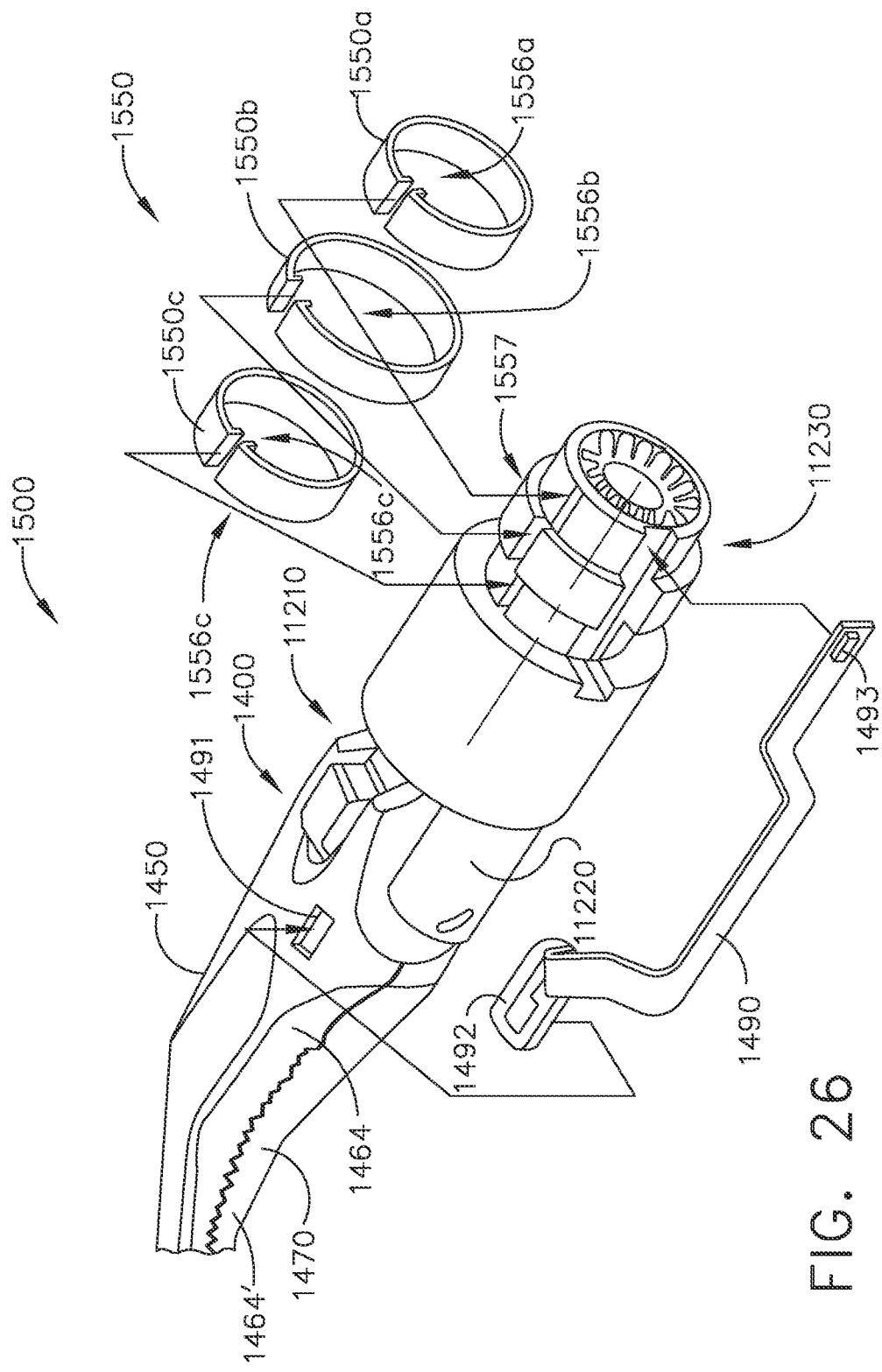
FIG. 26 illustrates a partial exploded view of an end effector of an electrosurgical instrument, in accordance with at least one aspect of the present disclosure.

Referring now to FIGS. 24-26, an electrosurgical instrument 1500 includes an end effector 1400 configured to deliver monopolar energy and/or bipolar energy to tissue grasped by the end effector 1400, as described in greater detail below. The end effector 1400 is similar in many respects to the end effector 1200. For example, the end effector 1400 includes a first jaw 1450 and a second jaw 1470. At least one of the first jaw 1450 and the second jaw 1470 is movable relative to the other jaw to transition the end effector 1400 from an open configuration to a closed configuration to grasp the tissue therebetween. The grasped tissue can then be sealed and/or cut using monopolar and bipolar energies. As described below in greater details, the end effector 1400 utilizes GEM to adjust energy densities at a tissue treatment interface of the jaws 1450, 1470 to effect a desired tissue treatment.

Like the jaws 1250, 1270, the jaws 1450, 1470 include generally angular profiles formed from linear portions that are angled with respect to one another, yielding a bent or finger-like shape, as illustrated in FIG. 26. Furthermore, the jaws 1450, 1470 include conductive skeletons 1452, 1472 that have narrowing angular bodies extending distally along the angular profile of the jaws 1450, 1470. The conductive skeletons 1452, 1472 can be comprised of a conductive material such as, for example, Titanium. In certain aspects, each of the conductive skeletons 1453, 1473 comprise a thermally insulative portion and a thermally conductive portion integral with the thermally insulative portion. The thermally conductive portion defines a heat sink and the thermally insulative portion resists heat transfer. In certain examples, the thermally insulative portions of the skeletons 1453, 1473 define inner cores comprising inner gaps, voids, or pockets that effectively isolate the thermal mass of the outer surfaces of the jaws 1452, 1472 that are directly in contact with the tissue without compromising the electrical conductivity of the jaws 1450, 1470.

The thermally conductive portions comprise conductive outer layers 1469, 1469' that surround, or at least partially surround, the inner conductive cores. In at least one example, the inner conductive cores comprise gap-setting members, which can be in the form of pillars, columns, and/or walls extending between opposite sides of the outer layers 1469, 1469' of each of the jaws 1250, 1270 with gaps, voids, or pockets extending between the gap setting members. In at least one example, the gap-setting members form honeycomb-like lattice structures 1467, 1467'.

Further to the above, the conductive skeletons 1453, 1473 include first conductive portions 1453*a*, 1473*a* extending distally along the angular profile of the jaws 1450, 1470 and second conductive portions 1453*b*, 1473*b* defining a tapered electrodes protruding from the first conductive portions 1453*a*, 1473*a* and extending distally along at least a portion of the gradually narrowing body of the skeletons 1453, 1473. In at least on example, the first conductive portions 1453*a*, 1473*a* are thicker than the second conductive portions 1453*b*, 1473*b* in a transverse cross-section (e.g. FIG. 25) of the gradually narrowing bodies of the skeletons 1453, 1473. In at least one example, the second conductive portions 1453*b*, 1473*b* are integral with, or permanently attached to, the first conductive portions 1453*a*, 1473*a* such that electrical energy flows from the first conductive portions 1453*a*, 1473*a* to the tissue only through the second conductive portions 1453*b*, 1473*b*. Electrically insulative layers 1464, 1464' are configured to completely electrically insulate the first conductive portions 1453*a*, 1473*a* but not the second conductive portions 1453*b*, 1473*b*. At least outer surfaces of the second conductive portions 1453*b*, 1473*b*, which define electrodes 1452, 1472, are not covered by the electrically insulative layers 1464, 1464'. In the illustrated example, the electrodes 1452, 1472 and the electrically insulative layers 1464, 1464' define flush tissue treatment surfaces.

As described above, the first conductive portions 1453*a*, 1473*a* are generally thicker than the second conductive portions 1453*b*, 1473*b*, and are wrapped with the electrically insulative layers 1464, 1464', which causes the second conductive portions 1453*b*, 1473*b* to become high energy density areas. In at least one example, the electrically insulative layers 1464, 1464' are comprised of high temperature PolyTetraFluoroEthylene (e.g. Teflon®) coatings, DLC coatings, and/or ceramic coatings for insulation and resistance to char sticking. In various examples, the thicker first conductive portion 1453*a* conducts more potential power with a smaller resistance to the tissue-contacting second conductive portion 1453*b* yielding the higher energy density at the electrode 1452.

In various aspects, the outer surfaces of the electrodes 1452, 1472 include consecutive linear segments that extend along angled tissue treatment surfaces of the jaws 1450, 1470. The linear segments intersect at predefined angles, and comprise widths that gradually narrow as the linear segments extend distally. In the example illustrated in FIG. 24, the electrode 1452 includes segments 1452*a*, 1452*b*, 1452*c*, 1452*c*, 1452*d*, and the electrode 1472 includes segments 1472*a*, 1472*b*, 1472*c*, 1472*c*, 1472*d*. The electrode 1452 of the jaw 1450 is illustrated by dashed lines on the jaw 1470 of FIG. 24 to show the lateral position of the electrode 1452 with respect to the electrode 1452 in a closed configuration of the end effector 1400. The electrodes 1452, 1472 are laterally offset from one another in the closed configuration. In a bipolar energy mode, the electrical energy supplied by the generator (e.g. generator 1100) flows from the first conductive portion 1453*a* to the electrode 1452 of the second conductive portion 1453b, and from the electrode 1452 to the tissue grasped between the jaws 1450, 1470. The bipolar energy then flows from the tissue to the electrode 1472 of the second conductive portion 1473b, and from the electrode 1472 to the first conductive portion 1473a.

In various aspects, as illustrated in FIGS. 24, 25, the second jaw 1470 further includes an electrode 1474 spaced apart from the skeleton 1473. In at least one example, the electrode 1474 is a monopolar electrode configured to deliver monopolar energy to the tissue grasped between the jaws 1450, 1470 in the closed configuration. A return pad can be placed under the patient, for example, to receive the monopolar energy from the patient. Like the electrode 1472, the electrode 1474 includes consecutive linear segments 1474a, 1474b, 1474c, 1474d that extend distally along the angular profile defined by the second jaw 1470 from an electrode proximal end to an electrode distal end. Further, the electrode 1474 is laterally offset from the electrodes 1472, 1452.

The electrode 1474 includes a base 1474e positioned in a cradle 1480 extending distally along the angular profile of the second jaw 1470 from a cradle proximal 1480a and to a cradle distal end 1480b. The cradle 1480 is centrally situated with respect to lateral edges 1470e, 1470f of the second jaw 1470. The electrode 1474 further comprises a tapered edge 1474f extending from the base 1474e beyond sidewalls of the cradle 1480. In addition, the cradle 1480 is partially embedded in a valley defined in an outer tissue-treatment surface of the narrowing curved body. The cradle 1480 is spaced apart from the gradually narrowing body of the skeleton 1473 by the electrically insulative coating 1464'. As illustrated in FIG. 24, the base 1480 comprises widths that gradually narrow as the base extends along the angular profile from a base proximal end 1480a to a base distal end 1480b.

In various examples, the cradle 1480 is comprised of a compliant substrate. In an uncompressed state, as illustrated in FIG. 25, the sidewalls of the cradle 1480 extend beyond a tissue treatment surface of the jaw 1472. When tissue is compressed between the jaws 1450, 1470, the compressed tissue applies a biasing force against the sidewalls of the cradle 1480 further exposing the tapered edge 1474f of the electrode 1474.

One or more of the jaws described by the present disclosure include stop members or gap-setting members, which are features extending outwardly from one or both of the tissue treatment surfaces of the jaws of an end effector. The stop members help maintain a separation or a predetermined gap between the jaws in a closed configuration with no tissue between the jaws. In at least one example, the sidewalls of the cradle 1480 define such stop members. In another example, the stop members can be in the form of insulative pillars or laterally extending spring-biased features that allow the gap between opposing jaws and the closed configuration to vary based on clamping loads.

Most electrosurgery generators use constant power modes. With constant power modes, the power output remains constant as impedance increases. In constant power modes, the voltage increases as the impedance increases. Increased voltage causes thermal damage to tissue. GEM focuses the energy output of the jaws 1250, 1270, for example, by controlling the size and shape of the electrodes 1252, 1272, 1274, 1260, 1294, 1472, 1452, 1474, as described above, and modulating the power level based on tissue impedance to create a low voltage plasma.

In certain instances, GEM maintains a constant minimum voltage required for cutting at the surgical site. The generator (e.g. 1100) modulates the power in order to maintain the voltage as close as possible to the minimum voltage required for cutting at the surgical site. In order to obtain an arc plasma and cut, current is pushed by voltage from gradually narrowing portions of the electrodes 1252, 1272, 1274, 1260, 1294, 1472, 1452, 1474, to the tissue. In certain examples, a minimum voltage of approximately 200 Volts is maintained. Cutting with greater than 200 Volts increases thermal damage and cutting with less than 200 Volts results in minimal arcing and drag in the tissue. Accordingly, the generator (e.g. 1100) modulates the power to ensure utilizing the minimum voltage possible that will still form an arc plasma and cut.

Referring primarily to FIG. 26, a surgical instrument 1500 includes the end effector 1400. The surgical instrument 1500 is similar in many respects to other surgical instruments described in U.S. patent application Ser. No. 16/885,820, now U.S. Patent Application Publication No. 2021/0196301. Various actuation and articulation mechanisms described elsewhere in connection with such surgical instruments could be similarly utilized to articulate and/or actuate the surgical instrument 1500. For brevity, such mechanisms are not repeated herein.

The end effector 1400 comprises an end effector frame assembly 11210 that comprises a distal frame member 11220 that is rotatably supported in a proximal frame housing 11230. In the illustrated example, the distal frame member 11220 is rotatably attached to the proximal frame housing 11230 by an annular rib on the distal frame member 11220 that is received within an annular groove in the proximal frame housing 11230.

Electrical energy is transmitted to the electrodes 1452, 1472, 1474 of the end effector 1400 by one or more flex circuits extending distally through, or alongside, the distal frame member 11220. In the illustrated example, a flex circuit 1490 is fixedly attached to the first jaw 1450. More particularly, the flex circuit 1490 includes a distal portion 1492 that can be fixedly attached to an exposed portion 1491 of the first jaw 1450, which is not covered by the insulative layer 1464.

A slip ring assembly 1550 within the proximal frame housing 11230 allows free rotation of the end effector 1400 about a shaft of the surgical instrument 1500 without entanglement of the wires of the circuits transmitting electrical energy to the electrodes 1452, 1472, 1474. In the illustrated example, the flex circuit 1490 includes an electrical contact 1493 in movable engagement with a slip ring 1550a of the slip ring assembly 1550. Electrical energy is transmitted from the slip ring 1550a to the conductive skeleton 1453, and then to the electrode 1452, through the flex circuit 1490. Since the electrical contact 1493 is not fixedly attached to the slip ring 1550a, the rotation of the end effector 1400 about the shaft of the surgical instrument 1500 is permissible without losing the electrical connection between the electrical contact 1493 and the slip ring 1550a. Further, a similar electrical contact transmits the electrical energy to the slip ring 1550a.

In the example illustrated in FIG. 26, the slip ring 1550a is configured to transmit bipolar energy to the electrode 1452 of the jaw 1450. A slip ring 1550b cooperates with similar electrical contacts and the electrode 1472 to define a return path for the bipolar energy. In addition, a slip ring 1550c cooperates with similar electrical contacts and the electrode 1474 to provide a pathway for monopolar electrical energy into tissue. The bipolar and monopolar electrical energies can be delivered to the slip rings 1550a, 1550b through one or more electrical generators (e.g. generator 1100). The bipolar and monopolar electrical energies can be delivered simultaneously or separately, as described in greater detail elsewhere herein.

In various examples, the slip rings 1550a, 1550b, 1550c are integrated electrical slip rings with mechanical features 1556a, 1556b, 1556c configured to couple the slip rings 1550a, 1550b, 1550c to an insulative support structure 1557, or a conductive support structure coated with an insulative material, as illustrated in FIG. 26. Furthermore, the slip rings 1550a, 1550b, 1550c are sufficiently spaced apart to ensure that circuit shorting will not occur if a conductive fluid fills the space between the slip rings 1550a, 1550b, 1550c. In at least one example, a core flat stamped metallic shaft member includes a three dimensionally printed, or over-molded, nonconductive portion for supporting the slip ring assembly 1550.

Figure 27:
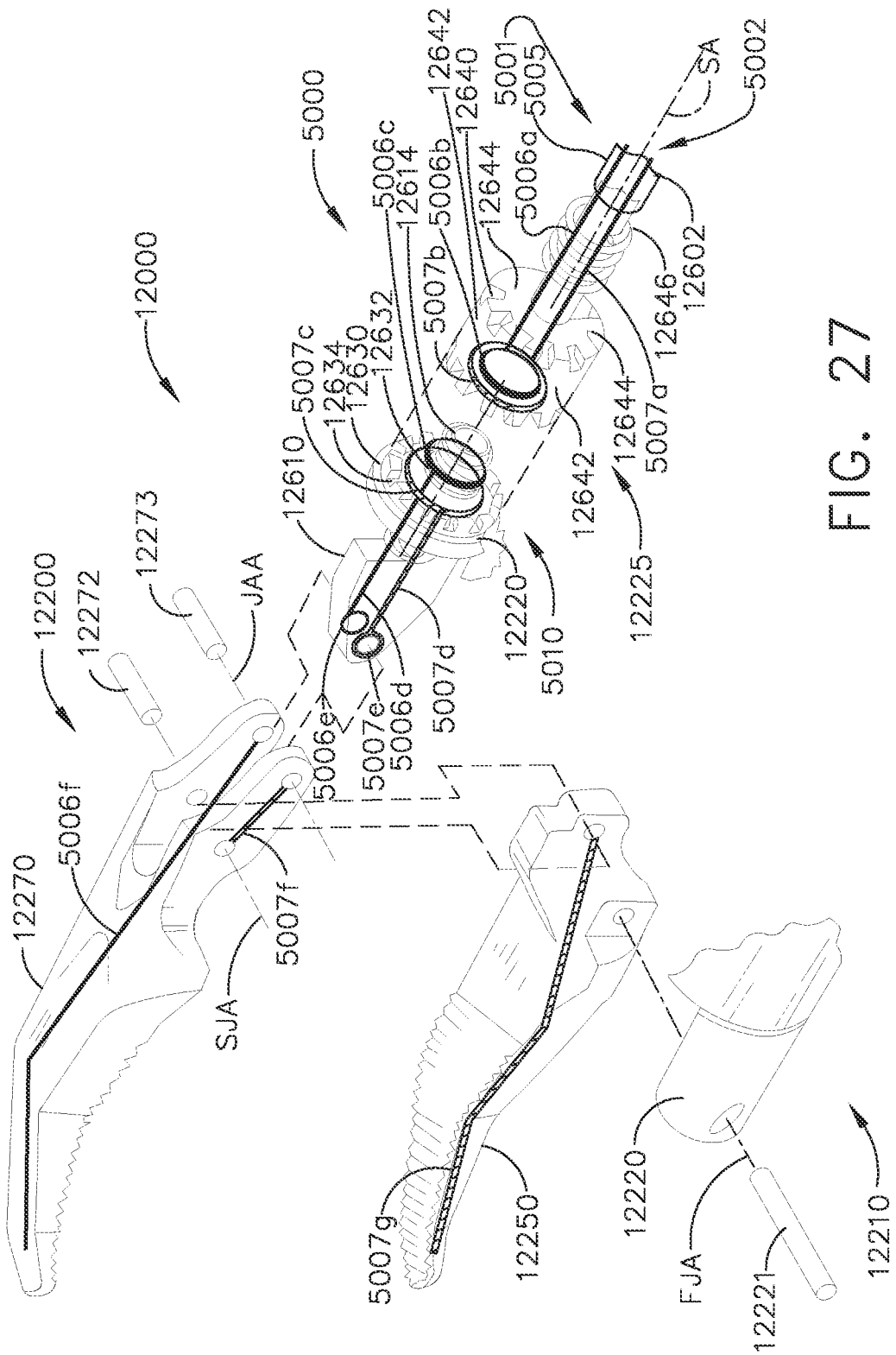
FIG. 27 illustrates an exploded perspective assembly view of a portion of an electrosurgical instrument including an electrical connection assembly, in accordance with at least one aspect of the present disclosure.

FIG. 27 illustrates a portion of an electrosurgical instrument 12000 that comprises a surgical end effector 12200 that may be coupled to a proximal shaft segment by an articulation joint in the various suitable manners. In certain instances, the surgical end effector 12200 comprises an end effector frame assembly 12210 that comprises a distal frame member 12220 that is rotatably supported in a proximal frame housing that is attached to the articulation joint.

The surgical end effector 12200 comprises a first jaw 12250 and a second jaw 12270. In the illustrated example, the first jaw 12250 is pivotally pinned to the distal frame member 12220 for selective pivotal travel relative thereto about a first jaw axis FJA defined by a first jaw pin 12221. The second jaw 12270 is pivotally pinned to the first jaw 12250 for selective pivotal travel relative to the first jaw 12250 about a second jaw axis SJA that is defined by a second jaw pin 12272. In the illustrated example, the surgical end effector 12200 employs an actuator yoke assembly 12610 that is pivotally coupled to the second jaw 12270 by a second jaw attachment pin 12273 for pivotal travel about a jaw actuation axis JAA that is proximal and parallel to the first jaw axis FJA and the second jaw axis SJA. The actuator yoke assembly 12610 comprises a proximal threaded drive shaft 12614 that is threadably received in a threaded bore 12632 in a distal lock plate 12630. The threaded drive shaft 12614 is mounted to the actuator yoke assembly 12610 for relative rotation therebetween. The distal lock plate 12630 is supported for rotational travel within the distal frame member 12220. Thus rotation of the distal lock plate 12630 will result in the axial travel of the actuator yoke assembly 12610.

In certain instances, the distal lock plate 12630 comprises a portion of an end effector locking system 12225. The end effector locking system 12225 further comprises a dual-acting rotary lock head 12640 that is attached to a rotary drive shaft 12602 of the various types disclosed herein. The lock head 12640 comprises a first plurality of radially arranged distal lock features 12642 that are adapted to lockingly engage a plurality of proximally-facing, radial grooves or recesses 12634 that are formed in the distal lock plate 12630. When the distal lock features 12642 are in locking engagement with the radial grooves 12634 in the distal lock plate 12630, rotation of the rotary lock head 12640 will cause the distal lock plate 12630 to rotate within the distal frame member 12220. Also in at least one example, the rotary lock head 12640 further comprises a second series of proximally-facing proximal lock features 12644 that are adapted to lockingly engage a corresponding series of lock grooves that are provided in the distal frame member 12220. A locking spring 12646 serves to bias the rotary lock head distally into locking engagement with the distal lock plate 12630. In various instances, the rotary lock head 12640 may be pulled proximally by an unlocking cable or other member in the manner described herein. In another arrangement, the rotary drive shaft 12602 may be configured to also move axially to move the rotary lock head 12640 axially within the distal frame member 12220. When the proximal lock features 12644 in the rotary lock head 12640 are in locking engagement with the series of lock grooves in the distal frame member 12220, rotation of the rotary drive shaft 12602 will result in rotation of the surgical end effector 12200 about the shaft axis SA.

In certain instances, the first and second jaws 12250, 12270 are opened and closed as follows. To open and close the jaws, as was discussed in detail above, the rotary lock head 12640 is in locking engagement with the distal lock plate 12630. Thereafter, rotation of the rotary drive shaft 12602 in a first direction will rotate the distal lock plate 12630 which will axially drive the actuator yoke assembly 12610 in the distal direction DD and move the first jaw 12250 and the second jaw 12270 toward an open position. Rotation of the rotary drive shaft 12602 in an opposite second direction will axially drive the actuator yoke assembly 12610 proximally and pull the jaws 12250, 12270 toward a closed position. To rotate the surgical end effector 12200 about the shaft axis SA, the locking cable or member is pulled proximally to cause the rotary lock head 12640 to disengage from the distal lock plate 12630 and engage the distal frame member 12220. Thereafter, when the rotary drive shaft 12602 is rotated in a desired direction, the distal frame member 12220 (and the surgical end effector 12200) will rotate about the shaft axis SA.

Figure 36:
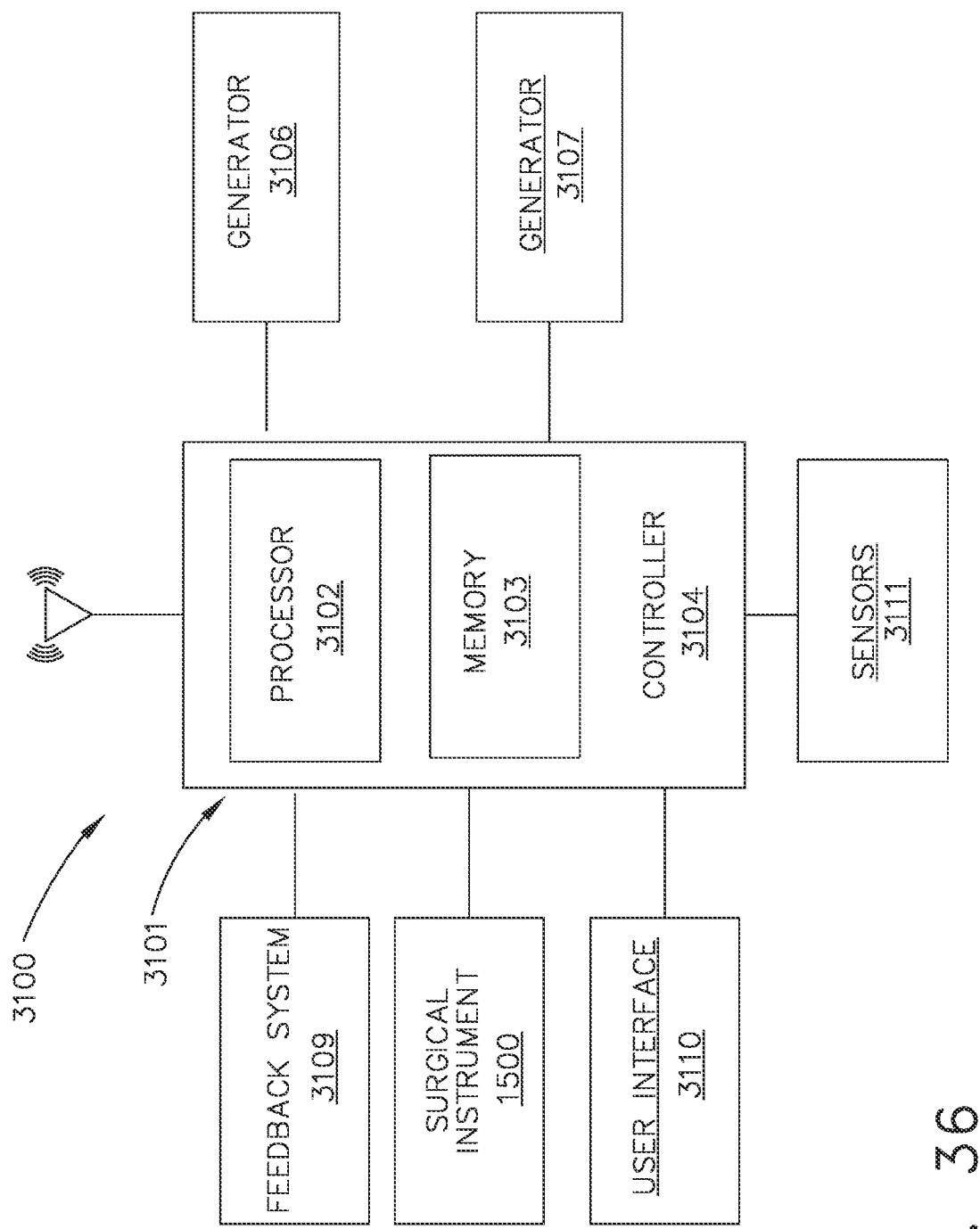
FIG. 36 is a schematic diagram of an electrosurgical system, in accordance with at least one aspect of the present disclosure.
Figure 38:
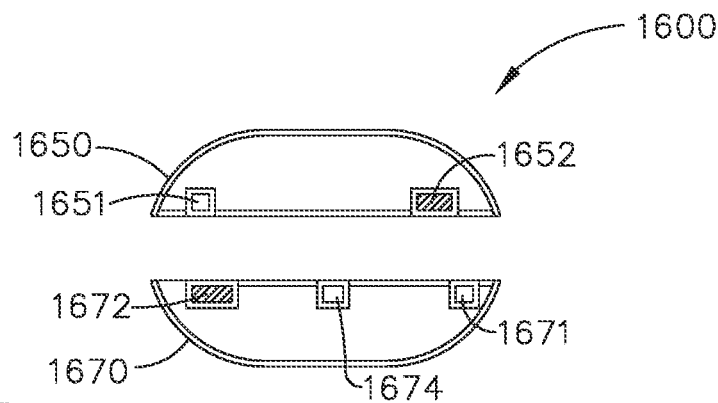
FIGS. 38-40 illustrate a tissue treatment cycle applied by an end effector to a tissue treatment region, in accordance with at least one aspect of the present disclosure.

FIG. 27 further illustrates an electrical connection assembly 5000 for electrically coupling the jaws 12250, 12270 to one or more power sources such as, for example, generators 3106, 3107 (FIG. 36). The electrical connection assembly 5000 defines two separate electrical pathways 5001, 5002 extending through the electrosurgical instrument 12000, as illustrated in FIG. 27. In a first configuration, the electrical pathways 5001, 5002 cooperate to deliver bipolar energy to the end effector 12200 where one of the electrical pathways 5001, 5002 acts as a return pathway. In addition, in a second configuration, the electrical pathways 5001, 5002 separately and/or simultaneously deliver monopolar energy 12200. Accordingly, in the second configuration, both of the electrical pathways 5001, 5002 can be used as supply pathways. Further, the electrical connection assembly 5000 can be utilized with other surgical instruments described elsewhere herein (e.g. the surgical instrument 1500) to electrically couple such surgical instruments with one or more power sources (e.g. generators 3106, 3107).

Figure 30:
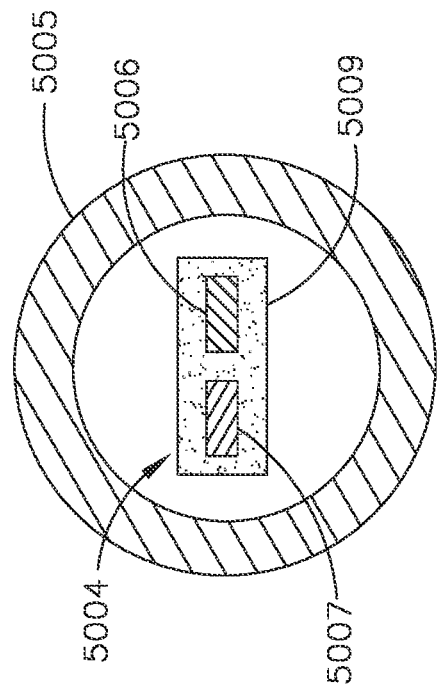
FIG. 30 illustrates a cross-sectional view of a flex circuit extending through a coil tube, in accordance with at least one aspect of the present disclosure.

In the illustrated example, the electrical pathways 5001, 5002 are implemented using a flex circuit 5004 extending, at least partially, through a coil tube 5005. As illustrated in FIG. 30, the flex circuit 5004 includes two separate conductive trace elements 5006, 5007 embedded in a PCB (printed circuit board) substrate 5009. In certain instances, a flex circuit 5004 could be attached to a core flat stamped metallic shaft member with a 3D printed or an over molded plastic casing to provide full shaft fill/support.

Figure 31:
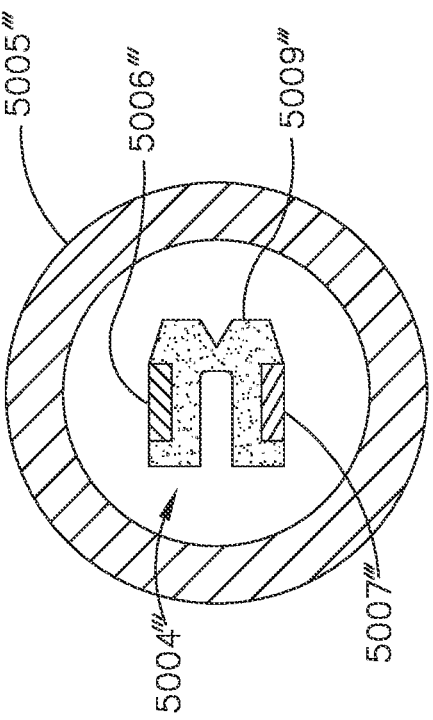
FIG. 31 illustrates a cross-sectional view of a flex circuit extending through a coil tube, in accordance with at least one aspect of the present disclosure.
Figure 33:
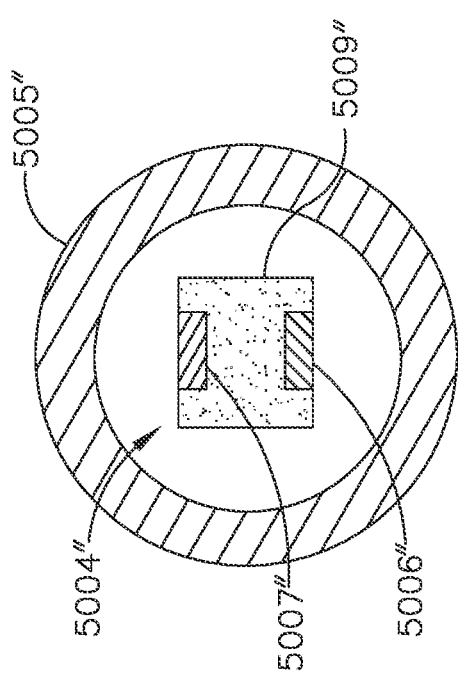
FIG. 33 illustrates a cross-sectional view of a flex circuit extending through a coil tube, in accordance with at least one aspect of the present disclosure.
Figure 32:
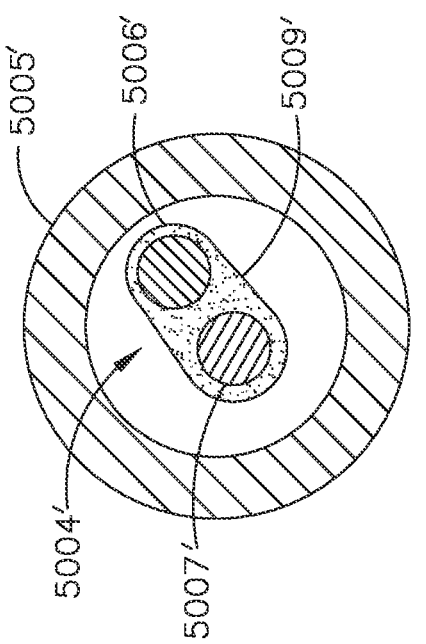
FIG. 32 illustrates a cross-sectional view of a flex circuit extending through a coil tube, in accordance with at least one aspect of the present disclosure.

In alternative examples, as illustrated in FIG. 32, a flex circuit 5004' extending through a coil tube 5005' can include conductive trace elements 5006', 5007' twisted in a PCB substrate 5009' in a helical profile resulting in a reduction of the overall size of the flex circuit 5004' and, in turn, a reduction in the inner/outer diameter of the coil tube 5005'. FIGS. 31 and 32 illustrate other examples of flex circuits 5004", 5004''' extending through coil tubes 5005", 5005''' and including conductive trace elements 5006", 5007" and 5006''', 5007''', respectively, which comprise alternative profiles for size reduction. For example, the flex circuit 5004''' comprises a folded profile while the flex circuit 5004" comprises trace elements 5006", 5007" on opposite sides of the PCB 5009".

Further to the above, the pathways 5001, 5002 are defined by trace portions 5006a-5006g, 5007a-5007g, respectively. The trace portions 5006b, 5006c and the trace portions 5007b, 5007c are in the form of rings that define a ring assembly 5010 which maintains electrical connections through the pathways 5001, 5002 while allowing rotation of the end effector 12200 relative to the shaft of the surgical instrument 12000. Further, trace portions 5006e, 5007e are disposed on opposite sides of the actuator yoke assembly 12610. In the illustrated example, the portions 5006e, 5007e are disposed around holes configured to receive the second jaw attachment pin 12273, as illustrated in FIG. 27. The trace portions 5006e, 5007e are configured to come into electrical contact with corresponding portions 5006f, 5007f disposed on the second jaw 12270. In addition, the trace portions 5007f, 5007g become electrically connected when the first jaw 12250 is assembled with the second jaw 12270.

Figure 29:
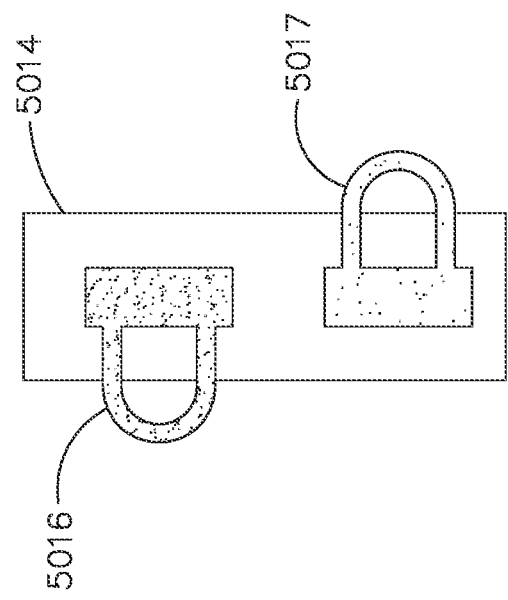
FIG. 29 illustrates a cross-sectional view of a flex circuit, in accordance with at least one aspect of the present disclosure.
Figure 28:
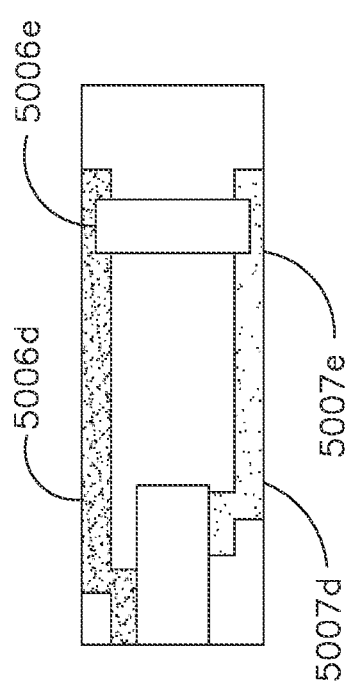
FIG. 28 illustrates a top view of electrical pathways defined in the surgical instrument portion of FIG. 27, in accordance with at least one aspect of the present disclosure.

Referring to FIG. 29, a flex circuit 5014 includes spring-biased trace elements 5016, 5017. The trace elements 5016, 5017 are configured to exert a biasing force against corresponding trace elements to ensure maintaining an electrical connection therewith particularly when corresponding trace portions are moving relative to one another. One or more of the trace portions of the pathways 5001, 5002 can be modified to include spring-biased trace elements in accordance with the flex circuit 5014.

Figure 34:
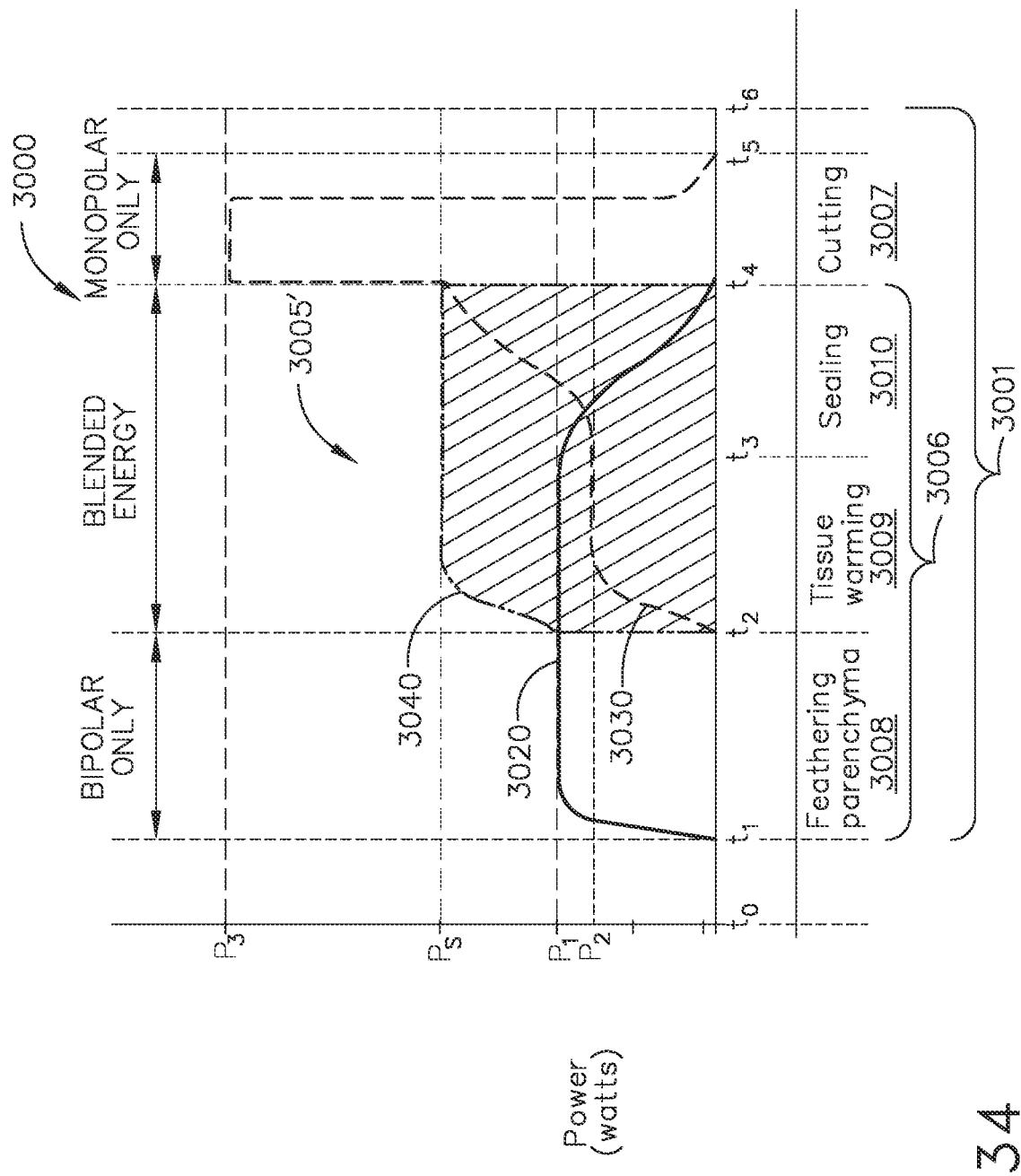
FIG. 34 is a graph illustrating a power scheme for coagulating and cutting a tissue treatment region in a treatment cycle applied by an end effector, in accordance with at least one aspect of the present disclosure.

Referring to FIG. 34, a graph 3000 illustrates a power scheme 3005' of a tissue treatment cycle 3001 applied by an end effector 1400, or any other suitable end effector of the present disclosure, to a tissue grasped by the end effector 1400. The tissue treatment cycle 3001 includes a tissue coagulation stage 3006 including a feathering segment 3008, a tissue-warming segment 3009, and a sealing segment 3010. The tissue treatment cycle 3001 further includes a tissue transection or cutting stage 3007.

FIG. 36 illustrates an electrosurgical system 3100 including a control circuit 3101 configured to execute the power scheme 3005'. In the illustrated example, the control circuit 3101 includes a controller 3104 with storage medium in the form of a memory 3103 and a processor 3102. The storage medium stores program instructions for executing the power scheme 3005'. The electrosurgical system 3100 includes a generator 3106 configured to supply monopolar energy to the end effector 1400, and a generator 3107 configured to supply bipolar energy to the end effector 1400, in accordance with the power scheme 3005'. In the illustrated example, control circuit 3101 is depicted separately from the surgical instrument 1500 and the generators 3106, 3107. In other examples, however, the control circuit 3101 can be integrated with the surgical instrument 1500, the generator 3106, or the generator 3107. In various aspects, the power scheme 3005' can be stored in the memory 3103 in the form of an algorism, equation, and/or look-up table, or any suitable other suitable format. The control circuit 3101 may cause the generators 3106, 3107 to supply monopolar and/or bipolar energies to the end effector 1400 in accordance with the power scheme 3005'.

In the illustrated example, the electrosurgical system 3100 further includes a feedback system 3109 in communication with the control circuit 3101. The feedback system 3109 can be a standalone system, or can be integrated with the surgical instrument 1500, for example. In various aspects, the feedback system 3109 can be employed by the control circuit 3101 to perform a predetermined function such as, for example, issuing an alert when one or more predetermined conditions are met. In certain instances, the feedback system 3109 may comprise one or more visual feedback systems such as display screens, backlights, and/or LEDs, for example. In certain instances, the feedback system 3109 may comprise one or more audio feedback systems such as speakers and/or buzzers, for example. In certain instances, the feedback system 3109 may comprise one or more haptic feedback systems, for example. In certain instances, the feedback system 3109 may comprise combinations of visual, audio, and/or haptic feedback systems, for example. Additionally, the electrosurgical system 3100 further includes a user interface 3110 in communication with the control circuit 3101. The user interface 3110 can be a standalone interface, or can be integrated with the surgical instrument 1500, for example.

The graph 3000 depicts power (W) on the y-axis and time on the x-axis. A bipolar energy curve 3020 spans the tissue coagulation stage 3005, and a monopolar energy curve 3030 starts in the tissue coagulation stage 3006 and terminates at the end of the tissue transection stage 3007. Accordingly, tissue treatment cycle 3001 is configured to apply a bipolar energy to the tissue throughout the tissue coagulation stage 3006, but not the tissue transection stage 3007, and apply a monopolar energy to the tissue in a portion of the coagulation stage 3006 and the transection stage 3007, as illustrated in FIG. 34.

In various aspects, a user input can be received by the control circuit 3101 from the user interface 3110. The user input causes the control circuit 3101 to initialize execution of the power scheme 3005' at time $t_1$. Alternatively, the initialization of the execution of the power scheme 3005' can be triggered automatically by sensor signals from one or more sensors 3111 in communication with the control circuit 3101. For example, the power scheme 3005' can be triggered automatically by the control circuit 3101 in response to a sensor signal indicative of a predetermined gap between the jaws 1450, 1470 of the end effector 1400.

During the feathering segment 3008, the control circuit 3101 causes generator 3107 to gradually increase the bipolar energy power supplied to the end effector 1400 to a predetermined power value P1 (e.g. 100 W), and to maintain the bipolar energy power at, or substantially at, the predetermined power value P1 throughout the remainder of the feathering segment 3008 and the tissue-warming segment 3009. The predetermined power value P1 can be stored in the memory 3103 and/or can be provided by a user through the user interface 3110. During the sealing segment 3010, the control circuit 3101 causes generator 3107 to gradually decrease the bipolar energy power. Bipolar energy application is terminated at the end of the sealing segment 3010 of the tissue coagulation stage 3006, and prior to the beginning of the cutting/transecting stage 3007.

Further to the above, at $t_2$, the control circuit 3101 causes generator 3107 to begin supplying monopolar energy power to the electrode 1474 of the end effector 1400, for example. The monopolar energy application to the tissue commences at the end of the feathering segment 3008 and the beginning of the tissue-warming segment 3009. The control circuit 3101 causes generator 3107 to gradually increase the monopolar energy power to a predetermined power level P2 (e.g. 75 W), and to maintain, or at least substantially maintain, the predetermined power level P2 for the remainder of the tissue-warming segment 3009 and a first portion of the sealing segment 3010. The predetermined power level P2 can also be stored in the memory 3103 and/or can be provided by a user through the user interface 3110.

During the sealing segment 3010 of the tissue coagulation stage 3006, the control circuit 3101 causes generator 3107 to gradually increase the monopolar energy power supplied to the end effector 1400. The beginning of the tissue transection stage 3007 is ushered by an inflection point in the monopolar energy curve 3030 where the previous gradual increase in monopolar energy, experienced during the sealing segment 3010, is followed by a step up to a predetermined maximum threshold power level P3 (e.g. 150 W) sufficient to transect the coagulated tissue.

At $t_4$, the control circuit 3101 causes generator 3107 to step up the monopolar energy power supplied to the end effector 1400 to the predetermined maximum threshold power level P3, and to maintain, or at least substantially maintain, predetermined maximum threshold power level P3 for a predetermined time period ($t_4$-$t_5$), or to the end of the tissue transection stage 3007. In the illustrated example, the monopolar energy power is terminated by the control circuit 3101 at t5. The tissue transection continues mechanically, as the jaws 1450, 1470 continue to apply pressure on the grasped tissue until the end of the issue transection stage 3007 at $t_6$. Alternatively, in other examples, the control circuit 3101 may cause the generator 3107 to continue supplying monopolar energy power to the end effector 1400 to the end of the tissue transection stage 3007.

Sensor readings of the sensors 3111 and/or a timer clock of the processor 3102 can be employed by the control circuit 3101 to determine when to cause the generator 3107 and/or the generator 3106 to begin, increase, decrease, and/or terminate energy supply to the end effector 1400, in accordance with a power scheme such as, for example, the power scheme 3005'. The control circuit 3101 may execute the power scheme 3005' by causing one or more timer clocks to count down from one or more predetermined time periods (e.g. $t_1$-$t_2$, $t_2$-$t_3$, $t_3$-$t_4$, $t_5$-$t_6$) that can be stored in the memory 3103, for example. Although the power scheme 3005' is time based, the control circuit 3101 may adjust predetermined time periods for any of the individual segments 3008, 3009, 3010 and/or the stages 3006, 3007 based on sensor readings received from one or more of the sensors 3111 such as, for example, a tissue impedance sensor.

The end effector 1400 is configured to deliver three different energy modalities to the grasped tissue. The first energy modality, which is applied to the tissue during the feathering segment 3008, includes bipolar energy but not monopolar energy. The second energy modality is a blended energy modality that includes a combination of monopolar energy and bipolar energy, and is applied to the tissue during the tissue warming stage 3009 and the tissue sealing stage 3010. Lastly, the third energy modality includes monopolar energy but not bipolar energy, and is applied to the tissue during the cutting stage 3007. In various aspects, the second energy modality comprises a power level that is the sum 3040 of the power levels of monopolar energy and bipolar energy. In at least one example, the power level of the second energy modality includes a maximum threshold Ps (e.g. 120 W).

In various aspects, the control circuit 3101 causes the monopolar energy and the bipolar energy to be delivered to the end effector 1400 from two different electrical generators 3106, 3107. In at least one example, energy from one of the generators 3106, 3107 can be detected using a return path of the other generator, or utilizing attached electrodes of the other generator to short to an unintended tissue interaction. Accordingly, a parasitic loss of energy through a return path that is not the intended can be detected by a generator connected to the return path. The inadvertent conductive path can be mitigated by effecting the voltage, power, waveform, or timing between uses.

Integrated sensors within the flex circuits of the surgical instrument 1500 can detect energizing/shorting of an electrode/conductive path when no potential should be present and the ability to prevent that conductive path once inadvertent use is sensed. Further, directional electronic gating elements that prevent cross talk from one generator down the source of the other generator can also be utilized.

One or more of the electrodes described by the present disclosure (e.g. electrodes 1452, 1472, 1474 in connection with the jaws 1450, 1470) may include a segmented pattern with segments that are linked together when the electrode is energized by a generator (e.g. generator 1100). However, when the electrode is not energized, the segments are separated to prevent circuit shorting across the electrode to other areas of the jaw.

In various aspects, thermal resistive electrode material are utilized with the end effector 1400. The material can be configured to inhibit electrical flow through electrodes that are at or above a predefined temperature level but continues to allow the energizing of other portions of the electrodes that are below the temperature threshold.

FIG. 37 illustrates a table representing an alternative power scheme 3005" that can be stored in the memory 3103, and can be executed by the processor 3102 in a similar manner to the power scheme 3005'. In executing the power scheme 3005", the control circuit 3101 relies on jaw aperture in addition to, or in lieu of, time in setting power values of the generators 3106, 3107. Accordingly, the power scheme 3005" is a jaw-aperture based power scheme.

In the illustrated example, jaw apertures $d_0$, $d_1$, $d_2$, $d_3$, $d_4$ from the power scheme 3005" correspond to the time values $t_1$, $t_2$, $t_3$, $t_4$ from the power scheme 3005'. Accordingly, the feathering segment corresponds to a jaw aperture from about $d_1$ to about $d_2$ (e.g. from about 0.700" to about 0.500"). In addition, the tissue-warming segment corresponds to a jaw aperture from about $d_2$ to about $d_3$ (e.g. from about 0.500" to about 0.300"). Further, the sealing segment corresponds to a jaw aperture from about $d_2$ to about $d_3$ (e.g. from about 0.030" to about 0.010"). Further, the tissue cutting stage corresponds to a jaw aperture from about $d_3$ to about $d_4$ (e.g. from about 0.010" to about 0.003").

Accordingly, the control circuit 3101 is configured to cause the generator 3106 to begin supplying bipolar energy power to the end effector 1400 when readings from one or more of the sensors 3111 corresponds to the predetermined jaw aperture d1, for example, thereby initializing the feathering segment. Likewise, the control circuit 3101 is configured to cause the generator 3106 to stop supplying bipolar energy power to the end effector 1400 when readings from one or more of the sensors 3111 corresponds to the predetermined jaw aperture d2, for example, thereby terminating the feathering segment. Likewise, the control circuit 3101 is configured to cause the generator 3107 to begin supplying monopolar energy power to the end effector 1400 when readings from one or more of the sensors 3111 corresponds to the predetermined jaw aperture d2, for example, thereby initializing the warming segment.

In the illustrated example, the jaw aperture is defined by the distance between two corresponding datum points on the jaws 1450, 1470. The corresponding datum points are in contact with one another when the jaws 1450, 1470 are in a closed configuration with no tissue therebetween. Alternatively, the jaw aperture can be defined by a distance between the jaws 1450, 1470 measured along a line intersecting the jaws 1450, 1470 and perpendicularly intersecting a longitudinal axis extending centrally through the end effector 1500. Alternatively, the jaw aperture can be defined by a distance between first and second parallel lines intersecting the jaws 1450, 1470, respectively. The distance is measured along a line extending perpendicularly to the first and second parallel lines, and extending through the intersection point between the first parallel line and the first jaw 1450, and through the intersection point between the second parallel line and the second jaw 1470.

Figure 35:
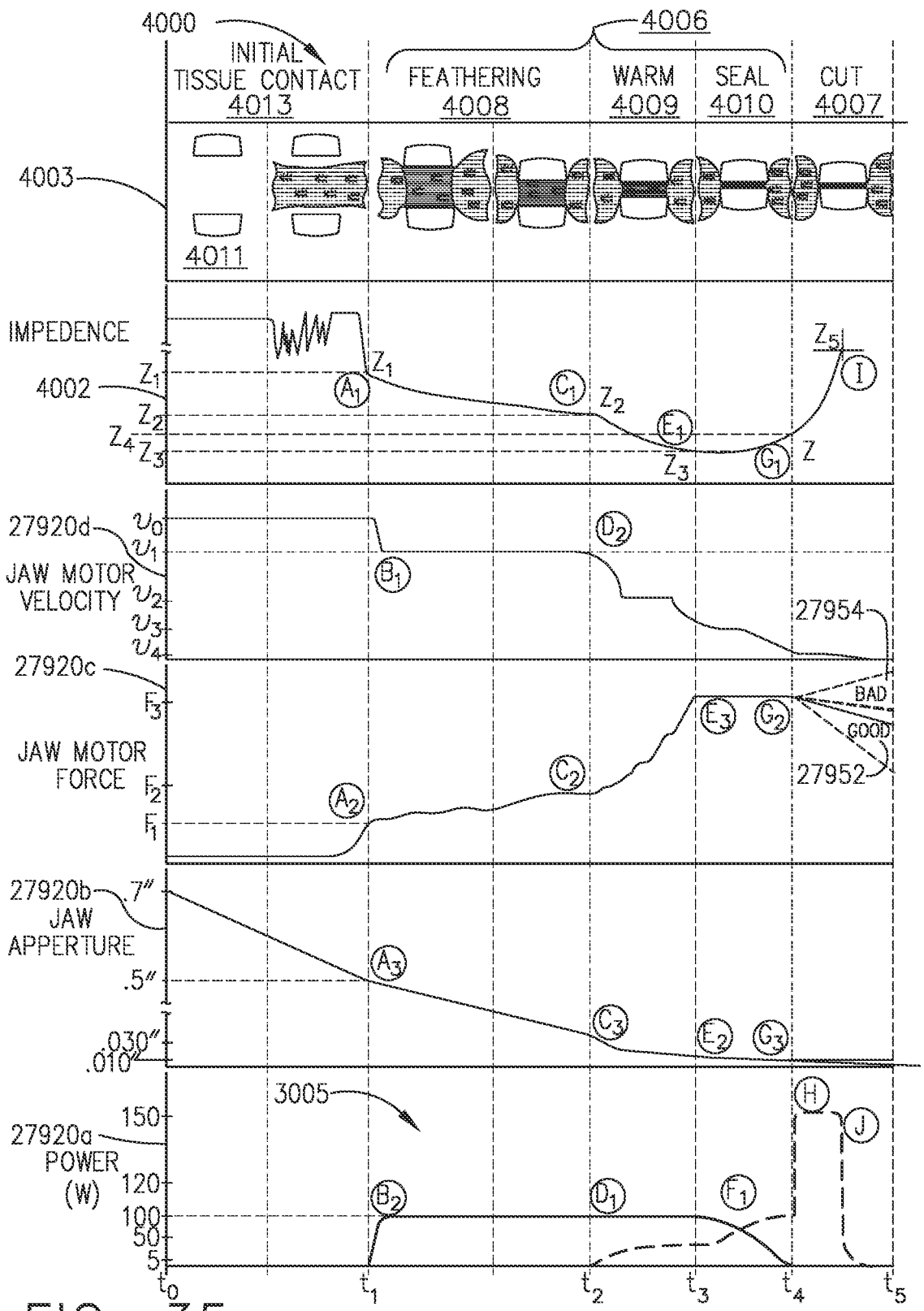
FIG. 35 is a graph illustrating a power scheme for coagulating and cutting a tissue treatment region in a treatment cycle applied by an end effector and a number of measured parameters of the end effector and the tissue, in accordance with at least one aspect of the present disclosure.

Referring to FIG. 35, in various examples, an electrosurgical system 3100 (FIG. 36) is configured to perform a tissue treatment cycle 4003 using a power scheme 3005. The tissue treatment cycle 4003 includes an initial tissue contacting stage 4013, a tissue coagulation stage 4006, and a tissue transection stage 4007. The tissue contacting stage 4013 include an open configuration segment 4011 where tissue is not between the jaws 1450 and 1470, and a proper orientation segment 4012 where the jaws 1450 and 1470 are properly positioned with respect to a desired tissue treatment region. The tissue coagulation stage 4006 includes a feathering segment 4008, a tissue-warming segment 4009, and the sealing segment 3010. The tissue transection stage 4007 includes a tissue-cutting segment. The tissue treatment cycle 4003 involves application of a bipolar energy and a monopolar energy separately and simultaneously to the tissue treatment region in accordance with a power scheme 3005. The tissue treatment cycle 4003 is similar in many respects to the tissue treatment cycle 3001, which are not repeated herein in the same level of detail for brevity.

FIG. 35 illustrates a graph 4000 that represents a power scheme 3005 similar in many respects to the power scheme 3005'. For example, the control circuit 3101 can execute the power scheme 3005, in a similar manner to the power scheme 3005', to deliver three different energy modalities to the tissue treatment region at three consecutive time periods of a tissue treatment cycle 4001. The first energy modality, which includes bipolar energy but not monopolar energy, is applied to the tissue treatment region from $t_1$ to $t_2$, in the feathering segment 4008. The second energy modality, which is a blended energy modality that includes a combination of monopolar energy and bipolar energy, is applied to the tissue treatment region from $t_2$ to $t_4$, in the tissue-warming segment 4009 and tissue-sealing segment. Lastly, the third energy modality, which includes monopolar energy but not bipolar energy 4010, is applied to the tissue from $t_4$ to $t_5$, in tissue transection stage 4007. Furthermore, the second energy modality comprises a power level that is the sum of the power levels of monopolar energy and bipolar energy. In at least one example, the power level of the second energy modality includes a maximum threshold (e.g. 120 W). In various aspects, the power scheme 3005 can be delivered to the end effector 1400 from two different electrical generators 3106, 3107. Additional aspects of the power scheme 3005 that are similar to aspects of the power scheme 3005' are not repeated herein in the same level of detail for brevity.

In various aspects, the control circuit 3101 causes the generators 3106, 3107 to adjust the bipolar and/or monopolar power levels of the power scheme 3005 applied to the tissue treatment region by the end effector 1400 based on one or more measured parameters including tissue impedance 4002, jaw motor velocity 27920d, jaw motor force 27920c, jaws aperture 27920b of the end effector 1400, and/or current draw of the motor effecting the end effector closure. FIG. 35 is a graph 4000 illustrating correlations between such measured parameters and the power scheme 3005 over time.

In various examples, the control circuit 3101 causes the generators 3106, 3107 to adjust the power levels of a power scheme (e.g. power schemes 3005, 3005') applied by the end effector 1400 to the tissue treatment region based on one or more parameters (e.g. tissue impedance 4002, jaw/closure motor velocity 27920d, jaw/closure motor force 27920c, jaws gap/aperture 27920b of the end effector 1400, and/or current draw of the motor) determined by one or more sensors 3111. For example, the control circuit 3101 may cause the generators 3106, 3107 to adjust the power levels based on the pressure within the jaws 1450, 1470.

In at least one example, the power levels are inversely proportional to the pressure within the jaws 1450, 1470. The control circuit 3101 may utilize such an inverse correlation to select the power levels based on the pressure values. In at least one example, current draw of the motor effecting the end effector closure is employed to determine the pressure values. Alternatively, the inverse correlation utilized by the control circuit 3101 can be directly based on the current draw as a proxy for the pressure. In various examples, the greater the compression applied by the jaws 1450, 1470 onto the tissue treatment region, the lower the power levels set by the control circuit 3101, which aids in minimizing sticking and inadvertent cutting of the tissue.

Graph 4000 provides several cues in the measured parameters of tissue impedance 4002, jaw/closure motor velocity 27920d, jaw/closure motor force 27920c, jaws gap/aperture 27920b of the end effector 1400, and/or current draw of the motor effecting the end effector closure, which can trigger an activation, an adjustment, and/or a termination of the bipolar energy and/or the monopolar energy application to tissue during the tissue treatment cycle 4003.

The control circuit 3101 may rely on one or more of such cues in executing and/or adjusting the default power scheme 3005 in the tissue treatment cycle 4003. In certain examples, the control circuit 3101 may rely on sensor readings of the one or more sensors 3111 to detect when one or more monitored parameters satisfy one or more predetermined conditions that can be stored in the memory 3103, for example. The one or more predetermined conditions can be reaching a predetermined threshold and/or detecting a meaningful increase and/or decrease in one or more of the monitored parameters. Satisfaction of the predetermined conditions, or the lack thereof, constitutes trigger/confirmation points for executing and/or adjusting portions of the default power scheme 3005 in the tissue treatment cycle 4003. The control circuit 3101 may rely exclusively on the cues in executing and/or adjusting a power scheme or, alternatively, use the cues to guide, or adjust, a timer clock of a time-based power scheme such as, for example, the power scheme 3005'.

For example, a sudden decrease ($A_1$) in tissue impedance to a predetermined threshold value ($Z_1$), occurring alone or coinciding with an increase ($A_2$) in jaw motor force to a predetermined threshold value ($F_1$) and/or a decrease ($A_3$) in jaw aperture to a predetermined threshold value (d1) (e.g. 0.5") may trigger the control circuit 3101 to begin the feathering segment 4008 of the tissue coagulation stage 4006 by activating the application of bipolar energy to the tissue treatment region. The control circuit 3101 may signal the generator 3106 to begin supplying bipolar power to the end effector 1400.

Furthermore, a decrease ($B_1$) in jaw motor velocity to a predetermined value (v1) following the activation of the bipolar energy triggers the control circuit 3101 to signal the generator 3106 to stabilize ($B_2$) the power level for bipolar energy at a constant, or at least substantially constant, value (e.g. 100 V).

In yet another example, the shifting from the feathering segment 4008 to the warming segment 4009 at $t_2$, which triggers an activation (D1) of the monopolar energy application to the tissue treatment region, coincides with an increase ($C_2$) in the jaw motor force to a predetermined threshold ($F_2$), a decrease ($C_3$) in the jaw aperture to a predetermined threshold (e.g. 0.03"), and/or a decrease (C1) in tissue impedance to a predetermined value $Z_2$. Satisfaction of one, or in certain instances two, or in certain instances all, of the conditions C1, C2, C3 causes the control circuit 3101 to cause the generator 3101 to begin application of monopolar energy to the tissue treatment region. In another example, satisfaction of one, or in certain instances two, or in certain instances all, of the conditions C1, C2, C3 at, or about, the time t2, triggers the application of monopolar energy to the tissue treatment region.

Activation of the monopolar energy by the generator 3107, in response to activation signals by the control circuit 3101, causes a blend ($D_1$) of the monopolar energy and bipolar energy to be delivered to the tissue treatment region, which causes a shift in the impedance curve characterized by a quicker decrease (E1) in impedance from $Z_2$ to $Z_3$ in comparison to a steady decrease (C1) prior to activation of the monopolar energy. In the illustrated example, the tissue impedance $Z_3$ defines a minimum impedance for the tissue treatment cycle 4003.

In the illustrated example, the control circuit 3101 determines that an acceptable seal is being achieved if ($E_1$) the minimum impedance value $Z_3$ coincides, or at least substantially coincides, with ($E_3$) a predetermined maximum jaw motor force threshold ($F_3$) and/or ($E_2$) a predetermined jaw aperture threshold range (e.g. 0.01"-0.003"). Satisfaction of one, or in certain instances two, or in certain instances all, of the conditions E1, E2, E3 signals the control circuit 3101 to shift from the warming segment 4009 to the sealing segment 4010.

Further to the above, beyond the minimum impedance value $Z_3$, the impedance level gradually increases to a threshold value Z4 corresponding to the end of the sealing segment 4010, at $t_4$. Satisfaction of the threshold value Z4 causes the control circuit 3101 to signal the generator 3107 to step up the monopolar power level to commence the tissue transection stage 4007, and signal the generator 3106 to terminate application of the bipolar energy application to the tissue treatment region.

In various examples, the control circuit 3101 can be configured to ($G_2$) verify that the jaw motor force is decreasing as ($G_1$) the impedance gradually increases from its minimum value $Z_3$, and/or ($G_3$) that the jaw aperture has decreased to a predetermined threshold (e.g. 0.01"-0.003"), prior to stepping up the power level of the monopolar energy to cut the tissue.

If, however, the jaw motor force continues to increase, the control circuit 3101 may pause application of the monopolar energy to the tissue treatment region for a predetermined time period to allow the jaw motor force to begin decreasing. Alternatively, the control circuit may signal the generator 3107 to deactivate the monopolar energy, and complete the seal using only the bipolar energy.

In certain instances, the control circuit 3101 may employ the feedback system 3109 to alert a user and/or provide instructions or recommendations to pause the application of the monopolar energy. In certain instances, the control circuit 3101 may instruct the user to utilize on a mechanical knife to transect the tissue.

In the illustrated example, the control circuit 3101 maintains (H) the stepped up monopolar power until a spike (I) is detected in tissue impedance. The control circuit 3101 may cause the generator 3107 to terminate (J) application of the monopolar energy to the tissue upon detection of the spike (I) in the impedance level to $Z_5$ following the gradual increase from $Z_3$ to $Z_4$. The spike indicates completion of the tissue treatment cycle 4003.

In various examples, the control circuit 3101 prevents the electrodes of the jaws 1450, 1470 from being energized before a suitable closure threshold is reached. The closure threshold can be based on a predetermined jaw aperture threshold and/or a predetermined jaw motor force threshold, for example, which can be stored in the memory 3103. In such examples, the control circuit 3101 may not act on user inputs through the user interface 3110 requesting of the treatment cycle 4003. In certain instances, the control circuit 3101 may respond by alerting the user through the feedback system 3109 that the suitable closure threshold has not been reached. The control circuit 3101 may also offer the user an override option.

Ultimately between time $t_4$ and $t_5$, monopolar energy is the only energy being delivered in order to cut the patient tissue. While the patient tissue is being cut, the force to clamp the jaws of the end effector may vary. In instances where the force to clamp the jaws decreases 27952 from its steady-state level maintained between time $t_3$ and $t_4$, an efficient and/or effective tissue cut is recognized by the surgical instrument and/or the surgical hub. In instances where the force to clamp the jaws increases 27954 from its steady-state level maintained between time $t_3$ and $t_4$, an inefficient and/or ineffective tissue cut is recognized by the surgical instrument and/or the surgical hub. In such instances, an error can be communicated to the user.

Figure 39:
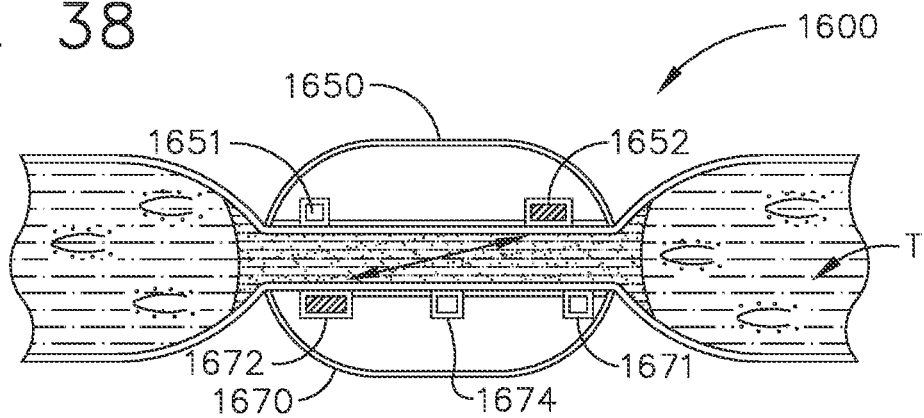
Figure 40:
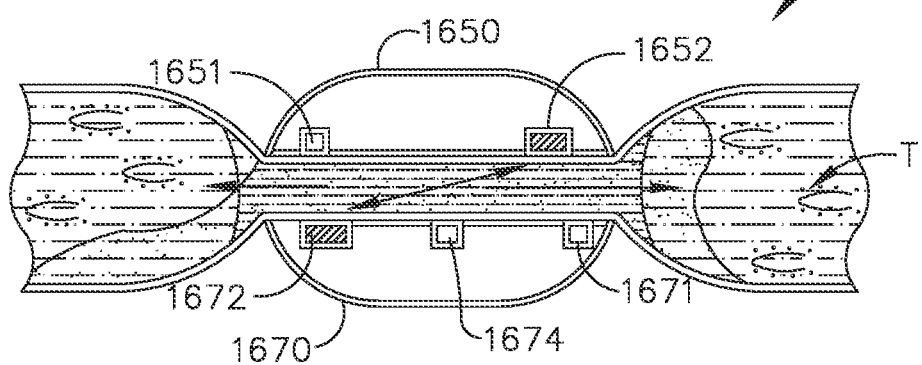
Figure 41:
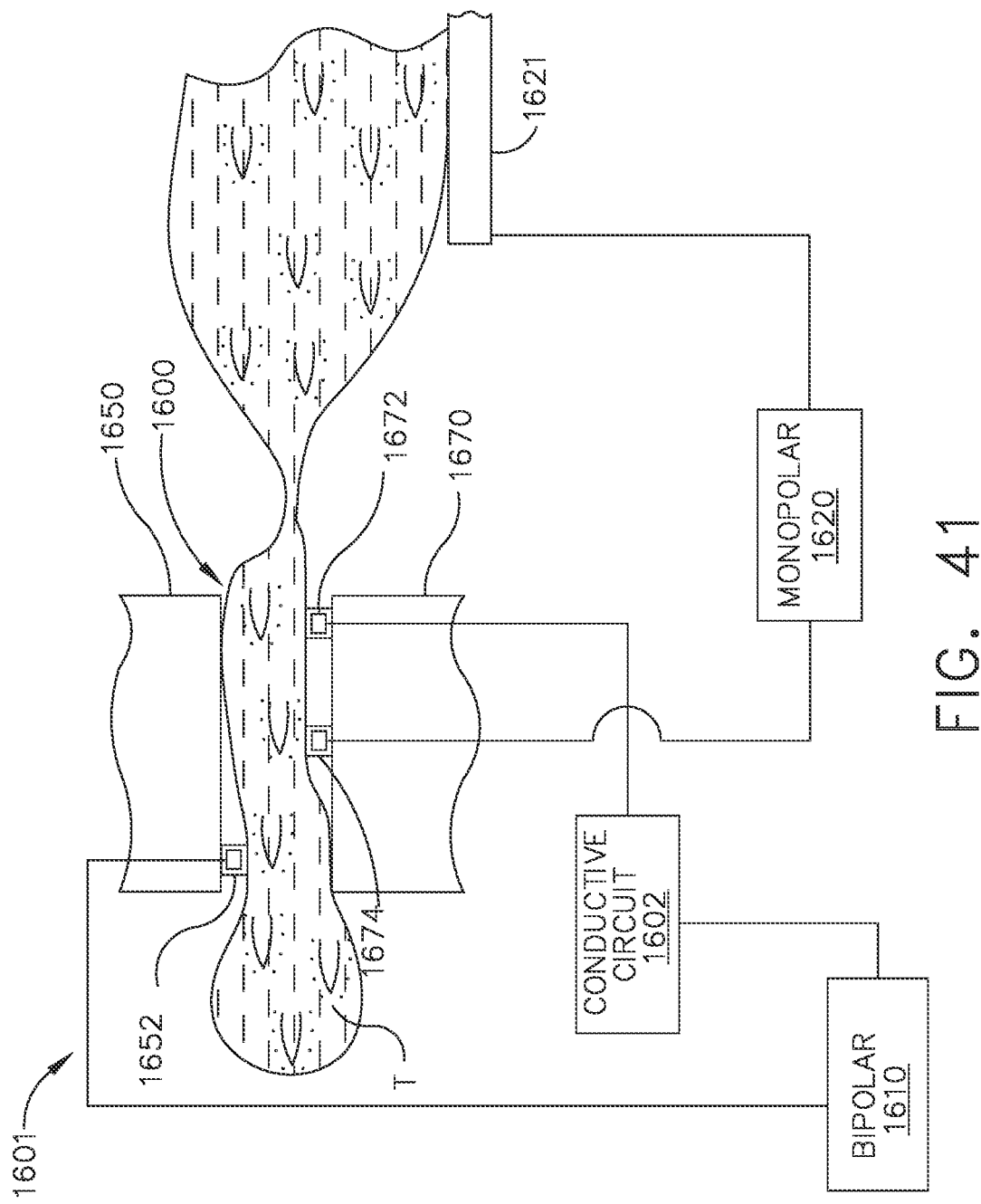
FIG. 41 illustrates an end effector applying therapeutic energy to a tissue grasped by the end effector, the therapeutic energy generated by a monopolar power source and a bipolar power source, in accordance with at least one aspect of the present disclosure.

Referring to FIGS. 38-42, a surgical instrument 1601 includes an end effector 1600 similar in many respects to the end effectors 1400, 1500, which are not repeated herein in the same level of detail for brevity. The end effector 1600 includes a first jaw 1650 and a second jaw 1670. At least one of the first jaw 1650 and the second jaw 1670 is movable to transition the end effector 1600 from an open configuration to a closed configuration to grasp tissue (T) between the first jaw 1650 and the second jaw 1670. Electrodes 1652, 1672 are configured to cooperate to deliver a bipolar energy to the tissue from a bipolar energy source 1610, as illustrated in FIG. 39. An electrode 1674 is configured to deliver a monopolar energy to the tissue from a monopolar energy source 1620. A return pad 1621 defines a return pathway for the monopolar energy. In at least one example, the monopolar energy and the bipolar energy are delivered to the tissue either simultaneously (FIG. 36), or in an alternating fashion, as illustrated in FIG. 36, to seal and/or cut the tissue, for example.

Figure 42:
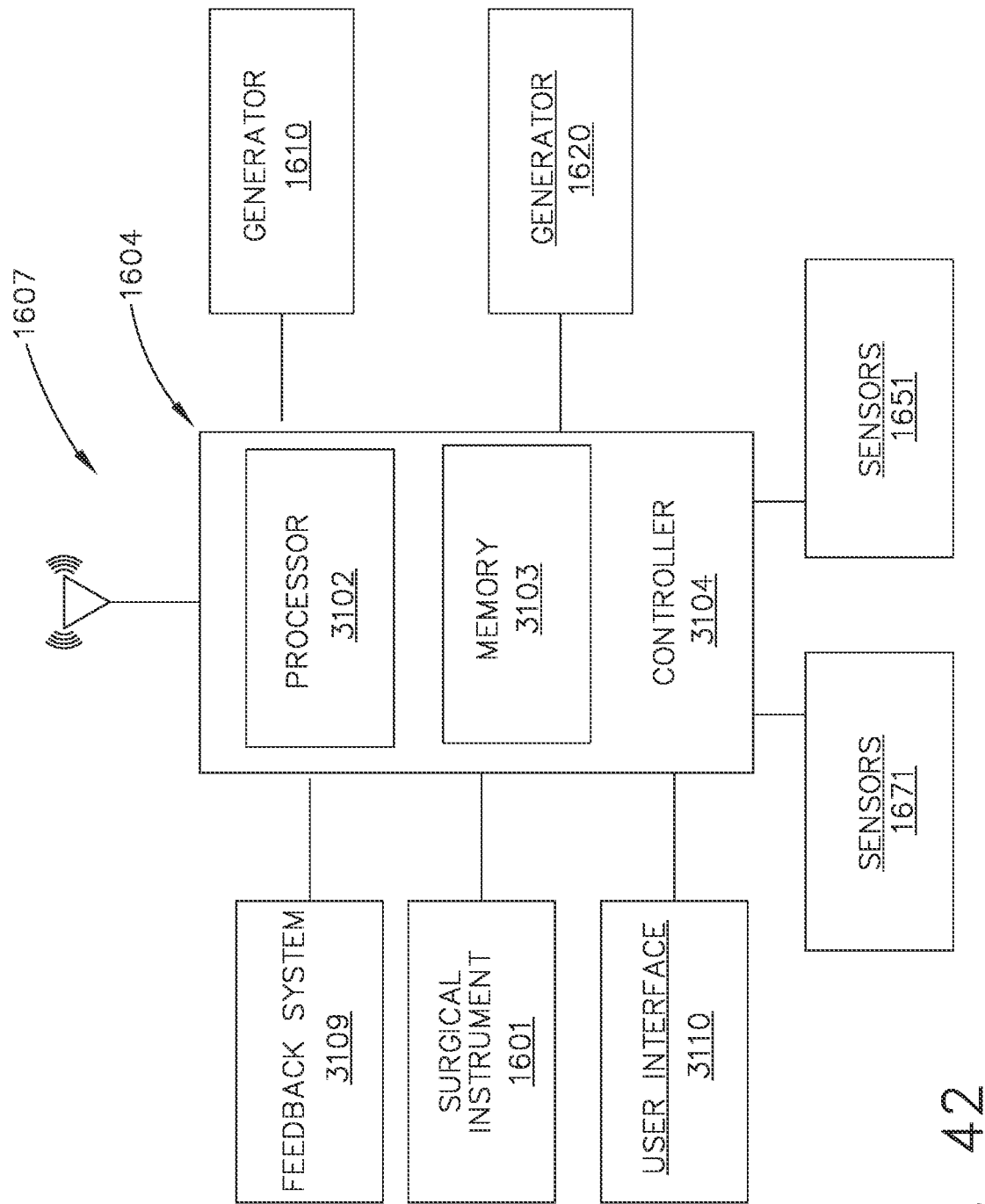
FIG. 42 illustrates a simplified schematic diagram of an electrosurgical system, in accordance with at least one aspect of the present disclosure.

FIG. 42 illustrates a simplified schematic diagram of an electrosurgical system 1607 includes a monopolar power source 1620 and bipolar power source 1610 connectable to an electrosurgical instrument 1601 that includes the end effector 1600. The electrosurgical system 1607 further includes a conductive circuit 1602 selectively transitionable between a connected configuration with the electrode 1672 and a disconnected configuration with the electrode 1672. The switching mechanism can be comprised of any suitable switch that can open and close the conductive circuit 1602, for example. In the connected configuration, the electrode 1672 is configured to cooperate with the electrode 1652 to deliver bipolar energy to the tissue, wherein the conductive circuit 1602 defines a return path for the bipolar energy after passing through the tissue. However, in the disconnected configuration, the electrode 1672 is isolated and therefore becomes an inert internally conductive and externally insulated structure on the jaw 1670. Accordingly, in the disconnected configuration the electrode 1652 is configured to deliver a monopolar energy to the tissue in addition to, or separate from, the monopolar energy delivered through the electrode 1674. In alternative examples, the electrode 1652, instead of the electrode 1672, can be transitionable between a connected configuration and a disconnected configuration with the conductive circuit 1602, allowing the electrode 1672 deliver monopolar energy to the tissue in addition to, or separate from, the monopolar energy delivered through the electrode 1674.

In various aspects, the electrosurgical instrument 1601 further includes a control circuit 1604 configured to adjust levels of the monopolar energy and the bipolar energy delivered to the tissue to minimize unintended thermal damage to surrounding tissue. The adjustments can be based on readings of at least one sensor such as, for example, a temperature sensor, an impedance sensor, and/or a current sensor. In the example illustrated in FIGS. 41 and 42, the control circuit 1604 is coupled to temperature sensors 1651, 1671 on the jaws 1650, 1670, respectively. The levels of the monopolar energy and the bipolar energy delivered to the tissue are adjusted by the control circuit 1604 based on temperature readings of the sensors 1651, 1671.

In the illustrated example, the control circuit 1604 includes a controller 3104 with a storage medium in the form of a memory 3103 and a processor 3102. The memory 3103 stores program instructions that, when executed by the processor 3102, cause the processor 3102 to adjust levels of the monopolar energy and the bipolar energy delivered to the tissue based on sensor readings received from one or more sensors such as, for example, the temperature sensors 1651, 1671. In various examples, as described in greater detail below, the control circuit 1604 may adjust a default power scheme 1701 based on readings from one or more sensors such as, for example, the temperature sensors 1651, 1671. The power scheme 1701 is similar in many respects to the power scheme 3005', which are not repeated herein in the same level of detail for brevity.

Figure 43:
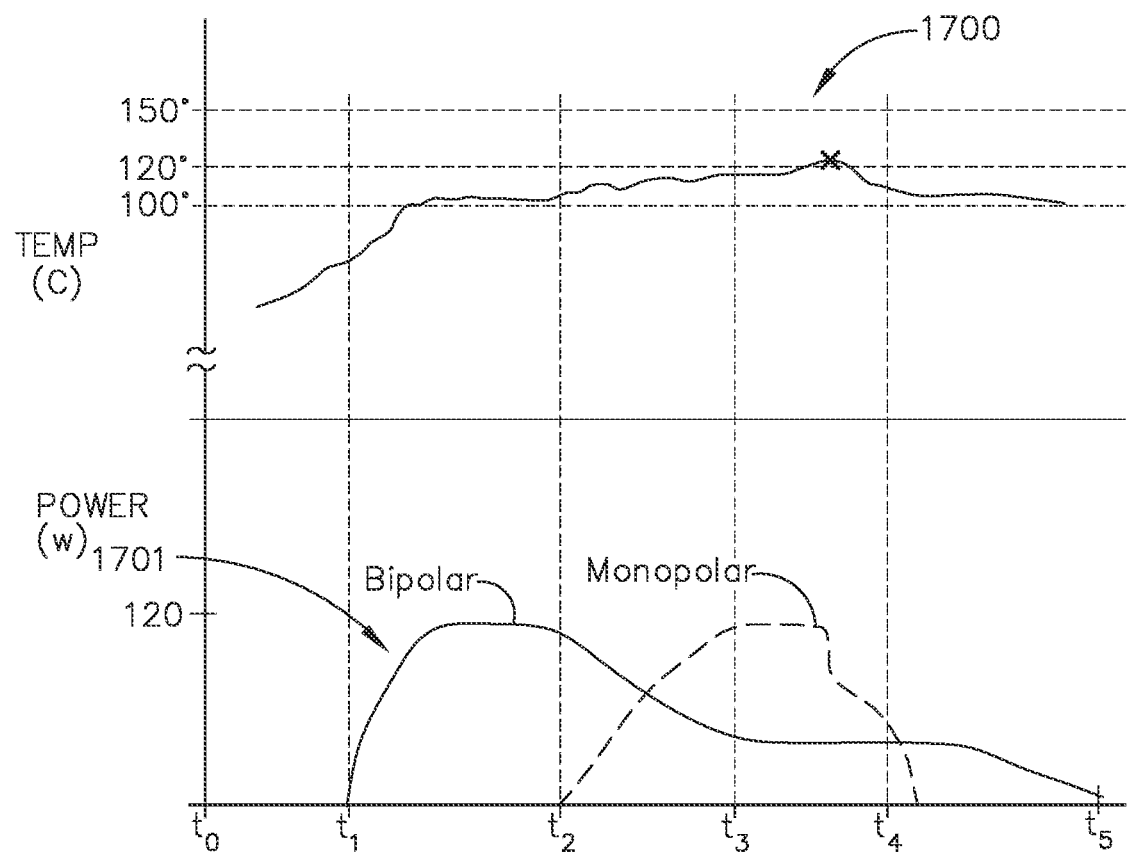
FIG. 43 is a graph illustrating a power scheme for coagulating and cutting a tissue treatment region in a treatment cycle applied by an end effector and corresponding temperature readings of the tissue treatment region, in accordance with at least one aspect of the present disclosure.

FIG. 43 illustrates a temperature-based adjustment of the power scheme 1701 for energy delivery to a tissue grasped by an end effector 1600. A graph 1700 depicts time on the x-axis, and power and temperature on the y-axis. In a tissue feathering segment ($t_1$-$t_2$), the control circuit 1604 causes the power level of the bipolar energy to gradually increase up to a predetermined threshold (e.g. 120 W), which causes the temperature of the tissue grasped by the end effector 1600 to gradually increase to a temperature within a predetermined range (e.g. 100° C.-120° C.). The power level of the bipolar energy is then maintained at the predetermined threshold as long as the tissue temperature remains within the predetermined range. In a tissue-warming segment ($t_2$-$t_3$), the control circuit 1604 activates the monopolar energy, and gradually decreases the power level of the bipolar energy, while gradually increasing the power level of the monopolar energy to maintain the tissue temperature within the predetermined range.

In the illustrated example, during a tissue-sealing segment ($t_3$-$t_4$), the control circuit 1604 detects that the tissue temperature has reached the upper limit of the predetermined range based on readings the temperature sensors 1651, 1671. The control circuit 1604 responds by stepping down the power level of the monopolar energy. In other examples, the reduction can be performed gradually. In certain examples, the reduction value, or a manner for determining the reduction value such as, for example, a table or an equation can be stored in the memory 3103. In certain examples, the reduction value can be a percentage of the present power level of the monopolar energy. In other examples, the reduction value can be based on a previous power level of the monopolar energy that corresponded to a tissue temperature within the predetermined range. In certain examples, the reduction can be performed in multiple steps that are temporally spaced apart. After each downward step, the control circuit 1604 allows a predetermined time period to pass before evaluating the tissue temperature.

In the illustrated example, the control circuit 1604 maintains the power level of the bipolar energy in accordance with the default power scheme 1701, but reduces the power level of the monopolar energy to maintain the temperature of the tissue within the predetermined range, while tissue sealing is completed. In other examples, the reduction in the power level of the monopolar energy is combined, or replaced, by a reduction in the power level of the bipolar energy.

Further to the above, an alert can be issued, through the feedback system 3109, to complete transection of the tissue using a mechanical knife, for example, instead of the monopolar energy to avoid unintended lateral thermal damage to surrounding tissue. In certain examples, the control circuit 1604 may temporarily pause the monopolar energy and/or the bipolar energy until the temperature of the tissue returns to a level within the predetermined temperature range. Monopolar energy can then be reactivated to perform a transection of the sealed tissue.

Figure 44:
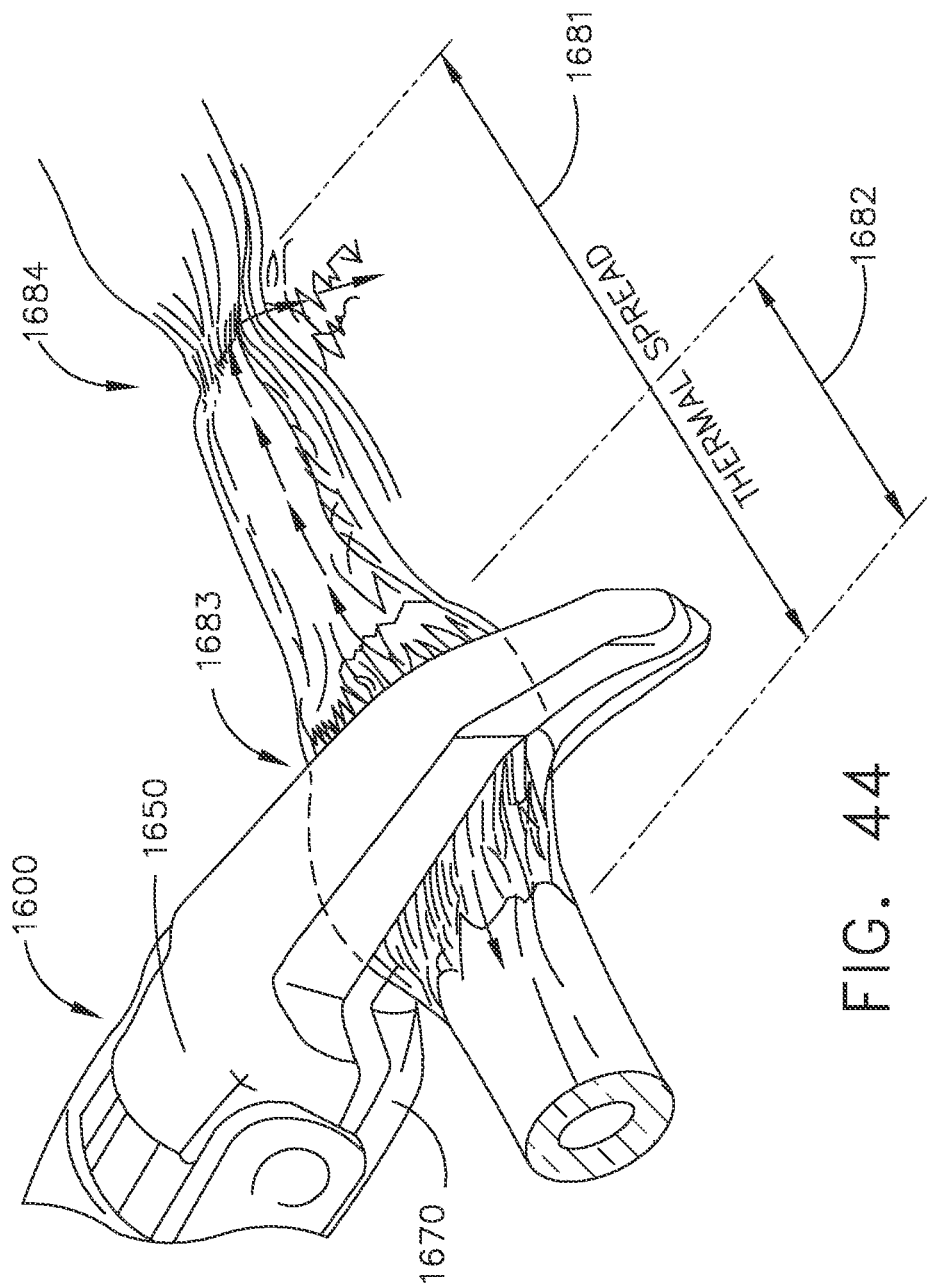
FIG. 44 illustrate an end effector treating an artery, in accordance with at least one aspect of the present disclosure.

Referring to FIG. 44, an end effector 1600 is applying monopolar energy to a tissue treatment region 1683 at a blood vessel such as, for example, an artery grasped by the end effector 1600. The monopolar energy flows from the end effector 1600 to the treatment region 1683, and eventually to a return pad (e.g. return pad 1621). Temperature of the tissue at the treatment region 1683 rises as monopolar energy is applied to the tissue. However, an actual thermal spread 1681 is greater than an expected thermal spread 1682, due to a constricted portion 1684 of the artery that inadvertently draws the monopolar energy, for example.

In various aspects, the control circuit 1604 monitors thermal effects at the treatment region 1683 resulting from application of the monopolar energy to the treatment region 1683. The control circuit 1604 can further detect a failure of the monitored thermal effects to comply with a predetermined correlation between the applied monopolar energy and thermal effects expected from application of the monopolar energy at the treatment region. In the illustrated example, the inadvertent energy draw at the constricted portion of the artery reduces the thermal effects at the treatment region, which is detected by the control circuit 1604.

In certain examples, the memory 3103 stores a predetermined correlation algorithm between monopolar energy level, as applied to a tissue treatment region grasped by the end effector 1600, and the thermal effects expected to result from application of the monopolar energy to the tissue treatment region. The correlation algorithm can be in the form of, for example, an array, lookup table, database, mathematical equation, or formula, etc. In at least one example, the stored correlation algorithm defines a correlation between power levels of the monopolar energy and expected temperatures. The control circuit 1604 can monitor the temperature of the tissue at the treatment region 1683 using the temperature sensors 1651, 1671, and can determine if a monitored temperature reading corresponds to an expected temperature reading at a certain power level.

The control circuit 1604 can be configured to take certain actions if a failure to comply with the stored correlation is detected. For example, the control circuit 1604 may alert a user of the failure. Additionally, or alternatively, the control circuit 1604 may reduce or pause delivery of the monopolar energy to the treatment region. In at least one example, the control circuit 1604 may adjust, or shift, from the monopolar energy to a bipolar energy application to the tissue treatment region to confirm the presence of a parasitic power draw. The control circuit 1604 may continue using bipolar energy at the treatment region if the parasitic power draw is confirmed. If, however, the control circuit 1604 refutes the presence of a parasitic power draw, the control circuit 1604 may reactivate, or re-increase, the monopolar power level. Changes to the monopolar and/or bipolar power levels can be achieved by the control circuit 1604 by signaling the monopolar power source 1620 and/or the bipolar power source 1610, for example.

Figure 45:
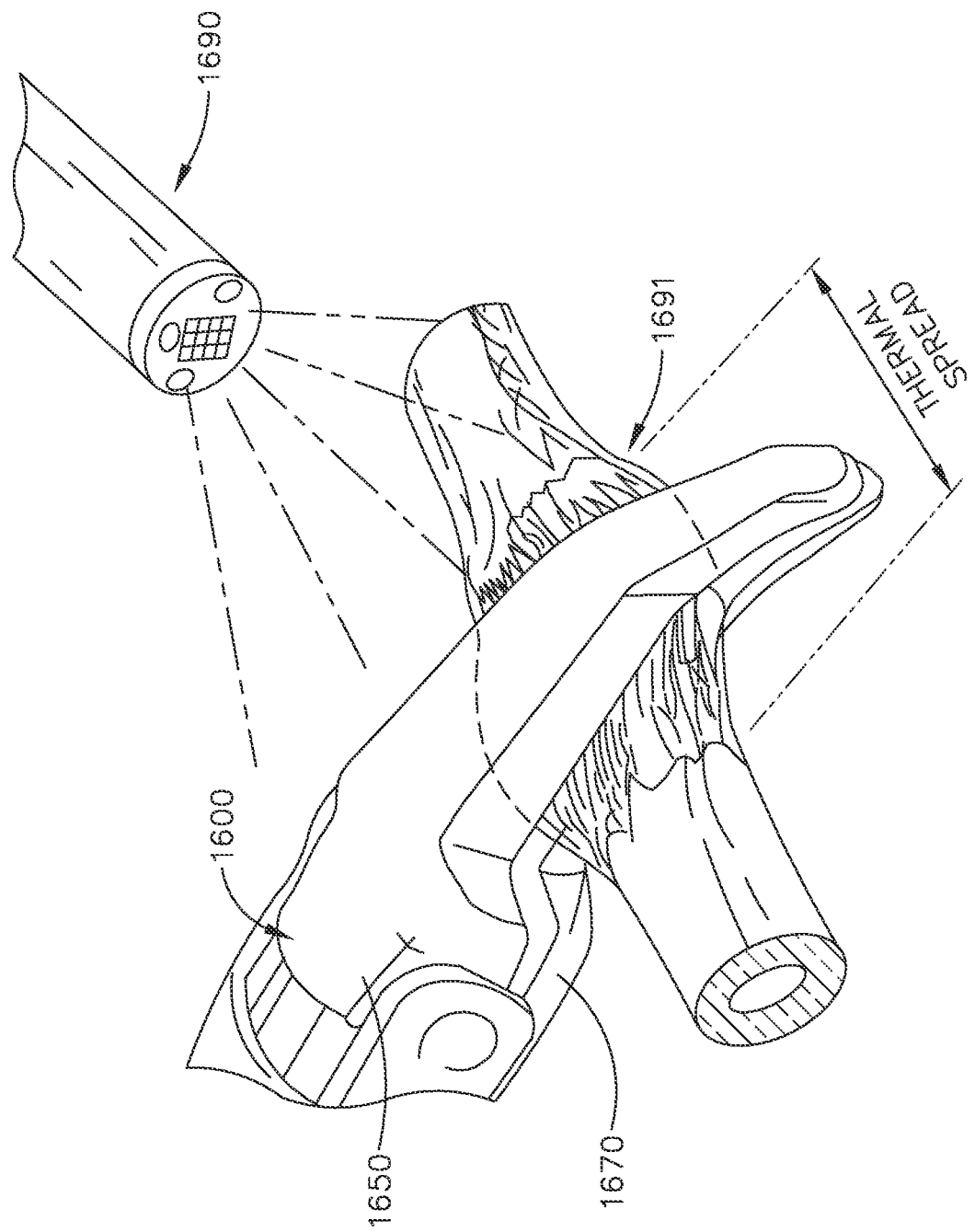
FIG. 45 illustrate an end effector treating an artery, in accordance with at least one aspect of the present disclosure.

In various aspects, one or more imaging devices such as, for example, a multi-spectral scope 1690 and/or an infrared imaging device can be utilized to monitor spectral tissue changes and/or the thermal effects at a tissue treatment region 1691, as illustrated in FIG. 45. Imaging data from the one or more imaging devices can be processed to estimate the temperature at the tissue treatment region 1691. For example, a user may direct the infrared imaging device at the treatment region 1691 as monopolar energy is being applied to the treatment region 1691 by the end effector of 1600. As the treatment region 1691 heats up, its infrared heat signature changes. Accordingly, changes in the heat signature correspond to changes in the temperature of the tissue at the treatment region 1691. Accordingly, the temperature of the tissue at the treatment region 1691 can be determined based on the heat signature captured by the one or more imaging devices. If the temperature estimated based on the heat signature at the treatment region 1691 associated with a certain part level is less than or equal to an expected temperature at the power level, the control circuit 1604 detects a discrepancy in the thermal effects at the treatment region 1691.

In other examples, the heat signature captured by the one or more imaging devices is not converted into an estimated temperature. Instead, it is directly compared heat signatures stored into the memory 3103 to assess whether a power level adjustment is needed.

In certain examples, the memory 3103 stores a predetermined a correlation algorithm between power levels of the monopolar energy, as applied to a tissue treatment region 1691 by the end effector 1600, and the heat signatures expected to result from application of the monopolar energy to the tissue treatment region. The correlation algorithm can be in the form of, for example, an array, lookup table, database, mathematical equation, or formula, etc. In at least one example, the stored correlation algorithm defines a correlation between power levels of the monopolar energy and expected heat signatures, or temperatures associated with the expected heat signatures.

Figure 46:
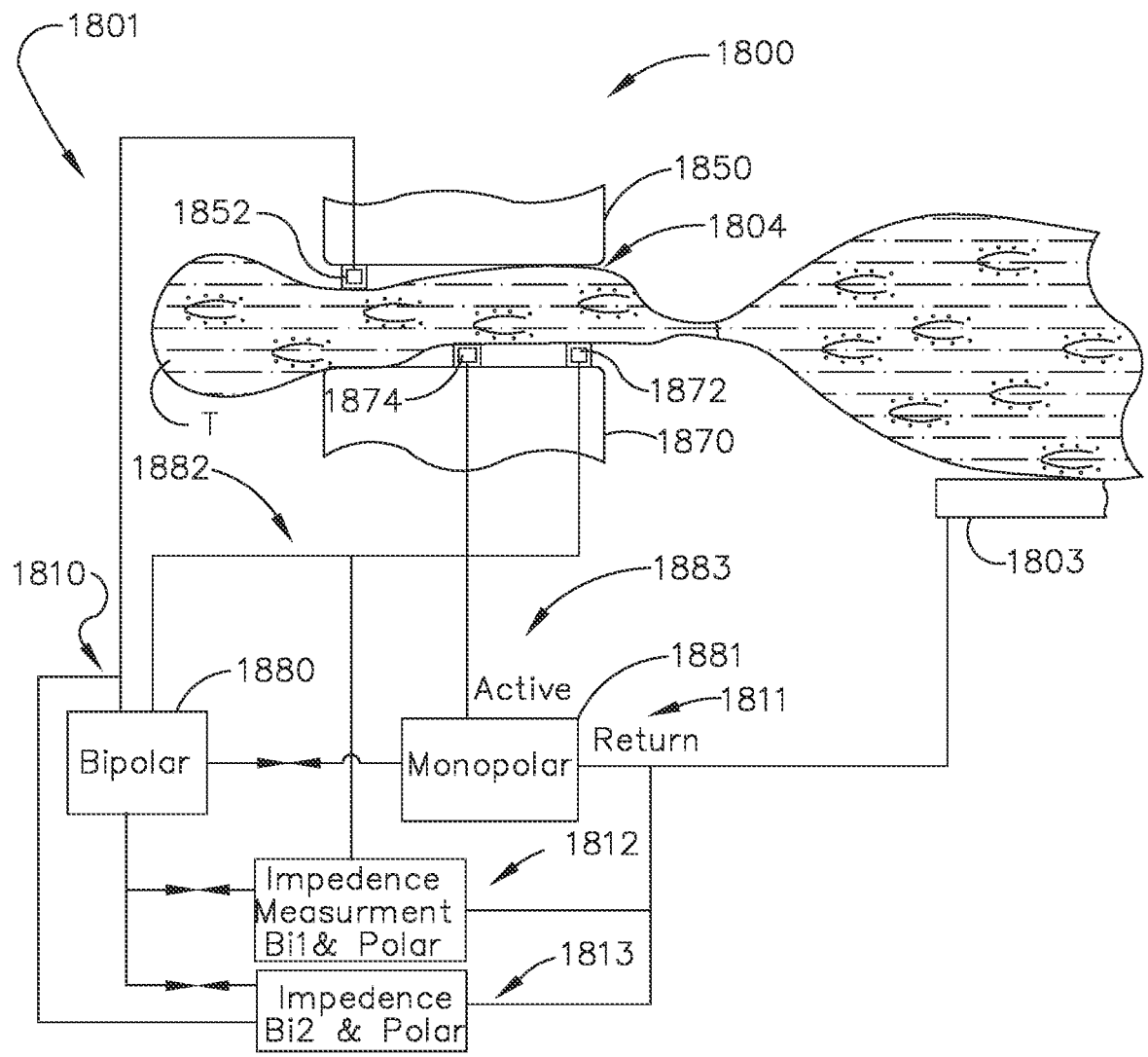
FIG. 46 illustrates an end effector applying therapeutic energy to a tissue grasped by the end effector, the therapeutic energy generated by a monopolar power source and a bipolar power source, in accordance with at least one aspect of the present disclosure.
Figure 47:
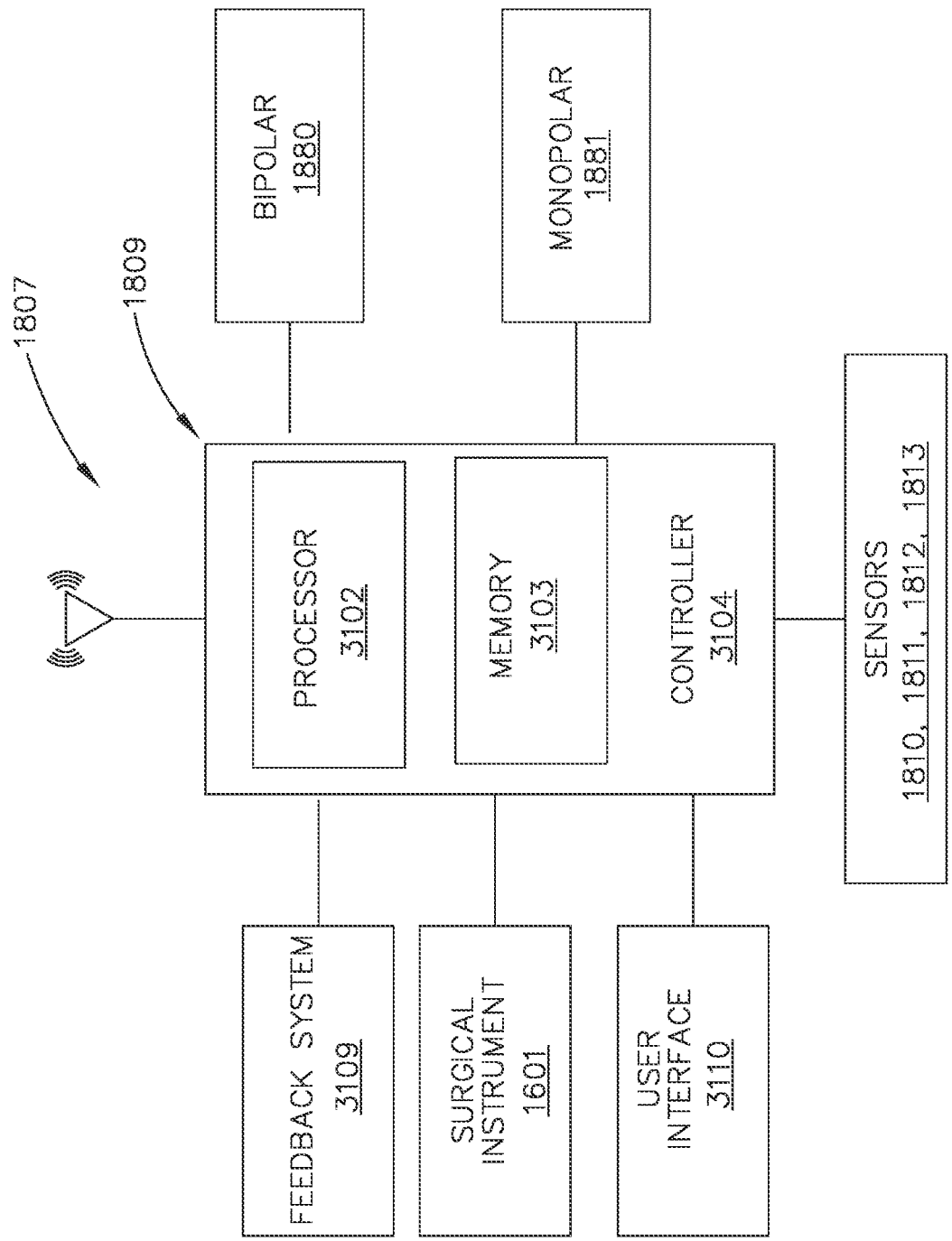
FIG. 47 illustrates a simplified schematic diagram of an electrosurgical system, in accordance with at least one aspect of the present disclosure.

Referring to FIGS. 46 and 47, an electrosurgical system includes an electrosurgical instrument 1801 that has an end effector 1800 similar to the end effectors 1400, 1500, 1600 in many respects, which are not repeated herein in the same level of detail for brevity. The end effector 1800 includes a first jaw 1850 and a second jaw 1870. At least one of the first jaw 1850 and the second jaw 1870 is movable to transition the end effector 1800 from an open configuration to a closed configuration to grasp tissue (T) between the first jaw 1850 and the second jaw 1870. Electrodes 1852, 1872 are configured to cooperate to deliver a bipolar energy to the tissue. An electrode 1874 is configured to deliver a monopolar energy to the tissue. In at least one example, the monopolar energy and the bipolar energy are delivered to the tissue either simultaneously, or in an alternating fashion, as illustrated in FIG. 34, to seal and/or cut the tissue, for example.

In the illustrated example, the bipolar energy and monopolar energy are generated by separate generators 1880, 1881, and are provided to the tissue by separate electrical circuits 1882, 1883 that connect the generator 1880 to the electrodes 1852, 1872, and the generator 1881 to the electrode 1874 and the return pad 1803, respectively. The power levels associated was the bipolar energy delivered to the tissue by the electrodes 1852, 1872 is set by the generator 1880, and the power levels associated with the monopolar energy delivered to the tissue by the electrode 1874 is set by the generator 1881, in accordance with the power scheme 3005', for example.

In use, as illustrated in FIG. 46, the end effector 1800 applies bipolar energy and/or monopolar energy to a tissue treatment region 1804 to seal and, in certain instances, transect the tissue. However, in certain instances, the energy is diverted from an intended target at the tissue treatment region 1804 causing an off-site thermal damage to surrounding tissue. To avoid, or at least reduce, such occurrences, the surgical instrument 1801 includes impedance sensors 1810, 1811, 1812, 1813, which are positioned between different electrodes and in different locations, as illustrated in FIG. 46, in order to detect off-site thermal damage.

In various aspects, the surgical system 1807 further includes a control circuit 1809 coupled to the impedance sensors 1810, 1811, 1812, 1813. The control circuit 1809 can detect an off-site, or an unintended, thermal damage based on one or more readings of the impedance sensors 1810, 1811, 1812, 1813. In response, the control circuit 1809 may alert a user to the off-site thermal damage, and instruct the user to pause energy delivery to the tissue treatment region 1804, or automatically pause the energy delivery, while maintaining the bipolar energy in accordance with a predetermined power scheme (e.g. power scheme 3005') to complete the tissue sealing. In certain instances, the control circuit 1809 may instruct the user to employ a mechanical knife to transect the tissue to avoid further off-site thermal damage.

Referring still to FIG. 46, the impedance sensor 1810 is configured to measure an impedance between the bipolar electrodes 1852, 1872. Further, the impedance sensor 1811 is configured to measure an impedance between the electrode 1874 and the return pad 1803. In addition, the impedance sensor 1812 is configured to measure an impedance between the electrode 1872 and the return pad 1803. In addition, the impedance sensor 1813 is configured to measure an impedance between the electrode 1852 and the return pad 1803. In other examples, additional impedance sensors are added inline between the monopolar and bipolar circuits 1882, 1883, which can be utilized to measure impedances at various locations to detect off-site thermal abnormalities with greater specificity as to the location and impedance path.

In various aspects, the off-site thermal damage occurs in tissue on one side (left/right) of the end effector 1800. The control circuit 1809 may detect the side on which the off-site thermal damage has occurred by comparing the readings of the impedance sensors 1810, 1811, 1812, 1813. In one example, a non-proportional change in the monopolar and bipolar impedance readings is indicative of an off-site thermal damage. On the contrary, if proportionality in the impedance readings is detected, the control circuit 1809 maintains that no off-site thermal damage has occurred. In one example, as described in greater detail below, the off-site thermal damage can be detected by the control circuit 1809 from a ratio of the bipolar to monopolar impedances.

FIG. 48 illustrates a graph 1900 depicting time on the x-axis and power on the y-axis. The graph 1900 illustrates a power scheme 1901 similar in many respects to the power scheme 3005' illustrated in FIG. 34, which are not repeated in the same level of detail herein for brevity. A control circuit 3101 causes the power scheme 1901 to be applied by the generators 1880 (GEN. 2), 1881 (GEN. 1) to effect a tissue treatment cycle by the end effector 1800. The power scheme 1901 includes a therapeutic power component 1902 and a nontherapeutic, or sensing, power component 1903. The therapeutic power component 1902 defines monopolar and bipolar power levels similar to the monopolar and bipolar power levels described in connection with the power scheme 3005'. The sensing power component 1903 includes monopolar 1905 and bipolar 1904 sensing pings delivered at various points throughout the tissue treatment cycle performed by the end effector 1800. In at least one example, the sensing pings 1903, 1904 of the sensing power component are delivered at a predetermined current value (e.g. 10 mA) or a predetermined range. In at least one example, three different sensing pings are utilized to determine location/orientation of a potential off-site thermal damage.

The control circuit 3101 may determine whether energy is being diverted to a non-tissue therapy directed site during a tissue treatment cycle by causing the sensing pings 1903, 1904 to be delivered at predetermined time intervals. The control circuit 3101 may then assess return-path conductivity based on the delivered sensing pings. If it is determined that energy is being diverted from a target site, the control circuit 3101 can take one or more reactive measures. For example, the control circuit 3101 can adjust the power scheme 1901 to be applied by the generators 1880 (GEN. 2), 1881 (GEN. 1). The control circuit 3101 may pause bipolar and/or monopolar energy application to the target site. Further, the control circuit 3101 may issue an alert to a user through feedback system 3109, for example. If, however, determines that no energy diversion is detected, the control circuit 3101 continues execution of the power scheme 1901.

In various aspects, the control circuit 3101 assesses return-path conductivity by comparing a measured return-conductivity to a predetermined return-path conductivity stored in the memory 3103, for example. If the comparison indicates that the measured and predetermined return-path conductivities are different beyond a predetermined threshold, the control circuit 3101 concludes that energy is being diverted to a non-tissue therapy directed site, and performs one or more of the previously described reactive measures.

FIG. 49 is a graph 2000 illustrating a power scheme 2001 interrupted, at t3', due to a detected off-site thermal damage. The power scheme 2001 is similar in many respects to the power schemes illustrated in FIGS. 34, 48, which are not repeated herein in the same level of detail for brevity. The control circuit 1809 causes the generators 1880 (curve line 2010), 1881 (curve line 2020) to apply the power scheme 2001 to effect a tissue treatment cycle by the end effector 1800, for example. In addition to the power scheme 2001, the graph 2000 further depicts bipolar impedance 2011 ($Z_{bipolar}$), monopolar impedance 2021 ($Z_{monopolar}$), and a ratio 2030 ($Z_{monopolar}/Z_{bipolar}$) of the monopolar impedance to the bipolar impedance on the y-axis. During normal operation, while the monopolar energy and the bipolar energy are being applied to the tissue simultaneously, values of the bipolar impedance 2011 ($Z_{bipolar}$) and monopolar impedance 2021 ($Z_{monopolar}$) remain proportional, or at least substantially proportional. It follows that a constant, or at least substantially constant, impedance ratio 2030 ($Z_{monopolar}/Z_{bipolar}$) of the monopolar impedance 2021 to the bipolar impedance 2011 is maintained within a predetermined range 2031 during normal operation.

In various aspects, the control circuit 1809 monitors the impedance ratio 2030 to assess whether the monopolar energy is diverting to non-tissue therapy directed site. The diversion changes the proportionality of the detected values of the bipolar impedance 2011 ($Z_{bipolar}$) and monopolar impedance 2021 ($Z_{monopolar}$), which changes the impedance ratio 2030. A change in the impedance ratio 2030 within the predetermined range 2031 may cause the control circuit 1908 to issue a warning. If, however, the change extends to, or below, a lower threshold of the predetermined range 2031 the control circuit 1908 may take additional reactive measures.

In the illustrated example, the impedance ratio 2030 ($Z_{monopolar}/Z_{bipolar}$) remains constant, or at least substantially constant, for an initial part of treatment cycle that involves a blended monopolar and bipolar energy application to the tissue. At B1, however, a discrepancy occurs where the monopolar impedance ($Z_{monopolar}$) drops unexpectedly, or un-proportionally with, the bipolar impedance ($Z_{bipolar}$) indicating a potential off-site thermal damage. In at least one example, the control circuit 1809 monitors changes in the ratio of ratio ($Z_{monopolar}/Z_{bipolar}$) of the monopolar impedance to the bipolar impedance, and detects an off-site thermal damage if the changes persist for a predetermined amount of time, and/or change in value to, or below, a lower threshold of the predetermined range 2031. At B1, since the detected the impedance ratio 2030 is still within the predetermined range 2031, the control circuit 3101 only issues a warning through the feedback system 3109 that an off-site thermal damage has been detected, and continues to monitor the impedance ratio 2030.

At t3', the control circuit 3101 further detects that the impedance ratio 2030 has changed to a value at, or below, a lower threshold of the predetermined range 2031. In response, the control circuit 3101 may issue another warning and, optionally, may instruct the user to pause energy delivery to the tissue, or automatically pause the energy delivery, at B2, while maintaining or adjusting the power level of the bipolar energy to complete the tissue sealing without monopolar energy. In certain examples, the control circuit 1809 further instructs the user to employ a mechanical knife (t4') to transect the tissue to avoid further off-site thermal damage. In the illustrated example, the control circuit 1809 further causes the generator 1880 to adjust its power level to complete the tissue sealing without monopolar energy, and increases the time period allotted for the tissue sealing segment from time t4 to time t4'. In other words, the control circuit 1809 increases the bipolar energy delivery to the tissue to compensate for the loss of monopolar energy by increasing the bipolar power level and its delivery time.

Various aspects of the subject matter described herein are set out in the following examples.

Various aspects of the subject matter described herein are set out in the following examples.

Example Set 1

Example 1—An electrosurgical instrument comprising an end effector. The end effector comprises a first jaw and a second jaw. At least one of the first jaw and the second jaw is movable to transition the end effector from an open configuration to a closed configuration to grasp tissue therebetween. The second jaw comprises a gradually narrowing body extending from a proximal end to a distal end. The gradually narrowing body comprises a conductive material. The gradually narrowing body comprises a first conductive portion extending from the proximal end to the distal end and a second conductive portion defining a tapered electrode protruding from the first conductive portion and extending distally along at least a portion of the gradually narrowing body. The second conductive portion is integral with the first conductive portion. The first conductive portion is thicker than the second conductive portion in a transverse cross-section of the gradually narrowing body. The second jaw further comprises an electrically insulative layer configured to electrically insulate the first conductive portion from the tissue but not the second conductive portion. The first conductive portion is configured to transmit an electrical energy to the tissue only through the second conductive portion.

Example 2—The electrosurgical instrument of Example 1, wherein the tapered electrode comprises an outer surface flush with an outer surface of the electrically insulative layer.

Example 3—The electrosurgical instrument of Examples 1 or 2, wherein the tapered electrode comprises a width that gradually narrows as the tapered electrode extends from the proximal end toward the distal end.

Example 4—The electrosurgical instrument of Examples 1, 2, or 3, wherein the electrical energy is delivered to the tissue through an outer surface of the tapered electrode.

Example 5—The electrosurgical instrument of Examples 1, 2, 3, or 4, wherein the first jaw comprises a first electrode extending distally along at least a portion of the first jaw, wherein the tapered electrode is a second electrode, and wherein the first electrode is laterally offset from the second electrode in the closed configuration.

Example 6—The electrosurgical instrument of Example 5, wherein the second jaw further comprises a third electrode spaced apart from the narrowing gradually body.

Example 7—The electrosurgical instrument of Example 6, wherein the third electrode extends distally along an angular profile defined by the second jaw from an electrode proximal end to an electrode distal end.

Example 8—The electrosurgical instrument of Example 7, wherein the third electrode comprises a base positioned in a cradle extending distally along the angular profile of the second jaw from a cradle proximal and to a cradle distal end.

Example 9—The electrosurgical instrument of Example 8, wherein the cradle is centrally situated with respect to lateral edges the second jaw.

Example 10—The electrosurgical instrument of Examples 8 or 9, wherein the third electrode further comprises a tapered edge extending from the base beyond sidewalls of the cradle.

Example 11—The electrosurgical instrument of Examples 8, 9, or 10, wherein the cradle is comprised of a compliant substrate.

Example 12—The electrosurgical instrument of Examples 8, 9, 10, or 11, wherein the cradle is partially embedded in a valley defined in the gradually narrowing body.

Example 13—The electrosurgical instrument of Examples 8, 9, 10, 11, or 12, wherein the cradle is spaced apart from the gradually narrowing body by an electrically insulative coating.

Example 14—The electrosurgical instrument of Examples 8, 9, 10, 11, 12, or 13, wherein the base comprises a base proximal end, a base distal end, and a width that gradually narrows as the base extends along the angular profile from the base proximal end to the base distal end.

Example 15—An electrosurgical instrument comprising an end effector. The end effector comprises a first jaw and a second jaw. At least one of the first jaw and the second jaw is movable to transition the end effector from an open configuration to a closed configuration to grasp tissue therebetween. The second jaw comprises a conductive body comprising a tapered angular profile extending from a proximal end to a distal end. The conductive body comprises a first conductive portion extending from the proximal end to the distal end and a second conductive portion defining a tapered electrode protruding from the first conductive portion and extending distally along at least a portion of the conductive body. The second conductive portion is integral with the first conductive portion. The first conductive portion is thicker than the second conductive portion. The second jaw further comprises an electrically insulative layer configured to electrically insulate the first conductive portion from the tissue but not the second conductive portion. The first conductive portion is configured to transmit an electrical energy to the tissue only through the second conductive portion.

Example 16—The electrosurgical instrument of Example 15, wherein the tapered electrode comprises a width that gradually narrows as the tapered electrode extends from the proximal end toward the distal end.

Example 17—The electrosurgical instrument of Examples 15 or 16, wherein the first jaw comprises a first electrode extending distally along at least a portion of the first jaw, wherein the tapered electrode is a second electrode, and wherein the first electrode is laterally offset from the second electrode in the closed configuration.

Example 18—The electrosurgical instrument of Examples 15, 16, or 17, wherein the second jaw further comprises a third electrode spaced apart from the conductive body.

Example 19—The electrosurgical instrument of Example 18, wherein the third electrode extends distally along at least a portion of the tapered angular profile.

Example 20—The electrosurgical instrument of Example 19, wherein the third electrode comprises a base positioned in a cradle extending distally along the at least a portion of the tapered angular profile from a cradle proximal and to a cradle distal end, and wherein the cradle is comprised of a compliant substrate.

Example Set 2

Example 1—An electrosurgical instrument comprising an end effector. The end effector comprises a first jaw and a second jaw. At least one of the first jaw and the second jaw is movable to transition the end effector from an open configuration to a closed configuration to grasp tissue therebetween. The second jaw comprises linear portions cooperating to form an angular profile and a treatment surface comprising segments extending along the angular profile. The segments comprise different geometries and different conductivities. The segments are configured to produce variable energy densities along the treatment surface.

Example 2—The electrosurgical instrument of Example 1, wherein the segments comprise a proximal segment and a distal segment. The proximal segment comprises a first surface area. The distal segment comprises a second surface area. The second surface area is smaller than the first surface area.

Example 3—The electrosurgical instrument of Examples 1 or 2, wherein at least one of the segments comprises conductive treatment regions longitudinally interrupted by nonconductive treatment regions.

Example 4—The electrosurgical instrument of Examples 1, 2, or 3, wherein the variable energy densities are predetermined based on a selection of the different geometries and different conductivities of the segments.

Example 5—The electrosurgical instrument of Examples 1, 2, 3, or 4, wherein at least one of the segments comprises a gradually narrowing width along its length.

Example 6—The electrosurgical instrument of Examples 1, 2, 3, 4, or 5, wherein the segments extend along a peripheral side of the second jaw.

Example 7—The electrosurgical instrument of Examples 1, 2, 3, 4, 5, or 6, wherein the segments are defined in the second jaw but not the first jaw.

Example 8—The electrosurgical instrument of Examples 1, 2, 3, 4, 5, 6, or 7, wherein the second jaw comprises an electrically conductive skeleton partially coated with a first material and a second material, wherein the first material is thermally conductive but electrically insulative, and wherein the second material is thermally and electrically insulative.

Example 9—The electrosurgical instrument of Example 8, wherein the first material comprises diamond-like carbon.

Example 10—The electrosurgical instrument of Examples 8 or 9, wherein the second material comprises PolyTetraFluoroEthylene.

Example 11—An electrosurgical instrument comprising an end effector. The end effector comprises a first jaw and a second jaw. At least one of the first jaw and the second jaw is movable to transition the end effector from an open configuration to a closed configuration to grasp tissue therebetween. The second jaw comprises a gradually narrowing body extending from a proximal end to a distal end. The gradually narrowing body comprises a tissue contacting surface. The tissue contacting surface comprises an insulative layer comprising a first material. The insulative layer extends on opposite sides of an intermediate area extending along a length of the gradually narrowing body. The tissue contacting surface further comprises segments configured to yield variable energy densities along the tissue contacting surface. The segments comprise conductive segments and insulative segments alternating with the conductive segments along the intermediate area. The insulative segments comprise a second material different from the first material.

Example 12—The electrosurgical instrument of Example 11, wherein the conductive segments comprise a proximal segment and a distal segment. The proximal segment comprises a first surface area. The distal segment comprises a second surface area. The second surface area is smaller than the first surface area.

Example 13—The electrosurgical instrument of Examples 11 or 12, wherein the second jaw comprises an electrically conductive skeleton partially coated with the first material.

Example 14—The electrosurgical instrument of Example 13, wherein the electrically conductive skeleton comprises an inner thermally-insulative core and an outer thermally-conductive layer at least partially surrounding the inner thermally-insulative core.

Example 15—The electrosurgical instrument of Examples 11, 12, 13, or 14, wherein the variable energy densities are predetermined based on a selection of different geometries and different conductivities of the conductive segments.

Example 16—The electrosurgical instrument of Examples 11, 12, 13, 14, or 15, wherein at least one of the segments comprises a gradually narrowing width along its length.

Example 17—The electrosurgical instrument of Examples 11, 12, 13, 14, 15, or 16, wherein the segments extend along a peripheral side of the second jaw.

Example 18—The electrosurgical instrument of Examples 11, 12, 13, 14, 15, 16, or 17, wherein the segments are defined in the second jaw but not the first jaw.

Example 19—The electrosurgical instrument of Examples 11, 12, 13, 14, 15, 16, 17, or 18, wherein the first material comprises diamond-like carbon.

Example 20—The electrosurgical instrument of Examples 11, 12, 13, 14, 15, 16, 17, 18, or 19, wherein the second material comprises PolyTetraFluoroEthylene.

Example Set 3

Example 1—An electrosurgical instrument comprising an end effector. The end effector comprises a first jaw, a second jaw, and an electrical circuit. The first jaw comprises a first electrically conductive skeleton, a first insulative coating selectively covering portions of the first electrically conductive skeleton, and first-jaw electrodes comprising exposed portions of the first electrically conductive skeleton. At least one of the first jaw and the second jaw is movable to transition the end effector from an open configuration to a closed configuration to grasp tissue therebetween. The second jaw comprises a second electrically conductive skeleton, a second insulative coating selectively covering portions of the second electrically conductive skeleton, and second-jaw electrodes comprising exposed portions of the second electrically conductive skeleton. The electrical circuit is configured to transmit a bipolar RF energy and a monopolar RF energy to the tissue through the first-jaw electrodes and the second-jaw electrodes. The monopolar RF energy shares a first electrical pathway and a second electrical pathway defined by the electrical circuit for transmission of the bipolar RF energy.

Example 2—The electrosurgical instrument of Example 1, wherein the electrical circuit defines a third electrical pathway separate from the first electrical pathway and the second electrical pathway.

Example 3—The electrosurgical instrument of Example 1 or 2, wherein the end effector comprises a cutting electrode electrically insulated from the first electrically conductive skeleton and the second electrically conductive skeleton.

Example 4—The electrosurgical instrument of Example 3, wherein the cutting electrode is configured to receive a cutting monopolar RF energy through the third electrical pathway.

Example 5—The electrosurgical instrument of Example 4, wherein the cutting electrode is configured to cut the tissue with the cutting monopolar RF energy after coagulation of the tissue has commenced with the bipolar RF energy.

Example 6—The electrosurgical instrument of Examples 3, 4 or 5, wherein the cutting electrode is centrally located in one of the first jaw and the second jaw.

Example 7—The electrosurgical instrument of Examples 4 or 5, wherein the end effector is configured to simultaneously deliver the cutting monopolar RF energy and the bipolar RF energy to the tissue.

Example 8—The electrosurgical instrument of Examples 1, 2, 3, 4, 5, 6, or 7, wherein the first-jaw electrodes comprise a first distal-tip electrode, and wherein the second-jaw electrodes comprise a second distal-tip electrode.

Example 9—The electrosurgical instrument of Example 8, wherein first electrically conductive skeleton and the second electrically conductive skeleton are energized simultaneously to deliver the monopolar RF energy to a tissue surface through the first distal-tip electrode and the second distal-tip electrode.

Example 10—The electrosurgical instrument of Examples 1, 2, 3, 4, 5, 6, 7, 8, or 9, wherein the second jaw comprises a dissection electrode extending along a peripheral surface of the second jaw.

Example 11—An electrosurgical instrument comprising an end effector and an electrical circuit. The end effector comprises at least two electrode sets, a first jaw, and a second jaw. At least one of the first jaw and the second jaw is movable to transition the end effector from an open configuration to a closed configuration to grasp tissue therebetween. The end effector is configured to deliver a combination of bipolar RF energy and monopolar RF energy to the grasped tissue from the at least two electrode sets. The electrical circuit is configured to transmit the bipolar RF energy and the monopolar RF energy. The monopolar RF energy shares an active pathway and a return pathway defined by the electrical circuit for transmission of the bipolar RF energy.

Example 12—The electrosurgical instrument of Example 11, wherein the at least two electrodes sets comprise three electrical interconnections that are used together in the electrical circuit.

Example 13—The electrosurgical instrument of Examples 11 or 12, wherein the at least two electrodes sets comprise three electrical interconnections that define at least a portion of the electrical circuit and another separate electrical circuit.

Example 14—The electrosurgical instrument of Example 13, wherein the separate electrical circuit leads to a cutting electrode of the at least two electrode sets that is isolated and centrally located in one of the first jaw and the second jaw.

Example 15—The electrosurgical instrument of Example 14, wherein the cutting electrode is configured to cut the tissue after coagulation of the tissue has commenced using second and third electrodes of the at least two electrode sets.

Example 16—The electrosurgical instrument of Examples 14 or 15, wherein the at least two electrode sets are configured to simultaneously deliver the monopolar RF energy and the bipolar RF energy to the tissue.

Example 17—An electrosurgical instrument comprising an end effector. The end effector comprises a first jaw and a second jaw. At least one of the first jaw and the second jaw is movable to transition the end effector from an open configuration to a closed configuration to grasp tissue therebetween. The second jaw comprises a composite skeleton of at least two different materials that are configured to selectively yield electrically conductive portions and thermally insulted portions.

Example 18—The electrosurgical instrument of Example 17, wherein the composite skeleton comprises a titanium ceramic-composite.

Example 19—The electrosurgical instrument of Examples 17 or 18, wherein the composite skeleton comprises a ceramic base and a titanium crown attachable to the ceramic base.

Example 20—The electrosurgical instrument of Examples 17, 18, or 19, wherein the composite skeleton is at least partially coated with an electrically insulative material.

Example 21—A method for manufacturing a jaw of an end effector of an electrosurgical instrument. The method comprises preparing a composite skeleton of the jaw by fusing a titanium powder with a ceramic powder in a metal injection molding process and selectively coating the composite skeleton with an electrically insulative material to yield a plurality of electrodes.

Example Set 4

Example 1—An electrosurgical instrument comprising a first jaw and a second jaw. The first jaw is configured to define a first electrode. The first jaw comprises a first electrically conductive skeleton and a first electrically insulative layer. The first electrically conductive skeleton comprises a first thermally insulative core and a first thermally conductive outer layer integral with and extending at least partially around the first thermally insulative core. The first electrode is defined by selective application of the first electrically insulative layer to an outer surface of the first thermally conductive outer layer. The second jaw is configured to define a second electrode. The second jaw comprises a second electrically conductive skeleton and a second electrically insulative layer. The second electrically conductive skeleton comprises a second thermally insulative core and a second thermally conductive outer layer integral with and extending at least partially around the second thermally insulative core. The second electrode is defined by selective application of the second electrically insulative layer to an outer surface of the second thermally conductive outer layer.

Example 2—The electrosurgical instrument of Example 1, wherein the first electrode is configured to transmit an RF energy to the second electrode through tissue positioned therebetween in a bipolar energy mode of operation.

Example 3—The electrosurgical instrument of Examples 1 or 2, wherein the first thermally insulative core comprises air pockets.

Example 4—The electrosurgical instrument of Examples 1, 2, or 3, wherein the first thermally insulative core comprises a lattice structure.

Example 5—The electrosurgical instrument of Examples 1, 2, 3, or 4, wherein the second jaw comprises a third electrode, and wherein the third electrode is defined by selective application of the second electrically insulative layer to the outer surface of the second thermally conductive outer layer.

Example 6—The electrosurgical instrument of Example 5, wherein the third electrode is configured to deliver an RF energy to tissue in contact with the third electrode in a monopolar energy mode of operation.

Example 7—The electrosurgical instrument of Examples 1, 2, 3, 4, 5, or 6, wherein at least one of the first electrically insulative layer and the second electrically insulative layer comprises a diamond-like material.

Example 8—The electrosurgical instrument of Examples 1, 2, 3, 4, 5, 6, or 7, wherein the first jaw comprises a tissue-contacting surface, and wherein the first thermally insulative core comprises a lattice structure including walls erected in a direction that transects the tissue-contacting surface.

Example 9—The electrosurgical instrument of Example 8, wherein the direction is perpendicular to the tissue-contacting surface.

Example 10—An electrosurgical instrument comprising a jaw configured to define an electrode. The jaw comprises a first electrically conductive portion, a second electrically conductive portion, and an electrically insulative layer. The first electrically conductive portion is configured to resist heat transfer therethrough. The second electrically conductive portion is integral with and extending at least partially around the first electrically conductive portion. The second electrically conductive portion is configured to define a heat sink. The electrode is defined by selective application of the electrically insulative layer to an outer surface of the second electrically conductive portion.

Example 11—The electrosurgical instrument of Example 10, wherein the electrode is configured to transmit an RF energy to tissue positioned against the electrode.

Example 12—The electrosurgical instrument of Examples 10 or 11, wherein the first electrically conductive portion comprises air pockets.

Example 13—The electrosurgical instrument of Examples 10, 11, or 12, wherein the first electrically conductive portion comprises a lattice structure.

Example 14—The electrosurgical instrument of Examples 10, 11, 12, or 13, wherein the electrically insulative layer comprises a diamond-like material.

Example 15—The electrosurgical instrument of Examples 10, 11, 12, 13, or 14, wherein the jaw comprises a tissue-contacting surface, and wherein the first electrically conductive portion comprises a lattice structure including walls erected in a direction that transects the tissue-contacting surface.

Example 16—The electrosurgical instrument of Example 15, wherein the direction is perpendicular to the tissue-contacting surface.

Example 17—An electrosurgical instrument comprising a jaw configured to define an electrode. The jaw comprises an electrically conductive skeleton and an electrically insulative layer. The electrically conductive skeleton comprises a thermally insulative core and a thermally conductive outer layer integral with and extending at least partially around the thermally insulative core. The electrode is defined by selective application of the electrically insulative layer to an outer surface of the thermally conductive outer layer.

Example 18—The electrosurgical instrument of Example 17, wherein the thermally insulative core comprises a lattice structure.

Example 19—The electrosurgical instrument of Example 18, wherein the jaw comprises a tissue-contacting surface, and wherein the lattice structure includes walls erected in a direction that transects the tissue-contacting surface.

Example 20—The electrosurgical instrument of Example 19, wherein the direction is perpendicular to the tissue-contacting surface.

Example Set 5

Example 1—An electrosurgical instrument comprising an end effector. The end effector comprises a first jaw and a second jaw. The first jaw comprises a first electrode. At least one of the first jaw and the second jaw is movable to transition the end effector from an open configuration to a closed configuration to grasp tissue therebetween. The second jaw comprises a second electrode configured to deliver a first monopolar energy to the tissue, a third electrode, and a conductive circuit selectively transitionable between a connected configuration with the third electrode and a disconnected configuration with the third electrode. In the connected configuration, the third electrode is configured to cooperate with the first electrode to deliver bipolar energy to the tissue. The conductive circuit defines a return path for the bipolar energy. In the disconnected configuration, the first electrode is configured to deliver a second monopolar energy to the tissue.

Example 2—The electrosurgical instrument of Example 1, further comprising a switching mechanism for alternating between the connected configuration and the disconnected configuration.

Example 3—The electrosurgical instrument of Examples 1 or 2, further comprising a switching mechanism for alternating between delivering the bipolar energy and the second monopolar energy to the tissue through the first electrode.

Example 4—The electrosurgical instrument of Examples 1, 2 or 3, wherein the end effector is configured to deliver the bipolar energy and the first monopolar energy to the tissue simultaneously.

Example 5—The electrosurgical instrument of Examples 1, 2, 3, or 4, wherein the end effector is configured to deliver an energy blend of the bipolar energy and the first monopolar energy to the tissue.

Example 6—The electrosurgical instrument of Example 5, wherein levels of the bipolar energy and the first monopolar energy in the energy blend are determined based on at least one reading of a temperature sensor indicative of at least one temperature of the tissue.

Example 7—The electrosurgical instrument of Examples 5 or 6, wherein levels of the bipolar energy and the first monopolar energy in the energy blend are determined based on at least one reading of an impedance sensor indicative of at least one impedance of the tissue.

Example 8—The electrosurgical instrument of Examples 5, 6, or 7, wherein levels of the bipolar energy and the first monopolar energy in the energy blend are adjusted to reduce a detected lateral thermal damage beyond a tissue treatment region between the first jaw and the second jaw.

Example 9—An electrosurgical instrument comprising an end effector and a control circuit. The end effector comprises a first jaw, a second jaw, and at least one sensor. The first jaw comprises a first electrode. At least one of the first jaw and the second jaw is movable to transition the end effector from an open configuration to a closed configuration to grasp tissue therebetween. The second jaw comprises a second electrode configured to deliver a monopolar energy to the tissue and third electrode configured to cooperate with the first electrode to deliver a bipolar energy. The control circuit is configured to execute a predetermined power scheme to seal and cut the tissue in a tissue treatment cycle. The power scheme comprises predetermined power levels of the monopolar energy and the bipolar energy. The control circuit is further configured to adjust at least one of the predetermined power levels of the monopolar energy and the bipolar energy based on readings of at least one sensor during the tissue treatment cycle.

Example 10—The electrosurgical instrument of Example 9, wherein the predetermined power scheme comprises a simultaneous application and a separate application of the bipolar energy and the monopolar energy to the tissue in the tissue treatment cycle.

Example 11—The electrosurgical instrument of Examples 9 or 10, wherein the predetermined power scheme comprises an application of the bipolar energy but not the monopolar energy to the tissue in a feathering segment of the tissue treatment cycle and a simultaneous application of the bipolar energy and the monopolar energy to the tissue in a tissue warming segment and a tissue sealing segment of the tissue treatment cycle.

Example 12—The electrosurgical instrument of Example 11, wherein the power scheme further comprises an application of the monopolar energy but not the bipolar energy to the tissue in a tissue transection segment of the tissue treatment cycle.

Example 13—The electrosurgical instrument of Examples 9, 10, 11, or 12, wherein the at least one sensor comprises impedance sensors.

Example 14—The electrosurgical instrument of Example 13, wherein the control circuit is configured to monitor an impedance ratio of a monopolar tissue-impedance to a bipolar tissue-impedance based on readings from the impedance sensors.

Example 15—The electrosurgical instrument of Example 14, wherein a change in the impedance ratio within a predetermined range causes the control circuit to issue a warning.

Example 16—The electrosurgical instrument of Example 15, wherein a change in the impedance ratio to, or below, a lower threshold of the predetermined range causes the control circuit to adjust the predetermined power scheme.

Example 17—The electrosurgical instrument of Examples 15 or 16, wherein a change in the impedance ratio to, or below, a lower threshold of the predetermined range causes the control circuit to pause an application of the monopolar energy to the tissue.

Example 18—The electrosurgical instrument of Example 17, wherein the change in the impedance ratio to, or below, a lower threshold of the predetermined range further causes the control circuit to adjust an application of the bipolar energy to the tissue to complete sealing the tissue.

Example 19—An electrosurgical instrument comprising an end effector and a control circuit. The end effector comprises a first jaw and a second jaw. The first jaw comprising a first electrode. At least one of the first jaw and the second jaw is movable to transition the end effector from an open configuration to a closed configuration to grasp tissue therebetween. The tissue being at a target site. The second jaw comprises a second electrode configured to deliver a monopolar energy to the tissue and a third electrode configured to cooperate with the first electrode to deliver a bipolar energy. The control circuit is configured to execute a predetermined power scheme to seal and cut the tissue in a tissue treatment cycle. The power scheme comprises predetermined power levels of the monopolar energy and the bipolar energy. The control circuit is further configured to detect an energy diversion off the target site and adjust at least one of the predetermined power levels of the monopolar energy and the bipolar energy to mitigate the energy diversion.

Example 20—The electrosurgical instrument of Example 19, wherein the predetermined power scheme comprises a simultaneous application and a separate application of the bipolar energy and the monopolar energy to the tissue in the tissue treatment cycle.

Example 21—The electrosurgical instrument of Examples 19 or 20, wherein the predetermined power scheme comprises an application of the bipolar energy but not the monopolar energy to the tissue in a feathering segment of the tissue treatment cycle and a simultaneous application of the bipolar energy and the monopolar energy to the tissue in a tissue warming segment and a tissue sealing segment of the tissue treatment cycle.

Example Set 6

Example 1—An electrosurgical system comprising an end effector and a control circuit. The end effector comprises a first jaw and a second jaw. At least one of the first jaw and the second jaw is movable to transition the end effector from an open configuration to a closed configuration to grasp tissue therebetween. The control circuit is configured to cause an application of two different energy modalities to the tissue simultaneously and separately during a tissue treatment cycle comprising a tissue coagulation stage and a tissue transection stage.

Example 2—The electrosurgical system of Example 1, wherein the first energy modality is a monopolar energy modality.

Example 3—The electrosurgical system of Example 2, wherein the second energy modality is a bipolar energy modality.

Example 4—The electrosurgical system of Examples 2 or 3, wherein the control circuit is configured to activate the application of the monopolar energy modality to the tissue prior to a completion of the tissue coagulation stage by the bipolar energy modality.

Example 5—The electrosurgical system of Examples 2 or 3, wherein the control circuit is configured to activate the application of the monopolar energy modality to the tissue prior to deactivation of the bipolar energy modality application to the tissue.

Example 6—The electrosurgical system of Examples 3, 4, or 5, wherein the control circuit is configured to cause a simultaneous application of the monopolar energy modality and the bipolar energy modality to the tissue during the tissue coagulation stage.

Example 7—The electrosurgical system of Examples 1, 2, 3, 4, 5, or 6, wherein the control circuit comprises a processor and a storage medium, and wherein the application of the two different energy modalities to the tissue is based on a default power scheme stored in the storage medium.

Example 8—The electrosurgical system of Example 7, further comprising at least one sensor, and wherein the control circuit is configured to modify the default power scheme based on one more sensor readings of the at least one sensor.

Example 9—An electrosurgical instrument comprising an end effector. The end effector comprises a first jaw and a second jaw. At least one of the first jaw and the second jaw is movable to transition the end effector from an open configuration to a closed configuration to grasp tissue therebetween. The end effector is configured to cause an application of three different energy modalities to the tissue during a tissue treatment cycle comprising a tissue coagulation stage and a tissue transection stage.

Example 10—The electrosurgical instrument of Example 9, wherein the first energy modality comprises a bipolar energy.

Example 11—The electrosurgical instrument of Example 10, wherein the second energy modality comprises an energy blend of a monopolar energy and the bipolar energy.

Example 12—The electrosurgical instrument of Example 11, wherein the third energy modality comprises the monopolar energy but not the bipolar energy.

Example 13—The electrosurgical instrument of Examples 11 or 12, wherein an activation of the monopolar energy application to the tissue is configured to begin prior to a completion of the tissue coagulation stage.

Example 14—The electrosurgical instrument of Examples 12 or 13, wherein an activation of the monopolar energy application to the tissue is configured to begin prior to a deactivation of the application of the bipolar energy modality to the tissue.

Example 15—The electrosurgical instrument of Examples 9, 10, 11, 12, 13, or 14, further comprising a control circuit, wherein the control circuit comprises a processor and a storage medium, and wherein the application of the two different energy modalities to the tissue is based on a default power scheme stored in the storage medium.

Example 16—The electrosurgical instrument of Example 15, further comprising at least one sensor, wherein the control circuit is configured to adjust the default power scheme during the tissue treatment cycle based on one more sensor readings of the at least one sensor.

Example 17—An electrosurgical system comprising a first generator configured output a bipolar energy, a second generator configured to output a monopolar energy, a surgical instrument electrically coupled to the first generator and the second generator, and a control circuit. The surgical instrument comprises an end effector. The end effector comprises a first jaw and a second jaw. At least one of the first jaw and the second jaw is movable to transition the end effector from an open configuration to a closed configuration to grasp tissue therebetween. The control circuit comprises a processor and a storage medium comprising program instructions that, when executed by the processor, causes the processor to cause the first generator and the second generator to apply a predetermined power scheme to the end effector. The power scheme comprises a simultaneous application and a separate application of the bipolar energy and the monopolar energy to the tissue in a tissue treatment cycle.

Example 18—The electrosurgical system of Example 17, further comprising at least one sensor, wherein the control circuit is configured to adjust the power scheme during the tissue treatment cycle based on one more sensor readings of the at least one sensor.

Example 19—The electrosurgical system of Examples 17 or 18, wherein the power scheme comprises an application of the bipolar energy but not the monopolar energy to the tissue in a feathering segment of the tissue treatment cycle, and a simultaneous application of the bipolar energy and the monopolar energy to the tissue in a tissue warming segment and a tissue sealing segment of the tissue treatment cycle.

Example 20—The electrosurgical system of Examples 17, 18, or 19, wherein the power scheme further comprises an application of the monopolar energy but not the bipolar energy to the tissue in a tissue transection segment of the tissue treatment cycle.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

With respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

In this specification, unless otherwise indicated, terms "about" or "approximately" as used in the present disclosure, unless otherwise specified, means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In this specification, unless otherwise indicated, all numerical parameters are to be understood as being prefaced and modified in all instances by the term "about," in which the numerical parameters possess the inherent variability characteristic of the underlying measurement techniques used to determine the numerical value of the parameter. At the very least, and not as an attempt to limit the application of the doctrine of equivalents to the scope of the claims, each numerical parameter described herein should at least be construed in light of the number of reported significant digits and by applying ordinary rounding techniques.

Any numerical range recited herein includes all sub-ranges subsumed within the recited range. For example, a range of "1 to 10" includes all sub-ranges between (and including) the recited minimum value of 1 and the recited maximum value of 10, that is, having a minimum value equal to or greater than 1 and a maximum value equal to or less than 10. Also, all ranges recited herein are inclusive of the end points of the recited ranges. For example, a range of "1 to 10" includes the end points 1 and 10. Any maximum numerical limitation recited in this specification is intended to include all lower numerical limitations subsumed therein, and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited. All such ranges are inherently described in this specification.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

What is claimed is:

1. An electrosurgical instrument, comprising:
   an end effector, comprising:
      a first jaw; and
      a second jaw, wherein at least one of the first jaw and the second jaw is movable to transition the end effector from an open configuration to a closed configuration to grasp tissue therebetween, and wherein the second jaw comprises:
         linear portions cooperating to form an angular profile; and
         a treatment surface comprising segments extending along the angular profile, wherein the segments comprise different geometries and different conductivities, and wherein the segments are configured to produce variable energy densities along the treatment surface.

2. The electrosurgical instrument of claim 1, wherein the segments comprise:
   a proximal segment comprising a first surface area; and
   a distal segment comprising a second surface area, wherein the second surface area is smaller than the first surface area.

3. The electrosurgical instrument of claim 1, wherein at least one of the segments comprises conductive treatment regions longitudinally interrupted by nonconductive treatment regions.

4. The electrosurgical instrument of claim 1, wherein the variable energy densities are predetermined based on a selection of the different geometries and different conductivities of the segments.

5. The electrosurgical instrument of claim 1, wherein at least one of the segments comprises a gradually narrowing width along its length.

6. The electrosurgical instrument of claim 1, wherein the segments extend along a peripheral side of the second jaw.

7. The electrosurgical instrument of claim 1, wherein the segments are defined in the second jaw but not the first jaw.

8. The electrosurgical instrument of claim 1, wherein the second jaw comprises an electrically conductive skeleton partially coated with a first material and a second material, wherein the first material is thermally conductive but electrically insulative, and wherein the second material is thermally and electrically insulative.

9. The electrosurgical instrument of claim 8, wherein the first material comprises diamond-like carbon.

10. The electrosurgical instrument of claim 9, wherein the second material comprises PolyTetraFluoroEthylene.

11. An electrosurgical instrument, comprising:
an end effector, comprising:
a first jaw; and
a second jaw, wherein at least one of the first jaw and the second jaw is movable to transition the end effector from an open configuration to a closed configuration to grasp tissue therebetween, wherein the second jaw comprises a gradually narrowing body extending from a proximal end to a distal end, and wherein the gradually narrowing body comprises a tissue contacting surface comprising:
an insulative layer comprising a first material, wherein the insulative layer extends on opposite sides of an intermediate area extending along a length of the gradually narrowing body; and
segments configured to yield variable energy densities along the tissue contacting surface, wherein the segments comprise:
conductive segments; and
insulative segments alternating with the conductive segments along the intermediate area, wherein the insulative segments comprise a second material different from the first material.

12. The electrosurgical instrument of claim 11, wherein the conductive segments comprise:
a proximal segment comprising a first surface area; and
a distal segment comprising a second surface area, wherein the second surface area is smaller than the first surface area.

13. The electrosurgical instrument of claim 11, wherein the second jaw comprises an electrically conductive skeleton partially coated with the first material.

14. The electrosurgical instrument of claim 13, wherein the electrically conductive skeleton comprises an inner thermally-insulative core and an outer thermally-conductive layer at least partially surrounding the inner thermally-insulative core.

15. The electrosurgical instrument of claim 11, wherein the variable energy densities are predetermined based on a selection of different geometries and different conductivities of the conductive segments.

16. The electrosurgical instrument of claim 11, wherein at least one of the segments comprises a gradually narrowing width along its length.

17. The electrosurgical instrument of claim 11, wherein the segments extend along a peripheral side of the second jaw.

18. The electrosurgical instrument of claim 11, wherein the segments are defined in the second jaw but not the first jaw.

19. The electrosurgical instrument of claim 11, wherein the first material comprises diamond-like carbon.

20. The electrosurgical instrument of claim 11, wherein the second material comprises PolyTetraFluoroEthylene.

21. An electrosurgical instrument, comprising:
an end effector configurable between an open configuration and a closed configuration, wherein the end effector comprises:
a first jaw; and
a second jaw, comprising:
a first linear portion;
a second linear portion extending transversely from the first linear portion;
a first segment extending along the first linear portion, wherein the first segment comprises a first geometry and a first conductivity; and
a second segment extending along the second linear portion, wherein the second segment comprises a second geometry different than the first geometry and a second conductivity different than the first conductivity.

22. The electrosurgical instrument of claim 21, wherein first segment and the second segment are configured to produce variable energy densities along the second jaw.

23. The electrosurgical instrument of claim 21, wherein:
the first segment comprises a first surface area; and
the second segment comprises a second surface area, wherein the second surface area is smaller than the first surface area.

24. The electrosurgical instrument of claim 21, wherein at least one of the first segment and the second segment comprises conductive treatment regions longitudinally interrupted by nonconductive treatment regions.

25. The electrosurgical instrument of claim 21, wherein at least one of the first segment and the second segment comprises a gradually narrowing width along its length.

26. The electrosurgical instrument of claim 21, wherein the first segment and the second segment extend along a peripheral side of the second jaw.

27. The electrosurgical instrument of claim 21, wherein the first segment and the second segment are defined in the second jaw but not the first jaw.

28. The electrosurgical instrument of claim 21, wherein the second jaw comprises an electrically conductive skeleton partially coated with a first material and a second material, wherein the first material is thermally conductive but electrically insulative, and wherein the second material is thermally and electrically insulative.

29. The electrosurgical instrument of claim 28, wherein the first material comprises diamond-like carbon.

30. The electrosurgical instrument of claim 29, wherein the second material comprises PolyTetraFluoroEthylene.

31. An electrosurgical instrument, comprising:
an end effector configurable between an open configuration and a closed configuration, wherein the end effector comprises:
a first jaw; and a second jaw comprising a tissue contacting surface, wherein the tissue contacting surface comprises:
   an insulative layer comprising a first material; and
   segments configured to yield variable energy densities along the tissue contacting surface, wherein the segments comprise:
      conductive segments; and
      insulative segments selectively interrupting the conductive segments along the tissue contacting surface, wherein the insulative segments comprise a second material different from the first material.

32. The electrosurgical instrument of claim 31, wherein the insulative layer extends on opposite sides of an intermediate area of the second jaw.

33. The electrosurgical instrument of claim 31, wherein the second jaw comprises:
   a proximal end defining a first width; and
   a distal end defining a second width smaller than the first width, wherein the width of the second jaw narrows from the first width to the second width along the length thereof.

34. The electrosurgical instrument of claim 31, wherein the conductive segments comprise:
   a proximal segment comprising a first surface area; and
   a distal segment comprising a second surface area, wherein the second surface area is smaller than the first surface area.

35. The electrosurgical instrument of claim 31, wherein the second jaw comprises an electrically conductive skeleton partially coated with the first material.

36. The electrosurgical instrument of claim 35, wherein the electrically conductive skeleton comprises an inner thermally-insulative core and an outer thermally-conductive layer at least partially surrounding the inner thermally-insulative core.

37. The electrosurgical instrument of claim 31, wherein the variable energy densities are predetermined based on a selection of different geometries and different conductivities of the conductive segments.

38. The electrosurgical instrument of claim 31, wherein at least one of the segments comprises a gradually narrowing width along its length.

39. The electrosurgical instrument of claim 31, wherein the segments extend along a peripheral side of the second jaw.

40. The electrosurgical instrument of claim 31, wherein the segments are defined in the second jaw but not the first jaw.

41. The electrosurgical instrument of claim 31, wherein the first material comprises diamond-like carbon.

42. The electrosurgical instrument of claim 31, wherein the second material comprises PolyTetraFluoroEthylene.

* * * * *